(12) United States Patent
Hendricks et al.

(10) Patent No.: US 10,251,882 B2
(45) Date of Patent: Apr. 9, 2019

(54) AZA-PYRIDONE COMPOUNDS AND USES THEREOF

(71) Applicant: Alios BioPharma, Inc., South San Francisco, CA (US)

(72) Inventors: Robert Than Hendricks, San Carlos, CA (US); Leonid Beigelman, San Mateo, CA (US); David Bernard Smith, San Mateo, CA (US); Antitsa Dimitrova Stoycheva, Half Moon Bay, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

(21) Appl. No.: 15/141,387

(22) Filed: Apr. 28, 2016

(65) Prior Publication Data

US 2016/0228438 A1    Aug. 11, 2016

Related U.S. Application Data

(62) Division of application No. 14/482,886, filed on Sep. 10, 2014, now Pat. No. 9,328,119.

(60) Provisional application No. 62/031,673, filed on Jul. 31, 2014, provisional application No. 62/011,784, filed on Jun. 13, 2014, provisional application No. 61/877,151, filed on Sep. 12, 2013.

(51) Int. Cl.

| | |
|---|---|
| *A61K 31/5025* | (2006.01) |
| *C07D 487/04* | (2006.01) |
| *A61K 31/13* | (2006.01) |
| *A61K 31/196* | (2006.01) |
| *A61K 31/215* | (2006.01) |
| *A61K 31/351* | (2006.01) |
| *A61K 31/4965* | (2006.01) |
| *A61K 31/5377* | (2006.01) |
| *A61K 31/7056* | (2006.01) |
| *A61K 38/21* | (2006.01) |
| *C07B 59/00* | (2006.01) |

(52) U.S. Cl.
CPC .......... *A61K 31/5025* (2013.01); *A61K 31/13* (2013.01); *A61K 31/196* (2013.01); *A61K 31/215* (2013.01); *A61K 31/351* (2013.01); *A61K 31/4965* (2013.01); *A61K 31/5377* (2013.01); *A61K 31/7056* (2013.01); *A61K 38/212* (2013.01); *C07B 59/002* (2013.01); *C07D 487/04* (2013.01); *C07B 2200/05* (2013.01)

(58) Field of Classification Search
CPC .. A61K 45/06; A61K 31/5025; A61K 31/706; C07D 487/04; C07D 519/00; C07H 17/02
See application file for complete search history.

(56) References Cited

U.S. PATENT DOCUMENTS

| | | | |
|---|---|---|---|
| 7,211,572 B2 | 5/2007 | Miyazaki et al. | |
| 8,383,638 B2 | 2/2013 | Kuduk et al. | |
| 8,455,475 B2 | 6/2013 | Schunk et al. | |
| 9,328,119 B2* | 5/2016 | Hendricks | C07D 487/04 |
| 2005/0054645 A1 | 3/2005 | Miyazaki et al. | |
| 2006/0052596 A1 | 3/2006 | Muller et al. | |
| 2007/0135525 A1 | 6/2007 | Liang et al. | |
| 2009/0099168 A1 | 4/2009 | Donghi et al. | |
| 2009/0281107 A1 | 11/2009 | Congy et al. | |
| 2010/0143301 A1 | 6/2010 | Desai et al. | |
| 2010/0197651 A1 | 8/2010 | Taniguchi et al. | |
| 2011/0275608 A1 | 11/2011 | Rodriguez et al. | |
| 2012/0022255 A1 | 1/2012 | Fujishita et al. | |
| 2012/0184734 A1 | 7/2012 | Akiyama et al. | |
| 2013/0197219 A1 | 8/2013 | Takahashi et al. | |
| 2013/0231327 A1 | 9/2013 | Schunk et al. | |
| 2015/0072982 A1 | 3/2015 | Hendricks et al. | |
| 2016/0221963 A1 | 8/2016 | Beigelman et al. | |
| 2016/0264581 A1* | 9/2016 | Hendricks | C07D 487/04 |
| 2017/0260189 A1 | 9/2017 | Welch et al. | |

FOREIGN PATENT DOCUMENTS

| | | |
|---|---|---|
| AU | 2007330652 | 7/2009 |
| CL | 201603024 | 11/2016 |
| CN | 1594300 A | 3/2005 |
| CN | 101340902 A | 1/2009 |
| CN | 102803260 A | 11/2012 |
| EP | 1544199 A1 | 6/2005 |
| EP | 2042402 A1 | 4/2009 |
| EP | 2042502 | 4/2009 |
| EP | 2444400 | 4/2012 |
| JP | 2007-528379 A | 10/2007 |

(Continued)

OTHER PUBLICATIONS

Bunce, R.A. et al., "A Synthesis of Diphenyl Methyl Ketones" Synthetic Communications (1990) 20(19), 3007-3014.

(Continued)

*Primary Examiner* — Alexander R Pagano
*Assistant Examiner* — Ebenezer O Sackey
(74) *Attorney, Agent, or Firm* — Morrison & Foerster LLP

(57) ABSTRACT

Disclosed herein are aza-pyridone compounds, pharmaceutical compositions that include one or more aza-pyridone compounds, and methods of synthesizing the same. Also disclosed herein are methods of ameliorating and/or treating a disease and/or a condition, including an orthomyxovirus infection, with an aza-pyridone compounds. Examples of an orthomyxovirus viral infection include an influenza infection.

33 Claims, 4 Drawing Sheets

Specification includes a Sequence Listing.

(56) References Cited

FOREIGN PATENT DOCUMENTS

| WO | WO 1995/020583 | 8/1995 |
|----|----------------|--------|
| WO | WO 2005/016927 | 2/2005 |
| WO | WO 2005/099688 | 10/2005 |
| WO | WO 2008/068424 | 6/2008 |
| WO | WO 2008/077188 | 7/2008 |
| WO | WO 2009/053799 | 4/2009 |
| WO | WO-2009/087379 A2 | 7/2009 |
| WO | WO 2010/080864 | 7/2010 |
| WO | WO 2010/090737 | 8/2010 |
| WO | WO 2010/096338 | 8/2010 |
| WO | WO 2010/108651 | 9/2010 |
| WO | WO 2010/110231 | 9/2010 |
| WO | WO 2010/138419 | 12/2010 |
| WO | WO-2010/147068 A1 | 12/2010 |
| WO | WO 2011/084371 | 7/2011 |
| WO | WO-2011/105590 A1 | 9/2011 |
| WO | WO 2011/120153 | 10/2011 |
| WO | WO 2012/009194 | 1/2012 |
| WO | WO 2012/039414 | 3/2012 |
| WO | WO 2013/049352 | 4/2013 |
| WO | WO 2014/108406 | 7/2014 |
| WO | WO 2015/038655 | 3/2015 |
| WO | WO 2015/038660 | 3/2015 |
| WO | WO 2017/223231 | 12/2017 |

OTHER PUBLICATIONS

Carey, Francis, Organic Chemistry, 2nd ed., McGraw Hill, Inc., New York (1992), pp. 328-331.
CAS Reg. No. 1259366-34-1, Entry Date Jan. 14, 2011, Retrieved on Dec. 2, 2014.
CAS Reg. No. 1422050-75-6, Entry Date Feb. 28, 2013, Retrieved on Dec. 2, 2014.
Clark, J.A., et al., "Substituted 3-amino-1,1-diaryl-2-propanols as potential antidepressant agents" J. Med. Chem. (1979) 22(11), 1373-1379.
Gilchrist, T.L., et al., "Formation of Pyridazino[6,1-c][1,4]oxazin-8(7H)-ones by Intramolecular Cycloaddition of Azoalkenes" Journal of the Chemical Society, Perkin Transactions I (1987) 11:2517-2522.
Gopishetty et. al., "An improved asymmetric synthetic route to a novel triple uptake inhibitor antidepressant (2S,4R,5R)-2-benzhydryl-5-((4-methoxybenzyl)amino)tetrahydro-2H-pyran-4-ol (D-142)" Tetrahedron: Asymmetry (2011) 22(10):1081-1086.
Greene, et al., Protective Groups in Organic Synthesis, 3. Ed., John Wiley & Sons, (1999) Cover & Contents pages.
Hassall, C.H., et al, "Amino-acids and Peptides. Part XII. The Molecular Structures of the Monamycins, Cyclodepsipeptide Antibiotics" Journal of the Chemical Society C: Organic (1971) 3:526-532.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
Kumazawa, T. et al., "Inhibitors of Acyl-CoA:Cholesterol Acyltransferase. 1. Synthesis and Hypocholesterolemic Activity of Dibenz[b,e]oxepin-11-carboxanilides" J. Med. Chem. (1994) 37(6), 804-810.
Martz, K.E., et. al., "Targeting the Hinge Glycine Flip and the Activation Loop: Novel Approach to Potent p38α Inhibitors" J. Med. Chem. (2012) 55(17):7862-7874.
McMurry, Organic Chemistry, 5th ed., Brooks/Cole, Pacific Grove, CA (2000), Chapter 11.5, pp. 398 and 408.
Mcomie, J. F. W., Protective Groups in Organic Chemistry, Plenum Press, 1973. Cover & Contents pages only.
Prichard, M. N. et al., "A three-dimensional model to analyze drug-drug interactions" Antiviral Res. (1990) 14(4-5):181-205.
Snieckus et. al., "Regioselective N-methyl carbon lithiation of N-boc-methylalkylamines. Expedient synthesis of unsymmetrical amines" Tet. Lett. (1994) 35(24):4067-4070.
Streitwieser et al., Introduction to Organic Chemistry, 2nd ed., Macmillan Publishing Co. Inc., New York, NY, 1981, pp. 169-171.
International Search Report and Written Opinion dated Dec. 1, 2014 for PCT Application No. PCT/US2014/055012 filed Sep. 10, 2014.
International Preliminary Report on Patentability dated Mar. 15, 2016 for PCT Application No. PCT/US2014/055012, filed Sep. 10, 2014.
Office Action dated Nov. 19, 2015 for U.S. Appl. No. 14/482,886, filed Sep. 10, 2014.
Office Action dated Apr. 12, 2016 for Colombian Application No. 16-71186-1, filed Sep. 10, 2014.
Extended European Search Report dated Feb. 16, 2017 for EP Application No. 14844961.4, filed Sep. 10, 2014.
Notification-Demand dated Mar. 21, 2017 for Georgian Application No. 14114/01, filed Sep. 10, 2014.
Notification-Demand dated Oct. 20, 2016 for Georgian Application No. 14114/01, filed Sep. 10, 2014.
Search Report and Written Opinion dated Mar. 7, 2017 for Singapore Application No. 11201601571W, filed Sep. 10, 2017.
Office Action dated Feb. 21, 2017 for Chinese Application No. 201480061771.X, filed Sep. 10, 2014.
Office Action dated Dec. 2, 2016 for Eurasian Application No. 201690372, filed Sep. 10, 2014.
Song et al., "Advances in Research on Anti-Influenza Virus Drugs" Foreign Medical Sciences Section of Pharmacy (2005) 32(2):111-115.
Written Opinion dated Dec. 5, 2017 for Singapore Application No. 11201601571W, filed Sep. 10, 2017.
Zhang et al., "Synthesis and Evaluation of 1,4,5,6-Tetrahydropyridazine Derivatives As Influenza Neuraminidase Inhibitors" Bioorganic & Medicinal Chemistry Letters (1999) 9(13):1751-1756.
Office Action dated Jul. 14, 2017 for Chilean Application No. 2016-000539, filed Sep. 10, 2014.
Office Action dated Aug. 16, 2017 for Colombian Application No. 16-71186-1, filed Sep. 10, 2014.
Examination Report dated Nov. 23, 2017 for Australian Application No. 2014318832, filed Sep. 10, 2014.
Communication dated Mar. 28, 2018 for EP Application No. 14844961.4, filed Sep. 10, 2014.
Office Action dated Jan. 12, 2018 for Chinese Application No. 201480061771.X, filed Sep. 10, 2014.
Chilean Office Action dated Apr. 11, 2018 for Chilean Application No. 2016-000539, filed Sep. 10, 2014, (Machine Translation of the Office Action is provided).
Israeli Office Action dated Jul. 16, 2018 for IL Application No. 24432 filed Sep. 10, 2014.
Japanese Office Action dated Jun. 19, 2018 for JP Application No. 2016-542073 filed Sep. 10, 2014.
Singapore Examination Report dated Sep. 6, 2018 for Singapore Application No. 11201601571W, filed Sep. 10, 2017.
Singapore Notice of Eligibility for Grant dated Sep. 11, 2018 for Singapore Application No. 11201601571W, filed Sep. 10, 2017.
Taiwanese Office Action dated May 30, 2018 for TW Application No. 103131647, filed Sep. 10, 2014.
Uzbekistan Office Action dated on Aug. 17, 2018 for UZ Application No. IAP20160128, filed Sep. 10, 2017.
Japanese Notice of Allowance dated Nov. 6, 2018 for JP Application No. 2016-542073 filed Sep. 10, 2014.
Thailand Office Action dated Oct. 29, 2018 for TH Application No. 1601001372, filed Sep. 10, 2014.
Australian Notice of Acceptance for Patent Application dated Nov. 20, 2018 for Australian Application No. 2014318832, filed Sep. 10, 2014.
Georgian Notice of Allowance dated Nov. 15, 2018 for Georgian Application No. 14114/01, filed Sep. 10, 2014.
Philippines Substantive Examination Report dated Dec. 14, 2018 for PH Application No. 1/2016/500486 filed Mar. 11, 2016.
Taiwanese Notice of Allowance dated Dec. 10, 2018 for TW Application No. 103131647, filed Sep. 10, 2014.
European Office Action dated Jan. 15, 2019 for EP Application No. 14844961.4, filed Sep. 10, 2014.

* cited by examiner

| Name or CAS No. | IUPAC Name | Structure |
|---|---|---|
| amantadine | adamantan-1-amine | 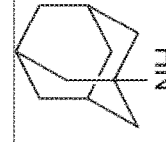 |
| rimantadine | (RS)-1-(1-adamantyl)ethanamine | 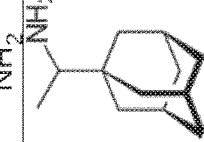 |
| zanamivir | (2R,3R,4S)-4-guanidino-3-(prop-1-en-2-ylamino)-2-((1R,2R)-1,2,3-trihydroxypropyl)-3,4-dihydro-2H-pyran-6-carboxylic acid | 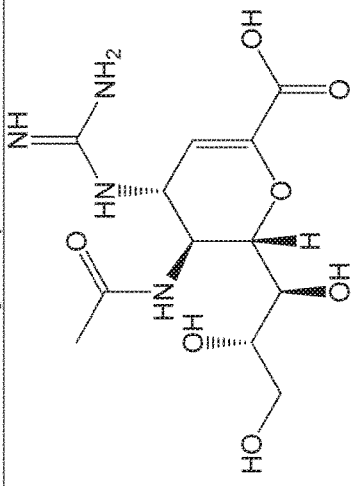 |
| oseltamivir | ethyl (3R,4R,5S)-5-amino-4-acetamido-3-(pentan-3-yloxy)-cyclohex-1-ene-1-carboxylate | 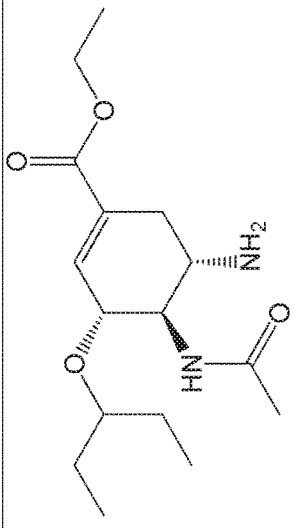 |

| Name or CAS No. | IUPAC Name | Structure |
|---|---|---|
| peramivir | (1S,2S,3S,4R)-3-[(1S)-1-acetamido-2-ethylbutyl]-4-(diaminomethylideneamino)-2-hydroxycyclopentane-1-carboxylic acid | 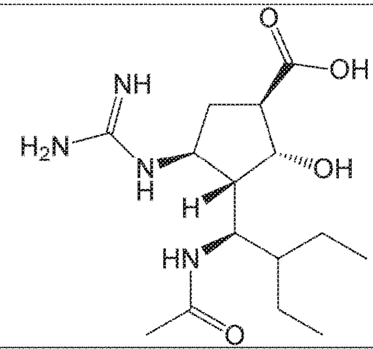 |
| laninamivir | (4S,5R,6R)-5-acetamido-4-carbamimidamido-6-[(1R,2R)-3-hydroxy-2-methoxypropyl]-5,6-dihydro-4H-pyran-2-carboxylic acid | 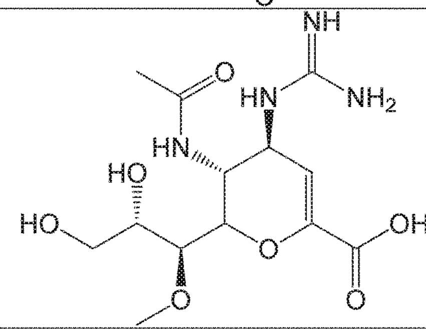 |
| laninamivir octanoate | (3R,4S)-3-acetamido-4-guanidino-2-((1S,2S)-2-hydroxy-1-methoxy-3-(octanoyloxy)propyl)-3,4-dihydro-2H-pyran-6-carboxylic acid | 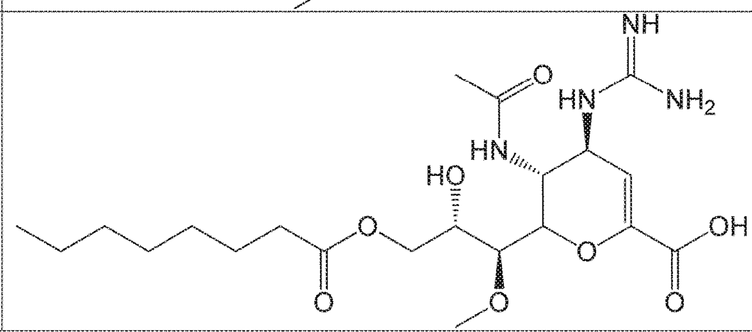 |

(cont.)

| Name or CAS No. | IUPAC Name | Structure |
|---|---|---|
| favipiravir | 6-fluoro-3-hydroxy-2-pyrazinecarboxamide | 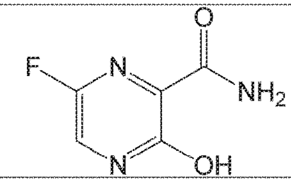 |
| beraprost | 4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid | 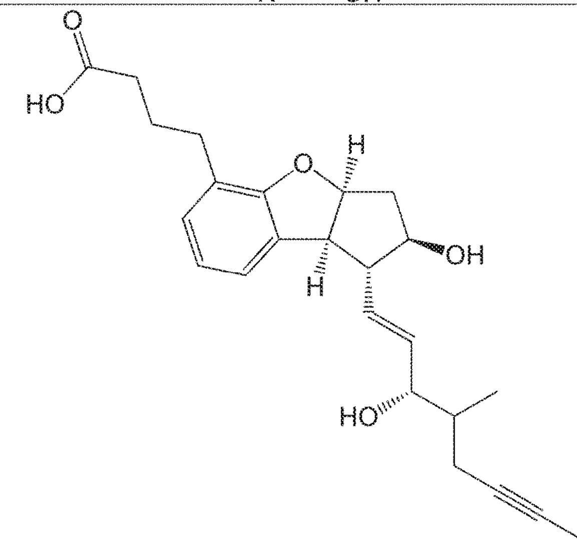 |
| ribavirin | 1-[(2R,3R,4S,5R)-3,4-dihydroxy-5-(hydroxymethyl)oxolan-2-yl]-1H-1,2,4-triazole-3-carboxamide | 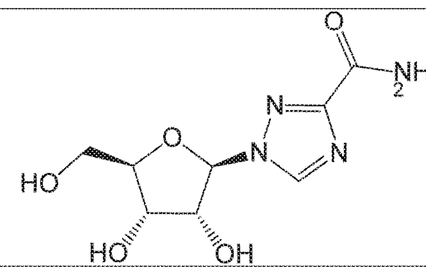 |

(cont.)

| Name or CAS No. | IUPAC Name | Structure |
|---|---|---|
| 1422050-75-6 | (R)-3-((5-fluoro-2-(5-fluoro-1H-pyrrolo[2,3-b]pyridin-3-yl)pyrimidin-4-yl)amino)-4,4-dimethylpentanoic acid | 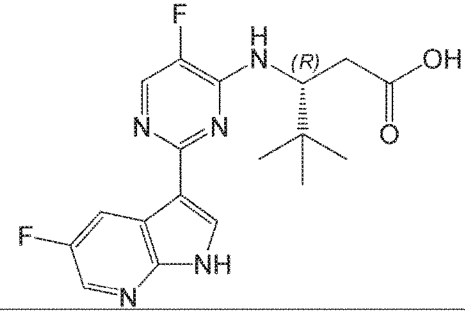 |
| VX-787 | (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid | 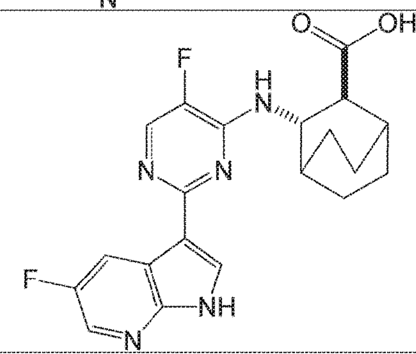 |

SEQUENCE LISTING

<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<223> OTHER INFORMATION: synthetic oligoribonucleotide

<400> SEQUENCE: 1
auuuuguuuu uaauauuuc 19

AZA-PYRIDONE COMPOUNDS AND USES THEREOF

CROSS REFERENCE TO RELATED APPLICATIONS

This application is a division application of U.S. patent application Ser. No. 14/482,886, filed on Sep. 10, 2014, now U.S. Pat. No. 9,328,119, which claims the benefit of U.S. Provisional Application Nos. 62/031,673, filed Jul 31, 2014, 62/011,784, filed Jun. 13, 2014, and 61/877,151, filed Sep. 12, 2013.

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

SEQUENCE LISTING

The present application is being filed along with a Sequence Listing in electronic format. The Sequence Listing is provided as a file entitled ALIOS078, created Apr. 28, 2016, which is 4 kb bytes in size. The information in the electronic format of the Sequence Listing is incorporated herein by reference in its entirety.

BACKGROUND

Field

The present application relates to the fields of chemistry, biochemistry and medicine. More particularly, disclosed herein are aza-pyridone compounds, pharmaceutical compositions that include one or more aza-pyridone compounds, and methods of synthesizing the same. Also disclosed herein are methods of ameliorating and/or treating an orthomyxovirus viral infection with one or more aza-pyridone compounds.

Description

The viruses of the Orthomyxoviridae family are negative-sense, single-stranded RNA viruses. The Orthomyxoviridae family contains several genera including Influenzavirus A, Influenzavirus B, Influenzavirus C, Isavirus and Thogotovirus. Influenzaviruses can cause respiratory viral infections, including upper and lower respiratory tract viral infections. Respiratory viral infections are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

SUMMARY

Some embodiments disclosed herein relate to a compound of Formula (I), or a pharmaceutically acceptable salt thereof.

Some embodiments disclosed herein relate to methods of ameliorating and/or treating an orthomyxovirus viral infection that can include administering to a subject suffering from the orthomyxovirus viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating an orthomyxovirus viral infection. Still other embodiments described herein relate to a compound of Formula (I), or a pharmaceutically acceptable salt thereof, that can be used for ameliorating and/or treating an orthomyxovirus viral infection. Yet still other embodiments disclosed herein relate to methods of ameliorating and/or treating an orthomyxovirus viral infection that can include contacting a cell infected with the orthomyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. Some embodiments disclosed herein relate to methods of preventing an orthomyxovirus infection that can include administering to a subject an effective amount of one or more compounds of Formula (I), or a pharmaceutically acceptable salt thereof, or a pharmaceutical composition that includes one or more compounds of Formula (I), or a pharmaceutically acceptable salt thereof. For example, the orthomyxovirus viral infection can be an influenza viral infection (such as influenza A, B and/or C).

Some embodiments disclosed herein relate to methods of inhibiting the replication of an orthomyxovirus that can include contacting a cell infected with the orthomyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. For example, the orthomyxovirus viral infection can be an influenza viral infection (such as influenza A, B and/or C). Other embodiments disclosed herein relate to a method for inhibiting endonuclease activity of an influenza endonuclease that can include contacting the active site of the endonuclease with an effective amount of one or more compounds of Formula (I), or a pharmaceutically acceptable salt thereof, or a pharmaceutical composition that includes one or more compounds of Formula (I), or a pharmaceutically acceptable salt thereof. These and other embodiments are described in greater detail below.

BRIEF DESCRIPTION OF THE DRAWINGS

FIG. 1 shows example anti-influenza agents.

DETAILED DESCRIPTION

Influenza is a negative sense, single stranded RNA virus and a member of the Orthomyxoviridae family. There are currently three species of influenza; influenza A, influenza B and influenza C. Influenza A has a lipid membrane derived from the host cell, which contains the hemagglutinin, neuramididase and M2 proteins that project from the surface of the virus. Influenza A has been further classified based the hemagglutinin (H or HA) and the neuramididase (N). There are approximately 16 H antigens (H1 to H16) and 9 N antigens (N1 to N9). Influenza A includes several subtypes, including H1N1, H1N2, H2N2, H3N1, H3N2, H3N8, H5N1, H5N2, H5N3, H5N8, H5N9, H7N1, H7N2, H7N3, H7N4, H7N7, H7N9, H9N2 and H10N7. The influenza virus polymerase is a heterotrimer composed of three subunits, polymerase acid (PA), polymerase basic 1 (PB1) and polymerase basic 2 (PB2). This polymerase is responsible for replication and transcription of the viral RNA in the nuclei of infected cells. The PA subunit contains the endonuclease active site. The endonuclease activity of the PA cleaves the cellular mRNA, which is then used by the PB1 subunit as a primer for the viral mRNA synthesis.

Influenza viruses can be transmitted from person to person via direct contact with infected secretions and/or contaminated surfaces or objections. Complications from an influenza viral infection include pneumonia, bronchitis, dehydration, and sinus and ear infections. Medications currently approved by the FDA against an influenza infection include a limited number of neuraminidase inhibitors and M2 protein inhibitors. Examples of approved neuraminidase inhibitors and M2 protein inhibitors include amantadine, rimantadine, Relenza® (zanamivir, GlaxoSmithKline) and Tamiflu® (oseltamivir, Genentech).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^{3a}$, $R^{3b}$, $R^4$, $R^5$ and $R^6$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^a R^b$ group are indicated to be "taken together," it means that they are covalently bonded to one another to form a ring:

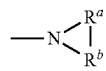

In addition, if two "R" groups are described as being "taken together" with the atom(s) to which they are attached to form a ring as an alternative, the R groups may not be limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl (straight and branched) and hexyl (straight and branched). The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) mono-cyclic or multi-cyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a mono-cyclic or multi-cyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered mono-cyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and/or aryl group of an aryl (alkyl) may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and/or heteroaryl group of heteroaryl(alkyl) may be substituted or unsubstituted. Examples include but are not limited to 2-thienyl (alkyl), 3-thienyl(alkyl), furyl(alkyl), thienyl(alkyl), pyrrolyl(alkyl), pyridyl(alkyl), isoxazolyl(alkyl), imidazolyl (alkyl), and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and/or heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is alkyl, alkenyl, alkynyl, cycloalkyl, cycloalkenyl, aryl, heteroaryl, heterocyclyl, cycloalkyl(alkyl), aryl (alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group of the formula —O— alkyl in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SW" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$W" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl and isobutyryl); arylalkylcarbonyls and arylalkoxycarbonyls (e.g., benzyloxycarbonyl); substituted methyl ether (e.g. methoxymethyl ether and tetrahydropyranyl ether); substituted ethyl ether; a substituted benzyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl and t-butyldiphenylsilyl); esters (e.g. benzoate ester); carbonates (e.g. methoxymethylcarbonate); sulfonates (e.g. tosylate and mesylate); acyclic ketal (e.g. dimethyl acetal and diisopropyl acetal); cyclic ketals (e.g., 1,3-dioxane and 1,3-dioxolane); acyclic acetal; cyclic acetal; acyclic hemiacetal; cyclic hemiacetal; dithioacetals (both cyclic and acyclic); dithioketals (both cyclic and acyclic) (e.g., S,S'-dimethyl, S,S'-diethyl, S,S'-diisopropyl, 1,3-dithiane and 1,3-dithiolane); orthoesters (including cyclic orthoesters, such as cyclic orthoformates); carbamates (e.g., N-phenylcarbamate) and triarylmethyl groups (e.g., trityl, monomethoxytrityl (MMTr), 4,4'-dimethoxytrityl (DMTr), and 4,4',4''-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, trifluoroacetates and halogens (e.g., I, Br, and Cl). Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof,

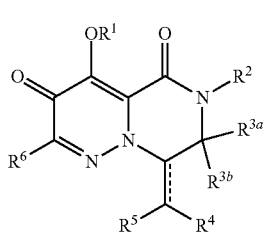

(I)

wherein: ----- can be a single bond or double bond; $R^1$ can be selected from hydrogen, an unsubstituted $C_{1-4}$ alkyl, —C(=O)$Y^1$, —C(=O)—O—$Y^1$, —(CH$_2$)—O—(C=O)—$Y^1$, —(CH$_2$)—O—(C=O)—O—$Y^1$, —(CHCH$_3$)—O—(C=O)—$Y^1$ and —(CHCH$_3$)—O—(C=O)—O—$Y^1$; $R^2$ can be selected from hydrogen, an optionally substituted $C_{1-6}$ alkyl, an optionally substituted heterocyclyl, an optionally substituted cycloalkyl($C_{1-6}$ alkyl), an optionally substituted aryl($C_{1-6}$ alkyl), an optionally substituted heteroaryl($C_{1-6}$ alkyl) and an optionally substituted heterocyclyl($C_{1-6}$ alkyl); $R^{3a}$ and $R^{3b}$ can be independently hydrogen or an optionally substituted $C_{1-4}$ alkyl; $R^4$ and $R^5$ can be independently selected from hydrogen, an optionally substituted aryl, an optionally substituted aryl($C_{1-6}$ alkyl) an optionally substituted heteroaryl and an optionally substituted heteroaryl($C_{1-6}$ alkyl), provided that at least one of $R^4$ and $R^5$ is not hydrogen; or $R^4$ and $R^5$ can be taken together to form an optionally substituted tricyclic cycloalkenyl or an optionally substituted tricyclic heterocyclyl; $R^6$ can be selected from hydrogen, halogen, —CN, an optionally substituted $C_{1-6}$ alkyl, an optionally substituted aryl, an optionally substituted heteroaryl, —CH$_2$OH, —CH($Y^2$)(OH) and —C(O)$Y^2$; and $Y^1$ and $Y^2$ can be independently selected from an optionally substituted $C_{1-6}$ alkyl, an optionally substituted $C_{3-6}$ cycloalkyl, an optionally substituted aryl an optionally substituted heteroaryl, an optionally substituted heterocyclyl, a mono-substituted amino group, a di-substituted amino and —C($R^7$)NH$R^8$; and $R^7$ and $R^8$ can be independently hydrogen or an optionally substituted $C_{1-4}$ alkyl.

Various groups can be present for $R^4$ and $R^5$. In some embodiments, $R^4$ can be hydrogen. In other embodiments, $R^4$ can be an optionally substituted aryl, such as an optionally substituted phenyl or an optionally substituted naphthyl. When the phenyl ring is substituted, it can be substituted 1, 2, or 3 or more times. When $R^4$ is a mono-substituted phenyl, the mono-substituted phenyl can be ortho-substituted, meta-substituted or para-substituted. In still other embodiments, $R^4$ can be an optionally substituted aryl($C_{1-6}$ alkyl). For example, $R^4$ can be an optionally substituted benzyl. The phenyl ring of the benzyl group can be unsubstituted or substituted 1, 2, or 3 or more times. In yet still other embodiments, $R^4$ can be an optionally substituted heteroaryl. In some embodiments, $R^4$ can be an optionally substituted heteroaryl($C_{1-6}$ alkyl). Examples of optionally substituted heteroaryls include, but are not limited to, an optionally substituted imidazole

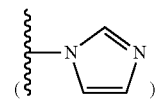

and an optionally substituted pyrazole

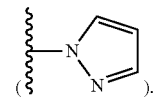

The heteroaryl ring of an optionally substituted heteroaryl and an optionally substituted heteroaryl($C_{1-6}$ alkyl) can be unsubstituted or substituted with 1, 2 or 3 or more substituents.

In some embodiments, including those of the preceding paragraph, $R^5$ can be an optionally substituted aryl. For example, $R^5$ can be an optionally substituted phenyl or an optionally substituted naphthyl. When $R^5$ is a mono-substituted phenyl, the mono-substituted phenyl can be ortho-substituted, meta-substituted or para-substituted. In still other embodiments, $R^5$ can be an optionally substituted aryl($C_{1-6}$ alkyl), such as an optionally substituted benzyl. The optionally substituted aryl and aryl ring of the an optionally substituted aryl($C_{1-6}$ alkyl) can be unsubstituted or substituted with 1, 2 or 3 or more substituents. In still other embodiments, $R^4$ can be an optionally substituted heteroaryl. For example, $R^4$ can be an optionally substituted pyridinyl, an optionally substituted imidazolyl or an optionally substitute pyrazolyl. In yet still other embodiments, $R^4$ is an optionally substituted heteroaryl($C_{1-6}$ alkyl). When substituted, the optionally substituted heteroaryl and the optionally substituted heteroaryl($C_{1-6}$ alkyl) can be substituted 1, 2 or 3 or more times. In some embodiments, $R^4$ and/or $R^5$ can be substituted with one or more substituents selected from halo (such as fluoro, chloro and iodo), $C_{1-4}$ alkyl (for example, methyl, ethyl, n-propyl, iso-propyl, n-butyl, iso-butyl, tert-butyl), $C_{2-4}$ alkynyl, a haloalkyl (such as CF$_3$), hydroxy, $C_{1-4}$ alkoxy (for example, methoxy, ethoxy, n-propoxy, iso-propoxy, cyclopropoxy and

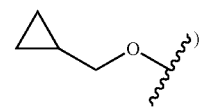 [SMILES: *OCC1CC1]

and an optionally substituted aryl (for example, an optionally substituted phenyl), cyano, NC—(CH$_2$)—, H$_2$N—C(=O)—(CH$_2$)—, O-amido(CH$_2$)— and an optionally substituted heteroaryl($C_{1-6}$ alkyl) (such as

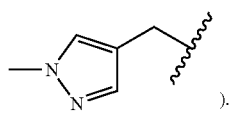 [SMILES: *Cc1cnn(C)c1]

In some embodiments, $R^4$ and $R^5$ can each be an optionally substituted phenyl. For example, $R^4$ and $R^5$ can be each a substituted phenyl substituted with one or more group selected from halo (such as fluoro, chloro and iodo), $C_{1-4}$ alkyl (for example, methyl, ethyl, n-propyl, iso-propyl, n-butyl, iso-butyl, tert-butyl), $C_{2-4}$ alkynyl, a haloalkyl (such as $CF_3$), hydroxy, $C_{1-4}$ alkoxy (for example, methoxy, ethoxy, n-propoxy, iso-propoxy, cyclopropoxy and

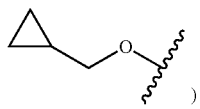 [SMILES: *OCC1CC1]

and an optionally substituted aryl (for example, an optionally substituted phenyl), cyano, $NC(C_{1-4}$ alkyl) (for example, $NC-(CH_2)-$), O-amido($C_{1-4}$ alkyl)- (for example, $H_2N-C(=O)-(CH_2)-$), and an optionally substituted heteroaryl($C_{1-6}$ alkyl) (such as

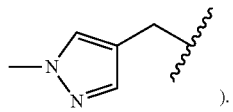 [SMILES: *Cc1cnn(C)c1]

In some embodiments, $R^4$ and $R^5$ can each be a deuterated phenyl. The deuteratd phenyl can include one or more deuteriums (for example, 1, 2, 3, 4 or 5 deuteriums). In some embodiments, $R^4$ and $R^5$ can be the same. For example, $R^4$ and $R^5$ can both be an unsubstituted phenyl. In other embodiments, $R^4$ and $R^5$ can be different. As an example, $R^4$ can be an optionally substituted heteroaryl (such as an optionally substituted mono-cyclic heteroaryl), and $R^5$ can be an optionally substituted aryl (such as an optionally substituted phenyl). As an another example, $R^4$ can be an optionally substituted aryl (such as an optionally substituted phenyl), and $R^5$ can be an optionally substituted aryl($C_{1-6}$ alkyl) (such as an optionally substituted benzyl).

Instead of being separate groups, $R^4$ and $R^5$ can be taken together to form a tricyclic ring group. In some embodiments, $R^4$ and $R^5$ can be taken together to form an optionally substituted tricyclic cycloalkenyl. In some embodiments, $R^4$ and $R^5$ can be taken together to form an optionally substituted tricyclic heterocyclyl. One, two or more than to heteroatoms can be present in the optionally substituted tricyclic heterocyclyl such as nitrogen (N), oxygen (O) and sulfur (S), including oxidized versions of sulfur (e.g., S=O and S=$O_2$). The optionally substituted tricyclic heterocyclyl can be two aryl rings and one heterocyclyl ring, wherein the aryl rings can be the same or different. Alternatively, the optionally substituted tricyclic heterocyclyl can be two heteroaryl rings and one cycloalkenyl ring, wherein the heteroaryl rings can be the same or different; one aryl ring, one cycloalkenyl ring and one heterocyclyl ring; two heterocyclyl rings and one cycloalkenyl or cycloalkyl ring. When substituted, one or more of the rings of the optionally substituted tricyclic cycloalkenyl and/or the optionally substituted tricyclic heterocyclyl can be substituted one or more times. Various groups can be substituted on an optionally substituted tricyclic heterocyclyl, such as halogen (such as fluoro, chloro and iodo) and/or $C_{1-4}$ alkyl (for example, methyl, ethyl, n-propyl, iso-propyl, n-butyl, iso-butyl and tert-butyl). Examples of the optionally substituted tricyclic cycloalkenyl and the optionally substituted tricyclic heterocyclyl include, but are not limited to, the following optionally substituted moieties:

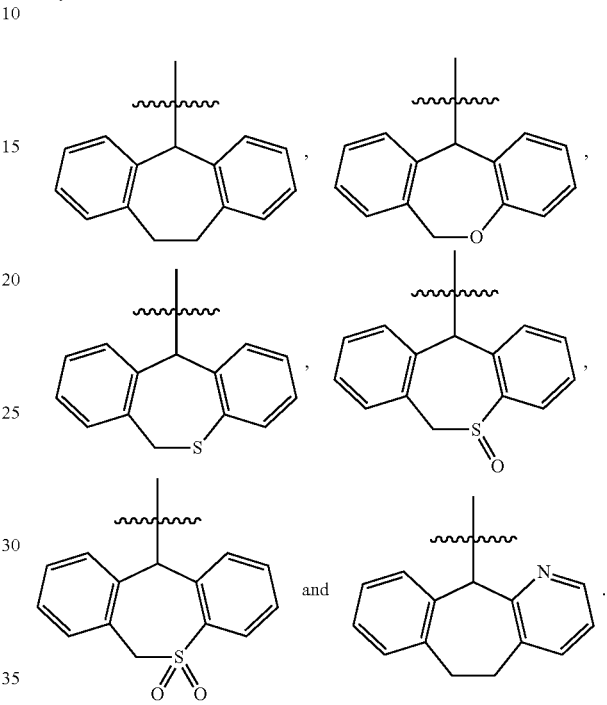

In some embodiments, $R^2$ can be hydrogen. In other embodiments, $R^2$ can be an optionally substituted $C_{1-6}$ alkyl. In some embodiments, $R^2$ can be an unsubstituted $C_{1-6}$ alkyl. The $C_{1-6}$ alkyl can be methyl, ethyl, n-propyl, isopropyl, n-butyl, iso-butyl, tert-butyl, pentyl (straight or branched) or hexyl (straight or branched). In some embodiments, $R^2$ can be a substituted $C_{1-6}$ alkyl. Various substituents can substitute the $C_{1-6}$ alkyl of $R^2$. In some embodiments, the substituted $C_{1-6}$ alkyl of $R^2$ can be substituted one or more times with a substituents selected from halogen, haloalkyl (such as $CF_3$), hydroxy and alkoxy. When substituted, in some embodiments, the one or more substituents on $R^2$ may not be present on the carbon closest to the nitrogen of the fused ring system. When $R_2$ is substituted at the carbon attached to the carbon closest to the nitrogen of the fused ring system of Formula (I), the carbon may be a chiral center. In some embodiments, the chiral center can be a (S)-chiral center. In other embodiments, the chiral center can be a (R)-chiral center.

In some embodiments, $R^2$ can be an optionally substituted cycloalkyl($C_{1-6}$ alkyl). In other embodiments, $R^2$ can be an optionally substituted heterocyclyl. In other embodiments, $R^2$ can be an optionally substituted aryl($C_{1-6}$ alkyl), such as an optionally substituted benzyl. The phenyl ring of the benzyl ring can be substituted 1, 2 or 3 or more times. When the phenyl ring of the benzyl group is mono-substituted, the phenyl ring can be substituted at the ortho-, meta- or para-position. In still other embodiments, $R^2$ can be an optionally substituted heteroaryl($C_{1-6}$ alkyl). In yet still other embodiments, $R^2$ can be an optionally substituted heterocyclyl($C_{1-6}$ alkyl). Examples of $R^2$ groups include, but are not limited to, hydrogen, methyl, ethyl, n-propyl, iso-propyl, n-butyl, isobutyl,

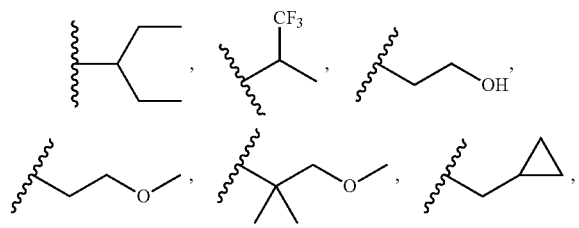

tetrahydro-2H-pyran and benzyl.

Various groups can be present at the $R^1$ position. In some embodiments, $R^1$ can be hydrogen. In other embodiments, $R^1$ can be an unsubstituted $C_{1-4}$ alkyl. For example, $R^1$ can be methyl, ethyl, n-propyl, iso-propyl, n-butyl, iso-butyl and t-butyl. In still other embodiments, $R^1$ can be a group that in vivo is capable of providing a compound of Formula (I), wherein $R^1$ is hydrogen or absent. Those skilled in the art understand that when $R^1$ is absent, the oxygen adjacent to $R^1$ can possess as associated negative charge. Examples of $R^1$ moieties that are capable of providing a compound of Formula (I), wherein $R^1$ is hydrogen or absent, include —C(=O)$Y^1$ and —C(=O)—O—$Y^1$. Additional examples of $R^1$ moieties that are capable of providing a compound of Formula (I), wherein $R^1$ is hydrogen or absent, include —(CH$_2$)—O—(C=O)—$Y^1$, —(CH$_2$)—O—(C=O)—O—$Y^1$, —(CHCH$_3$)—O—(C=O)—$Y^1$ or —(CHCH$_3$)—O—(C=O)—O—$Y^1$. In some embodiments, $R^1$ can be a group that is enzymatically cleaved to provide a compound of Formula (I), wherein $R^1$ is hydrogen or absent.

As described herein, $Y^1$ can be a variety of substituents. In some embodiments, $Y^1$ can be a substituted $C_{1-6}$ alkyl. In other embodiments, $Y^1$ can be an unsubstituted $C_{1-6}$ alkyl. In still other embodiments, $Y^1$ can be a substituted $C_{3-6}$ cycloalkyl. In yet still other embodiments, $Y^1$ can be an unsubstituted $C_{3-6}$ cycloalkyl. In some embodiments, $Y^1$ can be a substituted aryl (for example, a substituted phenyl). In other embodiments, $Y^1$ can be an unsubstituted aryl (for example, an unsubstituted phenyl). In still other embodiments, $Y^1$ can be a substituted heteroaryl (such as a substituted mono-cyclic heteroaryl). In yet still other embodiments, $Y^1$ can be an unsubstituted heteroaryl (such as an unsubstituted heteroaryl). In some embodiments, $Y^1$ can be a substituted heterocyclyl (such as a substituted mono-cyclic heterocyclyl). In other embodiments, $Y^1$ can be an unsubstituted heterocyclyl (such as an unsubstituted heterocyclyl). In still other embodiments, $Y^1$ can be a mono-substituted amino group. For example, the mono-substituted amino group can be

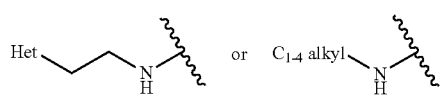

wherein Het can be an optionally substituted heteroaryl or an optionally substituted heterocyclyl. In yet still other embodiments, $Y^1$ can be a di-substituted amino group. In some embodiments, $Y^1$ can be —C($R^7$)NH$R^8$, wherein $R^7$ and $R^8$ can be independently hydrogen or an optionally substituted $C_{1-4}$ alkyl. For example, $Y^1$ can be:

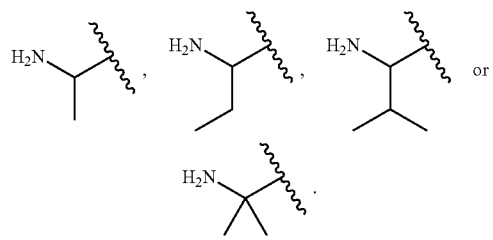

Example groups for $R^1$ include, but are not limited to, the following:

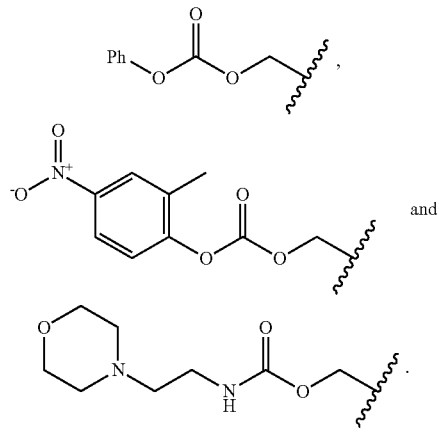

Various substituents can be present on the fused rings of Formula (I). For example, in some embodiments, $R^6$ can be hydrogen. In other embodiments, $R^6$ can be halogen. In still other embodiments, $R^6$ can be —CN. In yet still other embodiments, $R^6$ can be an optionally substituted $C_{1-6}$ alkyl. For example, $R^6$ can be methyl, ethyl, propyl (straight or branched), butyl (straight or branched), pentyl (straight or branched) or hexyl (straight or branched). In some embodiments, $R^6$ can be an optionally substituted aryl (such as a mono-, di- or 3 or more substituted phenyl). In other embodiments, $R^6$ can be an optionally substituted heteroaryl. In still other embodiments, $R^6$ can be —CH$_2$OH, —CH($Y^2$)(OH) or —C(O)$Y^2$. In some embodiments, a portion of $R^6$ can be enzymatically cleaved to provide a compound of Formula (I), wherein OH or O$^-$ is present at $R^6$.

In some embodiments, $R^{3a}$ and $R^{3b}$ can be independently hydrogen or an optionally substituted $C_{1-4}$ alkyl. In some embodiments, $R^{3a}$ and $R^{3b}$ can be both hydrogen. In other embodiments, at least one of $R^{3a}$ and $R^{3b}$ can be an optionally substituted $C_{1-4}$ alkyl. For example, one or both of $R^{3a}$ and $R^{3b}$ can be an unsubstituted or substituted $C_{1-4}$ alkyl. In some embodiments, $R^{3a}$ and $R^{3b}$ can be both an unsubstituted $C_{1-4}$ alkyl, for example, both $R^{3a}$ and $R^{3b}$ can be methyl. In some embodiments, $R^{3a}$ and $R^{3b}$ can be the same. In other embodiments, $R^{3a}$ and $R^{3b}$ can be different.

In some embodiments, ===== can be a single bond such that a compound of Formula (I) has the structure

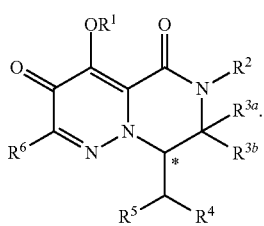
When ----- is a single bond, the bond indicated with an * can be a (S)-chiral center or a (R)-chiral center as shown herein:
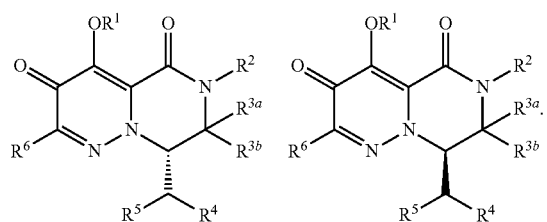
In other embodiments, ----- can be a double bond such that a compound of Formula (I) has the structure
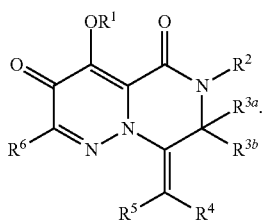
Examples of compounds of Formula (I) include the following:
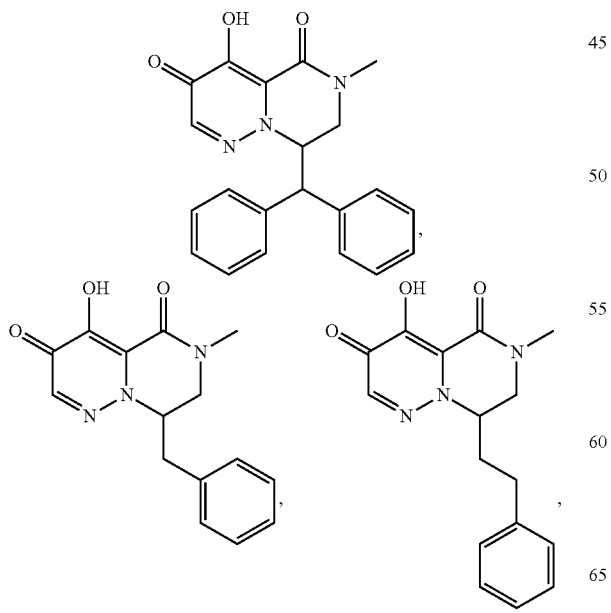
-continued
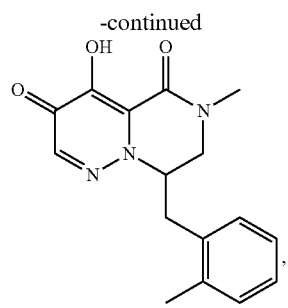
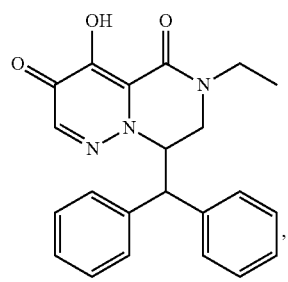
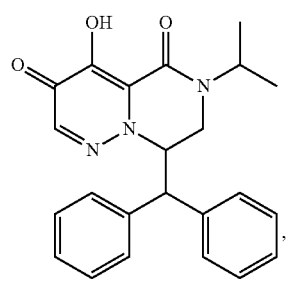
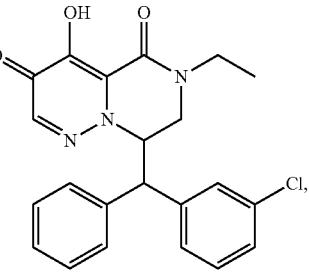
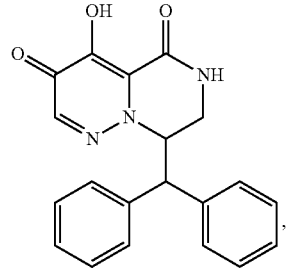
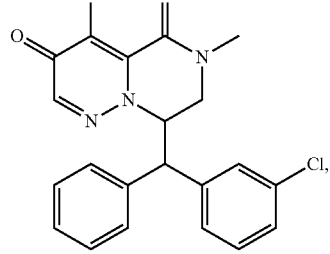

-continued

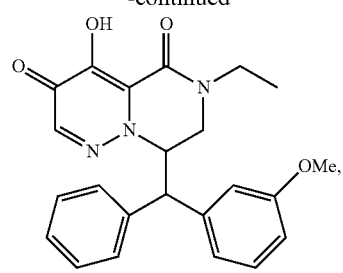
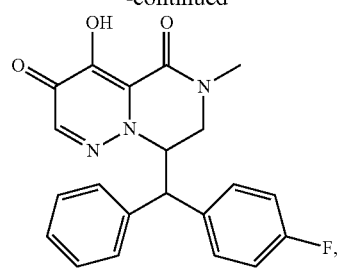

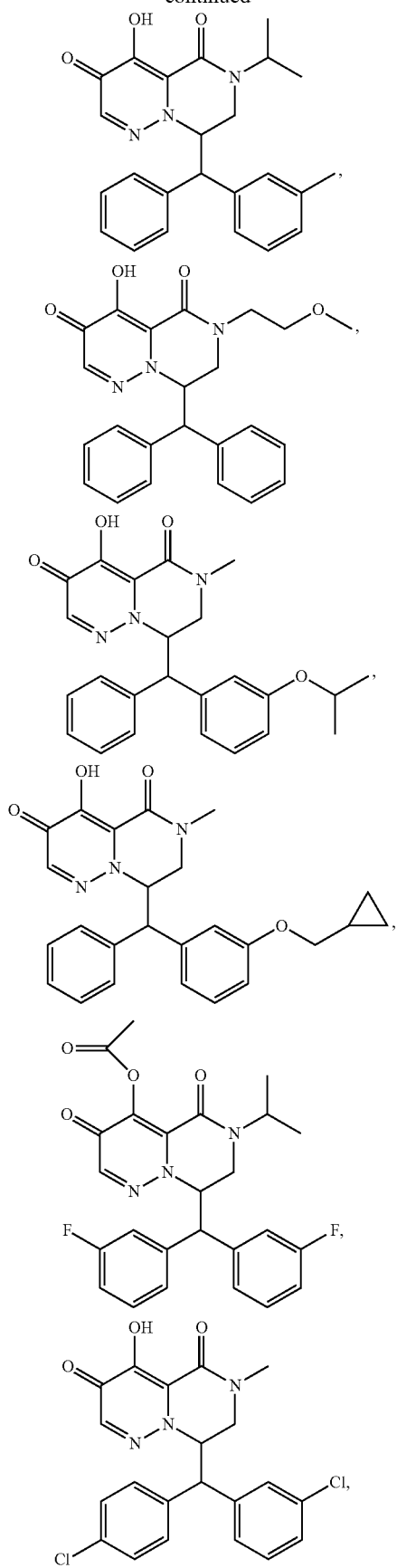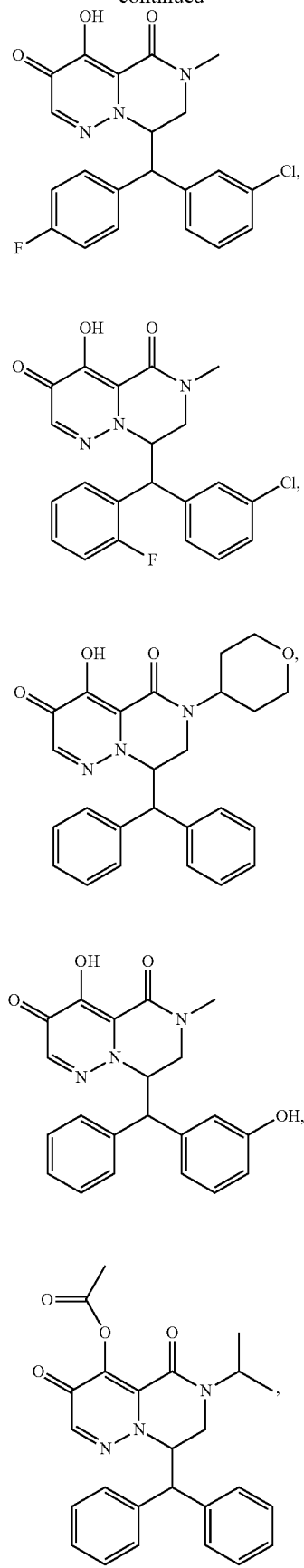

-continued
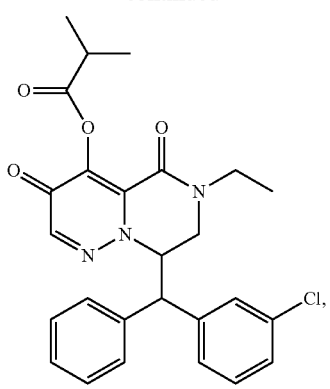
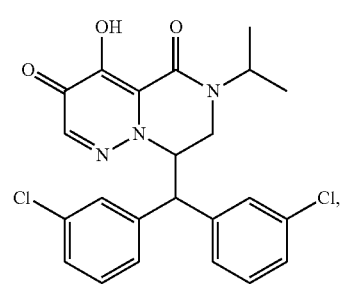
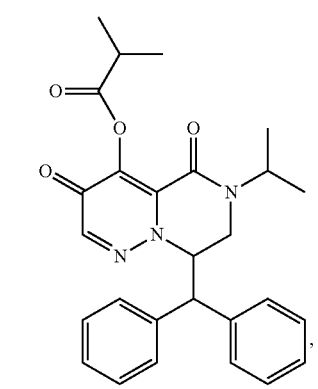
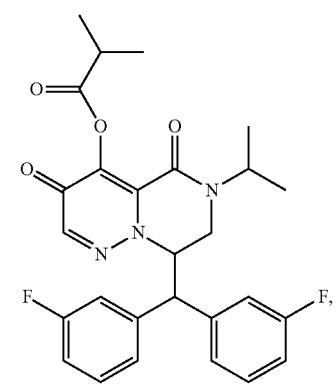
-continued
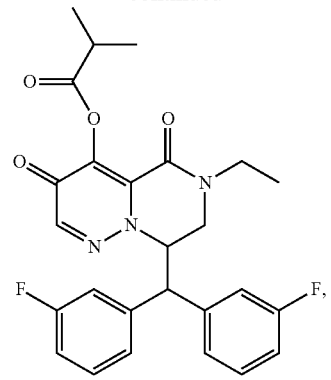
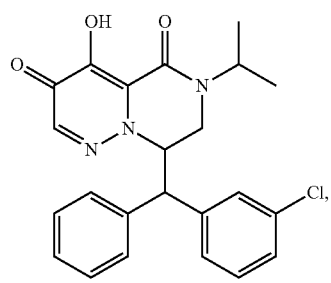
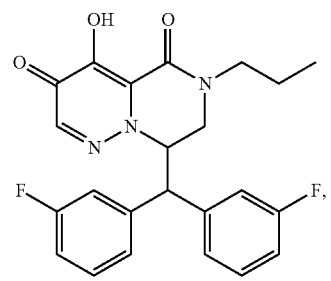
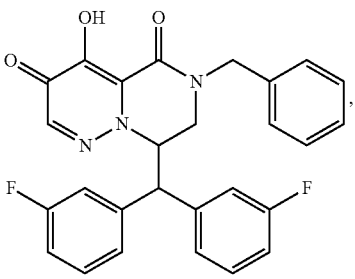
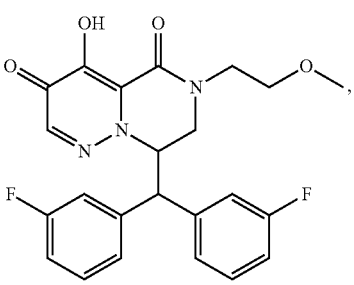

27
-continued
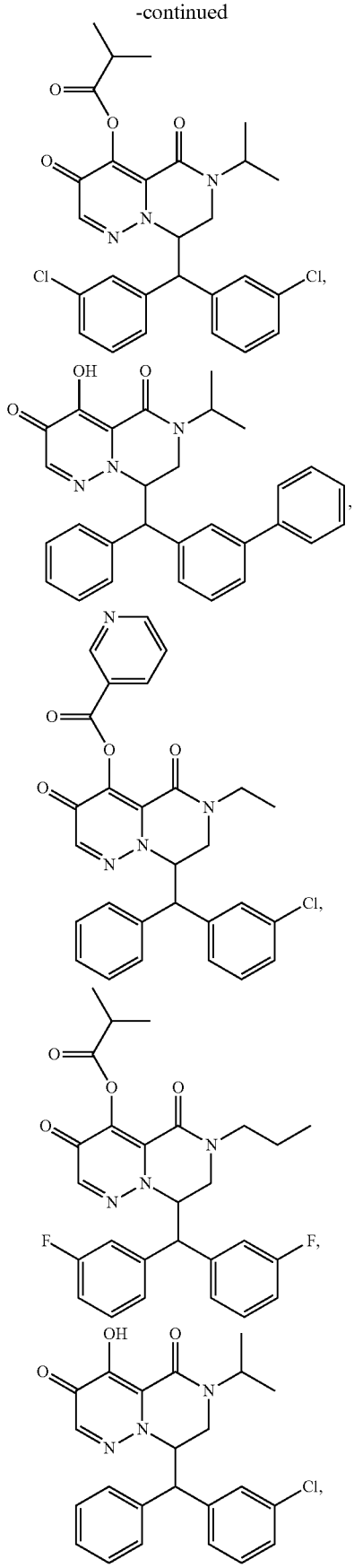
28
-continued
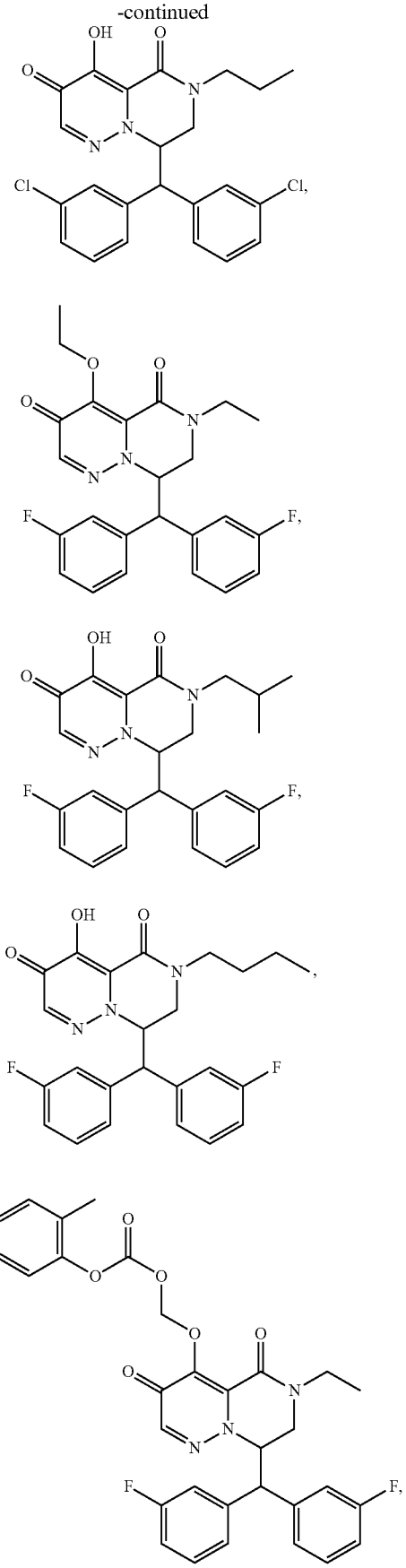

29
-continued
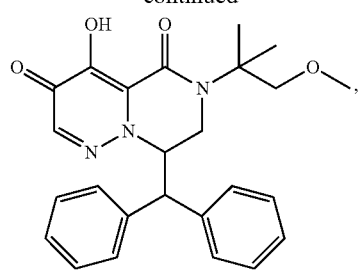
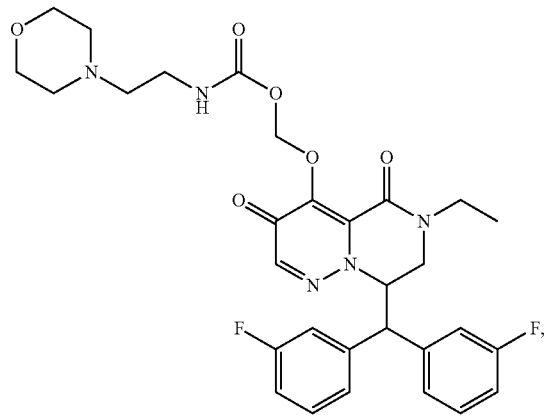
30
-continued
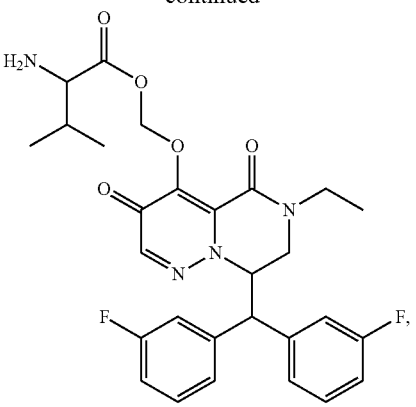
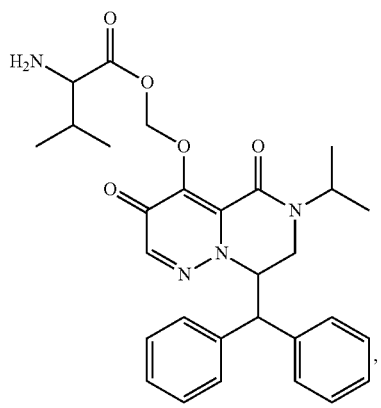
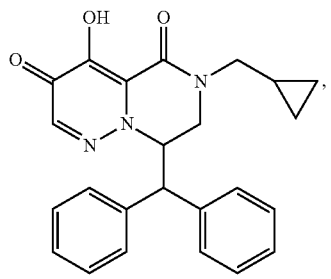
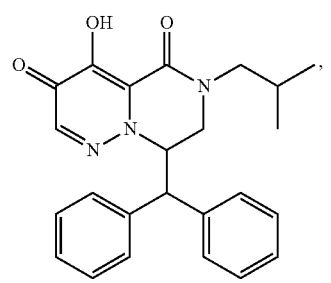
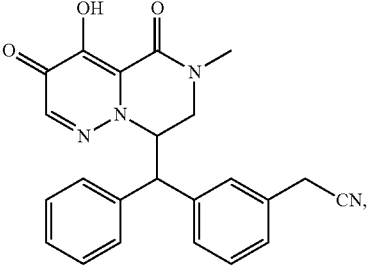

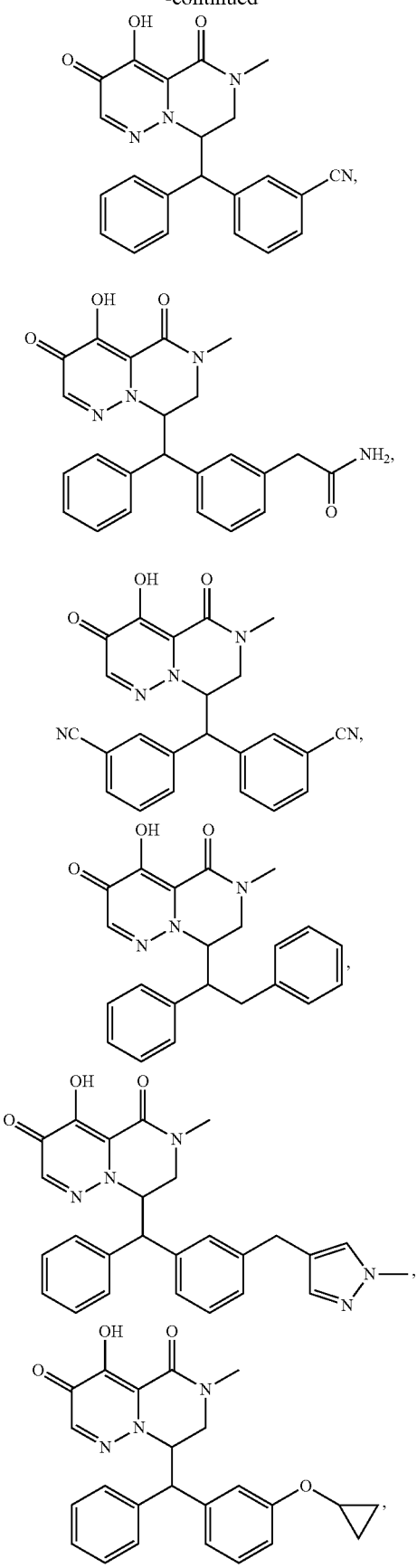
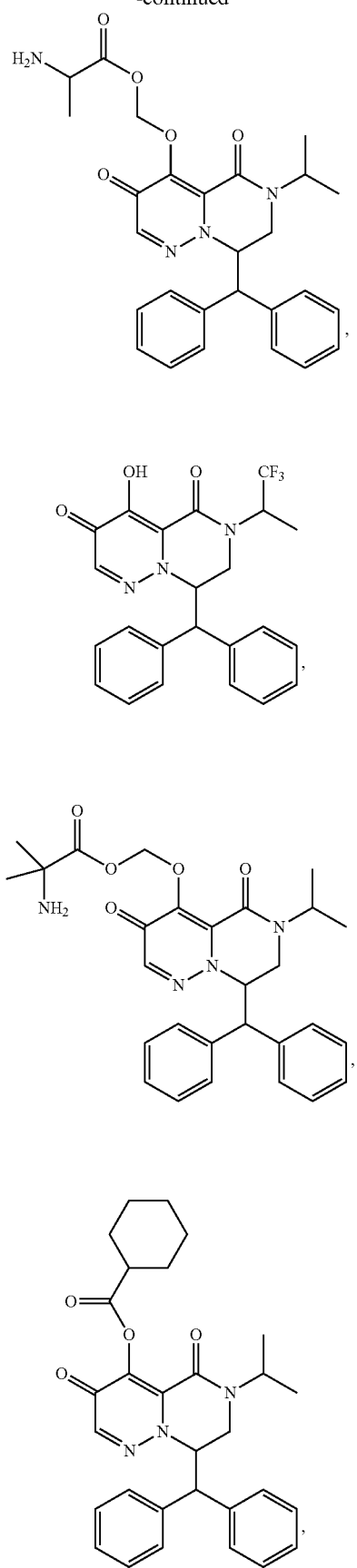

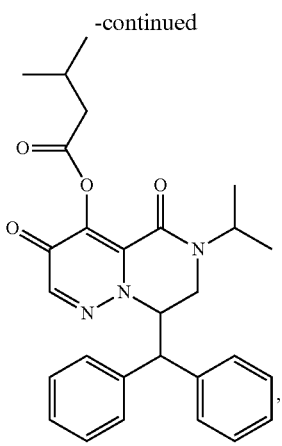
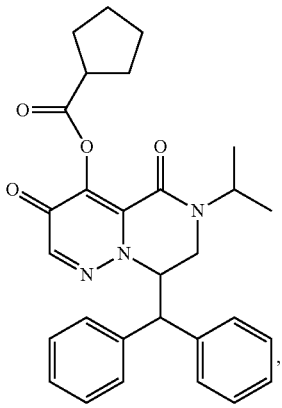
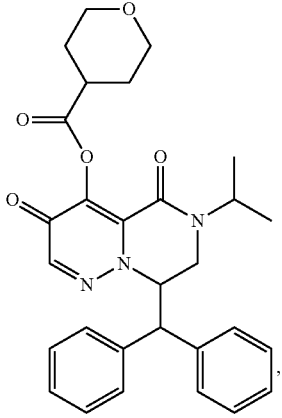
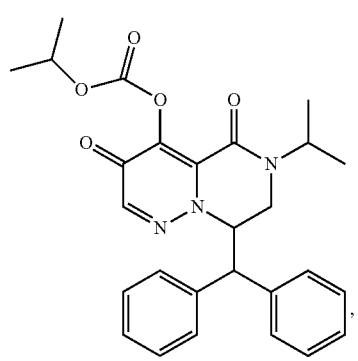
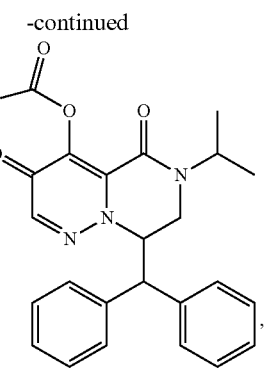
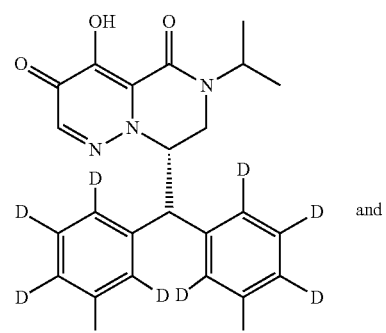
and
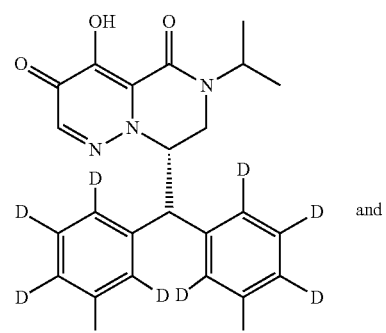
or a pharmaceutically acceptable salt of the foregoing.
Additionally examples of compounds of Formula (I) include the following:

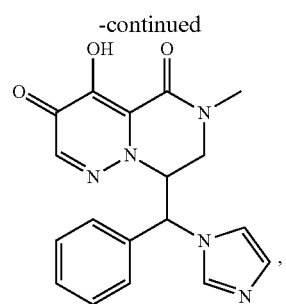
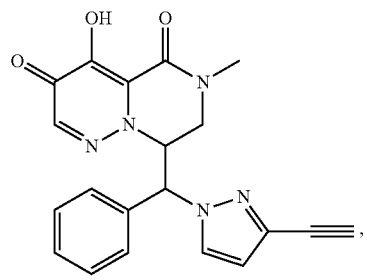
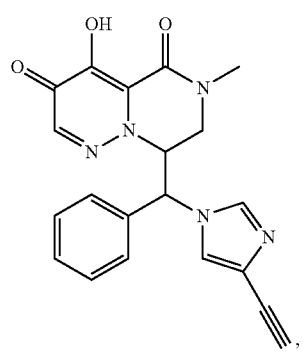
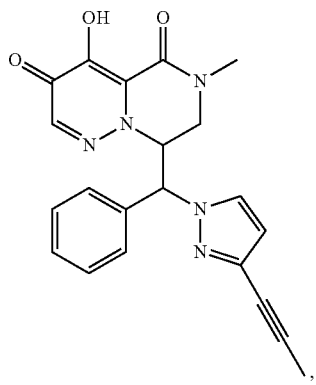
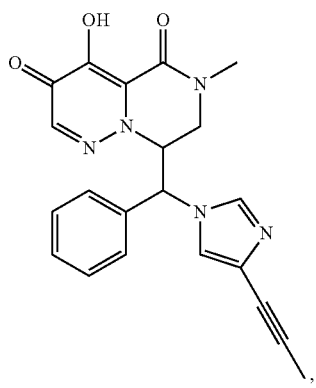
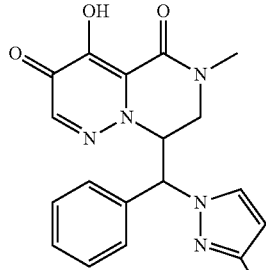
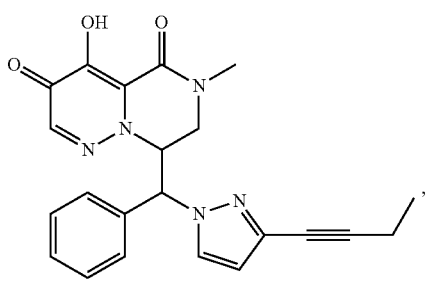
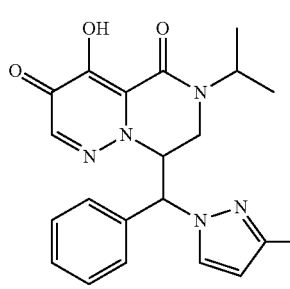
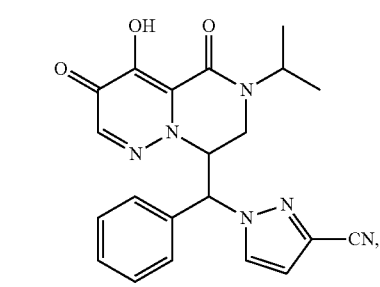
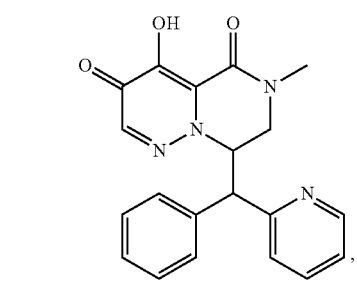

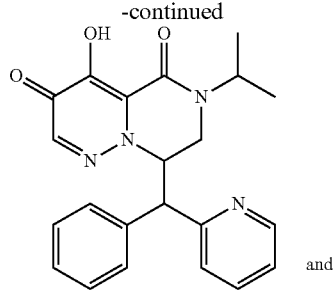
and
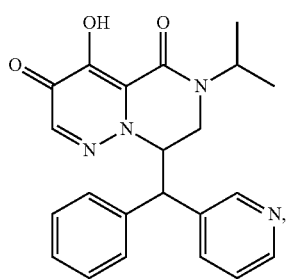
or a pharmaceutically acceptable salt of the foregoing.
Examples of compounds of Formula (I) also include the following:
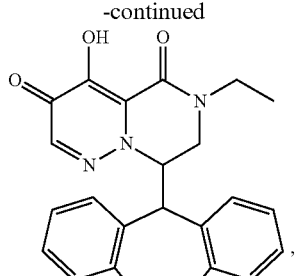
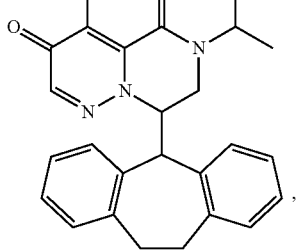
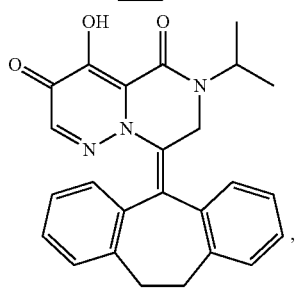
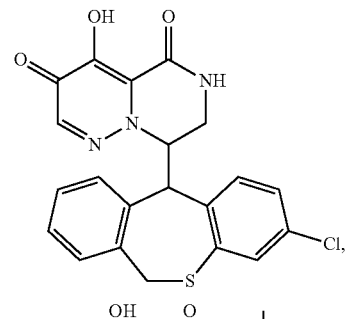
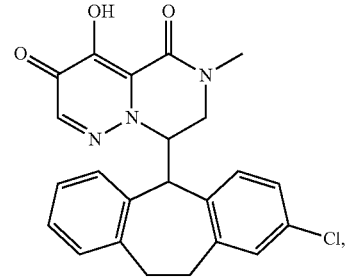
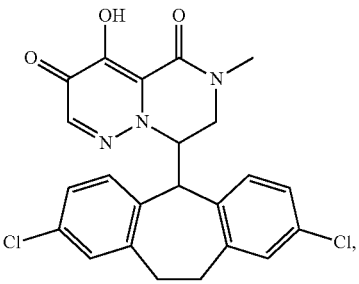

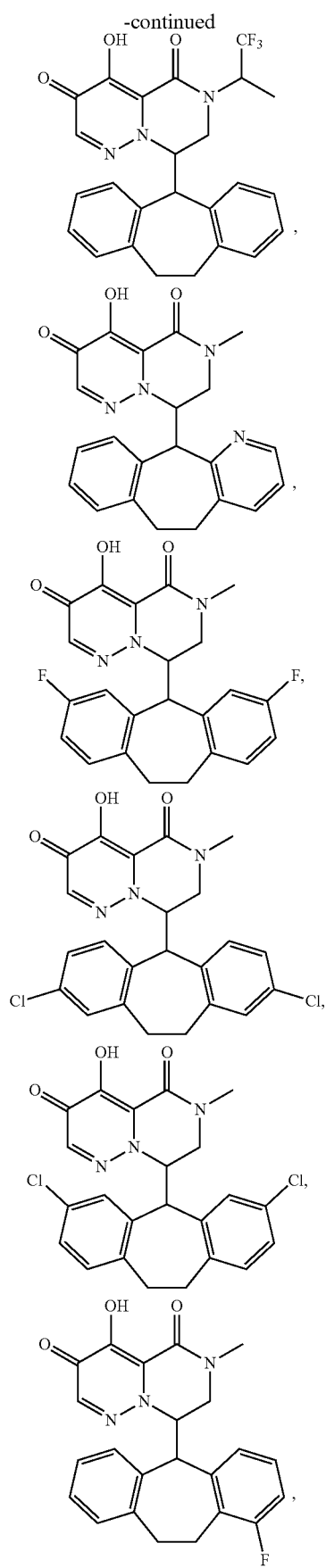
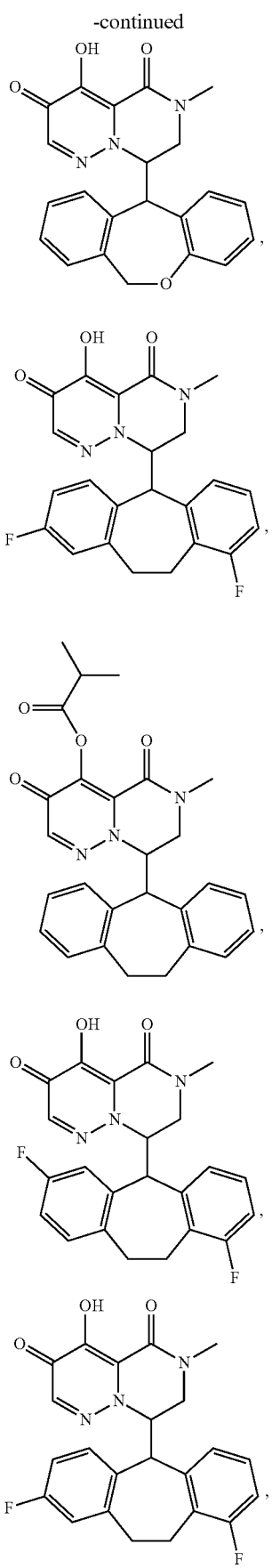

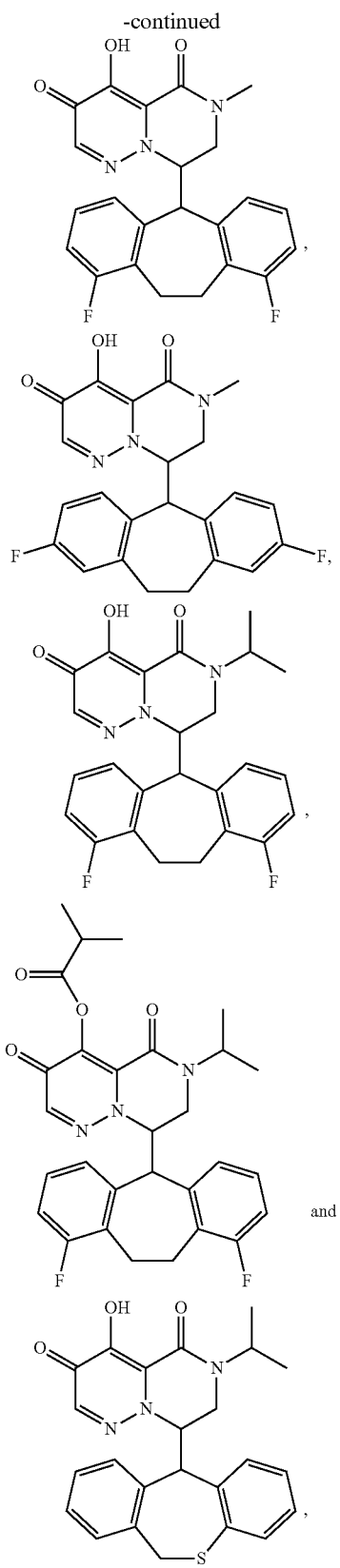

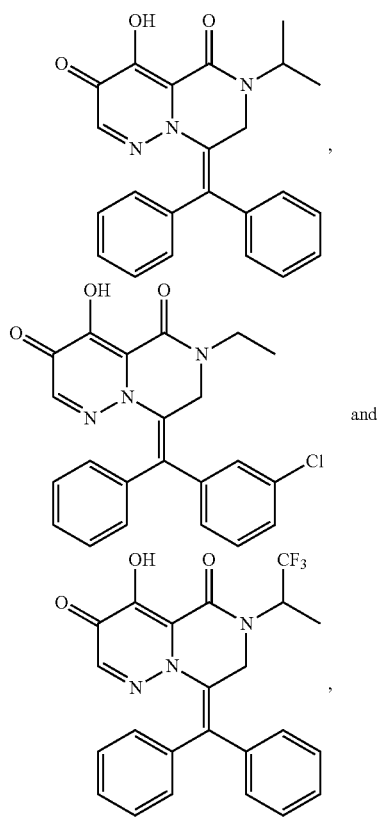

or a pharmaceutically acceptable salt of the foregoing.

As described herein, at any position of a compound of Formula (I) that has a hydrogen, the hydrogen can be an isotope of hydrogen, such as hydrogen-2 (deuterium). In some embodiments, a compound of Formula (I) can be a compound of Formula (Ia). Some embodiments of a compound of Formula (Ia) are provided in Table A.

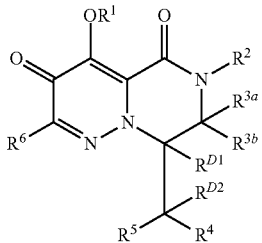

(Ia)

or a pharmaceutically acceptable salt of the foregoing.

Further examples of compounds of Formula (I) include the following:

TABLE A

| $R^{3a}$ | $R^{3b}$ | $R^6$ | $R^{D1}$ | $R^{D2}$ | $R^4$ | No. deuteriums on $R^4$ | $R^5$ | No. deuteriums on $R^5$ |
|---|---|---|---|---|---|---|---|---|
| D | D | D | D | D | phenyl | 0 | phenyl | 0 |
| H | D | D | D | D | phenyl | 0 | phenyl | 0 |
| D | H | D | D | D | phenyl | 0 | phenyl | 0 |
| D | D | H | D | D | phenyl | 0 | phenyl | 0 |
| D | D | D | H | D | phenyl | 0 | phenyl | 0 |
| D | D | D | D | H | phenyl | 0 | phenyl | 0 |
| H | H | D | D | D | phenyl | 0 | phenyl | 0 |
| H | D | H | D | D | phenyl | 0 | phenyl | 0 |

TABLE A-continued

| R$^{3a}$ | R$^{3b}$ | R$^6$ | R$^{D1}$ | R$^{D2}$ | R$^4$ | No. deuteriums on R$^4$ | R$^5$ | No. deuteriums on R$^5$ |
|---|---|---|---|---|---|---|---|---|
| H | D | D | H | D | phenyl | 0 | phenyl | 0 |
| H | D | D | D | H | phenyl | 0 | phenyl | 0 |
| D | H | H | D | D | phenyl | 0 | phenyl | 0 |
| D | H | H | H | D | phenyl | 0 | phenyl | 0 |
| D | H | H | D | H | phenyl | 0 | phenyl | 0 |
| D | D | H | H | D | phenyl | 0 | phenyl | 0 |
| D | D | H | D | H | phenyl | 0 | phenyl | 0 |
| D | D | D | H | H | phenyl | 0 | phenyl | 0 |
| H | H | D | H | D | phenyl | 0 | phenyl | 0 |
| H | H | D | D | H | phenyl | 0 | phenyl | 0 |
| D | H | H | H | D | phenyl | 0 | phenyl | 0 |
| D | H | H | H | H | phenyl | 0 | phenyl | 0 |
| D | D | H | H | H | phenyl | 0 | phenyl | 0 |
| D | H | D | H | H | phenyl | 0 | phenyl | 0 |
| H | D | H | H | H | phenyl | 0 | phenyl | 0 |
| H | H | D | H | H | phenyl | 0 | phenyl | 0 |
| H | H | H | D | H | phenyl | 0 | phenyl | 0 |
| H | H | H | H | D | phenyl | 0 | phenyl | 0 |
| H | H | H | H | H | phenyl | 0 | phenyl | 0 |
| D | D | D | D | D | phenyl | 1 | phenyl | 1 |
| H | D | D | D | D | phenyl | 1 | phenyl | 1 |
| D | H | D | D | D | phenyl | 1 | phenyl | 1 |
| D | D | H | D | D | phenyl | 1 | phenyl | 1 |
| D | D | D | H | D | phenyl | 1 | phenyl | 1 |
| D | D | D | D | H | phenyl | 1 | phenyl | 1 |
| H | H | D | D | D | phenyl | 1 | phenyl | 1 |
| H | D | H | D | D | phenyl | 1 | phenyl | 1 |
| H | D | D | H | D | phenyl | 1 | phenyl | 1 |
| H | D | D | D | H | phenyl | 1 | phenyl | 1 |
| D | H | H | D | D | phenyl | 1 | phenyl | 1 |
| D | H | D | H | D | phenyl | 1 | phenyl | 1 |
| D | H | D | D | H | phenyl | 1 | phenyl | 1 |
| D | D | H | H | D | phenyl | 1 | phenyl | 1 |
| D | D | H | D | H | phenyl | 1 | phenyl | 1 |
| D | D | D | H | H | phenyl | 1 | phenyl | 1 |
| H | H | H | D | D | phenyl | 1 | phenyl | 1 |
| H | H | D | H | D | phenyl | 1 | phenyl | 1 |
| H | H | D | D | H | phenyl | 1 | phenyl | 1 |
| D | H | H | H | D | phenyl | 1 | phenyl | 1 |
| D | H | H | D | H | phenyl | 1 | phenyl | 1 |
| D | H | D | H | H | phenyl | 1 | phenyl | 1 |
| H | D | H | H | H | phenyl | 1 | phenyl | 1 |
| H | H | D | H | H | phenyl | 1 | phenyl | 1 |
| H | H | H | D | H | phenyl | 1 | phenyl | 1 |
| H | H | H | H | D | phenyl | 1 | phenyl | 1 |
| H | H | H | H | H | phenyl | 1 | phenyl | 1 |
| D | D | D | D | D | phenyl | 2 | phenyl | 2 |
| H | D | D | D | D | phenyl | 2 | phenyl | 2 |
| D | H | D | D | D | phenyl | 2 | phenyl | 2 |
| D | D | H | D | D | phenyl | 2 | phenyl | 2 |
| D | D | D | H | D | phenyl | 2 | phenyl | 2 |
| D | D | D | D | H | phenyl | 2 | phenyl | 2 |
| H | H | D | D | D | phenyl | 2 | phenyl | 2 |
| H | D | D | H | D | phenyl | 2 | phenyl | 2 |
| H | D | D | D | H | phenyl | 2 | phenyl | 2 |
| D | H | H | D | D | phenyl | 2 | phenyl | 2 |
| D | H | D | D | H | phenyl | 2 | phenyl | 2 |
| D | D | H | D | H | phenyl | 2 | phenyl | 2 |
| D | D | D | H | H | phenyl | 2 | phenyl | 2 |
| H | H | H | D | D | phenyl | 2 | phenyl | 2 |
| H | H | D | H | D | phenyl | 2 | phenyl | 2 |
| H | H | D | D | H | phenyl | 2 | phenyl | 2 |
| D | H | H | H | D | phenyl | 2 | phenyl | 2 |
| D | H | H | D | H | phenyl | 2 | phenyl | 2 |
| H | H | D | H | H | phenyl | 2 | phenyl | 2 |
| H | H | H | D | H | phenyl | 2 | phenyl | 2 |
| H | H | H | H | D | phenyl | 2 | phenyl | 2 |
| H | H | H | H | H | phenyl | 2 | phenyl | 2 |
| D | D | D | D | D | phenyl | 3 | phenyl | 3 |
| H | D | D | D | D | phenyl | 3 | phenyl | 3 |
| D | H | D | D | D | phenyl | 3 | phenyl | 3 |
| D | D | H | D | D | phenyl | 3 | phenyl | 3 |
| D | D | D | H | D | phenyl | 3 | phenyl | 3 |
| D | D | D | D | H | phenyl | 3 | phenyl | 3 |
| H | H | D | D | D | phenyl | 3 | phenyl | 3 |
| H | D | H | D | D | phenyl | 3 | phenyl | 3 |
| H | D | D | H | D | phenyl | 3 | phenyl | 3 |
| H | D | D | D | H | phenyl | 3 | phenyl | 3 |
| D | H | H | D | D | phenyl | 3 | phenyl | 3 |
| D | H | D | H | D | phenyl | 3 | phenyl | 3 |
| D | H | D | D | H | phenyl | 3 | phenyl | 3 |
| D | D | H | H | D | phenyl | 3 | phenyl | 3 |
| D | D | H | D | H | phenyl | 3 | phenyl | 3 |
| D | D | D | H | H | phenyl | 3 | phenyl | 3 |
| H | H | H | D | D | phenyl | 3 | phenyl | 3 |
| H | H | D | H | D | phenyl | 3 | phenyl | 3 |
| H | H | D | D | H | phenyl | 3 | phenyl | 3 |
| D | H | H | H | D | phenyl | 3 | phenyl | 3 |
| D | H | H | D | H | phenyl | 3 | phenyl | 3 |
| D | H | D | H | H | phenyl | 3 | phenyl | 3 |
| H | D | H | H | H | phenyl | 3 | phenyl | 3 |
| H | H | D | H | H | phenyl | 3 | phenyl | 3 |
| H | H | H | D | H | phenyl | 3 | phenyl | 3 |
| H | H | H | H | D | phenyl | 3 | phenyl | 3 |
| H | H | H | H | H | phenyl | 3 | phenyl | 3 |
| D | D | D | D | D | phenyl | 4 | phenyl | 4 |
| H | D | D | D | D | phenyl | 4 | phenyl | 4 |
| D | H | D | D | D | phenyl | 4 | phenyl | 4 |
| D | D | H | D | D | phenyl | 4 | phenyl | 4 |
| D | D | D | H | D | phenyl | 4 | phenyl | 4 |
| D | D | D | D | H | phenyl | 4 | phenyl | 4 |
| H | H | D | D | D | phenyl | 4 | phenyl | 4 |
| H | D | H | D | D | phenyl | 4 | phenyl | 4 |
| H | D | D | H | D | phenyl | 4 | phenyl | 4 |
| H | D | D | D | H | phenyl | 4 | phenyl | 4 |
| D | H | H | D | D | phenyl | 4 | phenyl | 4 |
| D | H | D | H | D | phenyl | 4 | phenyl | 4 |
| D | H | D | D | H | phenyl | 4 | phenyl | 4 |
| D | D | H | H | D | phenyl | 4 | phenyl | 4 |
| D | D | H | D | H | phenyl | 4 | phenyl | 4 |
| D | D | D | H | H | phenyl | 4 | phenyl | 4 |
| H | H | H | D | D | phenyl | 4 | phenyl | 4 |
| H | H | D | H | D | phenyl | 4 | phenyl | 4 |
| H | H | D | D | H | phenyl | 4 | phenyl | 4 |
| D | H | H | H | D | phenyl | 4 | phenyl | 4 |
| D | H | H | D | H | phenyl | 4 | phenyl | 4 |
| D | H | D | H | H | phenyl | 4 | phenyl | 4 |
| H | D | H | H | H | phenyl | 4 | phenyl | 4 |
| H | H | D | H | H | phenyl | 4 | phenyl | 4 |
| H | H | H | D | H | phenyl | 4 | phenyl | 4 |
| H | H | H | H | D | phenyl | 4 | phenyl | 4 |
| H | H | H | H | H | phenyl | 4 | phenyl | 4 |
| D | D | D | D | D | phenyl | 5 | phenyl | 5 |
| H | D | D | D | D | phenyl | 5 | phenyl | 5 |
| D | H | D | D | D | phenyl | 5 | phenyl | 5 |
| D | D | H | D | D | phenyl | 5 | phenyl | 5 |
| D | D | D | H | D | phenyl | 5 | phenyl | 5 |
| D | D | D | D | H | phenyl | 5 | phenyl | 5 |
| H | H | D | D | D | phenyl | 5 | phenyl | 5 |
| H | D | H | D | D | phenyl | 5 | phenyl | 5 |
| H | D | D | H | D | phenyl | 5 | phenyl | 5 |
| H | D | D | D | H | phenyl | 5 | phenyl | 5 |
| D | H | H | D | D | phenyl | 5 | phenyl | 5 |
| D | H | D | H | D | phenyl | 5 | phenyl | 5 |
| D | H | D | D | H | phenyl | 5 | phenyl | 5 |
| D | D | H | H | D | phenyl | 5 | phenyl | 5 |
| D | D | H | D | H | phenyl | 5 | phenyl | 5 |
| D | D | D | H | H | phenyl | 5 | phenyl | 5 |
| D | H | D | D | H | phenyl | 5 | phenyl | 5 |

TABLE A-continued

| $R^{3a}$ | $R^{3b}$ | $R^6$ | $R^{D1}$ | $R^{D2}$ | $R^4$ | No. deuteriums on $R^4$ | $R^5$ | No. deuteriums on $R^5$ |
|---|---|---|---|---|---|---|---|---|
| D | H | H | D | H | phenyl | 5 | phenyl | 5 |
| D | D | H | H | H | phenyl | 5 | phenyl | 5 |
| D | H | H | H | H | phenyl | 5 | phenyl | 5 |
| H | D | H | H | H | phenyl | 5 | phenyl | 5 |
| H | H | D | H | H | phenyl | 5 | phenyl | 5 |
| H | H | H | D | H | phenyl | 5 | phenyl | 5 |
| H | H | H | H | D | phenyl | 5 | phenyl | 5 |
| H | H | H | H | H | phenyl | 5 | phenyl | 5 |

In some embodiments of Table A, $R^1$ can be hydrogen. In other embodiments of Table A, $R^1$ can be deuterium. In still other embodiments of Table A, $R^1$ can be —C(=O)Y$^1$, for example, $R^1$ can be —C(=O)— an optionally substituted $C_{1-6}$ alkyl. In some embodiments of Table A, $R^2$ can be an optionally substituted $C_{1-6}$ alkyl. In some embodiments of Table A, $R^1$ can be hydrogen and $R^2$ can be an unsubstituted $C_{1-6}$ alkyl. In other embodiments of Table A, $R^1$ can be —C(=O)$C_{1-6}$ alkyl and $R^2$ can be an unsubstituted $C_{1-6}$ alkyl. In some embodiments of Table A, $R^1$ can be

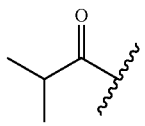

and $R^2$ can be isopropyl. In some embodiments, $R^1$ and/or $R^2$ can include one or more deuterium atoms. For example, $R^1$ can be deuterium or $R^1$ can be

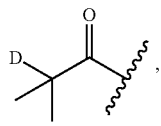

and/or $R^2$ can be —CH(CH$_3$)(CD$_3$) or $R^2$ can be —CH(CH$_3$)(CD$_3$).

Synthesis

Compounds of Formula (I), and those described herein may be prepared in various ways. General synthetic routes to compounds of Formula (I), and some examples of starting materials used to synthesize compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) can be prepared starting from various protected intermediates, including the two shown below.

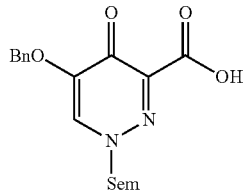

Intermediate A

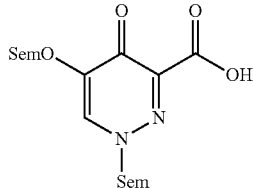

Intermediate B

Bn = benzyl
SEM = [2-(Trimethylsilyl)ethoxy]methyl

Methods for forming a compound of Formula (I) starting from an intermediate and an amino alcohol shown herein, such as Intermediate A or Intermediate B, is shown in Schemes 1, 2, 3, 4, 5 and 6. In Schemes 1, 2 and 3, $R^{2a}$, $R^{4a}$ and $R^{5a}$ can be the same as $R^2$, $R^4$ and $R^5$ as described herein for Formula (I), PG$^1$ can be a benzyl or SEM group and LG$^1$ can be a leaving group.

Scheme 1

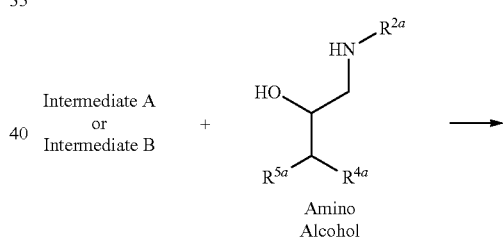

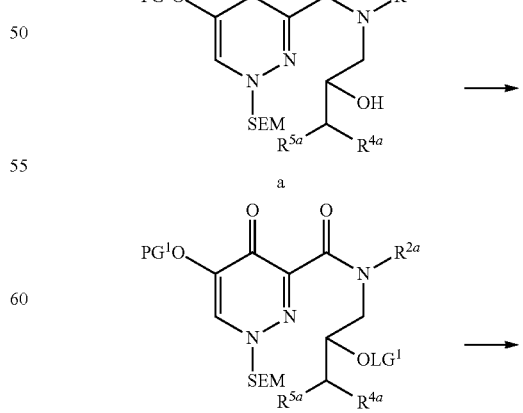

-continued

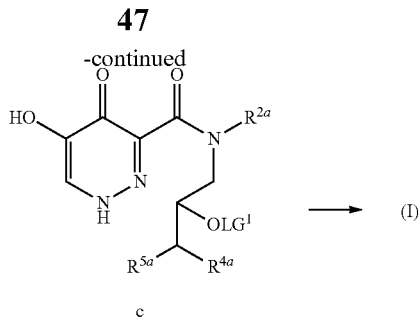

c

As shown in Scheme 1, Intermediate A or Intermediate B can be coupled with a 1,2-amino alcohol. Examples of suitable reaction conditions for coupling the aforementioned intermediate with a 1,2-amino alcohol include, but are not limited to, a carbodiimide (for example, N,N'-dicyclohexylcarbodiimide (DCC), N,N'-diisopropylcarbodiimide (DIC) or 1-ethyl-3-(3-dimethylaminopropyl)carbodiimide (EDCI)); O-(7-azabenzotriazol-1-yl)-N,N,N',N'-tetramethyluronium hexafluorophosphate (HATU), O-benzotriazole-N,N,N',N'-tetramethyl-uronium-hexafluoro-phosphate (HBTU) or O-(benzotriazol-1-yl)-N,N,N',N'-tetramethyluronium tetrafluoroborate (TBTU) in the presence of an amine base (such as N,N-diisopropylethylamine (DIPEA) or triethylamine (TEA)) in DMF; and propylphosphonic anhydride (T3P) in the presence of an amine base (such as those described herein).

The hydrogen of the unprotected secondary alcohol of compound a can be replaced to provide a suitable leaving group moiety. Suitable leaving groups are known to those skilled in the art. In some embodiments, the leaving group can be I, Br, Cl, a mesyl moiety and/or a tosyl moiety.

The $PG^1$ and the SEM group attached to the nitrogen of compound b can be removed using methods known to those skilled in the art. For example, the benzyl group can be removed via hydrogenolysis. Hydrogenolysis can be accomplished using various methods, such as a Pd or Pt catalyst (e.g., Pd/C or $PtO_2$) in combination with a hydrogen source (e.g., $H_2$ or formic acid), a strong acid, oxidation to the benzoate and subsequent hydrolysis under basic conditions and 2,3-dichloro-5,6-dicyano-p-benzoquinone (DDQ). The SEM group(s) can be removed using concentrated HF, tetra-n-butylammonium fluoride (TBAF), cesium fluoride, lithium tetrafluoroborate, trifluoroacetic acid (TFA) or pyridinium p-toluene sulfonate in ethanol at reflux temperature.

The leaving group moiety, $OLG^1$, can be removed and the compound can undergo cyclization using an acid or a base to form a compound of Formula (I). Suitable acids and bases are known to those skilled in the art. In some embodiments, the base can be potassium carbonate. Additional bases include sodium carbonate, calcium carbonate, cesium carbonate, sodium bicarbonate, potassium bicarbonate, calcium carbonate, cesium carbonate, triethylamine, diisopropyl ethyl amine, pyridine, KOH and NaOH. Suitable acids include sulfonic acids (e.g., methane sulfonic acid and p-toluenesulfonic acid), trifluoroacetic acid (TFA) and HCl. In some cases, the reagent(s) used to remove the $PG^1$ and SEM groups, for example, cesium fluoride or tetra-n-butylammonium fluoride (TBAF), can then promote cyclization to a compound of Formula (I).

Scheme 2

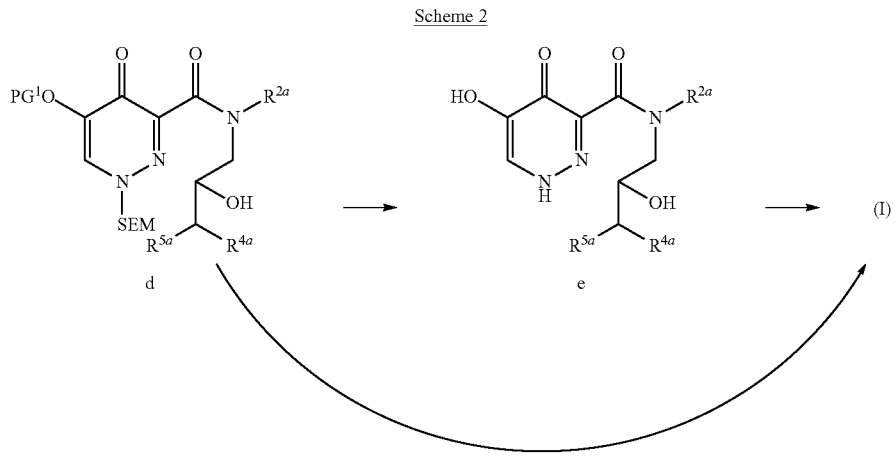

As shown in Scheme 2, the $PG^1$ and the SEM groups attached to the nitrogen can be removed from compound d using one or more methods described herein. A compound of Formula (I) can be then formed via a Mitsunobu ring-closure cyclization. The Mitsunobu ring-closure cyclization can be accomplished using a phosphine reagent (for example, triphenylphosphine, a tri-alkyl phosphine, a tri-aryl phosphine or polymer-supported triphenylphosphine) in combination with an azodicarboxylate, such as diethyl azodicarboxylate (DEAD) or diisopropyl azodicarboxylate (DIAD). Alternatively, the $PG^1$ and the SEM groups can be removed and the ring closed to form a compound of Formula (I) in a single step using a suitable acid, for example, trifluoroacetic acid, at an elevated temperature.

Scheme 3

Intermediate A or Intermediate B + 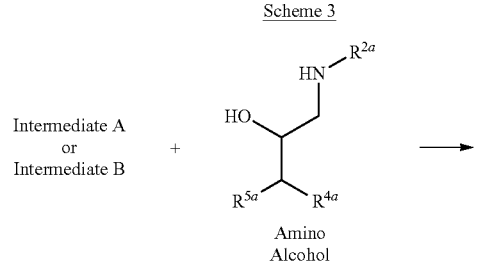

Amino Alcohol

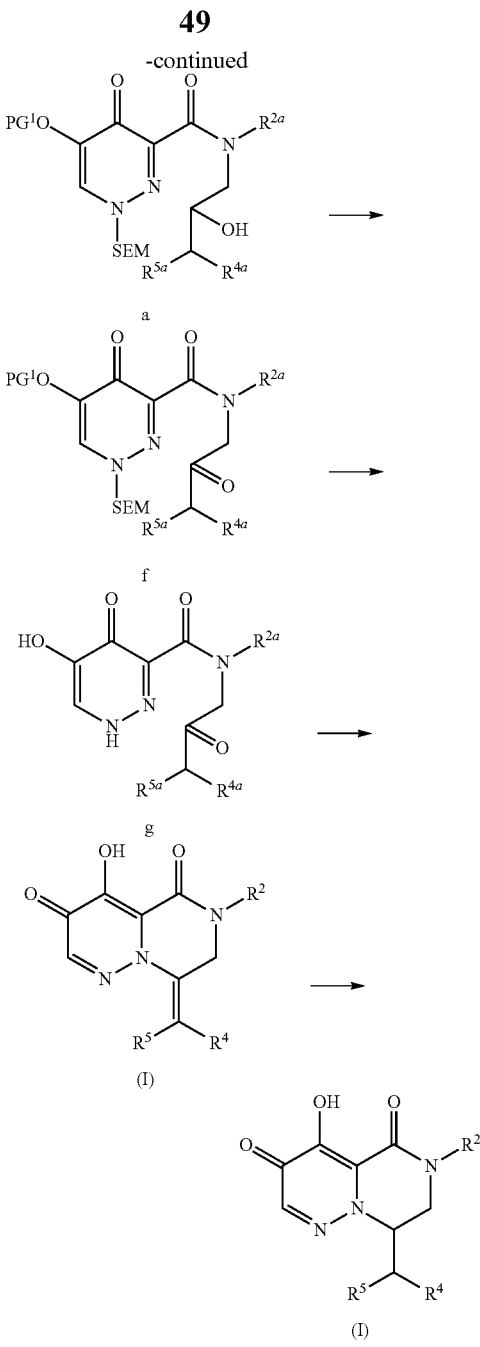

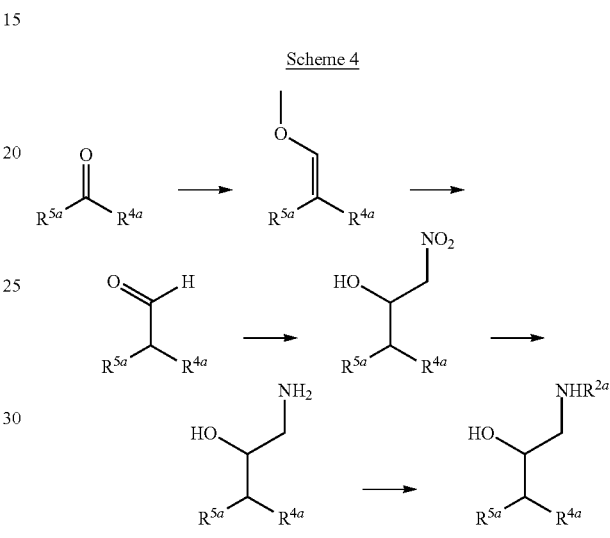

Scheme 4

As shown in Scheme 4, the ketone undergoes olefination using an alkoxy-based phosphonium halide under Wittig-type reaction conditions to form a vinyl alkoxy intermediate. The vinyl alkoxy intermediate can be hydrolyzed to an aldehyde using methods known to those skilled in the art, such as perchloric acid. Nitromethane can be added to the aldehyde via a nitro-aldol reaction. Utilizing methods and conditions known to those skilled in the art, the nitro group can be reduced to a $NH_2$ group. The $NH_2$ group can undergo reductive alkylation to form the amino alcohol.

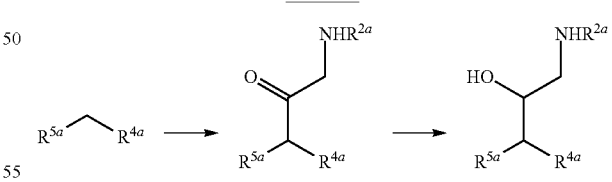

Scheme 5

Another method for forming the amino alcohol is shown in Scheme 5. An amino acid ester can be added to the anion of the starting material, generated using a method known to those skilled in the art, for example, using n-BuLi. The ketone can be reduced to a hydroxy group using one or more suitable reagents and conditions, such as those described herein. To minimize side reactions and/or facilitate the reaction(s), the nitrogen of the amino acid ester can be protected with a suitable protecting group. The protecting group can be removed before or after reduction of the ketone using methods known to those skilled in the alt provide compound g. The six-membered ring can be formed under acidic condition to provide a compound of Formula (I), wherein ==== is a double bond. Examples of suitable acids include, but are not limited to, sulfonic acids (e.g., methane sulfonic acid and p-toluenesulfonic acid), sulfuric acid, trifluoroacetic acid (TFA) and HCl. The double bond can be hydrogenated to a single bond using hydrogen gas in the presence of a palladium or platinum catalyst (such as Pd/C or $PtO_2$).

Amino alcohols that can be used in the preparation of a compound of Formula (I) can be commercially obtained or prepared according to a procedure provided herein, for example, a procedure shown in Schemes 4-6.

In Scheme 3, compound a can be formed as described herein. The secondary alcohol can be oxidized to a ketone using reagent(s) and conditions known to those skilled in the art. Examples of suitable oxidizing reagents and conditions include, but are not limited to, Dess-Martin periodinane, IBX (2-iodoxybenzoic acid), TPAP/NMO (tetrapropylammonium perruthenate/N-methylmorpholine N-oxide), Swern oxidation reagent, PCC (pyridinium chlorochromate), PDC (pyridinium dichromate), sodium periodate, Collin's reagent, Corey-Kim's reagent, Moffatt reagent, Jones' reagent, Oppenauer's reagent, ceric ammonium nitrate (CAN), $Na_2Cr_2O_7$ in water, $Ag_2CO_3$ on celite, hot $HNO_3$ in aqueous glyme, $O_2$-pyridine CuCl, $Pb(OAc)_4$-pyridine, potassium dichromate, and benzoyl peroxide-$NiBr_2$.

The $PG^1$ and the SEM group attached to the nitrogen can be removed using one or more methods described herein to Scheme 6

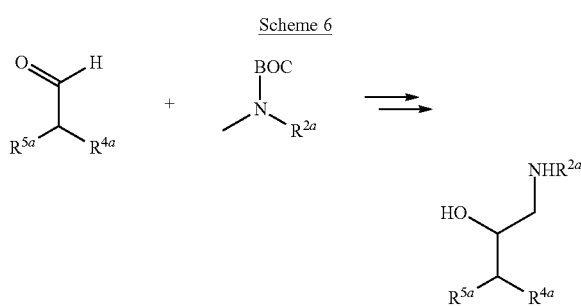

Scheme 6 shows a further method for forming the amino alcohol. The amino alcohol can be formed by a directed lithiation followed by a condensation-type reaction, using a method known to those skilled in the art, Snieckus et. al., *Tet. Lett.* (1994) 35(24):4067-4070.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intramuscular. In other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intranasal. In still other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intradermal. In yet still other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering orally.

When administered orally, one or more compounds described herein (e.g., a compound of Formula (I), or a pharmaceutically acceptable salt thereof) can be formulated as tablets, pills, dragees, capsules, liquids, gels, syrups, slurries, suspensions and the like, for oral ingestion by a subject to be treated. Injectables can be prepared in conventional forms, either as liquid solutions or suspensions, solid forms suitable for solution or suspension in liquid prior to injection, or as emulsions. Pharmaceutical compositions for intranasal delivery may also include drops and sprays often prepared to assist in simulating nasal secretions.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use:

Some embodiments described herein relate to a method of ameliorating, treating and/or preventing an orthomyxovirus infection, which can include administering an effective amount of one or more compounds described herein, or a pharmaceutical composition that includes one or more compounds described herein (e.g., a compound of Formula (I), or a pharmaceutically acceptable salt thereof).

Other embodiments described herein relate to a method of inhibiting an orthomyxovirus viral replication, which can include contacting a cell infected with the orthomyxovirus virus with an effective amount of a compound of Formula (I), or a pharmaceutically acceptable salt thereof and/or a pharmaceutical composition that includes one or more compounds described herein (e.g., a compound of Formula (I), or a pharmaceutically acceptable salt thereof).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate an influenza viral infection. In other embodiments, an effective amount of one or more compounds of Formula (I), or a pharmaceutically acceptable salt thereof and/or a pharmaceutical composition that includes one or more compounds described herein (e.g., a compound of Formula (I), or a pharmaceutically acceptable salt thereof) can be used to prevent an influenza viral infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication an influenza virus. In some embodiments, an effective amount of one or more compounds of Formula (I), or a pharmaceutically acceptable salt thereof and/or a pharmaceutical composition that includes one or more compounds described herein (e.g., a compound of Formula (I), or a pharmaceutically acceptable salt thereof) can be used to inhibit the influenza polymerase complex. In some embodiments, an effective amount of one or more compounds of Formula (I), or a pharmaceutically acceptable salt thereof and/or a pharmaceutical composition that includes one or more compounds described herein (e.g., a compound of Formula (I), or a pharmaceutically acceptable salt thereof) can be used for inhibiting and/or reducing the endonuclease activity of an influenza endonuclease that can include contacting the active site of the endonuclease with a compound of Formula (I), or a pharmaceutically acceptable salt thereof. In some embodiments, one or more compounds described herein inhibits and/or reduces the ability of the endonuclease to cleave the mRNA.

In some embodiments, including those embodiments in the previous paragraphs, the influenza viral infection can be an influenza A viral infection. In other embodiments, including those embodiments in the previous paragraphs, the influenza viral infection can be an influenza B viral infection. In still other embodiments, including those embodiments in the previous paragraphs, the influenza viral infection can be an influenza C viral infection. In some embodiments, a compound of Formula (I), or a pharmaceutically acceptable salt thereof, can be used to treat and/or ameliorate one or more subtypes of influenza. For example, a compound of Formula (I), or a pharmaceutically acceptable salt thereof, can be used to treat H1N1 and/or H3N2. In addition or in the alternative, a compound of Formula (I), or a pharmaceutically acceptable salt thereof, can be used to treat H2N2, H5N1 and/or H7N9. In some embodiments, a compound described herein (a compound of Formula (I), or a pharmaceutically acceptable salt thereof) can be effective against more than 1 subtype of influenza. For example, a compound described herein (a compound of Formula (I), or a pharmaceutically acceptable salt thereof can be effective against 2, 3, 4, and/or 5 or more subtypes of influenza.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection attributed to (directly and/or indirectly) an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection (directly and/or indirectly) an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an influenza virus infection (such as those described herein). In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate coup due to an influenza virus infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used lessen the severity of one or more symptoms of an influenza infection. Examples of symptoms include, but are not limited to, the following: fever, chills, cough, sore throat, runny nose, stuffy nose, muscle aches, body aches, headache, fatigue, vomiting and/or diarrhea.

As used herein, the terms "prevent" and "preventing," mean a subject does not develop an infection because the subject has an immunity against the infection, or if a subject becomes infected, the severity of the disease is less compared to the severity of the disease if the subject has not been administered/received the compound. Examples of forms of prevention include prophylactic administration to a subject who has been or may be exposed to an infectious agent, such as an orthomyxovirus (e.g., an influenza virus).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

Various indicators for determining the effectiveness of a method for treating an orthomyxovirus viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, an effective amount of a compound of Formula (I), or a pharmaceutically acceptable salt thereof, is an amount that is effective to reduce viral titers to a lower level, for example, from about 10E4 TCID50/mL (TCID=tissue culture infectious dose) to about 10E3 TCID50/mL, or to about 100 TCID50/mL, or to about 10 TCID50/mL. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. For example, wherein the viral load is measure before administration of the compound of Formula (I), or a pharmaceutically acceptable salt thereof, and again after initiation of the treatment regime with the compound of Formula (I), or a pharmaceutically acceptable salt thereof (for example, 10 days after initiation of treatment). In some embodiments, an effective amount of a compound of Formula (I), or a pharmaceutically acceptable salt thereof, can be an amount that is effective to reduce viral load to lower than about 10E4 TCID50/mL. In some embodiments, an effective amount of a compound of Formula (I), or a pharmaceutically acceptable salt thereof, is an amount that is effective to achieve a reduction in viral titer in a nasal/pharyngeal swab or nasal wash sample of the subject in the range of about 1.5-log to about a 2.5-log reduction or about a 3-log to about a 4-log reduction compared to the viral load before administration of the compound of Formula (I), or a pharmaceutically acceptable salt thereof. For example, wherein the viral load is measure before administration of the compound of Formula (I), or a pharmaceutically acceptable salt thereof, and again after initiation of the treatment regime with the compound of Formula (I), or a pharmaceutically acceptable salt thereof (for example, 10 days after initiation of treatment).

In some embodiments, a compound of Formula (I), or a pharmaceutically acceptable salt of the foregoing, can result in one or more overall quality of life health, such as reduced illness duration, reduced illness severity, reduced time to return to normal health and normal activity, and reduced time to alleviation of one or more symptoms of orthomyxovirus infection, compared to a subject who is untreated. In some embodiments, a compound of Formula (I), or a pharmaceutically acceptable salt of the foregoing, can result in a reduction in the length and/or severity of one or more symptoms associated with an orthomyxovirus infection compared to an untreated subject. Symptoms of an orthomyxovirus infection are described herein and include but not limited to cough, myalgia (muscle pain), nasal obstruction, sore throat, fatigue, headache and fever. In some embodiments, a compound of Formula (I), or a pharmaceutically acceptable salt of the thereof, can result in a reduction in one or more secondary complications associated with an orthomyxovirus infection, including but not limited to otitis media (ear inflammation), sinusitis, bronchitis and pneumonia compared to an untreated subject.

In some embodiments, a compound of Formula (I), or a pharmaceutically acceptable salt of the foregoing, can result in at least a 1, 2, 3, 4, 5, 10, 15, 20, 25, 50, 75, 100-fold or more reduction in the replication of an orthomyxovirus relative to pre-treatment levels in a subject, as determined after initiation of the treatment regime (for example, 10 days after initiation of treatment). In some embodiments, a compound of Formula (I), or a pharmaceutically acceptable salt of the foregoing, can result in a reduction of the replication of an orthomyxovirus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of orthomyxovirus replication in the range of 1 to 1.5 log, 1.5 log to 2 log, 2 log to 2.5 log, 2.5 to 3 log, or 3 to 3.5 log reduction of orthomyxovirus replication compared to the reduction of orthomyxovirus reduction achieved by oseltamivir (Tamiflu®), or may achieve the same reduction as that of oseltamivir (Tamiflu®) therapy in a shorter period of time, for example, in one day, two days, three days, or four days as compared to the reduction achieved after 5 days of oseltamivir (Tamiflu®) therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an influenza virus that is resistant to one or more different anti-influenza agents (for example, amantadine, rimantadine and/or oseltamivir). In some embodiments, a compound of Formula (I), or a pharmaceutically acceptable salt thereof, can be administered to a subject infected with an influenza virus that is resistant to a M2 protein inhibitor. In some embodiments, development of resistant influenza strains is delayed when subjects are treated with a compound of Formula (I), or a pharmaceutically acceptable salt thereof, compared to the development of influenza strains resistant to other influenza drugs.

In some embodiments, a compound of Formula (I), or a pharmaceutically acceptable salt thereof, can decrease the percentage of subjects that experience complications from an influenza viral infection compared to the percentage of subjects that experience complication being treated with oseltamivir. For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with oseltamivir.

In some embodiments, a compound of Formula (I), or a pharmaceutically acceptable salt thereof, or a pharmaceutical composition that includes a compound described herein, can be used in combination with one or more additional agent(s). In some embodiments, a compound of Formula (I), or a pharmaceutically acceptable salt thereof, can be used in combination with one or more agents currently used in a conventional standard of care for treating influenza. For example, the additional agent can be amantadine (adamantan-1-amine, Symmetrel), rimantadine (Flumadine), zanamivir (Relenza) and oseltamivir (Tamiflu). For the treatment of influenza, additional agents include but are not limited to a neuraminidase inhibitor, a M2 protein inhibitor, a polymerase inhibitor, a PB2 inhibitor, peramivir ((1S,2S,3S,4R)-3-[(1S)-1-acetamido-2-ethylbutyl]-4-(diaminomethylideneamino)-2-hydroxycyclopentane-1-carboxylic acid, BioCryst Pharmaceuticals), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), favipiravir (T-705, 6-fluoro-3-hydroxy-2-pyrazinecarboxamide), laninamivir octanoate ((3R,4S)-3-acetamido-4-guanidino-2-((1S,2S)-2-hydroxy-1-methoxy-3-(octanoyloxy)propyl)-3,4-dihydro-2H-pyran-6-carboxylic acid) fludase (DAS 181, NexBio), ADS-8902 (amantadine HCl/oseltamivir/ribavirin, Adamas Pharmaceuticals), an immuno-modulator (for example, a Type 1 interferon), beraprost (4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid), NEUGENE®, ribavirin, (R)-3-((5-fluoro-2-(5-fluoro-1H-pyrrolo[2,3-b]pyridin-3-yl)pyrimidin-4-yl)amino)-4,4-dimethylpentanoic acid (CAS Reg. No. 1422050-75-6), (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid (CAS Reg. No. 1259366-34-1, VX-787), FLUMIST QUADRIVALENT® (MedImmune), FLUARIX® QUADRIVALENT (GlaxoSmithKline), FLUZONE® QUADRIVALENT (Sanofi Pasteur), FLUCELVAX® (Novartis) and FLUBLOK® (Protein Sciences). In some embodiments, a compound of Formula (I), or a pharmaceutically acceptable salt thereof, or a pharmaceutical composition that includes a compound described herein, can be used in combination with oseltamivir.

Type 1 interferons are known to those skilled in the art. A non-limiting list of examples include: alpha-interferons, beta-interferons, delta-interferons, omega-interferons, tau-interferons, x-interferons, consensus interferons and asialo-interferons. Type 1 interferons can be pegylated. Examples of specific type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERON-PEG, Schering), interferon beta-1a (REBIF, Serono, Inc. and Pfizer), consensus interferon alpha (INFERGEN, Valeant Pharmaceutical).

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) can result in an additive effect. In some embodiments, the combination of a compound of Formula (I), or a pharmaceutically acceptable salt thereof, in combination with one or more additional agent(s) can result in a synergistic effect. In some embodiments, the combination of a compound of Formula (I), or a pharmaceutically acceptable salt thereof, in combination with one or more additional agent(s) can result in a strongly synergistic effect. In some embodiments, the combination of a compound of Formula (I), or a pharmaceutically acceptable salt thereof, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more of the additional agent(s) described above, including pharmaceutically acceptable salts and prodrugs thereof, may be a reduction in the required amount(s) of the one or more additional agents, including pharmaceutically acceptable salts and prodrugs thereof, that is effective in treating a disease condition disclosed herein (for example, influenza), as compared to the amount required to achieve the same therapeutic result when one or more of the additional agents, including pharmaceutically acceptable salts and prodrugs thereof, are administered without a compound of Formula (I), or a pharmaceutically acceptable salt thereof. For example, the amount of an additional agent described above, including a pharmaceutically acceptable salt and prodrug thereof, can be less when administered in combination with a compound of Formula (I), or a pharmaceutically acceptable salt thereof, compared to the amount of additional agent, including a pharmaceutically acceptable salt and prodrug thereof, needed to achieve the same viral load reduction when administered as a monotherapy. Another potential advantage of utilizing a compound of Formula (I), or a pharmaceutically acceptable salt thereof, in combination with one or more of the additional agent(s) described above, including pharmaceutically acceptable salts and prodrugs thereof, is that the use of two or more compounds having different mechanisms of action can create a higher barrier to the development of resistant viral strains compared to the barrier when a compound is administered as monotherapy.

Additional advantages of utilizing a compound of Formula (I), or a pharmaceutically acceptable salt thereof, in combination with one or more of the additional agent(s) described above, including pharmaceutically acceptable salts and prodrugs thereof, may include little to no cross resistance between a compound of Formula (I), or a pharmaceutically acceptable salt thereof, and the one or more additional agent(s) described above (including pharmaceutically acceptable salts and prodrugs thereof); different routes for elimination of a compound of Formula (I), or a pharmaceutically acceptable salt thereof, and the one or more additional agent(s) described above (including pharmaceutically acceptable salts and prodrugs thereof); little to no overlapping toxicities between a compound of Formula (I), or a pharmaceutically acceptable salt thereof, and the one or more additional agent(s) described above (including pharmaceutically acceptable salts and prodrugs thereof); little to no significant effects on cytochrome P450; and/or little to no pharmacokinetic interactions between a compound of Formula (I), or a pharmaceutically acceptable salt thereof, and the one or more additional agent(s) described above, including pharmaceutically acceptable salts and prodrugs thereof.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1A

Synthesis of Compound H

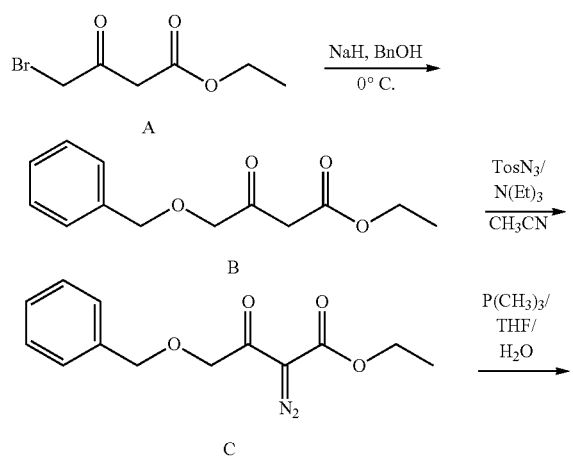

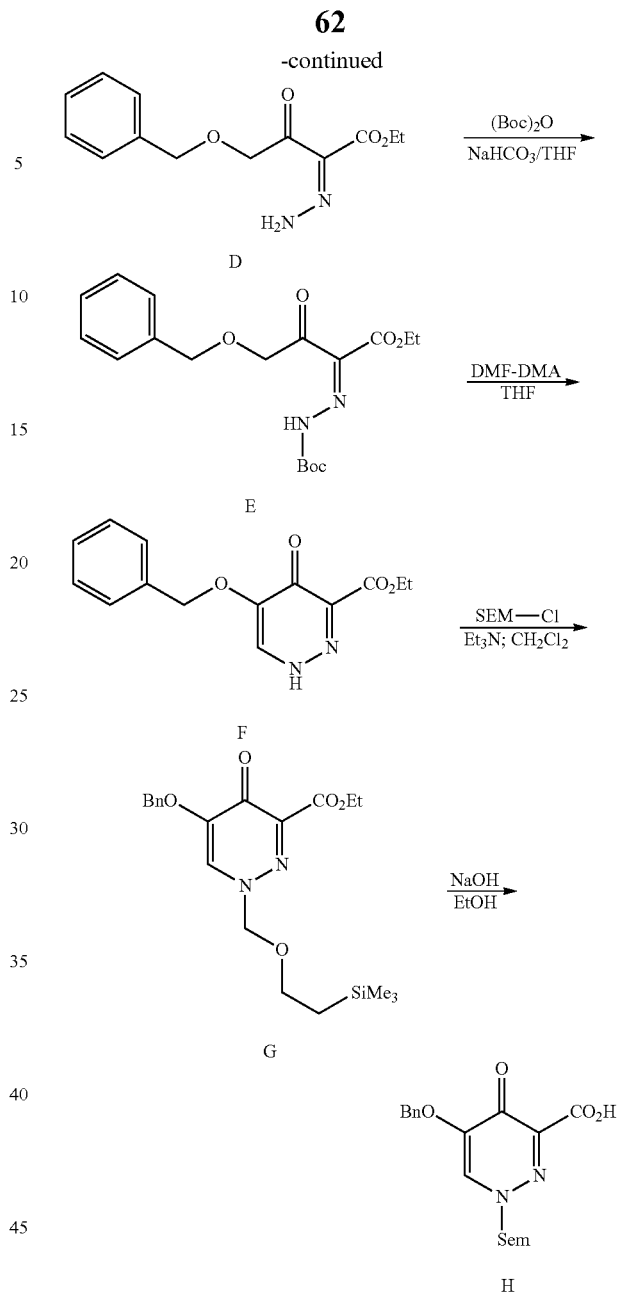

To a stirred solution of NaH (21.8 g, 912 mmol 3.0 eq.) in THF (300 mL) was added BnOH (32.8 g, 304.0 mmol 1.0 eq.) under a $N_2$ atmosphere at 0° C. After addition, the mixture was stirred for 30 min. Compound A (63.5 g, 304.0 mmol 1.0 eq.) was added portionwise. The mixture was allowed to warm to ambient temperature and stirred for another 12 h. The reaction was monitored by TLC (petroleum ether (PE):EtOAc=5:1). The mixture was poured into 2M HCl solution to a ~pH 6. The solution was exacted with EtOAc (200 mL×3). The combined organic phases were dried over $Na_2SO_4$, filtered and concentrated. The residue was purified by column chromatography on silica gel (PE:EtOAc=30:1 to 5:1) to give compound B as a colorless oil (46 g, 88.5%). $^1$H NMR ($CDCl_3$) δ 7.39-7.29 (m, 5H), 4.59 (s, 2H), 4.17-4.24 (q, 2H), 4.14 (s, 2H), 3.53 (s, 2H), 1.31-1.22 (t, 3H).

To a stirred solution of compound B (10.0 g, 42.3 mmol 1.0 eq.) in $CH_3CN$ (20 mL) under a $N_2$ atmosphere at 0° C., was added TosN₃ (8.35 g, 42.3 mmol 1.0 eq.) and TEA (12.84 g, 127.1 mmol 3.0 eq.). The mixture was stirred at 0° C. for 2 h. The mixture was warmed to room temperature (RT) and stirred for 6 h. The reaction was monitored by TLC (PE:EtOAc=5:1). After complete conversion was observed, the solvent was removed under reduced pressure, and the residue was purified by column chromatography on silica gel (PE:EtOAc=30:1 to 5:1) to give compound C as a colorless oil (4.5 g, 40.5%). ¹H NMR (CDCl₃) δ 7.39-7.26 (m, 5H), 4.64 (s, 2H), 4.60 (s, 2H), 4.29-4.24 (q, 2H), 1.32-1.28 (t, 3H).

To a solution of compound C (4.04 g, 15.4 mmol 1.0 eq.) in THF (5 mL) was added P(CH₃)₃/THF solution (16.9 mL, 16.9 mM, 1.1 eq.) at RT. The mixture was stirred for 15 min (indicated by TLC, PE:EtOAc=2:1) and then quenched with water (2.8 mL). The mixture was stirred for 15 min and concentrated under reduced pressure. The crude residue was purified by column chromatography on silica gel (PE:EtOAc=5:1 to 2:1) to give compound D as a yellow solid (4.0 g, 98.2%). ¹H NMR (CDCl₃) δ 7.39-7.24 (m, 5H), 4.66-4.66 (s, 1H), 4.66-4.61 (s, 2H), 4.53-4.53 (s, 1H), 4.31-4.24 (m, 2H), 1.35-1.29 (m, 3H).

To a stirred solution of compound D (20.0 g, 75.7 mmol, 1.0 eq.) in THF (100 mL) was added NaHCO₃ (19.1 g, 227.3 mmol 3.0 eq.) and (Boc)₂O (22.84 g, 113.6 mmol 1.5 eq.). The mixture was heated to reflux for 6 h and monitored by TLC (PE:EtOAc=2:1). After complete conversion was observed, the solution was concentrated under reduced pressure. The residue was dissolved in EtOAc (200 mL) and washed with water (80 mL×2). The organic layer was separated, dried over Na₂SO₄ and filtered. The mixture was concentrated under reduced pressure, and the residue was purified by column chromatography on silica gel (PE:EtOAc=8:1) to give compound E as a white solid (15 g, 54.30%). ¹H NMR (CDCl₃) δ 11.59 (s, 1H), 7.40-7.26 (m, 5H), 4.71-4.61 (m, 2H), 4.39 (s, 2H), 4.71-4.27 (q, 2H), 1.70-1.48 (m, 9H), 1.38-1.24 (t, 3H).

To a solution of compound E (4.2 g, 11.5 mmol 1 eq.) in THF (100 mL) at RT, was added DMF-DMA (6.15 g, 51.7 mmol, 4.5 eq.). The mixture was stirred at RT for 16 h. After complete conversion was observed as indicated by TLC, the reaction was treated with water (5-6 mL) and stirred for 30 min. The solvent was evaporated under reduced pressure at 40-50° C. The residue was crystallized from EtOAc to give the pure product as a white solid, (0.5 g). The mother liquor was concentrated and purified by column chromatography on silica gel (DCM:MeOH=50:1 to 10:1) to give compound F as a solid (2.4 g, total 75.95%). LCMS (ESI) m/z=275.2 [M+H]⁺ (calc.=274.1). Retention Time=1.097 min.

To a solution of compound F (2.74 g, 10 mmol) and TEA (3.03 g, 30 mmol) in DCM (40 mL) at 0° C., was added 2-trimethylsilylethyoxymethyl chloride (SEMCl, 2.86 g 0.20 mmol) dropwise. After addition, the mixture was stirred at 0° C. for 1 h. The solution was then slowly warmed to RT and stirred for 2 h. The mixture was quenched, washed with 1 M HCl aqueous solution (30 mL×3), saturated aq. NaHCO₃ (20 mL×2) and water. The organic layer was washed with brine, dried over Na₂SO₄, and concentrated to give a crude oil (3.8 g), which was then purified by column chromatography on silica gel to give compound G as a colorless oil (3.0 g, 74%).

To a stirred solution of compound G (2.02 g, 5.0 mmol) in MeOH (20 mL) at 0° C., was added aq. NaOH (1 M, 5 mL) dropwise. After addition, the mixture was stirred for 30 min. MeOH was removed under reduced pressure. The resulting aqueous solution was neutralized with 1 M HCl to pH ~2.0. A white solid was precipitated, which was then filtered, washed with water and dried in vacuum to get compound H (1.5 g, 83%) with a high purity. ¹H NMR (400 MHz, DMSO-d 6): δ 8.88 (s, 1H), 7.49-7.41 (m, 5H), 5.57 (s, 2H), 522 (s, 2H), 3.63 (t, J=8 Hz, 2H), 0.87 (t, J=8 Hz, 2H), 0.02 (S, 9H).

Example 1B

Synthesis of Compound F

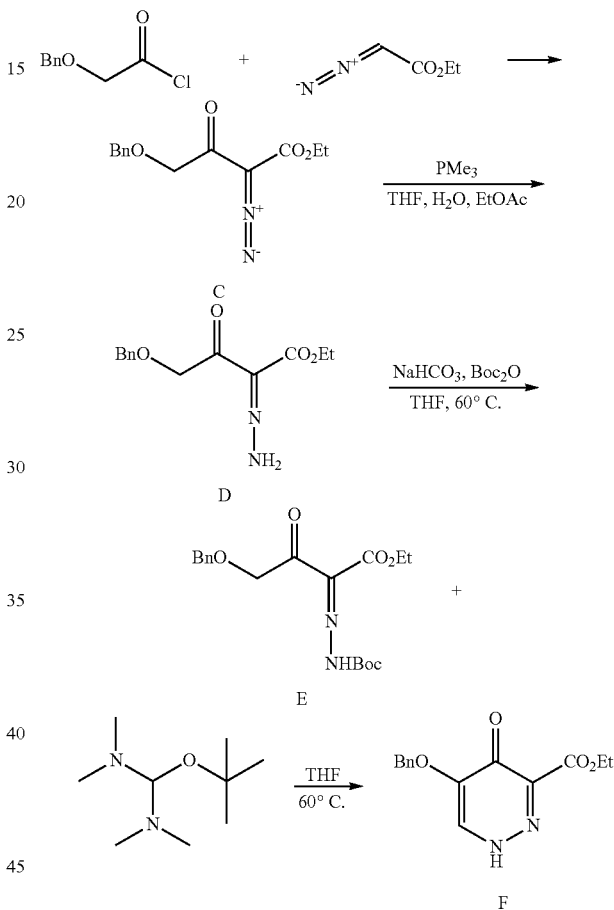

To a 100-mL flask with a teflon stir bar was added ethyl diazoacetate (7.81 g; 2.00 eq.). A bubbler was attached to vent gaseous by-products. The reaction was stirred and cooled with an ice bath during the addition of benzyloxyacetyl chloride (5.80 g; 1.00 eq.) to maintain the internal temperature near room temperature. Using intermittent cooling, the reaction was maintained at 20-25° C. for 70 min, and then stirred at RT overnight. Reaction progress was monitored by TLC (25% EtOAc/hexane; $R_F$ EDA ~0.6; $R_F$ product ~0.5) and was complete after 12 h. The reaction was diluted with EtOAc (45 mL), transferred to a separatory funnel, and washed successively with sat. aq. potassium carbonate (15 mL) and brine (15 mL). The organic layer was dried over sodium sulfate, filtered, and transferred into a 250-mL flask. Compound C was used without further purification.

A flask containing Compound C was purged with argon. PMe₃ (30 mL; 1.0 eq.; 1.0 M in THF) was added. The internal temperature was maintained near RT using an ice bath during the addition of PMe$_3$. The reaction was monitored by TLC (25% EtOAc/hexanes; R$_F$ starting material ~0.5; R$_F$ product ~0.1) and was determined to be complete after 5 min. The solution was transferred to a separatory funnel and washed with water (2×15-mL) and brine, and dried over sodium sulfate. The organic layer was concentrated under reduced pressure to yield compound D (9.63 g) as orange oil.

Compound D was dissolved in THF (75 mL). NaHCO$_3$ (7.51 g; 3.00 eq.) and Boc$_2$O (7.07 g; 1.09 eq.) were added. The mixture was stirred and heated to 60° C. The reaction was judged complete by TLC after 30 min (50% EtOAc/hex; R$_F$ starting material ~0.4, R$_F$ product ~0.9). The reaction was cooled to RT, filtered through a coarse-grade fritted glass filter, and washed with EtOAc (40 mL). The filtrate was washed with 1:1 brine:water (50 mL), and with brine. The organic layer was dried over sodium sulfate and concentrated under reduced pressure to give a yellow solid that was slurried with hexanes (75 mL) and filtered through a medium-grade fritted glass filter. The solid was slurried with additional hexanes (40 mL) and filtered to dryness (dried at 80° C.) to give compound E (6.60 g, 60.8% yield over 3 steps) as a pale yellow solid.

A solution of compound E (5.90 g; 1.0 eq.) in dry THF (18 mL) was placed into an addition funnel and added over 5 min to a 60° C., mechanically stirred solution of tert-butoxy bis(dimethylamino)methane (3 eq.) in dry THF (80 mL). After 10 min, the reaction was monitored by TLC (25% EtOAc/hexanes; R$_F$ s.m. ~0.5; R$_F$ product ~baseline) and judged to be complete within 30 min. The reaction was cooled in an ice bath to RT. Portions of 4 M HCl/dioxane (5-mL per portion) were added until samples that come into contact with wetted pH paper register as strongly acidic. During the addition, the temperature of the mixture was maintained near RT with an ice bath. The resulting thick slurry was diluted with THF (35 mL), collected by vacuum filtration (coarse-grade fritted glass filter), and washed with 1:1 acetone:water (2×17-mL). The filter cake was stirred with acetone (16 mL) and filtered 4 times to give compound F (3.8 g, 85.3%) as a white solid.

Example 2

Synthesis of Compound L

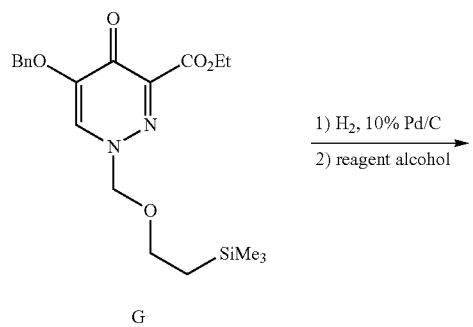

G

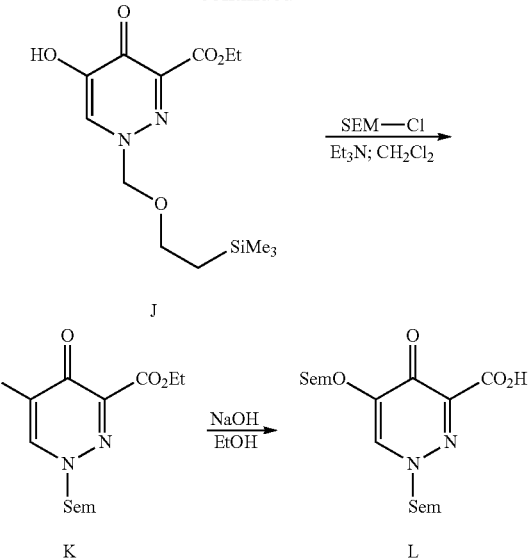

To a solution of compound G (9.0 g, 22.2 mmol) in reagent alcohol (110 mL) was added 10% Pd on carbon (700 mg; 3 mol %). The reaction flask was vacuum purged with hydrogen, and the suspension was rapidly stirred at RT under a hydrogen atmosphere (balloon pressure) for 2 h (LCMS analysis indicated complete conversion). The mixture was filtered through celite, followed by a rinse using 10% MeOH/CH$_2$Cl$_2$ (50 mL). The filtrate was concentrated to give compound J as a tan crystalline solid (6.9 g) that was used without further purification.

To a solution of compound J (6.9 g, 22 mmol) and triethylamine (9.2 mL g, 22 mmol) in DCM (80 mL) at 0° C., was added 2-trimethylsilylethoxymethyl chloride (SEMCl, 5.27 mL, 29.8 mmol), dropwise. After addition, the ice bath was removed and the mixture was stirred at RT overnight. TLC analysis indicated compound J was still present. Additional 2-trimethylsilylethoxymethyl chloride (SEMCl, 2 mL, 11.2 mmol) was added. TLC analysis after 2 h indicated the reaction was complete. The mixture was quenched with sat. aqueous NH$_4$Cl (100 mL) and 2 M HCl aqueous solution (20 mL, final pH ~7), and the layers were separated. The aqueous layer was extracted with DCM (80 mL) and the combined organic layers were washed with water, followed by brine, and dried over Na$_2$SO$_4$. The solution was concentrated to give an orange oil that was purified by column chromatography (silica gel; 45-75% EtOAc/hexanes) to give compound K as a colorless oil (7.95 g, 81%) that solidified on standing.

To a stirred solution of compound K (7.95 g, 17.9 mmol) in reagent alcohol (120 mL) at RT was added aq. NaOH (2 M, 54 mL, 108 mmol). The mixture was stirred for 3 h (LCMS indicated complete conversion) and was then concentrated to approx. half volume under reduced pressure (45° C.). The mixture was cooled at 0° C. and acidified with 2 M HCl to pH-2-3 (pH paper). An oily white solid precipitated during the acidification, which was extracted with DCM (150 mL). The layers were separated, and the aqueous layer was extracted with DCM (2×50 mL). The combined organic layers were washed with brine, dried over Na$_2$SO$_4$, and concentrated to give compound L (6.8 g) as an off-white solid. LCMS: m/z=415 [M–H]$^-$; $^1$H NMR (400 MHzCDCl$_3$): δ 8.38 (s, 1H), 5.57 (s, 2H), 5.40 (s, 2H), 3.8

(dd, J=8.8, 8.8 Hz, 2H), 3.68 (dd, J=8.4, 8.4 Hz, 2H), 0.965 (dd, J=16.8, 6.8 Hz, 4H), 0.01 (s, 18H).

Example 3

Synthesis of Amino Alcohol AA6

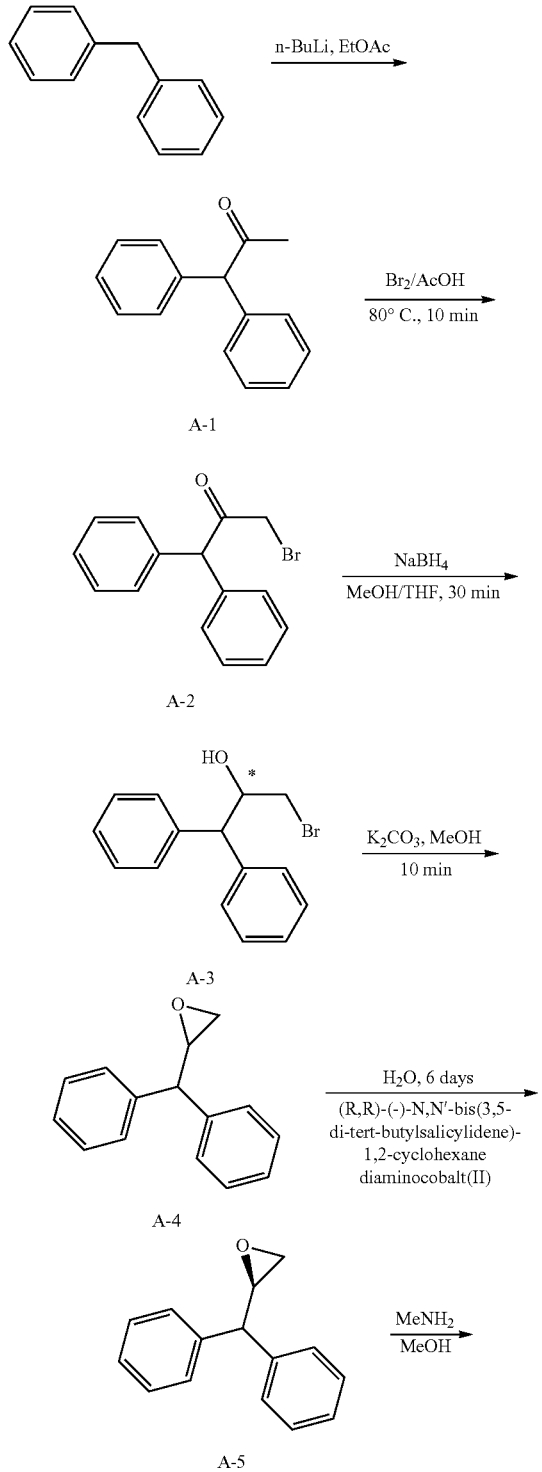

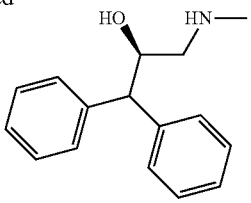

AA6

To a solution of diphenylmethane (250 g, 1.49 mol) in THF (1.5 L) at 0° C. under $N_2$ was added n-BuLi (549 ml, 1.49 mmol, 2.5 M) dropwise. After addition, the reaction was stirred for 1 h at the same temperature. AcOEt (196 g, 2.23 mol) was added dropwise, and then the mixture was kept stirring at 60° C. for 16 h. The reaction was quenched with water, extracted with EtOAc (3×200 mL). The organic phases were washed with brine, dried over anhydrous $Na_2SO_4$, filtered and concentrated. The residue was purified by flash column chromatography on silica gel (PE:EA=10:1) to give A-1 as a white solid (100 g, yield: 30%). $^1$H NMR (400 MHz, $CDCl_3$): δ 7.41-7.25 (m, 10H), 5.15 (s, 1H), 2.28 (s, 3H).

To a solution of A-1 (50 g, 237 mmol) in AcOH (250 mL) at 60° C. under $N_2$ was added $Br_2$ (38.0 g, 237 mmol) dropwise. After addition (30 min), the mixture was stirred at the same temperature for 1 h. The solution was then cooled to RT and then poured into ice-water (250 mL). The reaction was quenched with saturated aq. $Na_2SO_3$. The mixture was extracted with DCM (3×250 mL). The combined organic layers were washed with aq. $NaHCO_3$ and brine, and dried over $Na_2SO_4$. The mixture was filtered and concentrated. To the residue was added with PE (200 mL). The mixture was violently stirred for 20 mins and then filtered. The filtrate cake was washed with PE and dried in vacuum to provide crude A-2 as a white solid (52 g), which was used directly in the next step without further purification.

To a solution of A-2 (52.0 g, 179 mmol) in THF (300 mL) at 0° C., was added $NaBH_4$ (27.2 g, 719 mmol) in portions. After addition, the reaction was kept stirring for 2 h at RT. The reaction was quenched with water and extracted with EtOAc (3×200 mL). The organic phases were washed with brine, dried over $Na_2SO_4$ and concentrated. The residue was purified by flash column chromatography on silica gel (PE:EA=10:1) to give A-3 as a white solid (30 g, yield: 57.7%). $^1$H NMR (400 MHz, $CDCl_3$): δ 7.41-7.21 (m, 10H), 4.58-4.52 (m, 1H), 4.16-4.13 (d, J=12, 1 H), 3.57-3.53 (m, 1H), 3.36-3.32 (m, 1H).

To a stirred solution of A-3 (30.0 g, 103 mmol) in MeOH (30 mL) was added $K_2CO_3$ (42.7 g, 309 mmol) at RT. The reaction was monitored by TLC (PE:EtOAc=10:1). After 10 mins, the mixture was filtered. The filtrate cake was washed with MeOH (10 mL). The combined filtrates were concentrated to give a crude residue, which was purified by silica column chromatograph (PE:EA=50:1) give A-4 as a colorless oil (15 g, yield: 71.4%). $^1$H NMR (400 MHz, $CDCl_3$): δ 7.38-7.28 (m, 10H), 3.90-3.88 (d, J=8, 1H), 3.58-3.55 (m, 1H), 2.91-2.89 (t, J=4, 1H), 2.58-2.56 (m, 1H).

Compound A-5 was prepared according to the procedure described in Gopishetty et. al., *Tetrahedron: Asymmetry* (2011) 22(10):1081-1086, which is hereby incorporated by reference for the limited purpose of its disclosure of the preparation of A-5.

To a solution of A-5 (800 mg, 3.8 mmol) in MeOH (10 mL) in a screw-top tube, was added $MeNH_2$/MeOH (10 mL)

in one portion. The mixture was stirred at RT for 30 min. The mixture was then heated to 60° C. and stirred for 5 h. The mixture was cooled to RT, and the solvent was removed under reduced pressure to give AA6 as a yellowish solid (850 mg), which was used without further purification. ESI-MS: m/z=241.8 [M+H]+. Optionally, A-4 can be substituted for compound A-5, leading to amino alcohol AA6 as a racemic mixture.

1-(3-cyclopropoxyphenyl)-3-(methylamino)-1-phenyl-propan-2-ol was prepared following a similar procedure as in Example 3 and using 1-benzyl-3-cyclopropoxybenzene.

1-(methylamino)-3,4-diphenylbutan-2-ol was prepared following a similar procedure as in Example 3 starting from step 2 and using 3,4-diphenylbutan-2-one.

Example 4

Synthesis of Amino Alcohol (AA1)

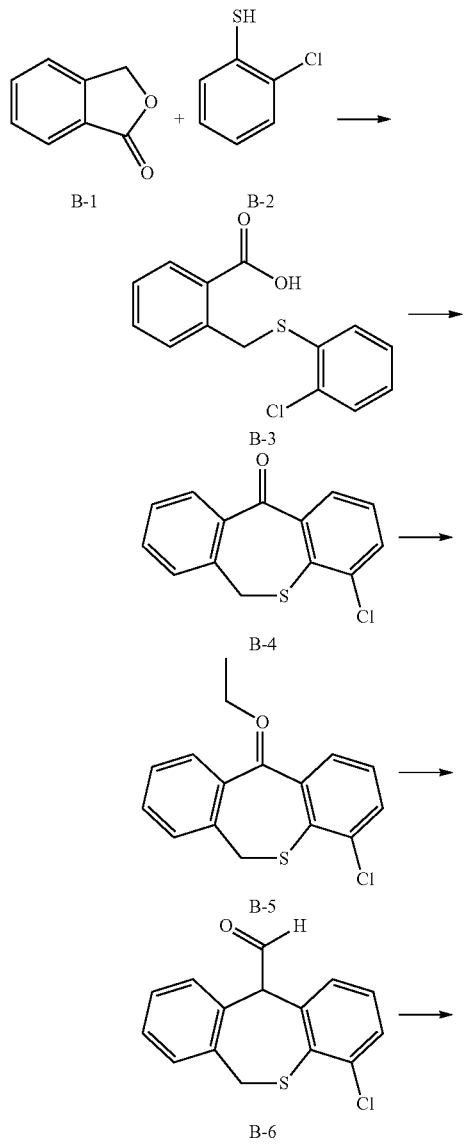

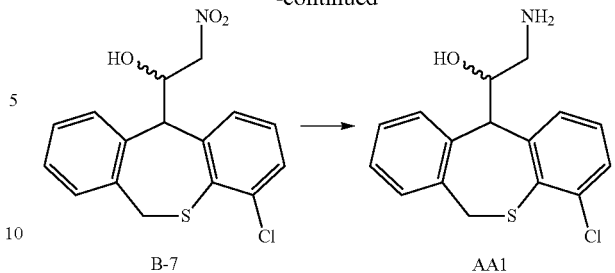

To a solution of B-2 (25 g, 0.17 mol) and K$_2$CO$_3$ (97.3 g, 0.7 mmol) in DMF (500 mL) was added B-1 (19 g, 0.14 mol). The mixture was stirred for 2 h at 150° C. The solution was poured into ice-water (2 L). The suspension was extracted with EtOAc (3×500 mL). The organic layers were washed with brine (2×300 mL), dried with Na$_2$SO$_4$ and concentrated to give B-3 (45 g), which was used directly in the next step. $^1$H NMR (400 MHz, d-DMSO): δ 13.08 (s, 1H), 7.83 (d, J=8.0 Hz, 1H), 7.45-7.39 (m, 5H), 7.27 (m, 1H), 7.14 (m, 1H), 4.61 (s, 2H).

A solution of B-3 (45 g, 0.16 mol) in polyphosphoric acid (PPA, 400 mL) was stirred at 150° C. for 3 h. The mixture was then slowly poured into 2 L of ice-water, and a white solid precipitated. The suspension was allowed to stand for 1 h, and then filtered. The solid was dried under vacuum to give B-4 (18 g, 48%). The filtrate was extracted with EtOAc. The organic layers were washed with brine, dried and concentrated. The residue was purified by re-crystallization (in EtOAc) to give additional B-4 (2.0 g) that was combined with the first batch of materials. $^1$H NMR (400 MHz, d-DMSO): δ 8.03 (dd, J=8 Hz, J=1.2 Hz, 1H), 7.70 (d, J=1.2 Hz, 1H), 7.70 (t, J=1.2 Hz, 1H), 7.44-7.35 (m, 4H), 4.30 (s, 2H).

To a mixture of (methoxymethyl) triphenylphosphonium chloride (43 g, 127 mmol) in THF (400 mL) was added n-BuLi (2.5 M, 51 mL, 127 mmol) dropwise at 0° C. A solution of B-4 (6.6 g, 25.38 mmol) in THF (50 mL) was added. The mixture was stirred for 5 h at 0° C. The mixture was warmed to room temperature and then stirred overnight. The mixture was quenched with sat. aq. NH$_4$Cl. The solution was extracted with EtOAc (3×200 mL). The combined organic phases were washed with brine, dried over with Mg$_2$SO$_4$ and concentrated. The residue was purified by flash column chromatography on silica gel to give compound B-5 as a colorless oil (6.0 g, a mixture of E/Z isomers, 82%). $^1$H NMR (400 MHz, CDCl$_3$): δ 7.30-7.28 (m, 1H), 7.16-7.07 (m, 5H), 6.90 (t, J=8 Hz, 1H), 6.10 (s, 1H), 4.50 (brs, 2H), 3.66 (s, 3H).

To a solution of B-5 (7 g, 24.3 mmol) in 1,4-dioxane (30 mL) was added HClO$_4$ (70% aq., 5 mL). The mixture was stirred for 30 min at 90° C. The reaction was cooled to RT, diluted with water (150 mL) and extracted with EtOAc (2×50 mL). The combined organic layers were washed with brine, dried over Na$_2$SO$_4$ and concentrated to give B-6 (7.5 g), which was used directly in the next step. $^1$H NMR (400 MHz, CDCl$_3$): δ 9.87 (s, 1H), 7.36-7.18 (m, 8H), 4.59 (s, 1H), 4.13 (d, J=16 Hz, 1H), 3.91 (d, J=16 Hz, 1H).

A mixture of B-6 (7.5 g, 27 mmol) and potassium carbonate (37.94 g, 273 mmol) in nitromethane (30 mL) was stirred for 3 h at 25° C. The solvent was removed under reduced pressure. To the residue was added EtOAc (200 mL) and water (100 mL). The separated organic phase was washed with brine (2×50 mL), dried and concentrated. The residue was purified by silica column chromatography (pet ether:EtOAc=10:1) to give B-7 as colorless oil (mixture of diastereoisomers, 4 g, 44%).

To a solution of B-7 (4.1 g, 12.2 mmol) in HOAc (30 mL), was added zinc powder (31.7 g, 489 mmol), and the mixture was stirred for 13 h at 25° C. The mixture was filtered through a pad of celite to give a clear solution, which was poured into ice-water (100 mL). The mixture was basified with K₂CO₃ to pH-10, and extracted with EtOAc (3×100 mL). The organic layer was washed with brine (2×50 mL), dried over with Na₂SO₄ and concentrated to give amino alcohol AA1 as a pale yellow solid (3 g, 81%). LCMS: m/z=306 [M+H]⁺.

Example 5

Synthesis of Amino Alcohol (AA2)

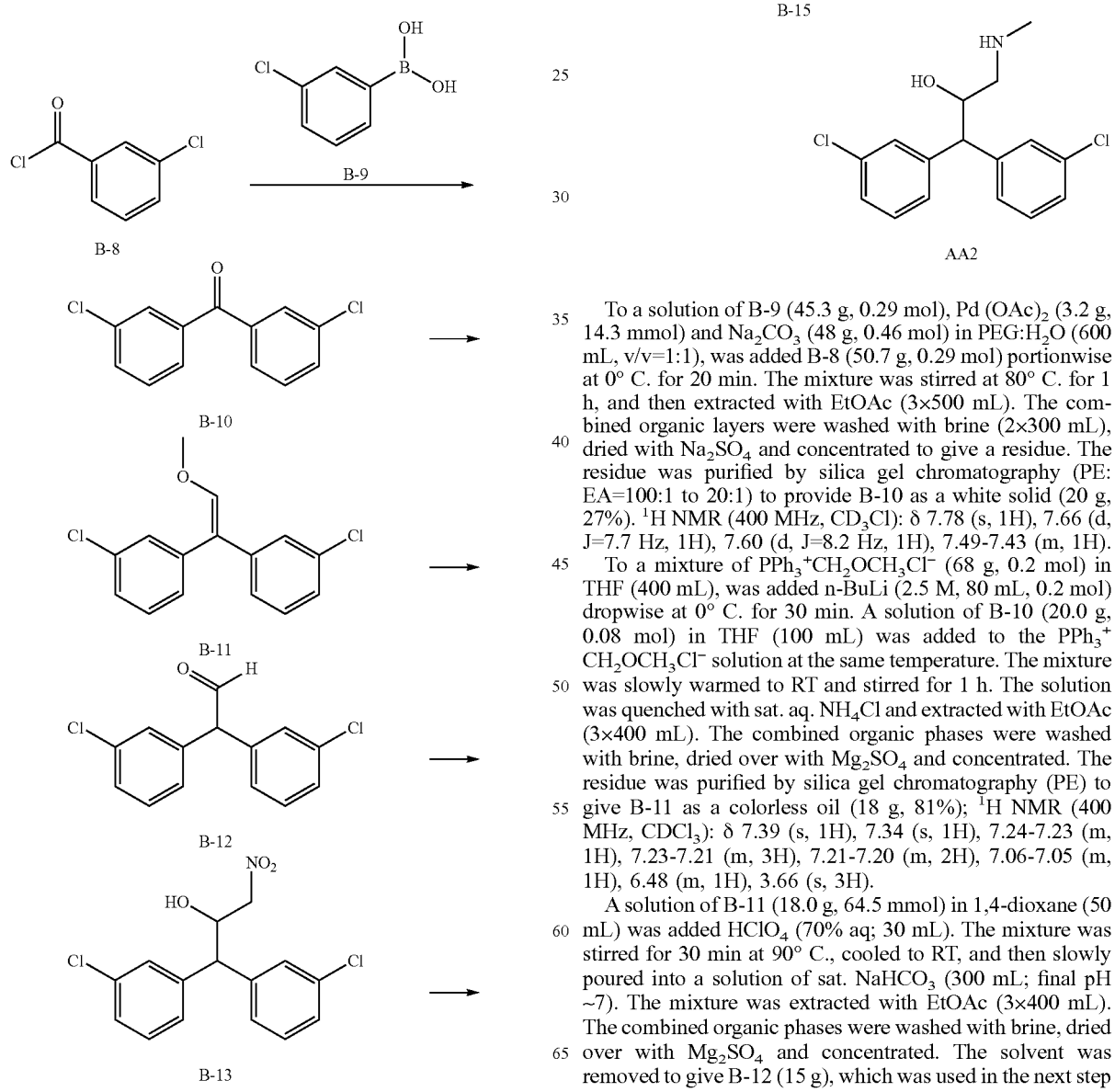

To a solution of B-9 (45.3 g, 0.29 mol), Pd (OAc)₂ (3.2 g, 14.3 mmol) and Na₂CO₃ (48 g, 0.46 mol) in PEG:H₂O (600 mL, v/v=1:1), was added B-8 (50.7 g, 0.29 mol) portionwise at 0° C. for 20 min. The mixture was stirred at 80° C. for 1 h, and then extracted with EtOAc (3×500 mL). The combined organic layers were washed with brine (2×300 mL), dried with Na₂SO₄ and concentrated to give a residue. The residue was purified by silica gel chromatography (PE: EA=100:1 to 20:1) to provide B-10 as a white solid (20 g, 27%). ¹H NMR (400 MHz, CD₃Cl): δ 7.78 (s, 1H), 7.66 (d, J=7.7 Hz, 1H), 7.60 (d, J=8.2 Hz, 1H), 7.49-7.43 (m, 1H).

To a mixture of PPh₃⁺CH₂OCH₃Cl⁻ (68 g, 0.2 mol) in THF (400 mL), was added n-BuLi (2.5 M, 80 mL, 0.2 mol) dropwise at 0° C. for 30 min. A solution of B-10 (20.0 g, 0.08 mol) in THF (100 mL) was added to the PPh₃⁺CH₂OCH₃Cl⁻ solution at the same temperature. The mixture was slowly warmed to RT and stirred for 1 h. The solution was quenched with sat. aq. NH₄Cl and extracted with EtOAc (3×400 mL). The combined organic phases were washed with brine, dried over with Mg₂SO₄ and concentrated. The residue was purified by silica gel chromatography (PE) to give B-11 as a colorless oil (18 g, 81%); ¹H NMR (400 MHz, CDCl₃): δ 7.39 (s, 1H), 7.34 (s, 1H), 7.24-7.23 (m, 1H), 7.23-7.21 (m, 3H), 7.21-7.20 (m, 2H), 7.06-7.05 (m, 1H), 6.48 (m, 1H), 3.66 (s, 3H).

A solution of B-11 (18.0 g, 64.5 mmol) in 1,4-dioxane (50 mL) was added HClO₄ (70% aq; 30 mL). The mixture was stirred for 30 min at 90° C., cooled to RT, and then slowly poured into a solution of sat. NaHCO₃ (300 mL; final pH ~7). The mixture was extracted with EtOAc (3×400 mL). The combined organic phases were washed with brine, dried over with Mg₂SO₄ and concentrated. The solvent was removed to give B-12 (15 g), which was used in the next step without further purification.

A mixture of B-12 (15.0 g, 56.8 mmol) and potassium carbonate (25.3 g, 184 mmol) in nitromethane (60 mL) was stirred for 30 min at 25° C. The mixture was filtered and the filtration was concentrated under reduced pressure. To the residue was added EtOAc (200 mL) and water (100 mL). The separated organic phase was washed with brine (2×50 mL), dried and concentrated. The residue was purified by silica column chromatography (PE:EtOAc=10:1) to give B-13 as a colorless oil (12 g, 67%). $^1$H NMR (400 MHz, CDCl$_3$): δ 7.37 (s, 1H), 7.31-7.25 (m, 6H), 7.19 (d, J=7.1 Hz, 1H), 5.10-5.01 (m, 1H), 4.39 (d, J=5.5 Hz, 2H), 3.96 (d, J=8.6 Hz, 1H), 2.77 (d, J=4.6 Hz, 1H).

A mixture of B-13 (4.0 g, 12.3 mmol) and Raney nickel (200 mg) in MeOH (40 mL) was rapidly stirred at RT under a hydrogen atmosphere (45 psi) for 2 h. The mixture was filtered through a pad of celite, and the filtrate was concentrated to give B-14 as a yellow oil (3.0 g, 83%). LCMS: m/z=296 [M+H]$^+$.

A solution of B-14 (2.96 g, 10 mmol) in ethyl formate (30 mL) was heated to reflux for 3 h. The mixture was concentrated to give B-15 as a yellow oil (3 g, 93%) that was used in the next step without further purification. LCMS: m/z=324 [M+H]$^+$.

To a solution of B-15 (3.2 g, 1.0 mmol) in THF (20 mL) under N$_2$ atmosphere at 0° C., was added a solution of BH$_3$ (1M THF solution, 5 mL) dropwise. The mixture was stirring for 10 min at the same temperature, warmed to RT, and then heated at reflux for 4 h. After complete conversion (as determined by TLC), the mixture was cooled in an ice-water bath, and quenched by adding MeOH (5 mL). The solvent was removed under reduced pressure. The residue was dissolved in EtOAc, washed with sat. NaHCO$_3$, water, and brine, and dried. The mixture was concentrated under reduced pressure to give amino alcohol AA2 (2 g, 64%). LCMS: m/z=310 [M+H]$^+$.

3-(methylamino)-1-phenyl-1-(m-tolyl)propan-2-ol was prepared following a similar procedure as in Example 5 starting with step 2 and using phenyl(m-tolyl)methanone.

3-(ethylamino)-1-phenyl-1-(m-tolyl)propan-2-ol was prepared following a similar procedure as in Example 5 starting with step 2 and using acetic anhydride and LAH.

3-(isopropylamino)-1-phenyl-1-(m-tolyl)propan-2-ol was prepared following a similar procedure as in Example 5 starting with step 2 and using acetone and NaBH$_4$.

1,1-bis(4-fluorophenyl)-3-(methylamino)propan-2-ol was prepared following a similar procedure as in Example 5 starting with step 2 and using bis(4-fluorophenyl)methanone.

1,1-bis(3-chlorophenyl)-3-(isopropylamino)propan-2-ol was prepared following a similar procedure as in Example 5 starting with step 2 and using acetone and sodium borohydride.

Example 6

Route 1

Synthesis of Amino Alcohol (AA3)

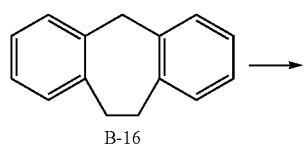

B-16

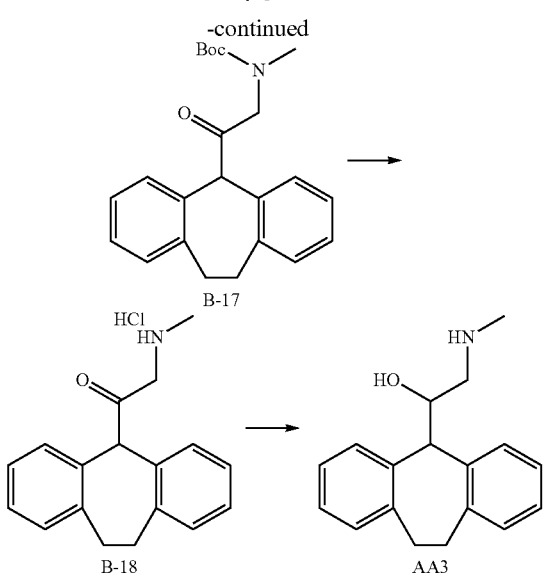

Glycine methyl ester hydrochloride (50.0 g, 0.398 mol, 1 eq.) was added to a 1 L flask containing water (300 mL) and THF (200 mL). Sodium bicarbonate (37.8 g, 0.438 mol) was added portionwise, followed by di-tert-butyl dicarbonate (83.4 g, 0.382 mol). The reaction was stirred for 18 h, and then the separated organic phase was concentrated. The mixture was redissolved in EtOAC, washed with brine, dried over Na$_2$SO$_4$, and evaporated to give an oily product (72 g, 95%). The oily product was dissolved in DMF (500 mL) and cooled to 0° C. To the mixture was added NaH (60%, 18.3 g, 0.457 mol) portionwise. The mixture was then stirred for 30 min and MeI (81.1 g, 0.571 mol) was added at such a rate as to maintain a reaction temperature below 20° C. The mixture was stirred at RT for 48 h. The mixture was poured into ice water (1.5 L), extracted with MTBE (300 mL×2). The combined organics were washed with brine, dried over Na$_2$SO$_4$, and evaporated. Silica gel chromatography (PE: EtOAc 7:1) gave N-Boc-N-methyl glycine methyl ester (21 g, 27%).

A solution of B-16 (10.0 g, 51.5 mmol) in THF (15 mL) was cooled to −10° C., and then n-BuLi (1.8 M in hexanes, 30 mL) was added dropwise. The mixture was transferred dropwise to a solution of N-Boc-N-methyl glycine methyl ester (5.75 g, 28.3 mmol) in THF (20 mL) while maintaining the temperature below 20° C. The reaction was stirred for 10 min. and then a sat. NH$_4$Cl solution was added. The organic layer was separated, dried over Na$_2$SO$_4$ and concentrated. Silica gel chromatography (PE:EA 10:1) afforded B-17 (5 g, 66%) as a yellow oil.

Dry hydrogen chloride gas was bubbled into a solution of B-17 (5.0 g, 13.7 mmol) in ethyl acetate (50 mL). The mixture was concentrated to give B-18 (3.3 g, 80%) as a white solid.

To a mixture of B-18 (4.3 g, 14.2 mmol) in MeOH (45 mL) was added NaBH$_4$ (1.6 g, 42.9 mmol) portionwise. The mixture was stirred for 1 h. A solution of sat. NH$_4$Cl was added, and the mixture was extracted with EtOAc (100 mL×2). The combined organic layer was washed with brine, dried over Na$_2$SO$_4$, and concentrated to give amino alcohol AA3 (1.9 g 50.7%) as a white solid; $^1$H NMR (400 MHz, CDCl3) δ (ppm) 7.11-7.27 (m, 8H), 4.43 (m, 1H), 3.84 (m, 1H), 4.50 (m, 2H), 4.29 (m, 2H), 2.48 (m, 2H), 2.34 (s, 3H).

Example 6

Synthesis of Amino Alcohol (AA3(HCl))—Route 2

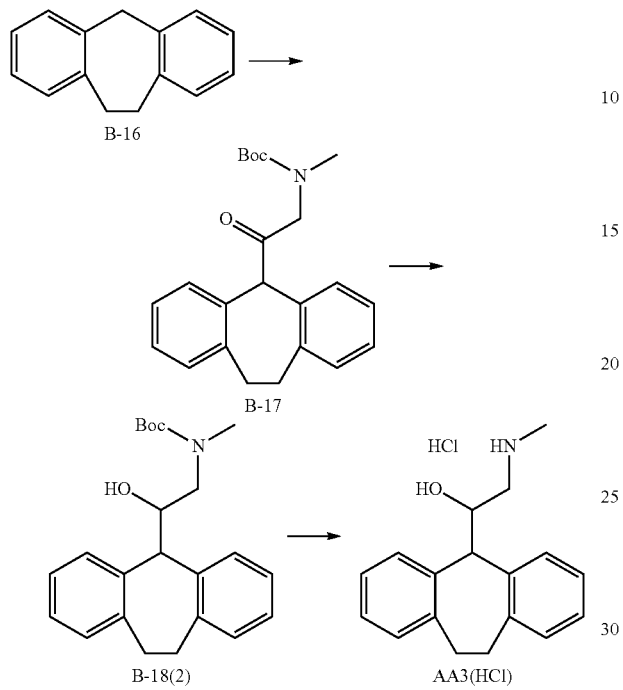

Compound B-16 (20 g; 103 mmol; 2 eq) was dissolved in dry THF (300 mL) under $N_2$ atmosphere. The mixture was chilled at 0° C. and n-BuLi (1.6 M, 103 mmol; 2 eq) was added dropwise. The mixture turned red and was stirred 30 min at 0° C. N-Boc sarcosine (1 eq.; 51.5 mmol; 10.4 g), dissolved in dry THF (30 mL), was added dropwise. After 20 mins, the reaction was quenched using sat. $NH_4Cl$ solution and extracted into EtOAc (2×). The organic phase was purified by silica gel chromatography (100:0 to 85:15, Cy:EtOAc) to give B-17 (16 g).

To a solution of B-17 (16 g; 44.8 mmol) dissolved in MeOH (200 mL) was added $NaBH_4$ (4 eq.; 6.6 g), portionwise, over 2 h. The reaction was partitioned between sat. $NH_4Cl$ solution and EtOAc. The organic solvent was dried over $Na_2SO_4$ and concentrated to give B-18(2) (16 g).

Compound B-18(2) (16 g) was dissolved in 4M HCl (160 mL) in dioxane. The mixture was stirred 1 h, and a heavy precipitation was formed. The mixture was diluted with $Et_2O$ (200 mL) and then filtered to give AA3(HCl) (12 g) as a white powder.

2-(benzylamino)-1-(10,11-dihydro-5H-dibenzo[a,d][7]annulen-5-yl)ethanol hydrochloride was prepared following a similar procedure as in Example 6 (Route 2) and using methyl [benzyl(tert-butoxycarbonyl)amino]acetate.

1-(10,11-dihydro-5H-dibenzo[a,d][7]annulen-5-yl)-2-(ethylamino)ethanol hydrochloride was prepared following a similar procedure as in Example 6 (Route 2) and using methyl [(tert-butoxycarbonyl)(ethyl)amino]acetate.

1-(10,11-dihydro-5H-dibenzo[a,d][7]annulen-5-yl)-2-(isopropylamino)ethanol hydrochloride was prepared following a similar procedure as in Example 6 (Route 2) and using methyl 2-{[(tert-butoxy)carbonyl](propan-2-yl)amino}acetate.

1-(1,9-difluoro-10,11-dihydro-5H-dibenzo[a,d][7]annulen-5-yl)-2-(isopropylamino)ethanol hydrochloride was prepared following a similar procedure as in Example 6 (Route 2) and using methyl 2-{[(tert-butoxy)carbonyl](propan-2-yl)amino}acetate.

3-(methylamino)-1-phenyl-1-(pyridin-2-yl)propan-2-ol dihydrochloride was prepared following a similar procedure as in Example 6 (Route 2) and using 2-benzylpyridine.

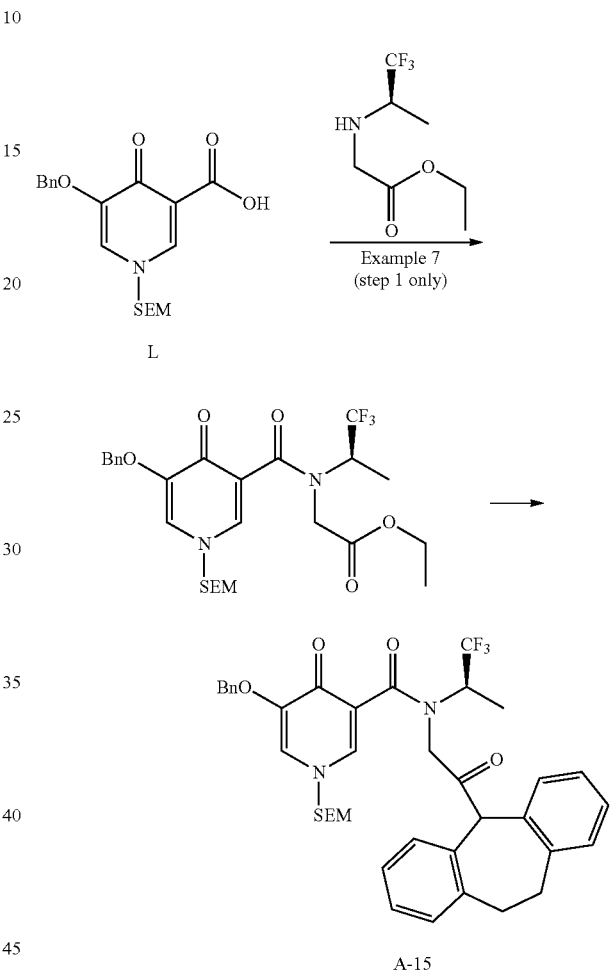

Compound A-15 was prepared following a similar procedure as in Example 6 (Route 2) and using (R)-ethyl 2-(5-(benzyloxy)-4-oxo-N-(1,1,1-trifluoropropan-2-yl)-1-((2-(trimethylsilyl)ethoxy)methyl)-1,4-dihydropyridazine-3-carboxamido)acetate.

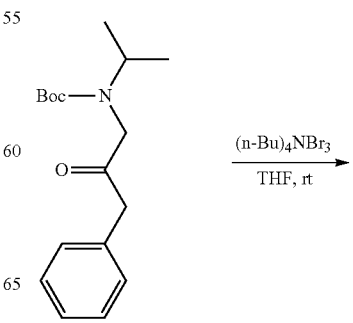

77
-continued

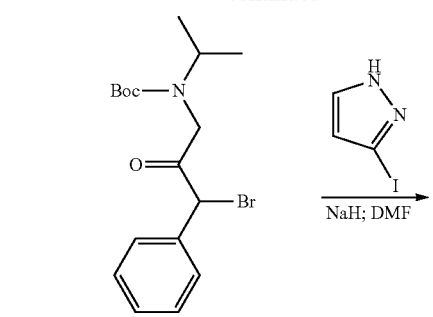

78
-continued

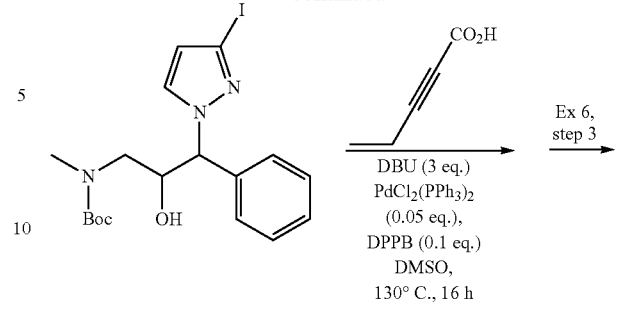

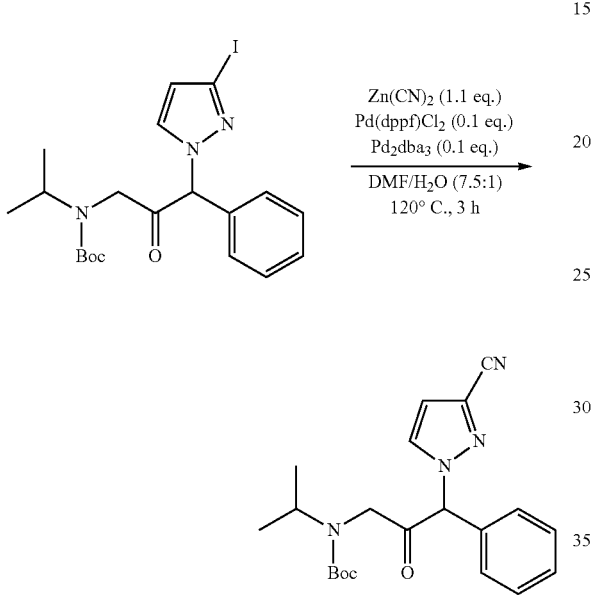

1-(2-hydroxy-3-(isopropylamino)-1-phenylpropyl)-1H-pyrazole-3-carbonitrile hydrochloride was prepared following a similar procedure as in Example 6 (Route 2) starting with step 2 and using tert-butyl (3-(3-cyano-1H-pyrazol-1-yl)-2-oxo-3-phenylpropyl)(isopropyl)carbamate.

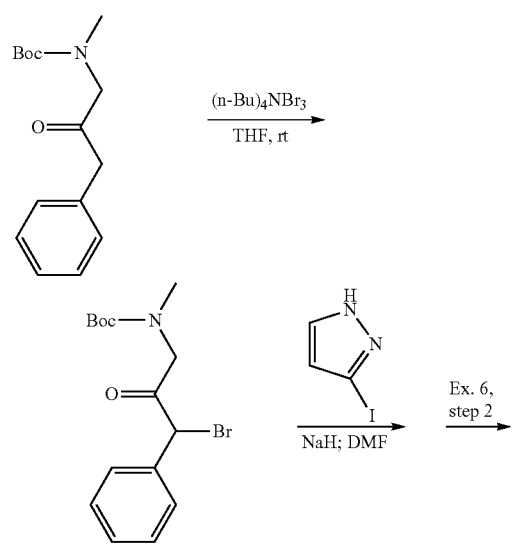

1-(3-(but-1-yn-1-yl)-1H-pyrazol-1-yl)-3-(methylamino)-1-phenylpropan-2-ol hydrochloride was prepared following a similar procedure as in Example 6 (Route 2) starting with step 2 and using tert-butyl (2-hydroxy-3-(3-iodo-1H-pyrazol-1-yl)-3-phenylpropyl)(methyl)carbamate, followed by acetylene coupling prior to step 3.

Example 7

Synthesis of Compound of Formula (I)—Route 1

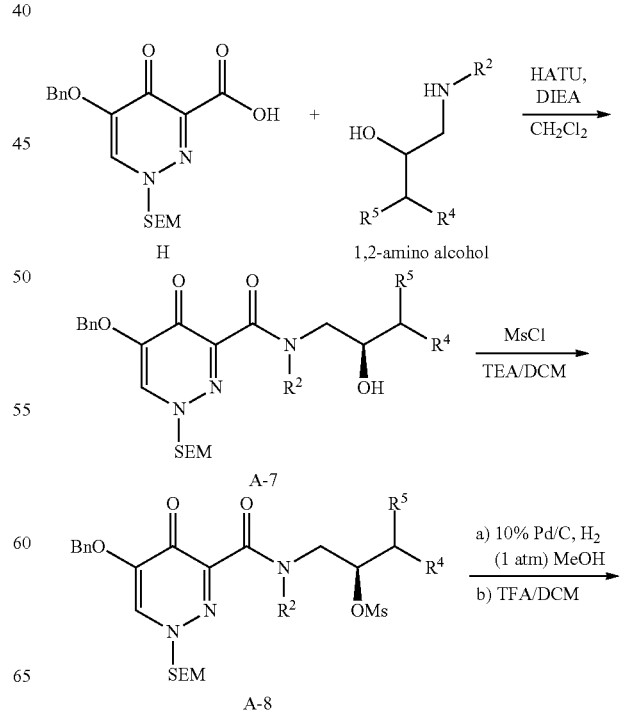

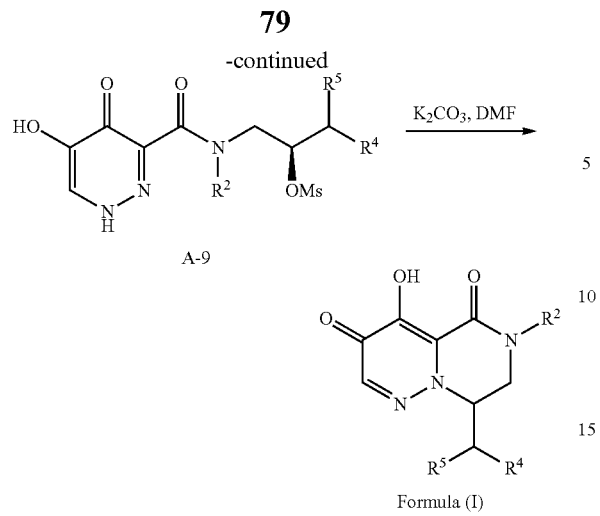

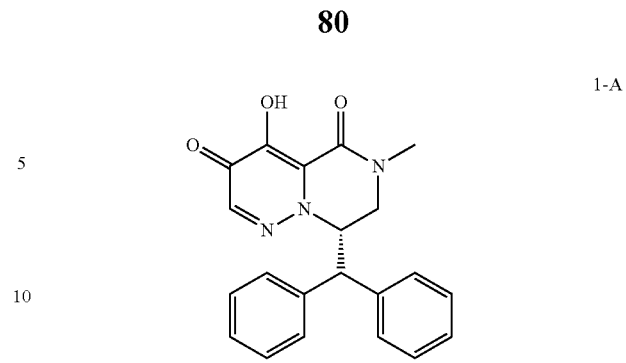

$R^2$ = a straight-chain optionally substituted alkyl,
an optionally substituted cycloalkyl ($C_{1-6}$ alkyl),
an optionally substituted aryl ($C_{1-6}$ alkyl),
an optionally substituted heteroaryl ($C_{1-6}$ alkyl) or
an optionally substituted heterocyclyl ($C_{1-6}$ alkyl)

A mixture of compound H (1.00 g, 2.67 mmol), HATU (1.21 g, 3.20 mmol) and DIEA (516 mg, 4.00 mmol) in DCM (20 mL) was stirred at RT for 30 min. The 1,2-aminoalcohol (for example, compound A-6, 584 mg, 2.42 mmol) was added, and the mixture was stirred for 1 h. The reaction was quenched with 1M HCl solution. The organic layer was washed with saturated $NaHCO_3$ solution and brine. The organic layer was dried and concentrated to give compound A-7 (1.0 g, 60%) as an oil. ESI-MS: m/z=600.1 $[M+H]^+$.

To a solution of A-7 (400 mg, 0.66 mmol) in DCM (10 mL) was added TEA (198 mg, 1.98 mmol) and MsCl (752 mg, 6.6 mmol) at 0° C. After 30 min, LCMS showed complete conversion to A-8. The mixture was washed with 1M HCl solution, saturated $NaHCO_3$ solution and brine. The organic layer was dried and concentrated to give A-9 (400 mg, 90%) as an oil. ESI-MS: m/z=678.1 $[M+H]^+$.

To a solution of A-9 (400 mg, 0.59 mmol) in MeOH (10 mL), was added 10% Pd/C (200 mg). The mixture was stirred at RT for 2 h under $H_2$ atmosphere ($H_2$ balloon). After complete conversion (as shown by LCMS), the mixture was filtered through a pad of celite and rinsed with 10% MeOH/$CH_2Cl_2$. The filtrate was concentrated to give the crude product as a pale brown solid (300 mg, 86%), which was used in the next step without further purification. ESI-MS: m/z=588.2 $[M+H]^+$.

To a solution of the crude product (300 mg, 0.51 mmol) in DCM (5 mL) was added trifluoroacetic acid (2 mL) dropwise at 0° C., and then stirred at 0° C. overnight. The solvent was removed under reduced pressure to give A-9 as a brown solid. (200 mg, 85%). ESI-MS: m/z=458.2 $[M+H]^+$.

To a solution of A-9 (200 mg, 0.43 mmol) in DMF (5 mL) was added $K_2CO_3$ (182 mg, 1.31 mmol). The mixture was stirred at RT until the reaction was complete as indicated by LCMS (approx. 1 h). The reaction solution was filtered and directly purified by RP-HPLC (0.1% formic acid/ACN) to give Formula (I). Further purification by chiral column chromatography, if needed, (either normal phase using Chiralpak AS-H 5 um chiral packing or SFC conditions using ChiralTech OD-H 3-5 um chiral packing) enables the separation and isolation of enantiomerically pure stereoisomers of Formula (IA).

Compound 1-A was obtained following the procedure for Formula (IA) using AA6 and compound H. Compound 1-A was obtained as a white solid (50 mg, 32%). ESI-MS: m/z=362 $[M+H]^+$.

Example 8

Synthesis of Compound of Formula (I)—Route 2

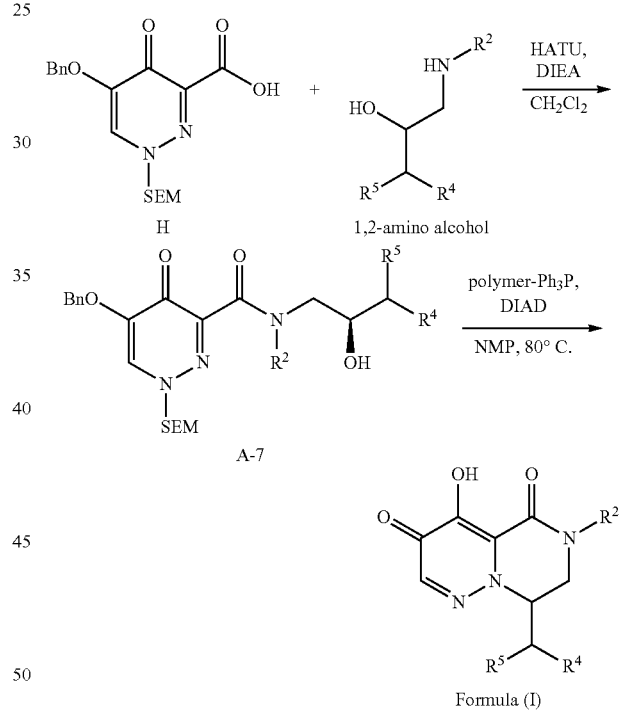

$R^2$ = a branched optionally substituted alkyl,
an optionally substituted cycloalkyl ($C_{1-6}$ alkyl),
an optionally substituted aryl ($C_{1-6}$ alkyl),
an optionally substituted heteroaryl ($C_{1-6}$ alkyl) or
an optionally substituted heterocyclyl ($C_{1-6}$ alkyl)

Compound A-7 was obtained following the procedure as described herein in Example 7.

A round bottom flask was charged with A-7, polymer supported triphenylphosphine (2.75 equiv., 100-200 mesh, 3.2 mmol/g loading) and dry N-methyl-2-pyrrolidinone (NMP, 6.5 mL). The flask was placed in an 85° C. oil bath and diisopropyl azodicarboxylate (DIAD, 2.5 eq.) was added via syringe in approximately 4 equal portions at 30 minute intervals. The reaction was monitored by LCMS. The reaction was heated for a total of 2.5 h, then cooled to ambient temperature and diluted with 1% MeOH/EtOAc (5 mL) and filtered through a plug of celite. The resin was rinsed with 1% MeOH/EtOAc (30 mL). The filtrate was shaken with an equal volume of 2% NH$_4$Cl (aq) in a separatory funnel. The EtOAc phase was collected, and the aqueous phase was further extracted with EtOAc (3×20 mL). The combined organic phases were washed with brine, dried (MgSO4), filtered and concentrated. The crude product was purified by Reverse Phase chromatography to provide Formula (I) following concentration and lyophilization (HPLC conditions: A: H$_2$O B: Acetonitrile; Phenomenex HydroRP C18 column 250×30 cm; 254 nM detection; flow rate: 24 mL/min; gradient: start at 5% B and increase from 5-75% B over 20 min, then 75-95% B over 2 min, then hold at 95% B for 5 min; RT=~21 min).

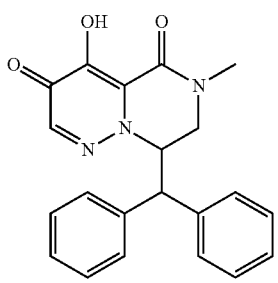 [SMILES: CN1CC(C(c2ccccc2)c2ccccc2)n2ncc(=O)c(O)c2C1=O]

Compound 1 was obtained following the procedure for Formula (I)—Route 2 of Example 8 using 4-hydroxy-N-(2-hydroxy-4,4-diphenylbutyl)-N-methyl-5-oxo-2,5-dihydro-pyridazine-3-carboxamide (222 mg, 0.59 mmol) and polymer-Ph$_3$P (505 mg). Compound 1 was obtained as a light brown powder (14 mg, 6.6%). MS m/z=362 [M+H]$^+$, 360 [M−H]$^-$.

Example 9

Synthesis of Compound 10

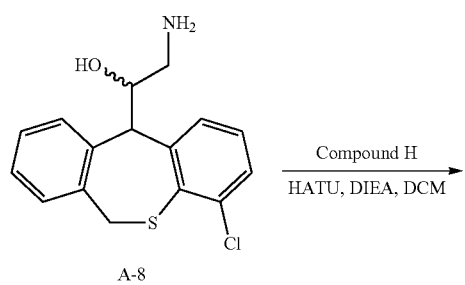

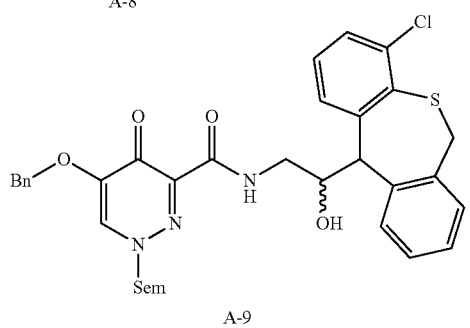

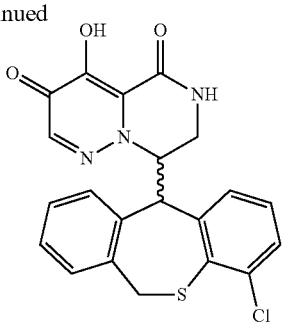

A mixture of compound H (2.03 g, 5.4 mmol), HATU (2.24 g, 5.8 mmol) and TEA (0.73 g, 7.35 mmol) in DCM (20 mL) was stirred for 0.5 h at 25° C. Compound AA1 (1.5 g, 4.9 mmol) was added to the mixture in a single portion. After 1 h, the mixture was washed with 1 M HCl solution (10 mL×3), sat. NaHCO$_3$ (10 mL×3), and brine (5 mL×2). The separated organic layer was dried and concentrated to give A-9 as a brown solid (2 g, 62%). LCMS: m/z=664 [M+H]$^+$.

A solution of A-9 (500 mg, 0.75 mmol) in TFA (5 mL) was heated to 90° C. for 2 h. The solvent was removed in vacuum, and the product was purified by prep-RPHPLC (C$_{18}$, 0.1% formic acid/ACN) to give compound 10 as a pair of partially separable isomers: (R$_t$=0.554 min, m/z=426, 10 mg; R$_t$=0.630 min, m/z=426, 10 mg; 6%). LCMS: m/z=426 [M+H]$^+$.

Example 10

Synthesis of Compounds 6 and 11

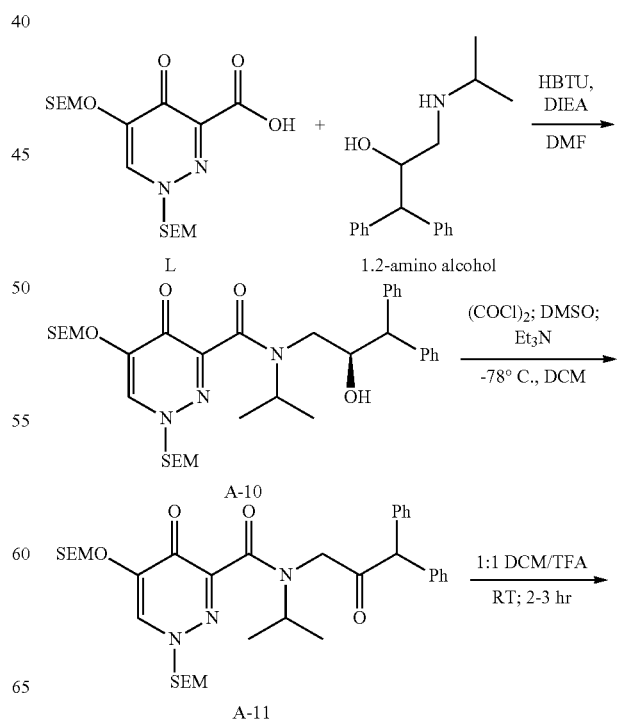

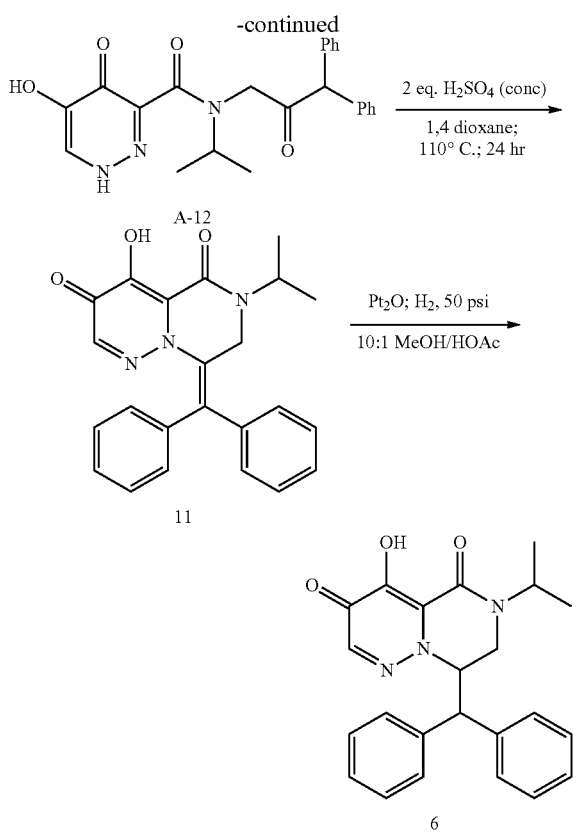

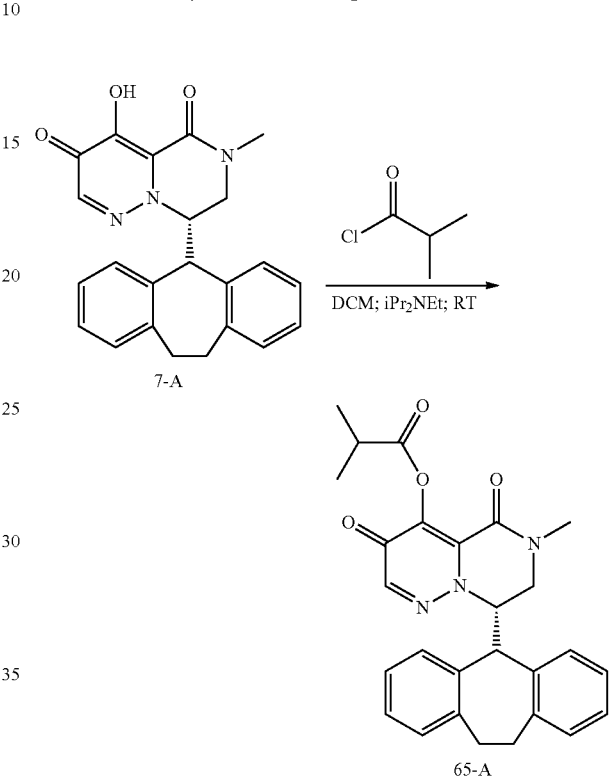

Compound A-10 was prepared as described herein in Example 7 by substituting compound H with compound L, and substituting HATU in DCM with HBTU in DMF.

To a −78° C. solution of oxalyl chloride (0.37 mL, 4.26 mmol) in dry DCM (12 mL) was added, dropwise, a solution of DMSO (0.31 mL, 4.26 mmol) in DCM (2 mL). The mixture was stirred for 5 min. A solution of A-10 (1.78 g, 2.66 mmol) in DCM (10 mL) was added, dropwise, over ~5 min, followed by a DCM rinse (2 mL) at −78° C. The mixture was stirred at −78° C. for 7 min, and then a solution of Et$_3$N (1.11 mL, 8 mmol) in DCM (3 mL) was added, dropwise. The orange solution was stirred at −78° C. for 5 min, and then allowed to warm to RT. The mixture was stirred at RT for 30 min. Water (50 mL) and DCM (50 mL) was added, and the layers were separated. The aqueous portion was extracted with DCM (25 mL) and the combined DCM portion was washed with brine, dried over sodium sulfate, and concentrated. Silica gel chromatography (1-5% MeOH in DCM) yielded A-11 (1.63 g, 92%) as a pale yellow oil.

A solution of A-11 (130 mg, 0.19 mmol) in DCM (1 mL) was treated with TFA (1 mL), and the solution was stirred at RT for 2.5 h. The reaction was monitored by LCMS and shows both SEM groups were cleaved. The solution was concentrated under reduced pressure to give A-12, which was used without further purification.

To a solution of A-12 in 1,4-dioxane (1 mL), was added sulfuric acid (37 gm, 0.38 mmol). The mixture was heated at 110° C. for 24 h. The reaction was cooled to RT, and water (2 mL) was added, dropwise, with stirring. The mixture was filtered and yielded compound 11 as a pale yellow solid (59 mg, 81%). MS: m/z=388 [M+H]$^+$.

To a solution of compound 11 (50 mg, 0.13 mmol) in MeOH (6 mL) and acetic acid (0.6 mL), was added PtO$_2$ (20 mg) in one portion. The mixture was stirred at RT under a H$_2$ atmosphere at 50 psi for 2 h. The mixture was filtered through a pad of celite, and the filtrate was concentrated purified by prep-RP-HPLC to give compound 6 as a white solid (13 mg, 26%). MS: m/z=390 [M+H]$^+$.

Example 11

Synthesis of Compound 65-A

To a solution of 7-A (125 mg, 0.32 mmol) in CH$_2$Cl$_2$ (2 mL) was added diisopropyl ethyl amine (0.078 ml, 0.45 mmol), followed by isobutryl chloride (0.042 mL, 0.4 mmol). The mixture was stirred 2 h at RT, diluted with CH$_2$Cl$_2$ (30 mL), and washed with dilute NaHCO$_3$ solution. The DCM layer was washed with brine, dried over sodium sulfate, and concentrated to give a pale, orange oil. A small volume of DCM (2.5 mL) was added, followed by the addition of hexane until just cloudy. A white solid crystallized after standing. Filtration gave compound 65-A as a white solid (85%). MS: m/z=458 [M+H]$^+$.

Compound 58-A was prepared following a similar procedure as in Example 11 and using 41-A and acetyl chloride. MS: m/z=463 [M+H]$^+$.

Compound 66-A was prepared following a similar procedure as in Example 11 and using 6-A and acetyl chloride. MS: m/z=432 [M+H]$^+$.

Compound 67-A was prepared following a similar procedure as in Example 11 and using 4-A. MS: m/z=480 [M+H]$^+$.

Compound 69-A was prepared following a similar procedure as in Example 11 and using 6-A. MS: m/z=460 [M+H]$^+$.

Compound 70-A was prepared following a similar procedure as in Example 11 and using 41-A. MS: m/z=496 [M+H]$^+$.

Compound 72-A was prepared following a similar procedure as in Example 11 and using 21-A. MS: m/z=482 [M+H]⁺.

Compound 114-A was prepared following a similar procedure as in Example 11 and using 51, followed by chiral SFC separation. MS: m/z=522 [M+H]⁺.

Example 12

Synthesis of Compound 96-A

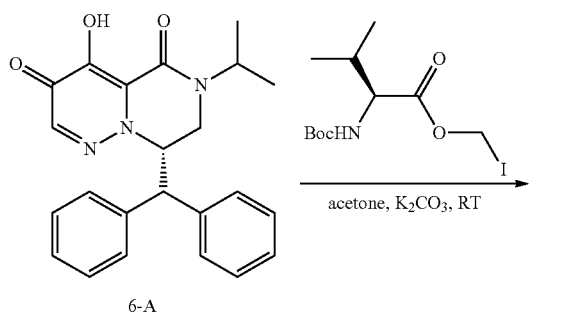

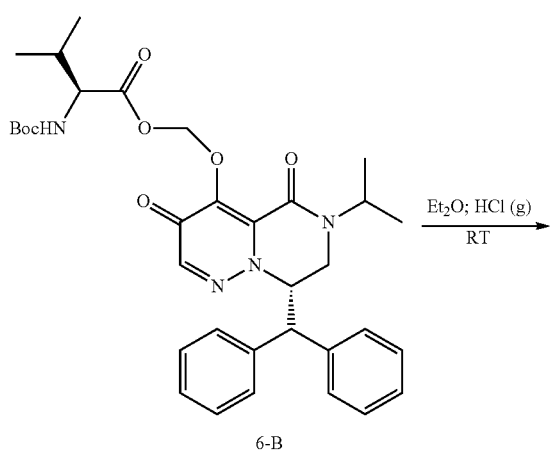

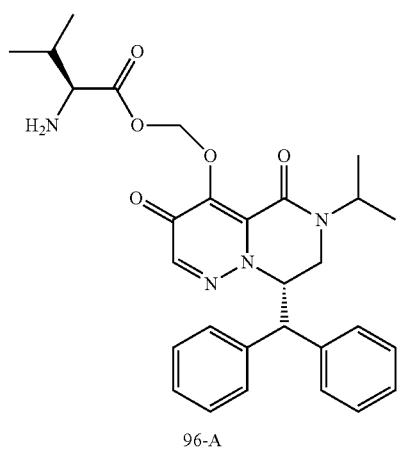

To a solution of N-Boc-valine (10 g, 46.08 mmol) in EtOH (70 mL) was added Cs$_2$CO$_3$ (14.97 g, 46.06 mmol) in a solution of H$_2$O (30 mL). The mixture was stirred at RT for 30 mins, co-evaporated with toluene to dryness, re-dissolved in DMF (100 mL) and cooled in an ice bath. Chloroiodomethane (81.1 g, 460.8 mmol) was added dropwise at 0° C. The mixture was stirred at RT in the dark (tin foil) for 12 h. The mixture was treated with H$_2$O (200 mL), extracted with EtOAc (3×100 mL). The combined organic layers were dried over Na$_2$SO$_4$, filtered and concentrated. The crude product was purified by column chromatography on silica gel eluted with PE:EA=100:1 to 60:1 to give (S)-chloromethyl 2-((tert-butoxycarbonyl)amino)-3-methylbutanoate (37%).

To a solution of (S)-chloromethyl 2-((tert-butoxycarbonyl)amino)-3-methylbutanoate (4.53 g, 17 mmol) in acetone (50 mL) was added NaI (7.67 g, 51 mmol). The mixture was heated to reflux for 12 h. The solution was diluted with H$_2$O (100 mL) and extracted with EtOAc (3×50 mL). The combined organic layers were dried over Na$_2$SO$_4$, filtered and concentrated. The crude product was purified by column chromatography on silica gel, eluted with PE:EA=100:1 to 50:1, to give (S)-iodomethyl 2-((tert-butoxycarbonyl)amino)-3-methylbutanoate (3 g, 49%) as a white solid. ¹H NMR (400 MHz, CDCl$_3$): δ ppm 6.06-6.05-7.30 (d, J=2.2, 1H), 5.86-5.85 (d, J=2.0, 1H), 4.97-4.95 (d, J=4.0, 1H), 4.25-4.22 (m, 1H), 2.20-2.18 (m, 1H), 1.46 (s, 9H), 1.01-1.00 (d, J=3.6, 3H), 0.94-0.93 (d, J=3.4, 3H).

To a solution of 6-A (300 mg, 0.77 mmol) in acetone (30 mL) was added K$_2$CO$_3$ (212.85 mg, 1.542 mmol) and (S)-iodomethyl 2-((tert-butoxycarbonyl)amino)-3-methylbutanoate (0.82 g, 2.31 mmol) at RT under N$_2$. The mixture was stirred at the same temperature for 12 h. The reaction was quenched with H$_2$O and extracted with EtOAc. The combined organic phases were dried over Na$_2$SO$_4$, filtered and concentrated. The crude product was purified by column chromatography on silica gel eluted with PE:EA=5:1 to 1:1 to give 6-B (55%) as a white solid. ⁺ESI-MS: m/z 619.3 [M+H]⁺.

To a solution of 6-B (260 mg, 0.42 mmol) in DCM (20 mL) at 0° C. was added to HCl/Et$_2$O (20 mL, 2N) dropwise. The mixture was stirred at 0° C. for 1 h and slowly warmed to RT. The mixture was stirred for 11 h. The solution was concentrated under reduced pressure. The crude product was washed with Et$_2$O (20 mL), and filtered to give compound 96-A (86%) as a beige solid. MS: m/z=519 [M+H]⁺.

Example 13

Synthesis of Compound 85-A

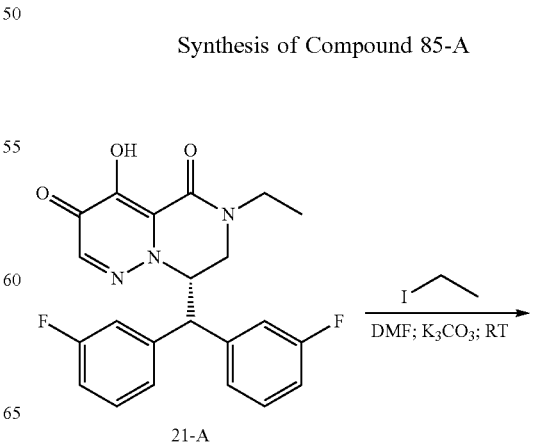

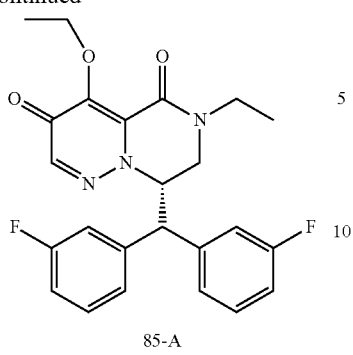

85-A

To a solution of 21-A (30 mg, 0.073 mol) in dry DMF (3 mL) was added K₂CO₃ (51 mg, 0.37 mol) and ethyl iodide (57 mg, 0.37 mol). The mixture was stirred at RT for 12 h. The mixture was diluted with water (10 mL) and dichloromethane (15 mL). The organic layer was separated, washed with water and brine, and dried of Na₂SO₄. Concentration of the mixture gave compound 85-A (29 mg) as a light brown solid. MS: m/z=440 [M+H]⁺.

Example 14

Synthesis of Amino Alcohol (AA4)

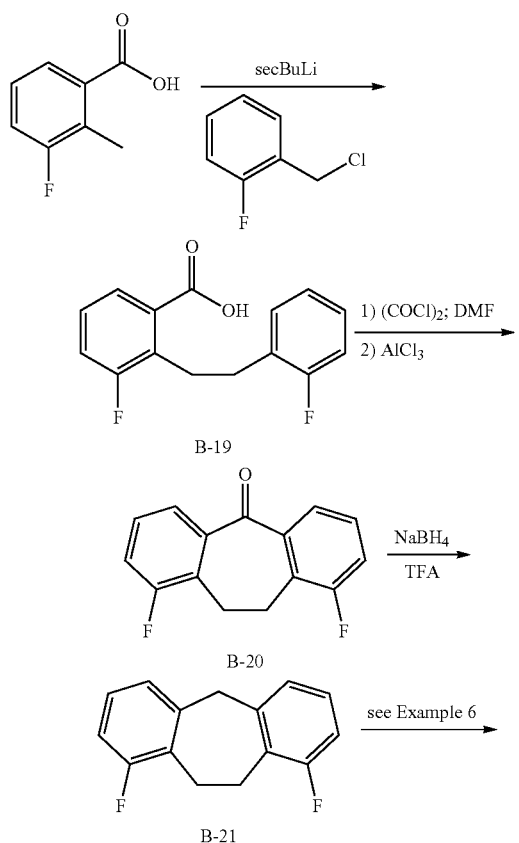

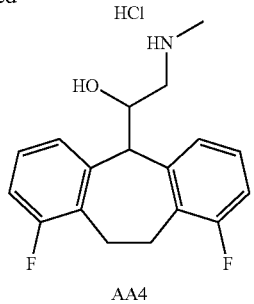

AA4

To a solution of 3-fluoro-2-methylbenzoic acid (1 g; 6.49 mmol) in dry THF (15 mL) at −60° C., s-BuLi in cyclohexane (2.5 eq.; 1.4M solution; 12 ml) was added. The deep red mixture was stirred for 1 h at −50/−60° C. To the mixture was added dropwise a cooled (−40° C.) solution of 2-fluorobenzyl chloride (1.13 g; 1.2 eq.) in THF (10 mL). The mixture was stirred at −40° C. After 30 mins, an UPLC check showed almost complete conversion to the desired compound: after 1 h. The reaction was quenched with 2M NaOH (7 mL) and concentrated in vacuo. The aqueous phase was washed with cyclohexane (2×). The organics were discarded, and the aqueous phase was acidified with 37% HCl. The mixture was extracted with ethyl acetate (2×). The organic phase was washed with brine, dried over Na₂SO₄, filtered and concentrated in vacuo to give B-19 (1.10 g), which was used in the next step without further purification.

Oxalyl chloride (1.1 eq.; 0.39 mL) and DMF (3 drops) were added at RT to a solution of B-19 (1.1 g; 4.19 mmol; 1 eq.) in DCM dry (35 mL). The mixture was stirred at RT. After 3 h, the mixture was diluted with DCM (30 mL) and AlCl₃ (1.5 eq.; 0.84 g) was added. After 12 h, an HPLC showed almost complete conversion to the desired compound. After 2 h, ice and water were added. The mixture was extracted with DCM (2×). The organic phase was washed with water, a 1N aqueous NaOH solution and water. The organic phase was dried over Na₂SO₄, filtered and concentrated in vacuo to give the crude (0.8 g). The crude was purified by flash chromatography (Biotage KP-Sil 100 g SNAP cartridge, gradient cyclohexane:EA from 100:0 to 95:5 in 10 CV, fraction size 42 mL) to give B-20 (0.52 g) as a yellow solid.

To a well-stirred solution of TFA (76 eq.; 12.46 mL) at 0° C., was added, dropwise, a solution of B-20 (0.52 g; 2.12 mmol) in DCM (8 mL). NaBH₄ was added portionwise (12 eq.; 962 mg; added in 4 portions). The ice-bath was removed, and the mixture was stirred overnight at RT. HPLC showed complete conversion to B-21. The mixture was poured into an ice-water, basified with solid NaOH, and extracted with DCM (2×). The organic phase was washed with water and dried over Na₂SO₄. The solvent was removed under vacuum. The crude material was purified by flash chromatography (Biotage KP-Sil 50 g SNAP cartridge, gradient cyclohexane:EA from 99:1 to 90:10 in 10 CV, fraction size 9 mL) gave B-21 as a white solid (0.40 g).

Following Example 6 (route 2), B-21 was converted to amino alcohol AA4.

1-(2,8-dichloro-10,11-dihydro-5H-dibenzo[a,d][7]annulen-5-yl)-2-(methylamino)ethanol hydrochloride was prepared following a similar procedure as in Example 14 and using 4-chloro-2-methylbenzoic acid and 3-chlorobenzylbromide.

1-(1,8-difluoro-10,11-dihydro-5H-dibenzo[a,d][7]annulen-5-yl)-2-(methylamino)ethanol hydrochloride was prepared following a similar procedure as in Example 14 and using 4-fluoro-2-methylbenzoic acid and 2-fluorobenzylbromide.

1-(1,8-difluoro-10,11-dihydro-5H-dibenzo[a,d][7]annulen-5-yl)-2-(methylamino)ethanol hydrochloride was prepared following a similar procedure as in Example 14 and using 4-fluoro-2-methylbenzoic acid and 2-fluorobenzyl bromide.

Example 15

Synthesis of Amino Alcohol (AA9)

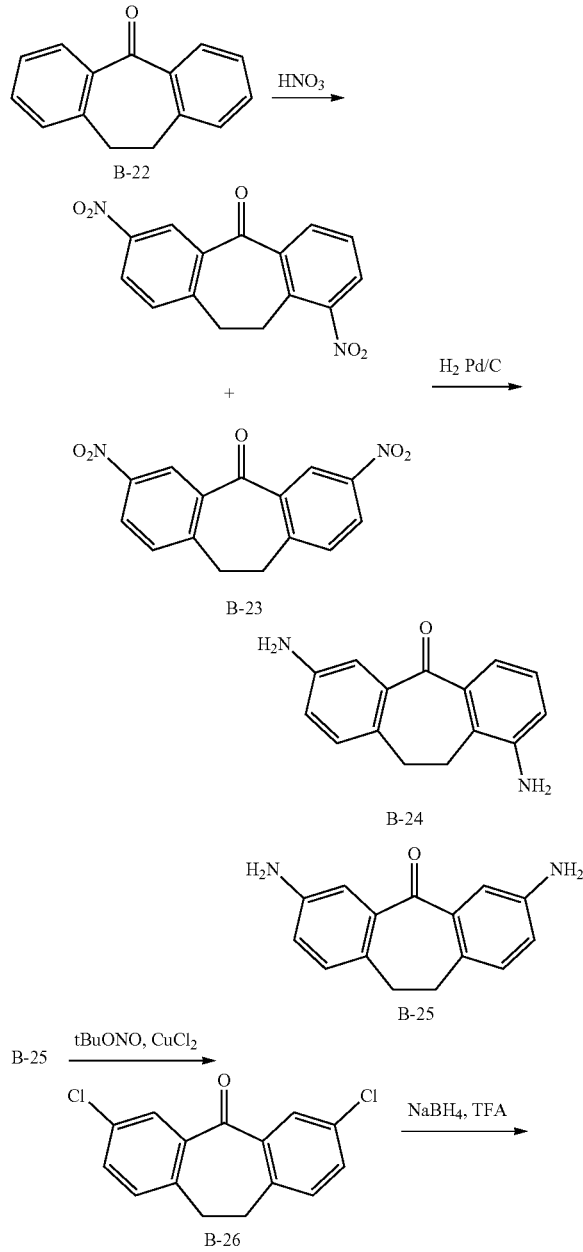

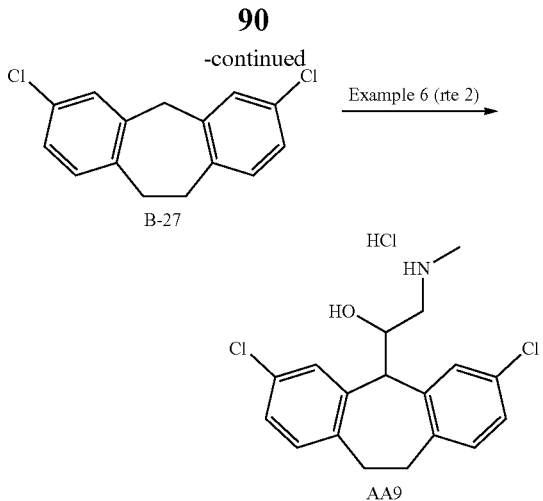

Nitric acid (110 mL) was added dropwise at 0° C. to B-22 (10 g) over 2 h. The mixture was stirred at 0° C. for 2 h and then slowly poured into chilled water (700 mL). The precipitate obtained was filtered to give a pale yellow solid (15.6 g). The solid was stirred in boiling in EtOH (2×40 mL) and filtered to give B-23 (12 g) as a pale yellow solid containing a mixture of 1,7- and 3,7-dinitro products that was used in the next step without further purification.

Pd/C 10% (2.5 g) was added to a suspension of B-23 (12 g) in EtOH (500 mL). The mixture was stirred under hydrogen (1 atm) at RT. After 3.5 h, the mixture was filtered and concentrated in vacuo. The residue was purified by silica gel flash chromatography (gradient $CH_2Cl_2$:MeOH from 100:0 to 90:10) to give B-24 (600 mg, as the first eluting spot) and B-25 (4.76 g, as second eluting spot). B-24—$^1$H NMR (400 MHz, $CDCl_3$) δ ppm 2.84-2.99 (m, 2H) 3.06-3.16 (m, 2H) 6.76 (dd, J=8.03, 2.51 Hz, 1H) 6.87 (dd, J=7.91, 1.13 Hz, 1H) 6.96-7.06 (m, 2H) 7.15 (t, J=7.78 Hz, 1H) 7.36-7.47 (m, 1H). B-25—$^1$H NMR (400 MHz, $CDCl_3$) δ ppm 3.08 (s, 4H) 6.80 (dd, J=8.16, 2.64 Hz, 2H) 7.04 (d, J=8.28 Hz, 2H) 7.27-7.38 (m, 2H).

Compound B-25 (830 mg) was added to a suspension of $CuCl_2$ (1.87 g) and tert-butyl nitrite (1.25 mL) in dry $CH_3CN$ (21 mL) at 0° C. The mixture was allowed to warm up at RT for 2.5 h, and then heated at 50° C. After 21 h, $CuCl_2$ and tert-butyl nitrite (same quantities as above) were added, and the mixture was heated again. After 25 h, a third addition of the same quantities of $CuCl_2$ and tert-butyl nitrite was made. After 28 h, the mixture was diluted with $CH_2Cl_2$ and filtered on a celite pad. The organic phase was washed with water, 2N aqueous HCl solution, sat. aqueous $NaHCO_3$ and brine. The organic layer was dried over $Na_2SO_4$, filtered and concentrated in vacuo. The crude material was purified by silica gel flash chromatography (cyclohexane:EA from 98:2 to 80:20) to give B-26 (966 mg) as a pale yellow solid.

To stirred, 0° C. TFA (11 mL) solution was added, dropwise, a solution of B-26 (517 mg) in dry $CH_2Cl_2$ (6.5 mL), followed by the portionwise addition of $NaBH_4$ (849 mg). The ice-bath was removed, and the mixture was stirred overnight at RT. The mixture was poured into ice, basified with 2N aqueous NaOH (100 mL) and extracted with diethyl ether (3×). The organic phase was washed with water and dried over $Na_2SO_4$. The solvent was removed under vacuum. The crude material (447 mg) was purified by silica gel flash chromatography (gradient cyclohexane:EA from 98:2 to 90:10) to give B-27 (366 mg) as a white solid.

Following Example 6 (route 2), B-27 was converted to amino alcohol AA9.

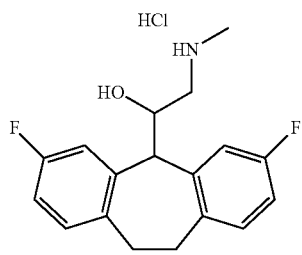

AA10

Amino alcohol AA10 was prepared following a similar procedure as in Example 15 and using HBF$_4$/NaNO$_2$.

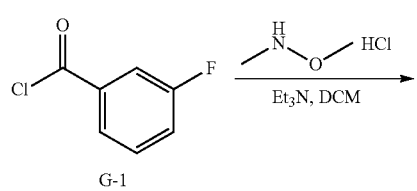

AA11

Amino alcohol AA11 was prepared following a similar procedure as in Example 15 and using HBF$_4$/NaNO$_2$.

Example 16

Synthesis of Amino Alcohol (AAg1)

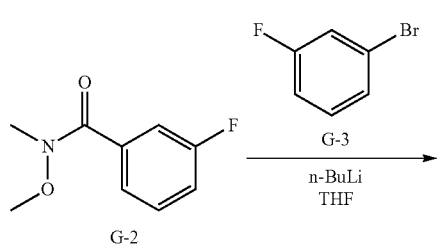

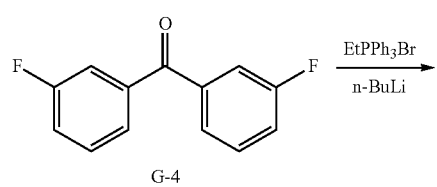

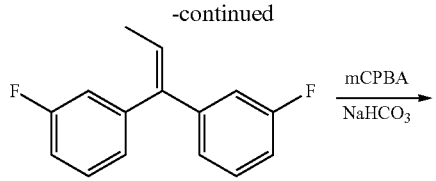

G-5

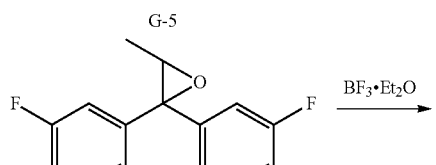

G-6

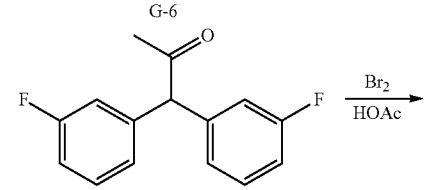

G-7

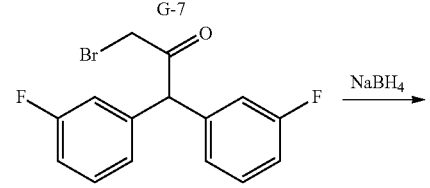

G-8

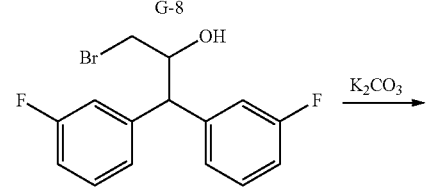

G-9

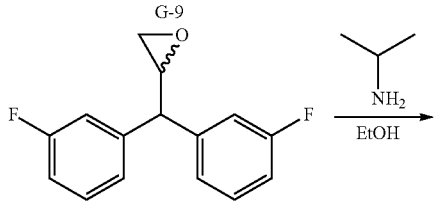

G-10

AAg1

To a solution of N, O-dimethylhydroxylamine hydrochloride (138 g, 1.42 mol) in DCM (1.5 L) was added Et$_3$N (383 g, 3.78 mol) at RT. To the stirred mixture, G-1 (150 g, 946 mmol) was added dropwise at 0° C. under N$_2$ atmosphere. The solution was stirred at the same temperature for 1 h, and then slowly warmed to RT for 10 h. The mixture was added to water (~1 L) and extracted with EtOAc (2×500 mL). The combined organic phases were dried with $Na_2SO_4$, filtered and concentrated. The residue was purified by flash column chromatography (eluent: PE) to give G-2 as a white solid (150 g, yield: 86.5%). $^1$H NMR (400 MHz, $CDCl_3$): δ 7.49-7.43 (1H, m), 7.41-7.32 (2H, m), 7.18-7.10 (1H, m), 3.54 (3H, s), 3.34 (3H, s).

To a solution of G-3 (133 g, 764 mmol) in THF (1 L) at −78° C. under $N_2$ atmosphere, was added n-BuLi (305 mL, 764 mmol) dropwise over 1 h. The solution was treated with a solution of G-2 (100 g, 546 mmol) in THF. After addition, the mixture was slowly warmed to RT and stirred for 16 h. The solution was quenched with water (1 L) and extracted with EtOAc (3×400 mL). The combined organic layers were dried over with $Na_2SO_4$, filtered and concentrated. The residue was purified by silica gel column chromatography (PE:EtOAc=50:1) to provide G-4 as a white solid (104 g, yield: 87.3%).

To a solution of $EtPPh_3Br$ (442 g, 1.19 mol) in THF (1.0 L) at 0° C. under $N_2$, was added n-BuLi (476 mL, 1.19 mol) dropwise over 1 h. The mixture was slowly warmed and a solution of G-4 (104 g, 476 mmol) in THF was added dropwise over 1 h. The reaction was quenched with water (1.0 L) and extracted with EtOAc (3×400 mL). The combined organic layers were dried over with $Na_2SO_4$, filtered and concentrated. The residue was purified by silica gel column chromatography (PE:EtOAc=100:1) to afford G-5 as a colorless oil (90 g, yield: 82%).

To a solution of G-5 (30 g, 130 mmol) in DCM (2.0 L) was added $NaHCO_3$ (23 g, 273 mmol). The stirred mixture was cooled to 0° C. and treated with m-CPBA (56.2 g, 325 mmol) portionwise. After addition, the mixture was stirred at the same temperature for 3 h. The reaction was quenched with sat. aq. $Na_2S_2O_4$ and extracted with DCM (3×500 mL). The combined organic layers were dried over with $Na_2SO_4$, filtered and concentrated. The residue was purified by silica gel column chromatography (PE:EtOAc=100:1) to provide G-6 as a yellow oil (13 g, 40.5%). $^1$H NMR ($CDCl_3$): δ 7.26-7.24 (m, 1H), 7.17-7.15 (m, 1H), 7.08-6.99 (m, 6H), 3.48-3.43 (m, 1H), 1.25-1.17 (m, 3H).

To a solution of G-6 (20 g, 81.2 mmol) in THF (300 mL) was added $BF_3/Et_2O$ (100 mL) at RT. The mixture was stirred at the same temperature for 2 h. After complete conversion, the reaction was quenched with sat. aq. $NaHCO_3$ and extracted with EtOAc (3×100 mL). The combined organic layers were dried over with $Na_2SO_4$, filtered and concentrated. The residue was purified by silica gel column chromatography (PE:EtOAc=10:1) to afford G-7 as a yellow oil (15 g, yield: 75%). $^1$H NMR (CDCl3): δ 7.35-7.29 (m, 2H), 7.02-7.96 (m, 6H), 5.10 (s, 1H), 2.27 (s, 3H).

To a solution of G-7 (15 g, 60.9 mmol) in AcOH (120 mL) at 60° C., was added $Br_2$ (9.73 g, 60.9 mmol) dropwise under $N_2$ atmosphere. The mixture was stirred at 60° C. for 2 h (indicated by TLC, PE: EtOAc=20:1). The mixture was slowly poured into ice-water (200 mL). The mixture was extracted with EA (3×50 mL). The combined organic layers were washed with $NaHCO_3$, brine, dried over with $Na_2SO_4$ and filtered. The solvent was removed under reduced pressure to give crude G-8 (25 g), which was used in the next step without further purification.

To a solution of crude G-8 (50 g) in THF (300 mL) at 0° C. under $N_2$ atmosphere, was added $NaBH_4$ (20 g, 529 mmol) portionwise. The mixture was stirred at RT for 3 h. The reaction was quenched with $H_2O$ (500 mL). The solution was extracted with EtOAc (3×300 mL). The combined organic layers were washed with brine, dried with $NaSO_4$, filtered and concentrated. The residue was purified by flash column chromatography to give G-9 as a colorless oil (36 g, yield: 71.6%). $^1$H NMR (CDCl3): δ 7.36-7.29 (m, 2H), 7.19-7.11 (m, 3H), 7.07-6.95 (m, 3H), 4.53-4.48 (m, 1H), 4.19-4.17 (m, 1H), 3.57-3.54 (m, 1H), 3.37-3.33 (m, 1H).

To a solution of G-9 (36 g, 110.72 mmol) in MeOH (200 mL) was added $K_2CO_3$ (39.54 g, 286.1 mmol) at RT. The mixture was stirred at the same temperature for 1 h (indicated by TLC, PE:EtOAc=10:1). The mixture was filtered, and the filtrate cake was washed with DCM. The combined filtrates were concentrated in vacuum. The residue was purified by flash column chromatography (PE:EtOAc=100:1) to give G-10 as a colorless oil (19 g, yield: 70.1%). $^1$H NMR ($CDCl_3$): δ 7.29-7.27 (m, 2H), 7.06-6.92 (m, 6H), 3.84-3.82 (d, J=6.8, 1H), 3.78-3.88 (m, 1H), 2.88-2.85 (t, J=4.4, 1H), 2.51-2.49 (m, 1H).

Compound G-10 (9.5 g, 38 mmol) was added into a solution of isopropylamine:EtOH (100 mL, v:v, 9:1). The mixture was stirred at RT overnight (indicated by TLC, PE:EtOAc=10:1). The mixture was concentrated under reduced pressure to afford amino alcohol AAg1 as an oil (10 g, yield: 86%).

1,1-bis(3-fluorophenyl)-3-(propylamino)propan-2-ol was prepared following a similar procedure as in Example 16 and using n-propylamine.

1,1-bis(3-fluorophenyl)-3-(butylylamino)propan-2-ol was prepared following a similar procedure as in Example 16 and using n-butylamine.

3-((2-(benzyloxy)ethyl)amino)-1,1-bis(3-fluorophenyl) propan-2-ol was prepared following a similar procedure as in Example 16 and using 2-(benzyloxy)ethanamine.

1,1-bis(3-fluorophenyl)-3-(isobutylamino)propan-2-ol was prepared following a similar procedure as in Example 16 and using 2-methylpropan-1-amine.

1-(3-chlorophenyl)-3-(isopropylamino)-1-phenylpropan-2-ol was prepared following a similar procedure as in Example 16 and using 3-chlorophenyl)(phenyl)methanone (prepared following step one of Example 5 using 3-chlorobenzoyl chloride and phenylboronic acid).

1-(3-chlorophenyl)-3-(methylamino)-1-phenylpropan-2-ol was prepared following a similar procedure as in Example 16 and using 3-chlorophenyl)(phenyl)methanone and methylamine.

1-(3-chlorophenyl)-3-(ethylamino)-1-phenylpropan-2-ol was prepared following a similar procedure as in Example 16 and using 3-chlorophenyl)(phenyl)methanone and ethylamine.

1-(3-methoxyphenyl)-3-(methylamino)-1-phenylpropan-2-ol was prepared following a similar procedure as in Example 16 and using 3-methoxyphenyl)(phenyl)methanone (prepared following step 1 of Example 5 using 3-methoxybenzoyl chloride and phenylboronic acid) and methylamine.

1-(3-methoxyphenyl)-3-(ethylamino)-1-phenylpropan-2-ol was prepared following a similar procedure as in Example 16 and using 3-methoxyphenyl)(phenyl)methanone and ethylamine.

1-(3-fluorophenyl)-3-(methylamino)-1-phenylpropan-2-ol was prepared following a similar procedure as in Example 16 and using (3-fluorophenyl)(phenyl)methanone (prepared following step 1 of Example 5 using 3-fluorobenzoyl chloride and phenylboronic acid) and methylamine.

3-(ethylamino)-1-(3-fluorophenyl)-1-phenylpropan-2-ol was prepared following a similar procedure as in Example 16 and using (3-fluorophenyl)(phenyl)methanone and ethylamine.

3-(methylamino)-1,1-di-m-tolylpropan-2-ol was prepared following a similar procedure as in Example 16 and using bis(3-methylphenyl)methanone (prepared following step one of Example 5 using 3-methylbenzoyl chloride and 3-methylphenylboronic acid) and methylamine.

3-(isopropylamino)-1,1-di-m-tolylpropan-2-ol was prepared following a similar procedure as in Example 16 and using bis(3-methylphenyl)methanone and isopropylamine.

1-(3-isopropoxyphenyl)-3-(methylamino)-1-phenylpropan-2-ol was prepared following a similar procedure as in Example 16 and using 3-isopropoxybenzoic acid and HATU to prepare the corresponding N,O-dimethyl amide.

1-(3-(cyclopropylmethoxy)phenyl)-3-(methylamino)-1-phenylpropan-2-ol was prepared following a similar procedure as in Example 16 and using 3-(cyclopropylmethoxy)benzoic acid and using HATU to prepare the corresponding N,O-dimethyl amide.

1,1-bis(3-chlorophenyl)-3-(isopropylamino)propan-2-ol was prepared following a similar procedure as in Example 16 and using 3-chlorobenzoyl chloride and 3-bromochlorobenzene.

1,1-bis(3-chlorophenyl)-3-(ethylamino)propan-2-ol was prepared following a similar procedure as in Example 16 and using 3-chlorobenzoyl chloride and ethylamine.

1,1-bis(3-chlorophenyl)-3-(propylamino)propan-2-ol was prepared following a similar procedure as in Example 16 and using 3-chlorobenzoyl chloride and propylamine.

Example 17

Synthesis of Amino Alcohol (AAj1)

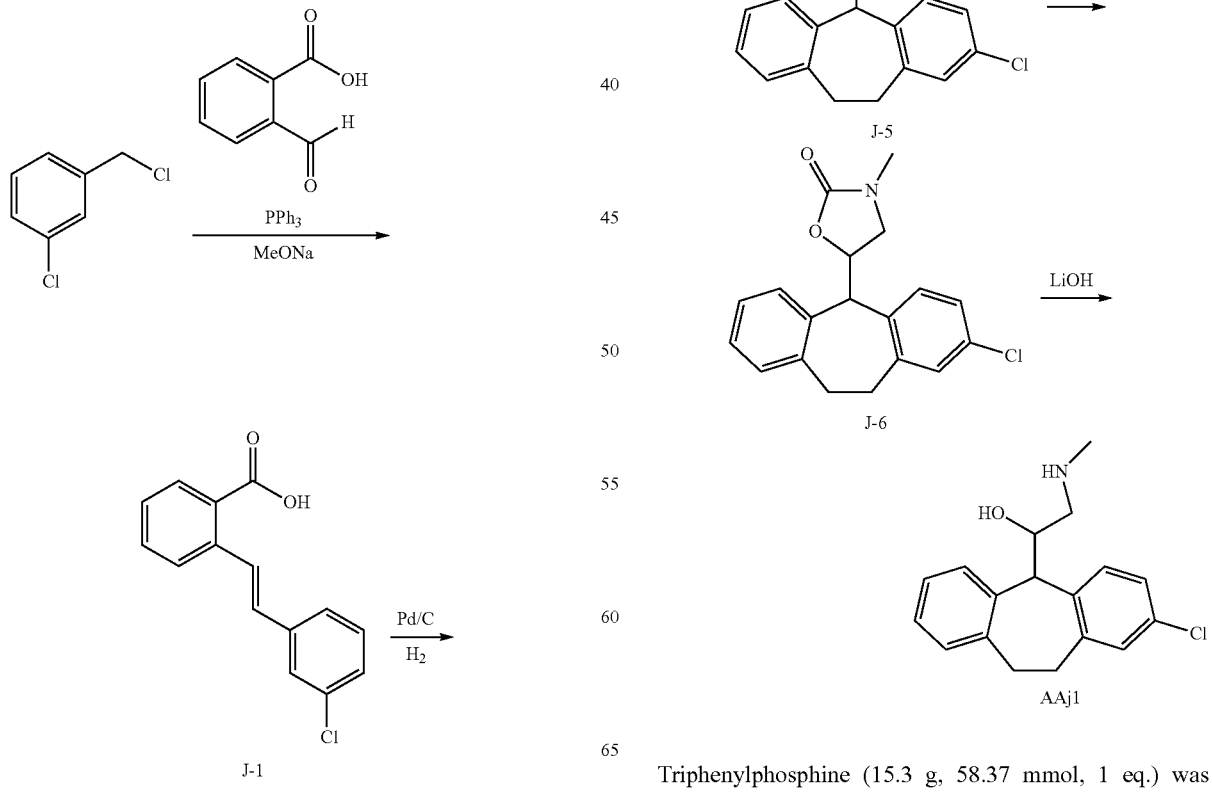

Triphenylphosphine (15.3 g, 58.37 mmol, 1 eq.) was diluted in MeOH (100 mL). 3-chlorobenzylchloride (9.4 g, 58.37 mmol, 1 eq.) diluted in MeOH (50 mL) was added dropwise to the stirred solution. The mixture was heated at reflux for 2 h. The mixture was cooled to 0° C. and 2-formylbenzoic acid (8.7 g, 58.37 mmol, 1 eq.) was added. Sodium methoxide (28% in MeOH; 28.0 g, 145 mmol, 2.5 eq.) was added dropwise at 0° C., over period of 45 mins. The mixture was stirred for 3 h at 0° C. The mixture was poured onto a stirred mixture of ice (75 g) and $H_2O$ (175 mL). The mixture was filtered, and the filtrate was washed several times with $H_2O$. The combined aqueous phases were washed several times with DCM. The aqueous phase was then acidified and extracted with DCM. The organic phase was concentrated in vacuo to give the crude product that was purified by silica-gel chromatography (340 g, 100% Cychex to 70/30 Cychex/EtOAc in 12 cv) to give J-1 (5.5 g) as a mixture of cis- and trans-isomers.

Compound J-1 (5.5 g, 21.26 mmol, 1 eq.) was dissolved in a mixture of EA (75 mL), $CH_3CN$ (75 mL) and Pd on activated carbon (1.5 g) was added. The mixture was stirred under $H_2$ atmosphere for 2 h at RT. The mixture was filtered, and the solvent was removed in vacuo to give J-2 (5.2 g).

Intermediate J-2 (5.2 g 19.95 mmol, 1 eq.) was dissolved in DCM (150 mL) containing a catalytic amount of DMF, and then oxalyl chloride (2.6 g, 19.95 mmol, 1 eq.) was added dropwise. The mixture was stirred at RT for 1 h under Ar atmosphere. The resulting acid chloride mixture was added to suspension of $AlCl_3$ (3.9 g 1.5 eq., 30 mmol) in DCM (50 mL). The mixture was stirred for 4 h at RT. The mixture was poured onto ice, extracted with DCM, washed NaOH and $H_2O$, and dried over $Na_2SO_4$. The solvent were removed in vacuo to give J-3 (4.7 g, see Martz, K. E., et. al., J. Med. Chem. (2012) 55(17):7862-7874). $^1$H NMR (400 MHz, $CDCl_3$) ppm 3.23 (s, 4H) 7.25-7.27 (m, 1H) 7.29 (s, 1H) 7.32-7.41 (m, 2H) 7.43-7.52 (m, 1H) 8.00-8.08 (m, 2H).

Following Example 5, steps 2-5, J-3 was converted to J-4.

A solution of J-4 (2.7 g, 9.38 mmol) in DCM (140 mL) was treated with DIPEA (28.08 mmol 4.88 mL) and triphosgene (1.11 g, 3.74 mmol). The mixture was stirred at RT for 1 h. The reaction was quenched with sat. $NH_4Cl$ solution and extracted with EtOAc (2×50 mL). The organic phases were dried over $Na_2SO_4$ and purified by silica gel column chromatography (Cychex:EtOAc: 80:20 to 50:50) to give J-5 (1.7 g).

NaH (28.5 mg, 1.19 mmol) was added at 0° C. to a solution of J-5 (300 mg, 0.95 mmol) in dry THF (8.6 mL). The mixture was stirred at this temperature for 15 mins, and then for 30 mins at RT. MeI (65.2 µl) was added, and the mixture was stirred at RT. After 1 h, an additional amount of NaH (0.3 eq.) and MeI (0.3 eq.) was added. The mixture was stirred overnight at RT. A sat. aq. $NH_4Cl$ solution was added, and the mixture was extracted with DCM (2×). The organic phase was washed with brine, dried over $Na_2SO_4$, filtered and concentrated in vacuo to give J-6 (260 mg) as a colorless oil, which was used without further purification.

Compound J-6, (260 mg; 0.79 mmol) was dissolved in 1:1 dioxane:water (36 mL) and LiOH (13.8 mL, 1.56 M) was added. The mixture was heated at 60° C. for 12 h. The organic solvent was concentrated in vacuo, and the mixture was extracted with EA (3×). The combined organics were washed with brine, dried over $Na_2SO_4$, filtered and concentrated in vacuo gave amino alcohol AAj1 (130 mg) as a colorless oil, which was used without further purification.

1-(2,8-difluoro-10,11-dihydro-5H-dibenzo[a,d][7]annulen-5-yl)-2-(methylamino)ethanol was prepared following a similar procedure as in Example 17, steps 4-7, using 2,8-difluoro-10,11-dihydro-5H-dibenzo[a,d][7]annulen-5-one (prepared following steps one and two of Example 14 using 3-fluorobenzoyl chloride and 4-fluoro-2-methylbenzoic acid).

Example 18

Synthesis of Amino Alcohol (AAk1)

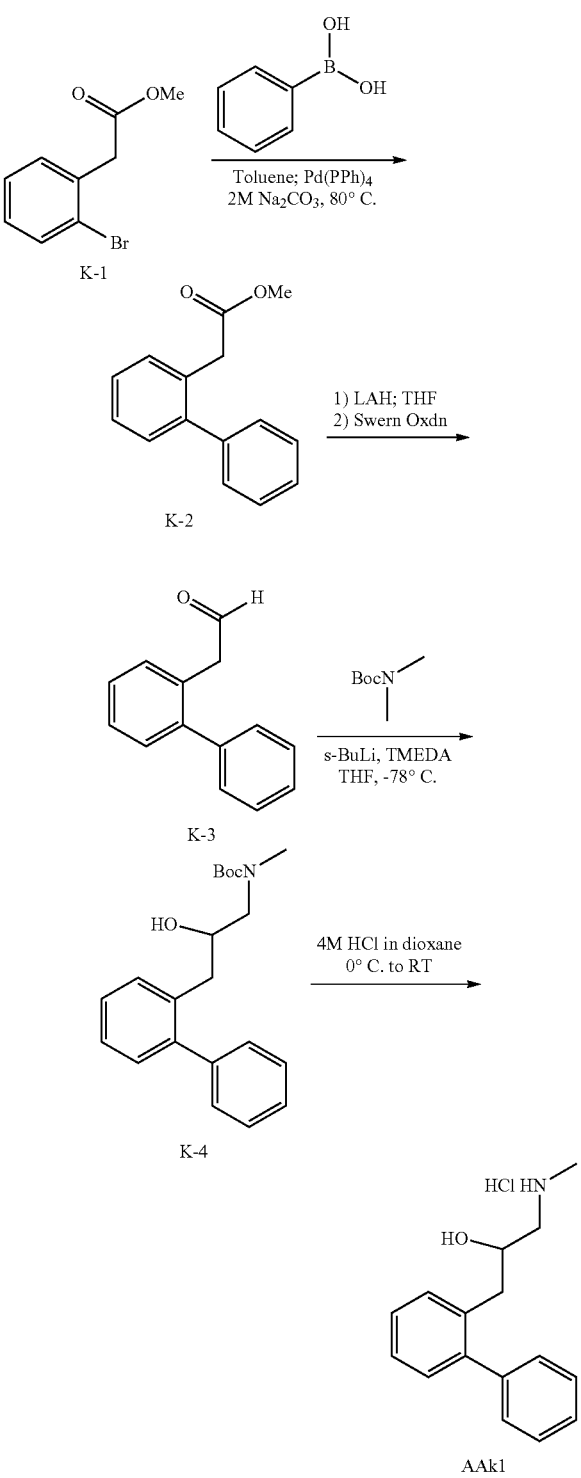

Aryl bromide K-1 (2 g, 8.73 mmol) and phenylboronic acid (1.6 g, 13.1 mmol) were taken up in toluene (120 mL). To this mixture was added a solution of 2M sodium carbonate (50 mL). The flask was evacuated and back filled with Ar (3 cycles). Tetrakis(triphenylphosphine)palladium (1.01 g, 0.873 mmol) was added. The flask was evacuated and back filled with argon (3 cycles). The flask was placed in an oil bath heated to 80° C. and stirred overnight. The flask was cooled to ambient. The mixture was diluted with EA and washed successively with water and a brine solution. The crude product was purified by flash chromatography (25 g silica column, elution gradient 2% to 5% EA:hexanes) to provide K-2 as a light yellow oil (1.82 g).

Methyl ester K-2 (1.82 g, 8.05 mmol) was taken up in dry tetrahydrofuran (20 mL) and cooled in an ice bath under an Ar balloon. To this mixture was added a 1 M solution of lithium aluminum hydride in THF (9.7 ml, 9.66 mmol) via a slow dropwise addition over 5 mins. The mixture was stirred for 1 h at 0° C. Water (0.16 mL) was added, and the mixture stirred for 10 mins. A solution of 5% NaOH (0.31 mL) was added, and the mixture stirred for 10 mins. Water (0.31 mL) was added, and the mixture stirred for 10 mins. The mixture was dried via addition of powdered magnesium sulfate. The mixture was filtered through a plug of celite, rinsing with CH$_2$Cl$_2$. The filtrate was transferred to a separatory funnel and shaken with water. The organic phase was collected, dried with magnesium sulfate and filtered. The solvent removed to provide the intermediate alcohol (1.519 g, semi-viscous white cloudy oil) which was used directly in the next step. An oven dried flask containing oxalyl chloride (0.55 mL, 9.80 mmol) in dry CH$_2$Cl$_2$ (12 mL) was cooled to −78° C. under Ar. To this mixture was added dimethylsulfoxide (1.13 mL, 15.83 mmol), via slow dropwise addition. The mixture was stirred for 30 mins at −78° C. A solution of intermediate alcohol (1.494 g, 7.54 mmol) in dry CH$_2$Cl$_2$ (3 mL) was added via slow dropwise addition. The mixture was stirred for 30 mins and then triethylamine (4.21 mL, 30.2 mmol) was added via dropwise addition. The flask was removed from the cooling bath, and stirred for 1.5 h. The mixture was taken up in CH$_2$Cl$_2$ and transferred to a separatory funnel. A solution of saturated sodium bicarbonate was added and the mixture was shaken. The organic phase was collected and washed with a 50% diluted brine solution. The organic phase was collected, dried with magnesium sulfate, filtered and stripped. The crude remainder was purified by flash chromatography (25 g silica gel column, elution gradient 2% to 8% EA:hexanes) to provide K-3 as a pale yellow oil (179 mg).

A oven dried flask was charged with N,N-dimethyl-tert-butoxycarbamate (64 mg, 0.44 mmol; see Snieckus, V., et. al., *Tet. Lett.* (1994) 35(24):4067-4070) and tetramethylethylenediamine (0.1 mL, 0.66 mmol) and taken up in dry THF (1.8 mL) under an Ar balloon. The mixture was cooled to −78° C. (acetone:dry ice bath). A solution of s-BuLi (0.39 mL, 0.46 mmol, 1.2M in cyclohexane) was added via dropwise addition over approx. 2 mins. The mixture was stirred at −78° C. for 75 mins. A solution of K-3 (173 mg, 0.88 mmol) in dry THF (1.5 mL) was added via slow, dropwise addition over 10 mins. The mixture was stirred for 2 h at −78° C. and then stirred in an ice bath for 15 mins. To the mixture was added a solution of sat. aq. ammonium chloride (10 mL), water (15 mL) and EA (25 mL). The biphasic solution was shaken in a separatory funnel, and the organic phase was collected. The aqueous phase was back extracted with EtOAc (2×20 mL). The combined organic phase was dried with magnesium sulfate, filtered. The solvent was removed, and the crude remainder was purified by preparative thin layer chromatography (2 plates) eluting with 25% EtOAc:hexane. The product band was collected, providing K-4 as a viscous yellow oil (86 mg). LCMS (ESI) m/z=342 [M+H]$^+$.

Compound K-4 (86 mg, 0.252 mmol) was taken up in dry dioxane (0.3 mL). The flask was cooled in an ice bath, and a solution of 4M hydrogen chloride in dioxane (0.63 mL) was added. The mixture was stirred for 5 mins, and the cooling bath was removed. The mixture was stirred at RT for 2 h. The mixture was concentrated, and the crude product was taken up in DCM (10 mL). The solvent was removed, and the remainder taken up in DCM (10 mL). The solvent was removed (2×) to give amino alcohol AAk1 as a gummy solid that was used directly in the next step without further purification.

Example 19

Synthesis of Amino Alcohol (AAm1)

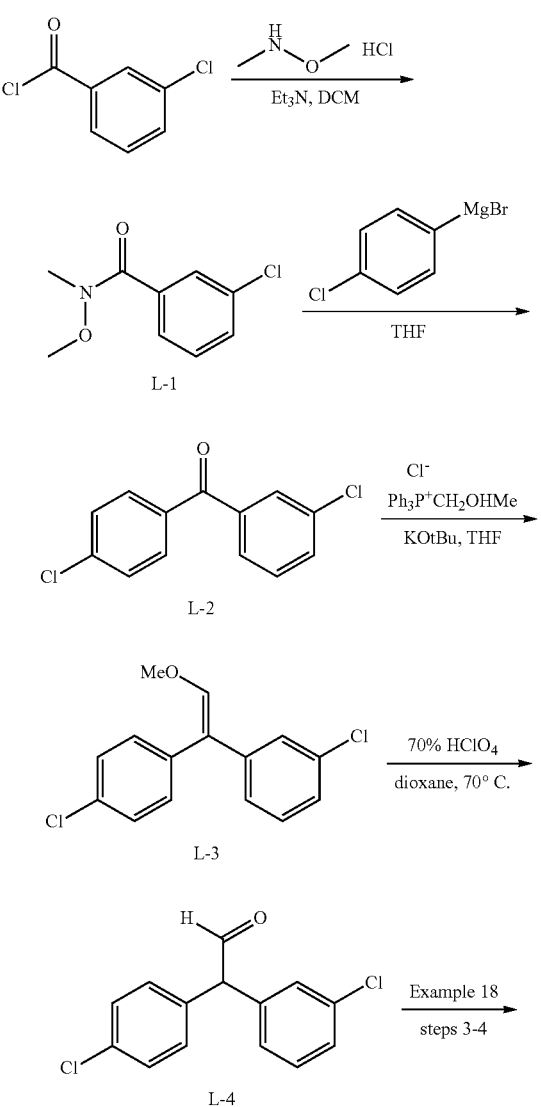

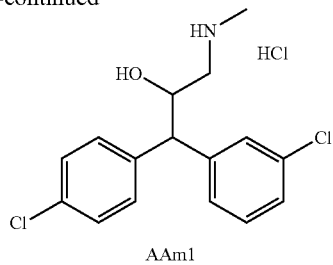

AAm1

To a cooled (ice bath) solution of N-methyl-O-methylhydroxylamine hydrochloride (6.131 g, 62.85 mmol) and triethylamine (20 mL, 142.85 mmol) in dry DCM (under Ar atmosphere) was added 3-chlorobenzoyl chloride (7.32 mL, 57.14 mmol) via slow dropwise addition. The mixture was stirred for 10 mins and then warmed to ambient temperature. After 2.5 h of stirring, the solvent was partially removed (condense about 80%—rotary evaporator). The remainder was taken up in EA, washed successively with 1N HCl (twice) and 2M aqueous sodium carbonate, and then diluted a brine solution. The aqueous phases were back-extracted. The organic phases were combined, dried with magnesium sulfate, filtered and concentrated to give L-1 (10.6 g), which was used directly in the next step without further purification.

Compound L-1 (2.04 g, 10.21 mmol) was taken up in dry THF (35 mL), and the flask was cooled to 0° C. (ice bath) under Ar. To this mixture was added a THF solution of 1.0 M 4-chlorophenylmagnesium bromide (20.42 mL, 20.42 mmol) via slow dropwise addition over 5 mins. The flask was warmed to ambient temperature, and the mixture was stirred for 3.5 h. The reaction was quenched with a solution of 5% aq. ammonium chloride (30 mL), water (30 mL) and EA (40 mL). The biphasic material was shaken, and the organic phase was collected. The mixture was washed with a diluted brine solution (60 mL), and the organic phase was collected. The aqueous phases were back-extracted with EA (2×40 mL). The organic phases were combined, dried with magnesium sulfate, filtered and concentrated to give L-2 (3.084 g) which was used directly in the next step without further purification.

To a suspension of potassium tert-butoxide (2.24 g, 20 mmol) in dry THF was added (methoxymethyl)triphenylphosphonium chloride (6.86 g, 20 mmol). The mixture was stirred at ambient temperature under Ar for 30 mins. To this mixture was added a solution of L-2 (3.08 g, 10 mmol) in THF (15 mL). The flask was heated at 70° C. for 2.5 h. The mixture was cooled to ambient temperature and about ⅔ of the solvent was removed with a rotary evaporator. The remainder was taken up in EA and washed successively with water (2×) and then a brine solution. The crude remainder was purified by flash chromatography (25 g silica column, elution gradient 1% to 2% EA:hexanes to provide L-3 as a clear oil (2.50 g, cis/trans mixture).

Compound L-3 (2.49 g, 8.92 mmol) was taken up in dioxane (75 mL). The solution was placed under mild vacuum and back-filled with Ar (4 cycles). To this mixture was added a solution of 70% HClO₄ (19 mL, 223 mmol), and the flask was heated at 70° C. via an oil bath for 90 mins. The mixture was cooled to ambient temperature and partitioned between water (300 mL) and EtOAc (150 mL). The organic phase was collected and washed consecutively with 50% diluted brine (2×200 mL). The organic phase was collected, and the aqueous phases were back extracted with EtOAc (2×100 mL). The EA phases were combined, dried with magnesium sulfate, filtered and concentrated. The crude product was purified by flash chromatography (25 g silica gel column, elution gradient 1% to 6% EA:hexanes) to provide L-4 as a pale yellow oil (1.04 g).

Compound L-4 was converted to AAm1 (320 mg) following Example 18, steps 3 and 4.

1-(4-chlorophenyl)-3-(methylamino)-1-phenylpropan-2-ol hydrochloride was prepared following a similar procedure as in Example 19 and using (4-chlorophenyl)(phenyl)methanone.

1-(4-fluorophenyl)-3-(methylamino)-1-phenylpropan-2-ol hydrochloride was prepared following a similar procedure as in Example 19 and using (4-fluorophenyl)(phenyl)methanone.

1-(3-chlorophenyl)-1-(4-fluorophenyl)-3-(methylamino)propan-2-ol hydrochloride was prepared following a similar procedure as in Example 19 and using 4-fluorophenylmagnesium bromide.

1-(3-chlorophenyl)-1-(2-fluorophenyl)-3-(methylamino)propan-2-ol hydrochloride was prepared following a similar procedure as in Example 19 and using 2-lithio fluorobenzene (prepared via lithiation of 2-bromofluorobenzene using n-BuLi at −78° C.).

Example 20

Synthesis of Amino Alcohol (AAf1)

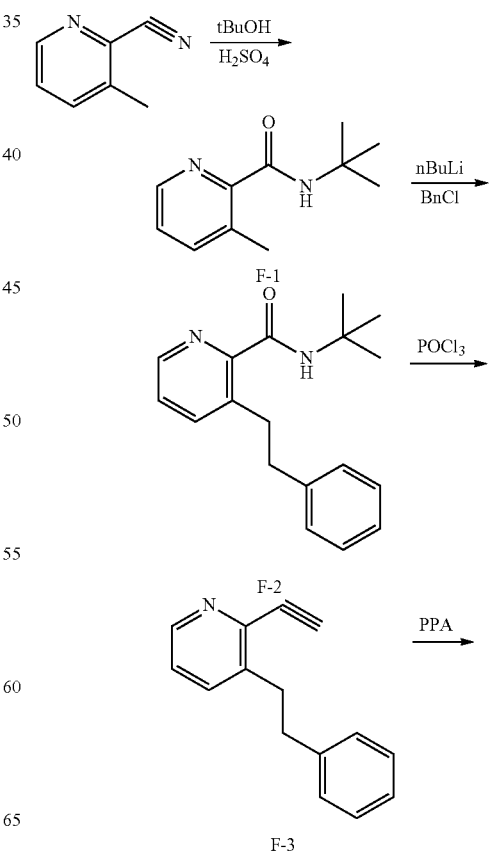

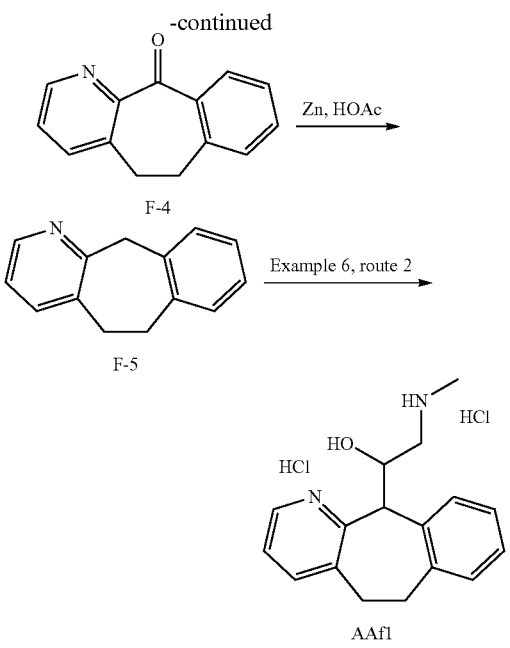

A suspension of 2-cyano-3-methylpyridine (1.9 g, 16.06 mmol) in tert-butyl alcohol (5 mL) was heated at 70° C. Concentrated sulfuric acid (1.9 mL) was added over 10 mins. The reaction was complete after 4 h at 75° C. The mixture was diluted with water and toluene, and brought to pH=10 with concentrated aqueous ammonia. The temperature was kept at 50-55° C. during workup. The toluene phase was separated, and the aqueous layer was extracted with water. Removal of the toluene yielded F-1 (3.3 gr) as a crystalline solid.

To a cold (−40° C.) solution of F-1 (3.3 g, 17.16 mmol) in dry THF (64 mL) was added n-butyllithium in hexanes 1.6M (2 eq., 22 mL) while the temperature was maintained at −40° C. The solution turned deep red after 1 eq. was added. Sodium bromide (0.1 eq., 176 mg) was added, and the mixture was stirred 10 mins. A solution of benzyl chloride (1 eq., 2 mL) in dry THF (12 mL) was added while the temperature was lowered to −40° C. The mixture was stirred for 30 mins. Water was added until the color dissipated. The mixture was extracted with EA, washed with water, dried on $Na_2SO_4$ and concentrated in vacuo to give F-2 (4.7 gr) as an oil.

Compound F-2 (4.7 g, 16.67 mmol) was dissolved in toluene (40 mL) and $POCl_3$ was added (10 eq., 15 mL). The mixture was refluxed for 5 h and then stirred at RT overnight. The mixture was poured into ice water (150 mL) and stirred for 0.5 h. The mixture was alkalized to pH=8 with 20% NaOH. The toluene phase was separated, and the aqueous layer was extracted with EA (3×). The organic layers were concentrated in vacuo to give F-3 (3.76 g, 18.08 mmol) as a brown oil.

Compound F-3, (2.5 g, 12 mmol) was added to polyphosphoric acid (50 g). The mixture was heated at 180° C. for 4 h. The mixture was poured into ice (50 g)-water (100 g). The mixture was made basic with 20% NaOH and extracted with EtOAc. The solvent was concentrated, and the crude product was purified by crystallization from hexane. F-4, (2 gr 9.56 mmol) as brown solid. $^1$H NMR (400 MHz, $CDCl_3$) ppm 3.20-3.26 (m, 2H) 3.27-3.32 (m, 2H) 7.27 (d, J=7.53 Hz, 1H) 7.38 (dd, J=7.28, 5.27 Hz, 2H) 7.46-7.54 (m, 1H) 7.65 (d, J=7.78 Hz, 1H) 8.09 (d, J=8.03 Hz, 1H) 8.66-8.76 (m, 1H).

To a mixture of F-4 (1 g, 1 eq., 4.78 mmol) and acetic anhydride in THF (6.8 mL) at −25° C. were sequentially added Zn dust (3.4 eq., 1.06 g, 16.27 mmol) and trifluoroacetic acid (2.2 eq., 1.19 g, 10.52 mmol) dropwise. The temperature of the mixture was slowly raised to RT and was stirred overnight. Additional Zn dust (3.4 eq.) and TFA (2.2 eq.) were added. The mixture was stirred at 70° C. for 40 mins. Toluene was added. The zinc and inorganic residue were filtered and washed with toluene. The filtrate was washed with water and 1M NaOH. The organic phase was concentrated under vacuum, and the residue was purified by silica-gel chromatography (100% Cychex to 50/50 Cychex/EtOAc in 12 CV) to give F-5 (820 mg). $^1$H NMR (400 MHz, $CDCl_3$) δ ppm 3.12-3.29 (m, 4H) 4.42 (s, 2H) 7.09 (dd, J=7.65, 4.89 Hz, 1H) 7.14-7.22 (m, 2H) 7.25-7.35 (m, 1H) 7.40 (d, J=7.28 Hz, 1H) 8.34 (dd, J=4.77, 1.51 Hz, 1H).

Following Example 6, route 2, F-5 was converted to amino alcohol AAf1.

Example 21

Synthesis of Compound 121

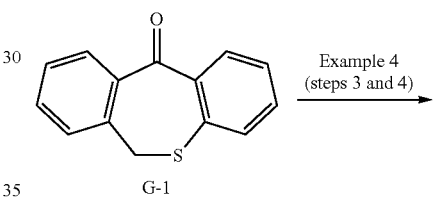

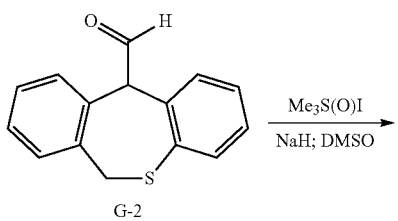

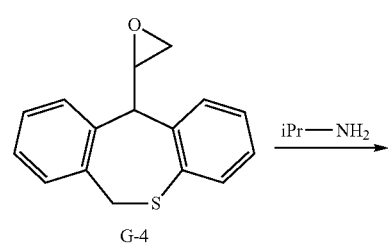

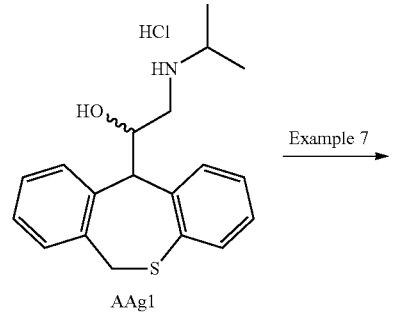

105

-continued

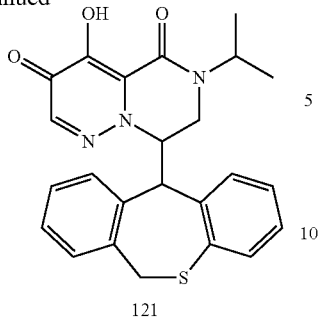

121

Trimethylsulfoxonium iodide (1.03 g, 4.68 mmol) was added to a mixture of NaH (95%; 112 mg, 4.6 mmol) in DMSO (8 mL) at RT. The mixture was stirred for 30 min, and then a solution of G-2 (0.75 g, 3.12 mmol) in DMSO (2 mL) was added. The solution was heated at 60° C. for 1.5 h and then diluted with water (75 mL) and hexane (50 mL). The aqueous layer was washed with hexane (2×30 mL), and the combined organic extract was washed with brine, dried over $Na_2SO_4$, and concentrated to give G-4 as a yellow oil (680 mg), that was used directly in the next step.

Crude G-4 was dissolved in reagent alcohol (5 mL) and transferred to a glass sealed tube reactor. Isopropyl amine (1.4 mL, 15.6 mmol) was added, and the mixture was heated at 60° C. for 12 h. Additional isopropyl amine (1 mL) was added, and the mixture was heated at 80° C. for 6 h and then concentrated. Ethyl acetate (5 mL) and 4M HCl in dioxane (xs) were added. Filtration gave AAg1 (228 mg, 21%) as a white solid.

Following a similar procedure as in Example 7, substituting trifluoroacetic anhydride for methanesulfonyl chloride and triethylamine in step 2 and substituting TFA at 75° C. for 10% Pd/C for step 3, AAg1 was converted to 121 (35 mg, 13%).

8-(1,9-difluoro-10,11-dihydro-5H-dibenzo[a,d][7]annulen-5-yl)-4-hydroxy-6-isopropyl-7,8-dihydro-3H-pyrazino[1,2-b]pyridazine-3,5(6H)-dione, was prepared following a similar procedure as in Example 21, step 4 and using 1-(1,9-difluoro-10,11-dihydro-5H-dibenzo[a,d][7]annulen-5-yl)-2-(isopropylamino)ethanol hydrochloride.

4-hydroxy-6-methyl-8-(phenyl(pyridin-2-yl)methyl)-7,8-dihydro-3H-pyrazino[1,2-b]pyridazine-3,5(6H)-dione, was prepared following a similar procedure as in Example 21, step 4 and using 3-(methylamino)-1-phenyl-1-(pyridin-2-yl)propan-2-ol dihydrochloride.

1-((4-hydroxy-6-isopropyl-3,5-dioxo-5,6,7,8-tetrahydro-3H-pyrazino [1,2-b]pyridazin-8-yl)(phenyl)methyl)-1H-pyrazole-3-carbonitrile was prepared following a similar procedure as in Example 21, step 4 and using 1-(2-hydroxy-3-(isopropylamino)-1-phenylpropyl)-1H-pyrazole-3-carbonitrile hydrochloride.

106

Example 22

Synthesis of Compound 129

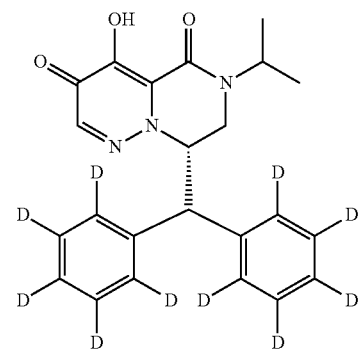

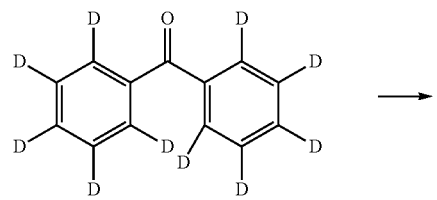

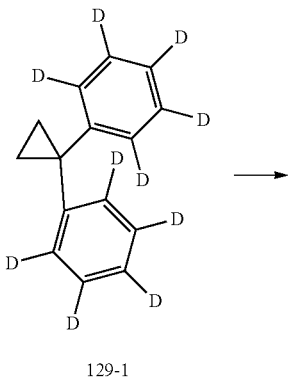

129-1

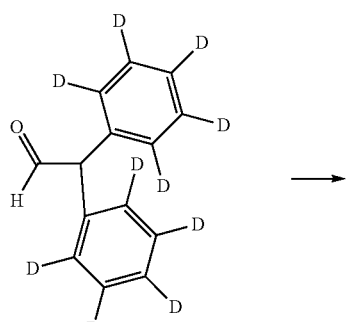

129-2

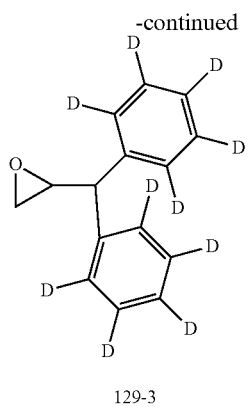

129-3

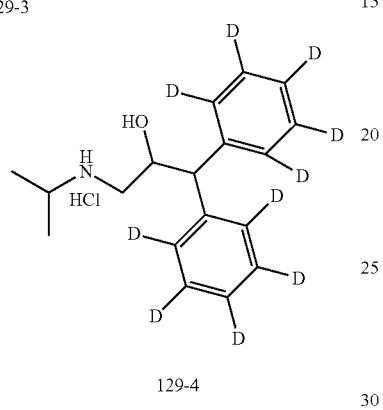

129-4

To a reactor flushed with Ar was loaded potassium t-butoxide (13.71 g, 1.30 eq.), trimethylsulfoxonium iodide (26.88 g, 1.30 eq.), and anhydrous DMSO (100 mL). The mixture was stirred for 0.5 h. Per-deuterated benzophenone (18 g) was added, and the mixture was heated to 50-60° C. for 45 mins. After cooling to RT, hexane (100 mL) was added. A solution of acetic acid (2.62 g) in water (100 mL) was used to wash the mixture. The aqueous phase was extracted with hexanes (100 mL). The combined organic phases were washed with aq. sat. sodium bicarbonate, dried with sodium sulfate and concentrated. After cooling, the colorless oil (17.25 g) solidified, which was used in the next step without further purification.

To a reactor flushed with Ar was added indium(III) chloride (2.16 g, 0.2 eq.). 129-1 (17.25 g) in anhydrous tetrahydrofuran (100 mL) was added. The mixture as stirred at 55° C. for 45 mins, cooled to RT and concentrated. The obtained concentrate was dissolved in hexane (100 mL), washed with water and brine, dried with sodium sulfate and concentrated to give 129-2 as a yellow oil (17.47 g), which was used in the next step without further purification.

To a reactor flushed with Ar was loaded trimethylsulfoxonium iodide (26.09 g, 1.40 eq.), potassium t-butoxide (13.30 g, 1.40 eq.), and anhydrous DMSO (100 mL). The mixture was stirred for 0.5 h. 129-2 (17.47 g) was added, and the mixture was rinsed with DMSO (25 mL). The mixture was heated to 50-60° C. for 45 mins, and then cooled to RT. The mixture was then diluted with hexane (100 mL). A solution of acetic acid (2.6 g) in water (100 mL) was used to wash the mixture. The organic phase was washed with water, dried with sodium sulfate and concentrated to obtain 129-3 as a yellow oil (15.0 g), which was used in the next step without further purification.

129-3 (14.3 g), isopropylamine (22 mL, 6 0.688; ~3.9 eq.), and reagent alcohol (22 mL) were combined. The mixture was heated in a 65-° C. oil bath for 10 mins, and then sealed and stirred overnight. The mixture was concentrated, and then dissolved in EA (150 mL). Hydrogen chloride (4 M) in dioxane (20 mL) was added and the precipitated white hydrochloride salt that formed was filtered, washed with EA and dried at 70° C. to give 129-4 (9.12 g).

Compound 129 was prepared following a similar procedure as in Example 21 (step 4) and using 129-4. m/z=400.2 [M+H]⁺.

Example 23

Synthesis of Compound 130

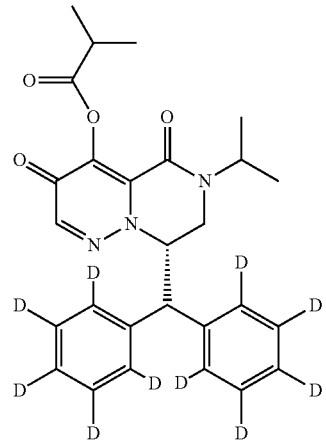

1-A

Compound 130 was prepared following a similar procedure as in Example 11 and using Compound 129. m/z=470.3 [M+H]⁺.

Example 24

Additional Compounds

The foregoing syntheses are exemplary and can be used as a starting point to prepare a large number of additional compounds, such as those in Table 1A. Examples of compounds of Formula (I) that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

The following compounds in Table 1A were prepared following one or methods described herein.

TABLE 1A

| Structure | # | General Procedure(s) | Mass |
|---|---|---|---|
| (structure) | 1 | Ex 3 & Ex 8 | M + H: 362 |
| (structure) | 1-A | Ex 3 & Ex 7 | M + H: 362 |
| (structure) | 1-B | Ex 3 & Ex 7 | M + H: 362 |
| (structure) | 2 | Ex 7 | M + H: 286 |
| (structure) | 3 | Ex 7 | M + H: 300 |

TABLE 1A-continued

| Structure | # | General Procedure(s) | Mass |
|---|---|---|---|
| 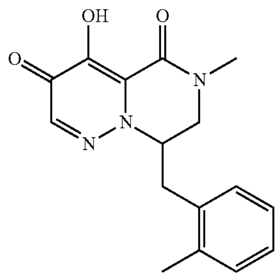 [SMILES: Cc1ccccc1CC1CN(C)C(=O)c2c(O)c(=O)cnn21] | 4 | Ex 7 | M + H: 300 |
| 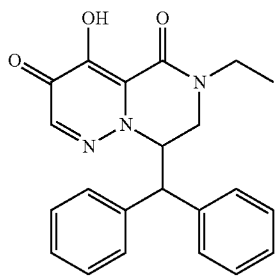 [SMILES: CCN1CC(C(c2ccccc2)c2ccccc2)n2ncc(=O)c(O)c2C1=O] | 5 | Ex 3 & Ex 7 | M + H: 376 |
| 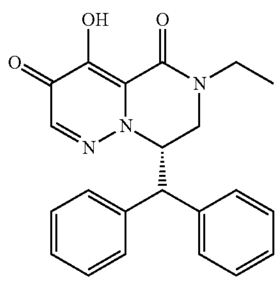 [SMILES: CCN1C[C@H](C(c2ccccc2)c2ccccc2)n2ncc(=O)c(O)c2C1=O] | 5-A | Ex 3 & Ex 7 | M + H: 376 |
| 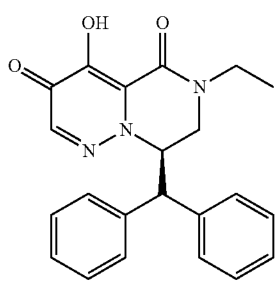 [SMILES: CCN1C[C@@H](C(c2ccccc2)c2ccccc2)n2ncc(=O)c(O)c2C1=O] | 5-B | Ex 3 & Ex 7 | M + H: 376 |
| 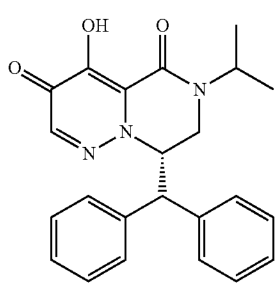 [SMILES: CC(C)N1C[C@H](C(c2ccccc2)c2ccccc2)n2ncc(=O)c(O)c2C1=O] | 6-A | Ex 3 & Ex 10 | M + H: 390<br>$CD_{230}$ = positive |

TABLE 1A-continued

| Structure | # | General Procedure(s) | Mass |
|---|---|---|---|
| 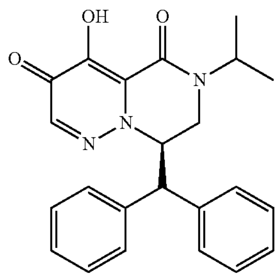 [SMILES: CC(C)N1C[C@@H](C(c2ccccc2)c2ccccc2)n2ncc(=O)c(O)c2C1=O] | 6-B | Ex 3 & Ex 10 | M + H: 390<br>$CD_{230}$ = negative |
| 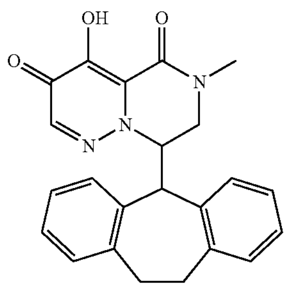 [SMILES: CN1CC(C2c3ccccc3CCc3ccccc32)n2ncc(=O)c(O)c2C1=O] | 7 | Ex 6 & Ex 7 | M + H: 388 |
| 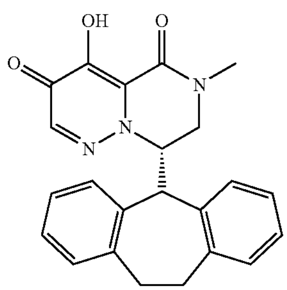 [SMILES: CN1C[C@H](C2c3ccccc3CCc3ccccc32)n2ncc(=O)c(O)c2C1=O] | 7-A | Ex 6 & Ex 7 | M + H: 388<br>$CD_{230}$ = positive |
| 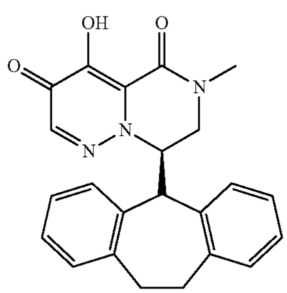 [SMILES: CN1C[C@@H](C2c3ccccc3CCc3ccccc32)n2ncc(=O)c(O)c2C1=O] | 7-B | Ex 6 & Ex 7 | M + H: 388<br>$CD_{230}$ = negative |
| 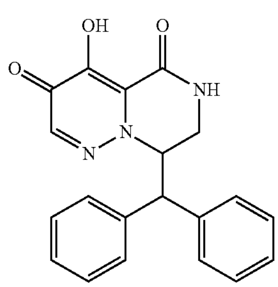 [SMILES: O=C1NCC(C(c2ccccc2)c2ccccc2)n2ncc(=O)c(O)c21] | 8 | Ex 3 & Ex 7 | M + H: 348 |

TABLE 1A-continued

| Structure | # | General Procedure(s) | Mass |
|---|---|---|---|
| 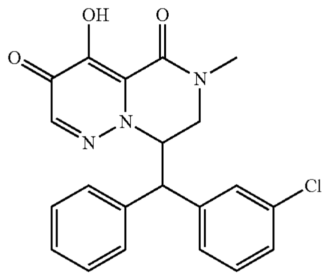 [SMILES: CN1CC(C(c2ccccc2)c2cccc(Cl)c2)n2ncc(=O)c(O)c2C1=O] | 9 | Ex 16 & Ex 7 | M + H: 396 |
| 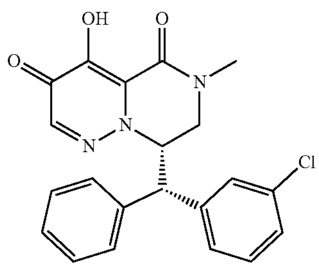 [SMILES: CN1C[C@H]([C@@H](c2ccccc2)c2cccc(Cl)c2)n2ncc(=O)c(O)c2C1=O] | 9-A | Ex 16 & Ex 7 | M + H: 396<br>CD$_{230}$ = positive |
| 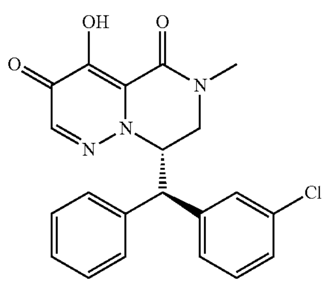 [SMILES: CN1C[C@H]([C@H](c2ccccc2)c2cccc(Cl)c2)n2ncc(=O)c(O)c2C1=O] | 9-B | Ex 16 & Ex 7 | M + H: 396<br>CD$_{230}$ = positive |
| 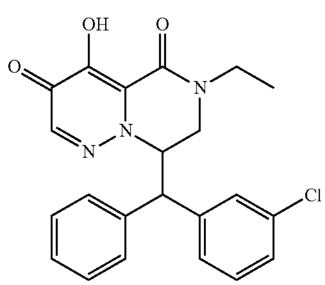 [SMILES: CCN1CC(C(c2ccccc2)c2cccc(Cl)c2)n2ncc(=O)c(O)c2C1=O] | 12 | Ex 16 & Ex 7 | M + H: 410 |
| 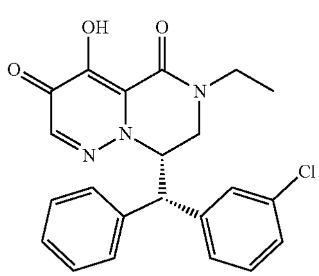 [SMILES: CCN1C[C@H]([C@@H](c2ccccc2)c2cccc(Cl)c2)n2ncc(=O)c(O)c2C1=O] | 12-A | Ex 16 & Ex 7 | M + H: 410<br>CD$_{230}$ = positive |

TABLE 1A-continued

| Structure | # | General Procedure(s) | Mass |
|---|---|---|---|
| 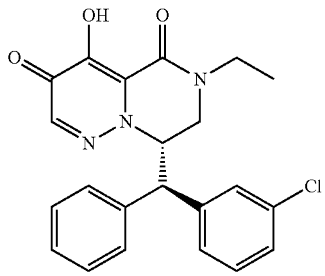 [SMILES: CCN1C[C@H]([C@H](c2ccccc2)c2cccc(Cl)c2)n2ncc(=O)c(O)c2C1=O] | 12-B | Ex 16 & Ex 7 | M + H: 410<br>$CD_{230}$ = positive |
| 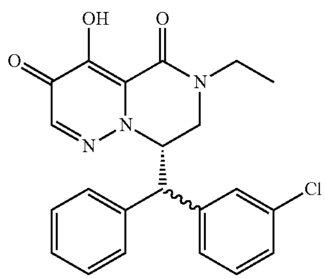 [SMILES: CCN1C[C@H](C(c2ccccc2)c2cccc(Cl)c2)n2ncc(=O)c(O)c2C1=O] | 12-C | Ex 16 & Ex 7 | M + H: 410 |
| 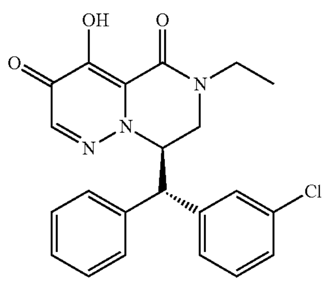 [SMILES: CCN1C[C@@H]([C@@H](c2ccccc2)c2cccc(Cl)c2)n2ncc(=O)c(O)c2C1=O] | 12-D | Ex 16 & Ex 7 | M + H: 410 |
| 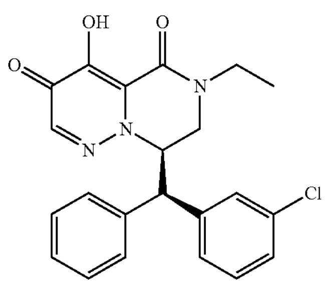 [SMILES: CCN1C[C@@H]([C@H](c2ccccc2)c2cccc(Cl)c2)n2ncc(=O)c(O)c2C1=O] | 12-E | Ex 16 & Ex 7 | M + H: 410 |
| 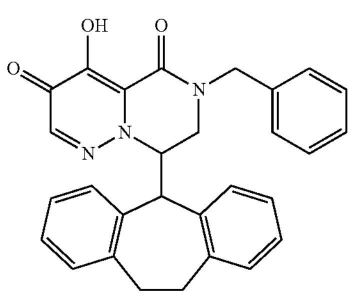 [SMILES: O=C1c2c(O)c(=O)cnn2C(C2c3ccccc3CCc3ccccc32)CN1Cc1ccccc1] | 13 | Ex 6 (rte 2) & Ex 7 | M + H: 464 |

TABLE 1A-continued

| Structure | # | General Procedure(s) | Mass |
|---|---|---|---|
| 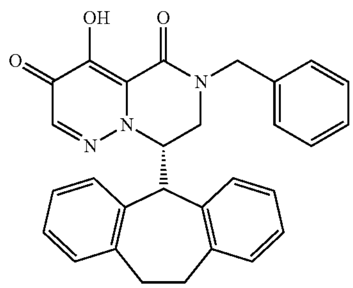 [SMILES: O=C1c2c(O)c(=O)cnn2[C@@H](C2c3ccccc3CCc3ccccc32)CN1Cc1ccccc1] | 13-A | Ex 6 (rte 2) & Ex 7 | M + H: 464 $CD_{230}$ = negative |
| 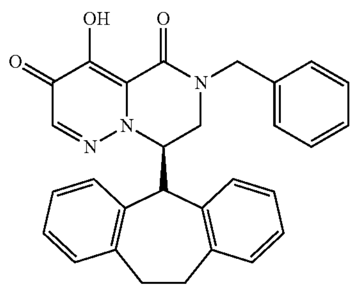 [SMILES: O=C1c2c(O)c(=O)cnn2[C@H](C2c3ccccc3CCc3ccccc32)CN1Cc1ccccc1] | 13-B | Ex 6 (rte 2) & Ex 7 | M + H: 464 $CD_{230}$ = positive |
| 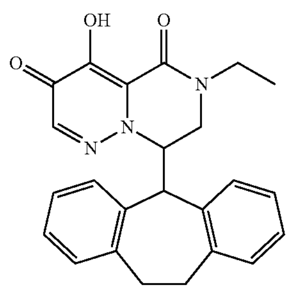 [SMILES: CCN1CC(C2c3ccccc3CCc3ccccc32)n2ncc(=O)c(O)c2C1=O] | 14 | Ex 6 (rte 2) & Ex 7 | M + H: 402 |
| 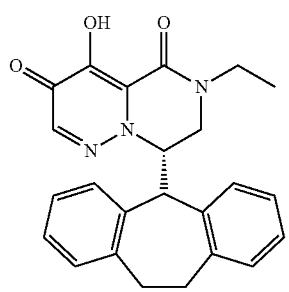 [SMILES: CCN1C[C@H](C2c3ccccc3CCc3ccccc32)n2ncc(=O)c(O)c2C1=O] | 14-A | Ex 6 (rte 2) & Ex 7 | M + H: 402 |
| 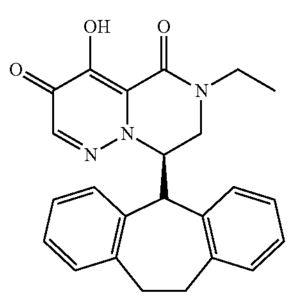 [SMILES: CCN1C[C@@H](C2c3ccccc3CCc3ccccc32)n2ncc(=O)c(O)c2C1=O] | 14-B | Ex 6 (rte 2) & Ex 7 | M + H: 402 |

TABLE 1A-continued

| Structure | # | General Procedure(s) | Mass |
|---|---|---|---|
| (structure) | 15 | Ex 3 & Ex 10 | M + H: 442 |
| (structure) | 16 | Ex 4 & Ex 8 | M + H: 426 |
| (structure) | 17 | Ex 6 (rte 2) & Ex 10 | M + H: 416 |
| (structure) | 17-A | Ex 6 (rte 2) & Ex 10 | M + H: 416 |
| (structure) | 17-B | Ex 6 (rte 2) & Ex 10 | M + H: 416 |

TABLE 1A-continued

| Structure | # | General Procedure(s) | Mass |
|---|---|---|---|
| (structure) | 18 | Ex 3 & Ex 10 | M + H: 444 |
| (structure) | 18-A | Ex 3 & Ex 10 | M + H: 444 |
| (structure) | 18-B | Ex 3 & Ex 10 | M + H: 444 |
| (structure) | 19 | Ex 18 & Ex 7 | M + H: 362 |
| (structure) | 20 | Ex 16 & Ex 10 | M + H: 424 |

TABLE 1A-continued

| Structure | # | General Procedure(s) | Mass |
|---|---|---|---|
| (structure) | 21 | Ex 16 & Ex 7 | M + H: 412 |
| (structure) | 21-A | Ex 16 & Ex 7 | M + H: 412 |
| (structure) | 21-B | Ex 16 & Ex 7 | M + H: 412 |
| (structure) | 22 | Ex 16 & Ex 7 | M + H: 398 |
| (structure) | 23 | Ex 16 & Ex 7 | M + H: 380 |

TABLE 1A-continued

| Structure | # | General Procedure(s) | Mass |
|---|---|---|---|
| 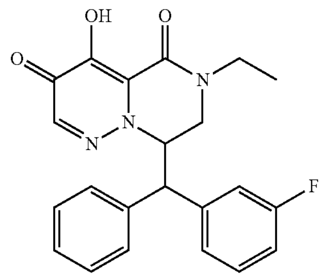 [SMILES: CCN1CC(C(c2ccccc2)c2cccc(F)c2)n2ncc(=O)c(O)c2C1=O] | 24 | Ex 16 & Ex 7 | M + H: 394 |
| 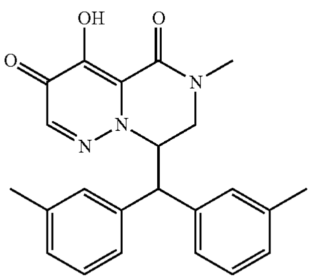 [SMILES: Cc1cccc(C(c2cccc(C)c2)C2CN(C)C(=O)c3c(O)c(=O)cnn32)c1] | 25 | Ex 16 & Ex 7 | M + H: 390 |
| 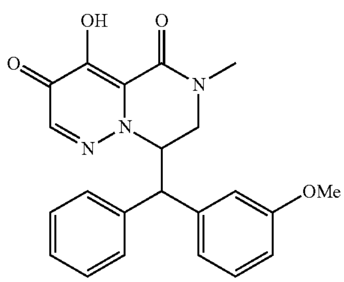 [SMILES: COc1cccc(C(c2ccccc2)C2CN(C)C(=O)c3c(O)c(=O)cnn32)c1] | 26 | Ex 16 & Ex 7 | M + H: 392 |
| 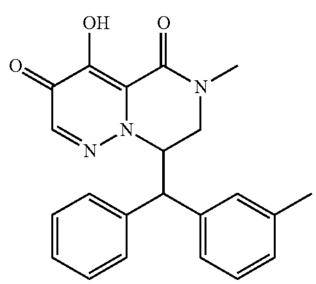 [SMILES: Cc1cccc(C(c2ccccc2)C2CN(C)C(=O)c3c(O)c(=O)cnn32)c1] | 27 | Ex 5 & Ex 7 | M + H: 376 |
| 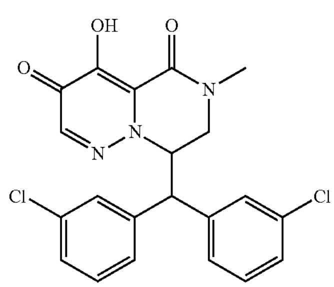 [SMILES: CN1CC(C(c2cccc(Cl)c2)c2cccc(Cl)c2)n2ncc(=O)c(O)c2C1=O] | 28 | Ex 5 & Ex 7 | M + H: 430 |

TABLE 1A-continued

| Structure | # | General Procedure(s) | Mass |
|---|---|---|---|
| 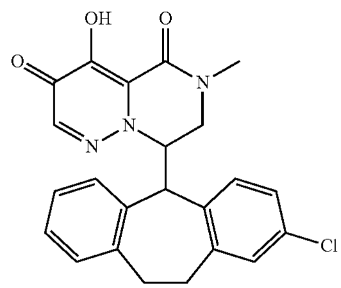 [SMILES: CN1CC(C2c3ccccc3CCc3cc(Cl)ccc32)n2ncc(=O)c(O)c2C1=O] | 29 | Ex 17 & Ex 7 | M + H: 422 |
| 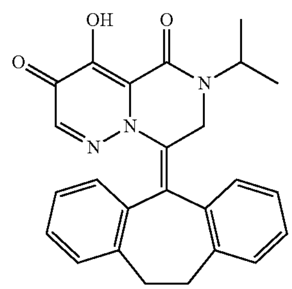 [SMILES: CC(C)N1CC(=C2c3ccccc3CCc3ccccc32)n2ncc(=O)c(O)c2C1=O] | 30 | Ex 6 & Ex 10 | M + H: 414 |
| 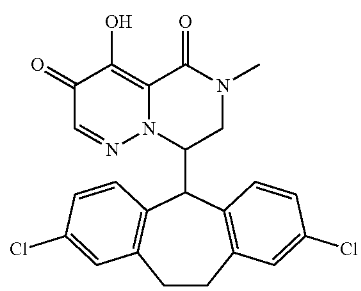 [SMILES: CN1CC(C2c3ccc(Cl)cc3CCc3cc(Cl)ccc32)n2ncc(=O)c(O)c2C1=O] | 31 | Ex 14 & Ex 7 (using PtO$_2$ in place of Pd/C) | M + H: 456 |
| 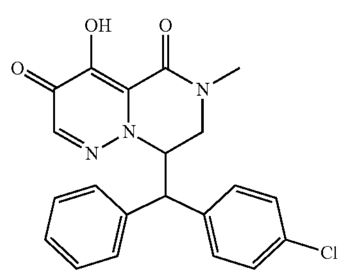 [SMILES: CN1CC(C(c2ccccc2)c2ccc(Cl)cc2)n2ncc(=O)c(O)c2C1=O] | 32 | Ex 19 & Ex 7 | M + H: 396 |
| 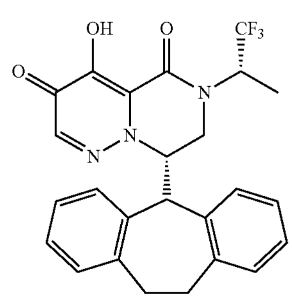 [SMILES: C[C@H](N1C[C@H](C2c3ccccc3CCc3ccccc32)n2ncc(=O)c(O)c2C1=O)C(F)(F)F] | 33-A | Ex 6 (rte 2) & Ex 10 | M + H: 470 |

TABLE 1A-continued
| Structure | # | General Procedure(s) | Mass |
|---|---|---|---|
| 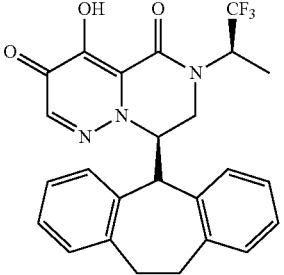 [SMILES: C[C@@H](N1C[C@@H](C2c3ccccc3CCc3ccccc32)n2ncc(=O)c(O)c2C1=O)C(F)(F)F] | 33-B | Ex 6 (rte 2) & Ex 10 | M + H: 470 |
| 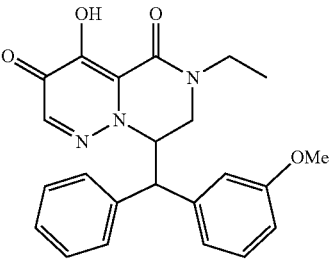 [SMILES: CCN1CC(C(c2ccccc2)c2cccc(OC)c2)n2ncc(=O)c(O)c2C1=O] | 34 | Ex 16 & Ex 7 | M + H: 406 |
| 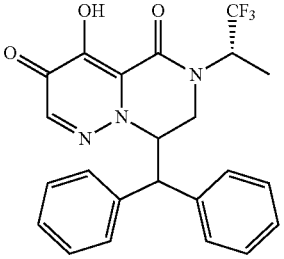 [SMILES: C[C@H](N1CC(C(c2ccccc2)c2ccccc2)n2ncc(=O)c(O)c2C1=O)C(F)(F)F] | 35-A | Ex 3 & Ex 10 | M + H: 444 |
| 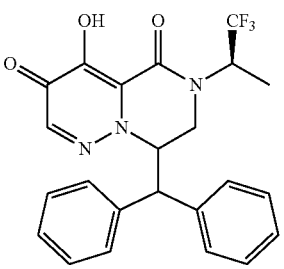 [SMILES: C[C@@H](N1CC(C(c2ccccc2)c2ccccc2)n2ncc(=O)c(O)c2C1=O)C(F)(F)F] | 35-B | Ex 3 & Ex 10 | M + H: 444 |
| 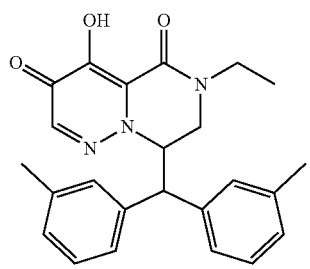 [SMILES: CCN1CC(C(c2cccc(C)c2)c2cccc(C)c2)n2ncc(=O)c(O)c2C1=O] | 36 | Ex 16 & Ex 7 | M + H: 404 |

TABLE 1A-continued

| Structure | # | General Procedure(s) | Mass |
|---|---|---|---|
| 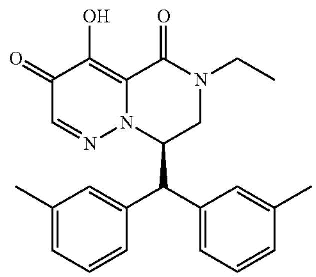 [SMILES: CCN1C[C@@H](C(c2cccc(C)c2)c2cccc(C)c2)n2ncc(=O)c(O)c2C1=O] | 36-B | Ex 16 & Ex 7 | M + H: 404 |
| 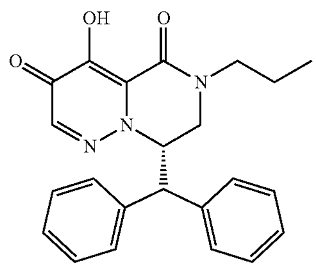 [SMILES: CCCN1C[C@H](C(c2ccccc2)c2ccccc2)n2ncc(=O)c(O)c2C1=O] | 37-A | Ex 3 & Ex 7 | M + H: 390 |
| 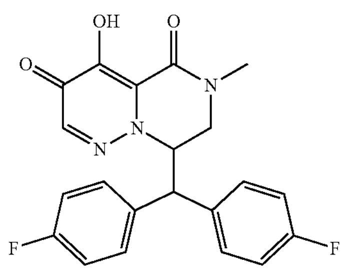 [SMILES: CN1CC(C(c2ccc(F)cc2)c2ccc(F)cc2)n2ncc(=O)c(O)c2C1=O] | 38 | Ex 5 & Ex 7 | M + H: 398 |
| 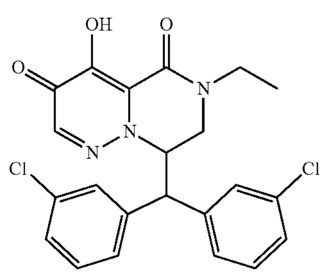 [SMILES: CCN1CC(C(c2cccc(Cl)c2)c2cccc(Cl)c2)n2ncc(=O)c(O)c2C1=O] | 39 | Ex 5 & Ex 7 | M + H: 444 |
| 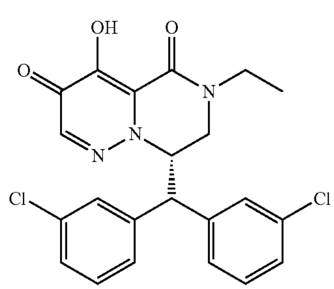 [SMILES: CCN1C[C@H](C(c2cccc(Cl)c2)c2cccc(Cl)c2)n2ncc(=O)c(O)c2C1=O] | 39-A | Ex 16 & Ex 7 | M + H: 444 |

TABLE 1A-continued

| Structure | # | General Procedure(s) | Mass |
|---|---|---|---|
| 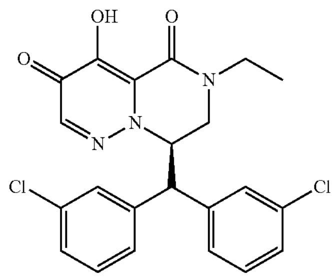 [SMILES: CCN1C[C@@H](C(c2cccc(Cl)c2)c2cccc(Cl)c2)n2ncc(=O)c(O)c2C1=O] | 39-B | Ex 5 & Ex 7 | M + H: 444 |
| 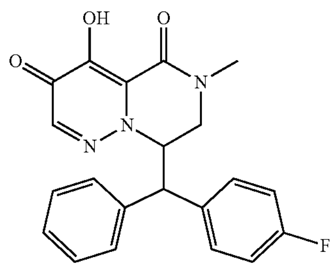 [SMILES: CN1CC(C(c2ccccc2)c2ccc(F)cc2)n2ncc(=O)c(O)c2C1=O] | 40 | Ex 19 & Ex 7 | M + H: 380 |
| 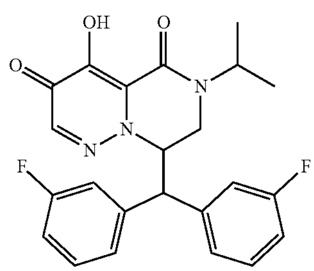 [SMILES: CC(C)N1CC(C(c2cccc(F)c2)c2cccc(F)c2)n2ncc(=O)c(O)c2C1=O] | 41 | Ex 16 & Ex 10 | M + H: 426 |
| 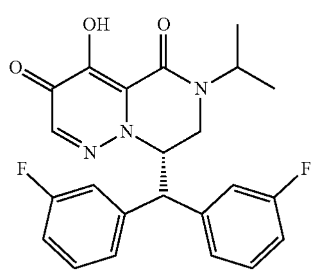 [SMILES: CC(C)N1C[C@H](C(c2cccc(F)c2)c2cccc(F)c2)n2ncc(=O)c(O)c2C1=O] | 41-A | Ex 16 & Ex 10 | M + H: 426 |
| 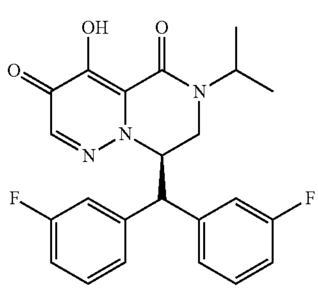 [SMILES: CC(C)N1C[C@@H](C(c2cccc(F)c2)c2cccc(F)c2)n2ncc(=O)c(O)c2C1=O] | 41-B | Ex 16 & Ex 10 | M + H: 426 |

TABLE 1A-continued

| Structure | # | General Procedure(s) | Mass |
|---|---|---|---|
| 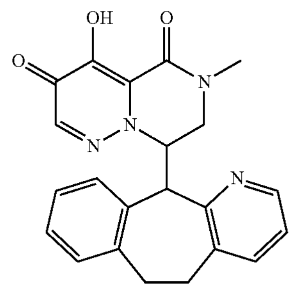 [SMILES: CN1CC(C2c3ccccc3CCc3cccnc32)n2ncc(=O)c(O)c2C1=O] | 42 | Ex 20 & Ex 7 | M + H: 389 |
| 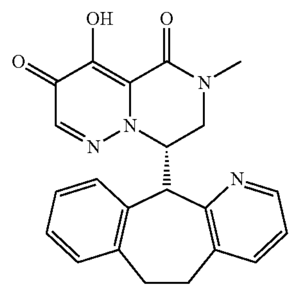 [SMILES: CN1C[C@H](C2c3ccccc3CCc3cccnc32)n2ncc(=O)c(O)c2C1=O] | 42-A | Ex 20 & Ex 7 | M + H: 389 |
| 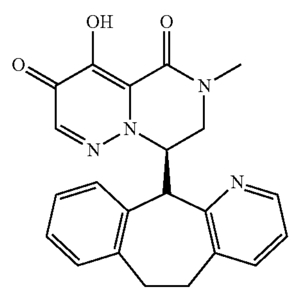 [SMILES: CN1C[C@@H](C2c3ccccc3CCc3cccnc32)n2ncc(=O)c(O)c2C1=O] | 42-B | Ex 20 & Ex 7 | M + H: 389 |
| 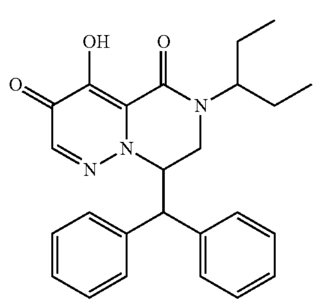 [SMILES: CCC(CC)N1CC(C(c2ccccc2)c2ccccc2)n2ncc(=O)c(O)c2C1=O] | 43 | Ex 3 & Ex 10 | M + H: 418 |
| 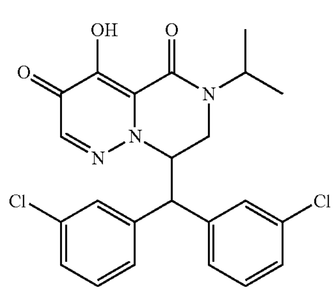 [SMILES: CC(C)N1CC(C(c2cccc(Cl)c2)c2cccc(Cl)c2)n2ncc(=O)c(O)c2C1=O] | 44 | Ex 5 & Ex 10 | M + H: 458 |

TABLE 1A-continued
| Structure | # | General Procedure(s) | Mass |
|---|---|---|---|
| 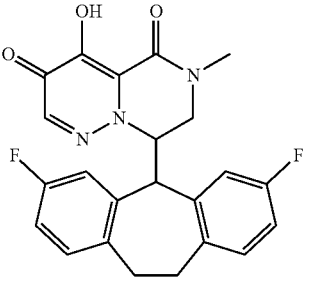 [SMILES: CN1CC(C2c3cc(F)ccc3CCc3ccc(F)cc32)n2ncc(=O)c(O)c2C1=O] | 45 | Ex 15 & Ex 7 | M + H: 424 |
| 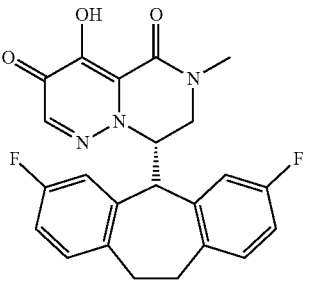 [SMILES: CN1C[C@H](C2c3cc(F)ccc3CCc3ccc(F)cc32)n2ncc(=O)c(O)c2C1=O] | 45-A | Ex 15 & Ex 7 | M + H: 424 |
| 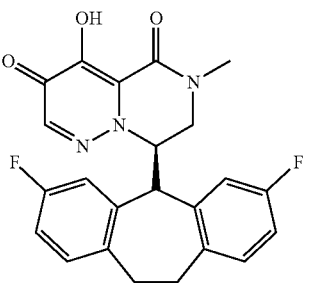 [SMILES: CN1C[C@@H](C2c3cc(F)ccc3CCc3ccc(F)cc32)n2ncc(=O)c(O)c2C1=O] | 45-B | Ex 15 & Ex 7 | M + H: 424 |
| 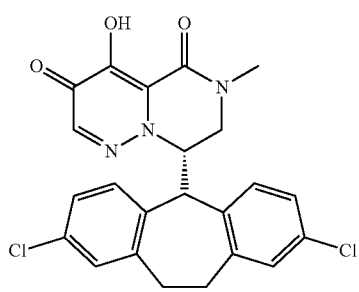 [SMILES: CN1C[C@H](C2c3ccc(Cl)cc3CCc3cc(Cl)ccc32)n2ncc(=O)c(O)c2C1=O] | 46-A | Ex 14 & Ex 7 (using Pt$_2$O in place of Pd/C) | M + H: 456<br>CD$_{230}$ = negative |
| 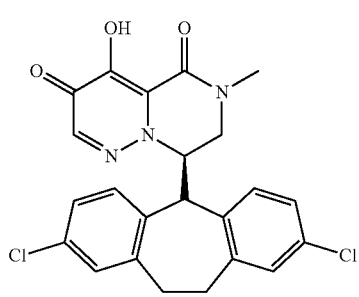 [SMILES: CN1C[C@@H](C2c3ccc(Cl)cc3CCc3cc(Cl)ccc32)n2ncc(=O)c(O)c2C1=O] | 46-B | Ex 14 & Ex 7 (using Pt$_2$O in place of Pd/C) | M + H: 456<br>CD$_{230}$ = positive |

TABLE 1A-continued

| Structure | # | General Procedure(s) | Mass |
|---|---|---|---|
| 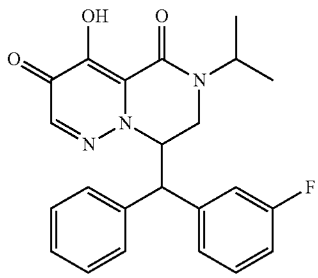 [SMILES: CC(C)N1CC(C(c2ccccc2)c2cccc(F)c2)n2ncc(=O)c(O)c2C1=O] | 47 | Ex 16 & Ex 10 | M + H: 408 |
| 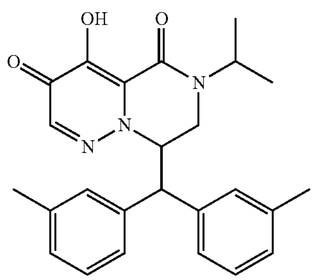 [SMILES: Cc1cccc(C(c2cccc(C)c2)C2CN(C(C)C)C(=O)c3c(O)c(=O)cnn32)c1] | 48 | Ex 16 & Ex 10 | M + H: 418 |
| 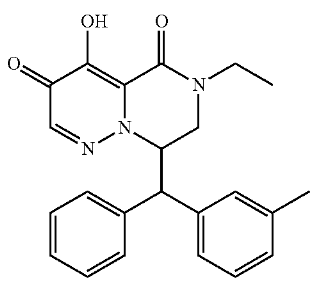 [SMILES: CCN1CC(C(c2ccccc2)c2cccc(C)c2)n2ncc(=O)c(O)c2C1=O] | 49 | Ex 5 & Ex 7 (using Compound L) | M + H: 390 |
| 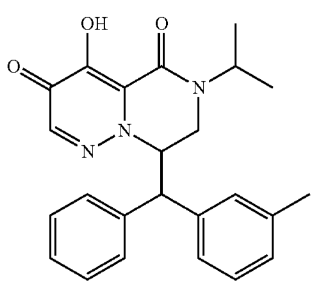 [SMILES: Cc1cccc(C(c2ccccc2)C2CN(C(C)C)C(=O)c3c(O)c(=O)cnn32)c1] | 50 | Ex 5 & Ex 10 (using Compound L) | M + H: 404 |
| 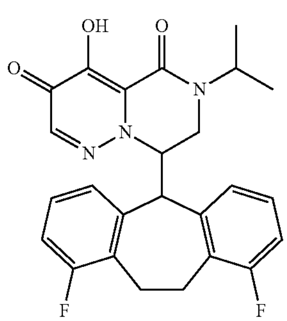 [SMILES: CC(C)N1CC(C2c3cccc(F)c3CCc3c(F)cccc32)n2ncc(=O)c(O)c2C1=O] | 51 | Ex 6 (rte 2) & Ex 21 (step 4) | M + H: 452 |

TABLE 1A-continued

| Structure | # | General Procedure(s) | Mass |
|---|---|---|---|
| 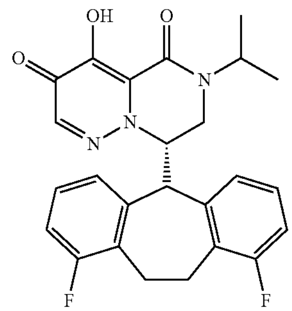 [SMILES: CC(C)N1C[C@H](C2c3cccc(F)c3CCc3c(F)cccc32)n2ncc(=O)c(O)c2C1=O] | 51-A | Ex 6 (rte 2) & Ex 21 (step 4) | M + H: 452 |
| 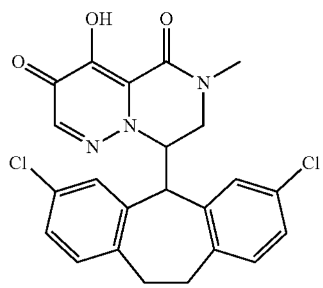 [SMILES: CN1CC(C2c3cc(Cl)ccc3CCc3ccc(Cl)cc32)n2ncc(=O)c(O)c2C1=O] | 52 | Ex 15 & Ex 7 (using Pt$_2$O in place of Pd/C) | M + H: 456 |
| 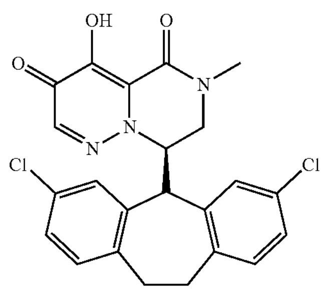 [SMILES: CN1C[C@@H](C2c3cc(Cl)ccc3CCc3ccc(Cl)cc32)n2ncc(=O)c(O)c2C1=O] | 52-A | Ex 15 & Ex 7 (using Pt$_2$O in place of Pd/C) | M + H: 456 |
| 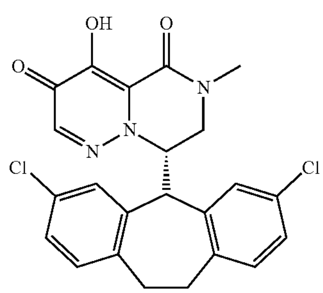 [SMILES: CN1C[C@H](C2c3cc(Cl)ccc3CCc3ccc(Cl)cc32)n2ncc(=O)c(O)c2C1=O] | 52-B | Ex 15 & Ex 7 (using Pt$_2$O in place of Pd/C) | M + H: 456 |
| 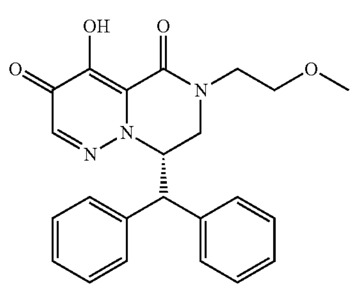 [SMILES: COCCN1C[C@H](C(c2ccccc2)c2ccccc2)n2ncc(=O)c(O)c2C1=O] | 53-A | Ex 3 & Ex 7 (using Compound L) | M + H: 406 |

TABLE 1A-continued

| Structure | # | General Procedure(s) | Mass |
|---|---|---|---|
| 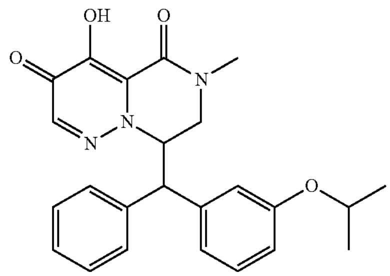 [SMILES: CC(C)Oc1cccc(C(c2ccccc2)C2CN(C)C(=O)c3c(O)c(=O)cnn32)c1] | 54 | Ex 16 & Ex 7 (using Compound L) | M + H: 420 |
| 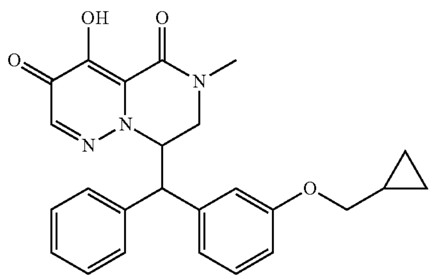 [SMILES: CN1CC(C(c2ccccc2)c2cccc(OCC3CC3)c2)n2ncc(=O)c(O)c2C1=O] | 55 | Ex 16 & Ex 7 (using Compound L) | M + H: 432 |
| 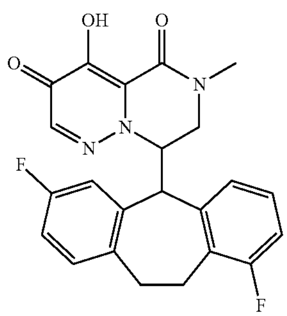 [SMILES: CN1CC(C2c3cc(F)ccc3CCc3c(F)cccc32)n2ncc(=O)c(O)c2C1=O] | 56 | Ex 15 & Ex 7 (using Pt$_2$O in place of Pd/C) | M + H: 424 |
| 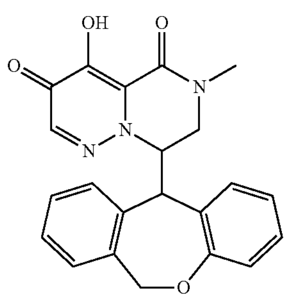 [SMILES: CN1CC(C2c3ccccc3COc3ccccc32)n2ncc(=O)c(O)c2C1=O] | 57 | Ex 3 & Ex 7 | M + H: 390 |
| 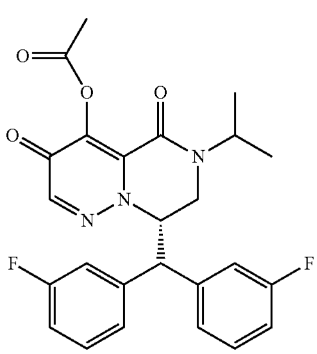 | 58-A | Ex 11 | M + H: 463 |

TABLE 1A-continued

| Structure | # | General Procedure(s) | Mass |
|---|---|---|---|
| 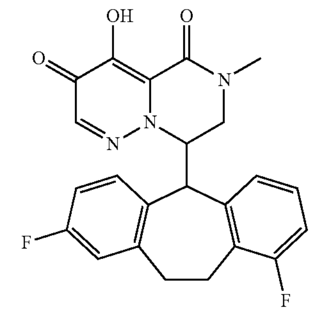 [SMILES: CN1CC(C2c3ccc(F)cc3CCc3c(F)cccc32)n2ncc(=O)c(O)c2C1=O] | 59-A | Ex 14 & Ex 7 (using Pt₂O in place of Pd/C) | M + H: 424 |
| 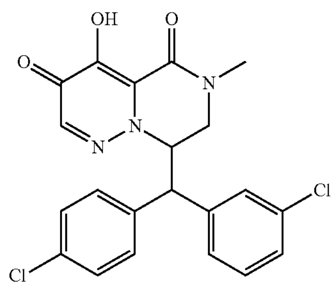 [SMILES: CN1CC(C(c2ccc(Cl)cc2)c2cccc(Cl)c2)n2ncc(=O)c(O)c2C1=O] | 60 | Ex 19 & Ex 7 (using Compound L) | M + H: 430 |
| 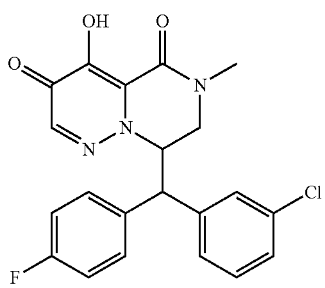 [SMILES: CN1CC(C(c2ccc(F)cc2)c2cccc(Cl)c2)n2ncc(=O)c(O)c2C1=O] | 61 | Ex 19 & Ex 7 (using Compound L) | M + H: 414 |
| 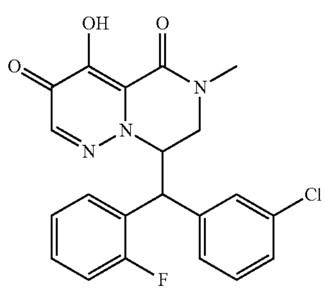 [SMILES: CN1CC(C(c2cccc(Cl)c2)c2ccccc2F)n2ncc(=O)c(O)c2C1=O] | 62 | Ex 19 & Ex 7 (using Compound L) | M + H: 414 |
| 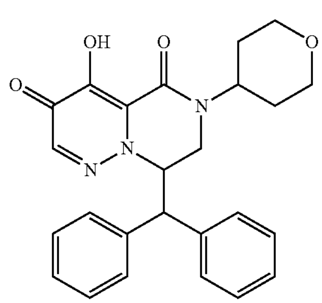 | 63 | Ex 3 & Ex 10 | M + H: 432 |

TABLE 1A-continued

| Structure | # | General Procedure(s) | Mass |
|---|---|---|---|
| 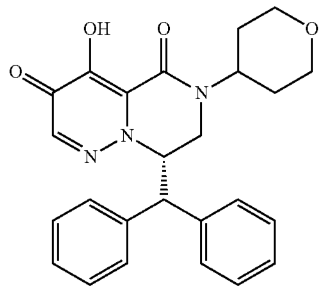 [SMILES: O=C1c2c(O)c(=O)cnn2[C@@H](C(c2ccccc2)c2ccccc2)CN1C1CCOCC1] | 63-A | Ex 3 & Ex 10 | M + H: 432 |
| 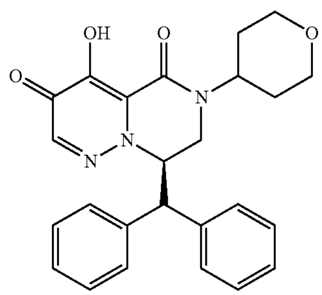 [SMILES: O=C1c2c(O)c(=O)cnn2[C@H](C(c2ccccc2)c2ccccc2)CN1C1CCOCC1] | 63-B | Ex 3 & Ex 10 | M + H: 432 |
| 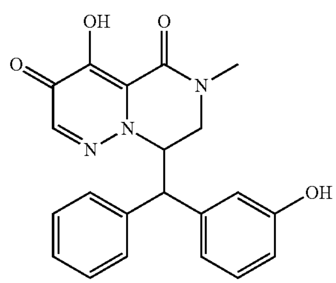 | 64 | Ex 16, Ex 7 and TFA | M + H: 378 |
| 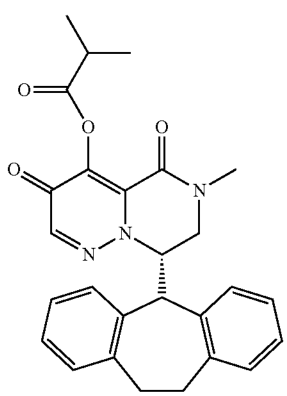 [SMILES: CC(C)C(=O)Oc1c2n(ncc1=O)[C@@H](C1c3ccccc3CCc3ccccc31)CN(C)C2=O] | 65-A | Ex 11 | M + H: 458 |

TABLE 1A-continued

| Structure | # | General Procedure(s) | Mass |
|---|---|---|---|
| 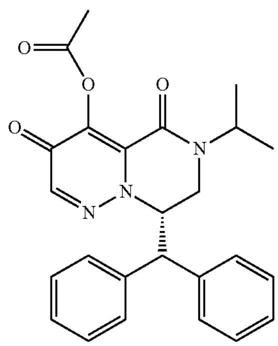 [SMILES: CC(=O)Oc1c2n(ncc1=O)[C@@H](C(c1ccccc1)c1ccccc1)CN(C(C)C)C2=O] | 66-A | Ex 11 | M + H: 432 |
| 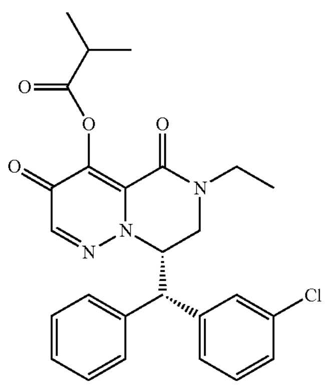 [SMILES: CCN1C[C@H]([C@@H](c2ccccc2)c2cccc(Cl)c2)n2ncc(=O)c(OC(=O)C(C)C)c2C1=O] | 67-A | Ex 11 | M + H: 480 |
| 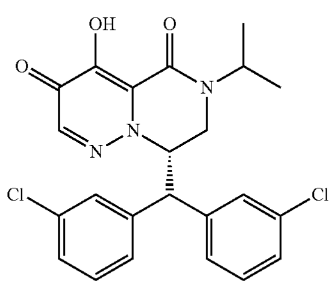 [SMILES: CC(C)N1C[C@H](C(c2cccc(Cl)c2)c2cccc(Cl)c2)n2ncc(=O)c(O)c2C1=O] | 68-A | Ex 16 & Ex 10 | M + H: 458 |
| 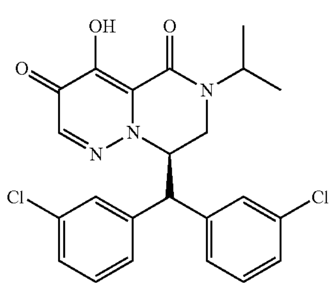 [SMILES: CC(C)N1C[C@@H](C(c2cccc(Cl)c2)c2cccc(Cl)c2)n2ncc(=O)c(O)c2C1=O] | 68-B | Ex 16 & Ex 10 | M + H: 458 |

TABLE 1A-continued

| Structure | # | General Procedure(s) | Mass |
|---|---|---|---|
| 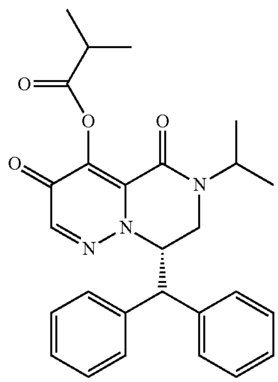 [SMILES: CC(C)C(=O)Oc1c2n(ncc1=O)[C@@H](C(c1ccccc1)c1ccccc1)CN(C(C)C)C2=O] | 69-A | Ex 11 | M + H: 460 |
| 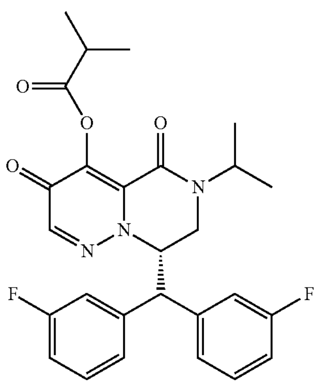 [SMILES: CC(C)C(=O)Oc1c2n(ncc1=O)[C@@H](C(c1cccc(F)c1)c1cccc(F)c1)CN(C(C)C)C2=O] | 70-A | Ex 11 | M + H: 496 |
| 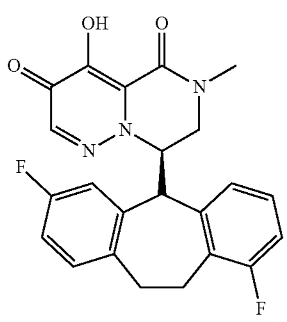 [SMILES: CN1C[C@@H](C2c3cc(F)ccc3CCc3c(F)cccc32)n2ncc(=O)c(O)c2C1=O] | 71 | Ex 15 & Ex 7 (using Pt₂O in place of Pd/C) | M + H: 424 |
| 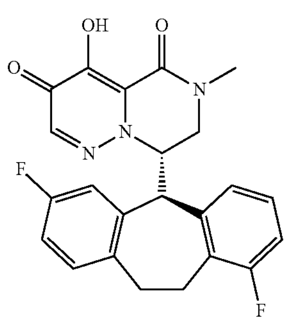 [SMILES: CN1C[C@H]([C@@H]2c3cc(F)ccc3CCc3c(F)cccc32)n2ncc(=O)c(O)c2C1=O] | 71-A | Ex 15 & Ex 7 (using Pt₂O in place of Pd/C) | M + H: 424 |

TABLE 1A-continued

| Structure | # | General Procedure(s) | Mass |
|---|---|---|---|
| 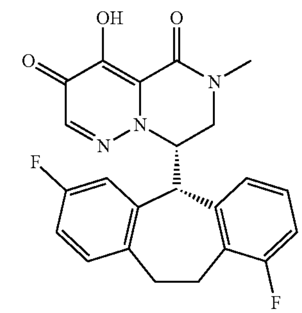 [SMILES: CN1C[C@H]([C@H]2c3cc(F)ccc3CCc3c(F)cccc32)n2ncc(=O)c(O)c2C1=O] | 71-B | Ex 15 & Ex 7 (using Pt₂O in place of Pd/C) | M + H: 424 |
| 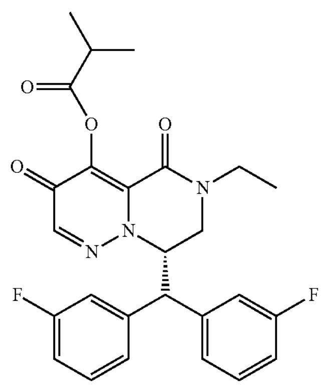 [SMILES: CCN1C[C@H](C(c2cccc(F)c2)c2cccc(F)c2)n2ncc(=O)c(OC(=O)C(C)C)c2C1=O] | 72-A | Ex 11 | M + H: 482 |
| 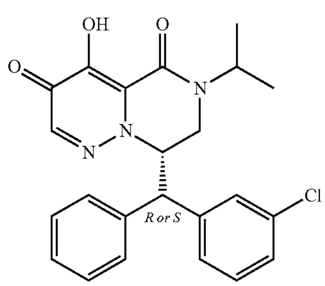 [SMILES: CC(C)N1C[C@H](C(c2ccccc2)c2cccc(Cl)c2)n2ncc(=O)c(O)c2C1=O] | 73-A | Ex 16 & Ex 10 | M + H: 424 |
| 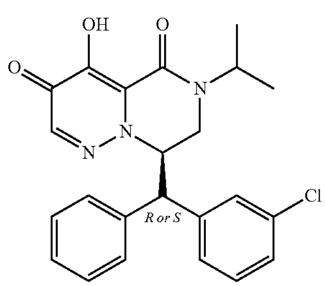 [SMILES: CC(C)N1C[C@@H](C(c2ccccc2)c2cccc(Cl)c2)n2ncc(=O)c(O)c2C1=O] | 73-B | Ex 16 & Ex 10 | M + H: 424 |
| 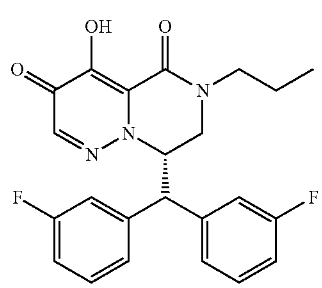 [SMILES: CCCN1C[C@H](C(c2cccc(F)c2)c2cccc(F)c2)n2ncc(=O)c(O)c2C1=O] | 74-A | Ex 16 & Ex 7 (using Compound L) | M + H: 426 |

TABLE 1A-continued

| Structure | # | General Procedure(s) | Mass |
|---|---|---|---|
| 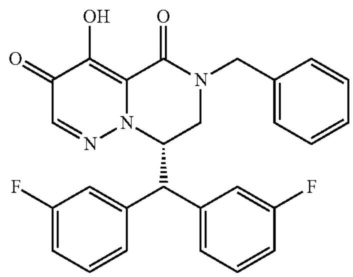 [SMILES: O=C1c2c(O)c(=O)cnn2[C@@H](C(c2cccc(F)c2)c2cccc(F)c2)CN1Cc1ccccc1] | 75-A | Ex 3 & Ex 7 | M + H: 474 |
| 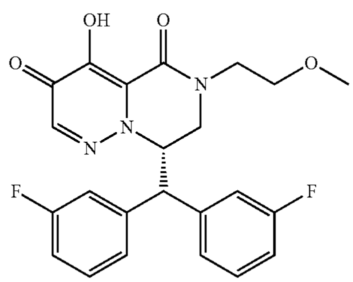 [SMILES: COCCN1C[C@H](C(c2cccc(F)c2)c2cccc(F)c2)n2ncc(=O)c(O)c2C1=O] | 76-A | Ex 3 & Ex 7 | M + H: 442 |
| 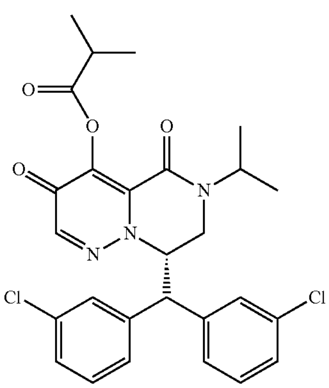 [SMILES: CC(C)C(=O)Oc1c2n(ncc1=O)[C@@H](C(c1cccc(Cl)c1)c1cccc(Cl)c1)CN(C(C)C)C2=O] | 77-A | Ex 11 | M + H: 528 |
| 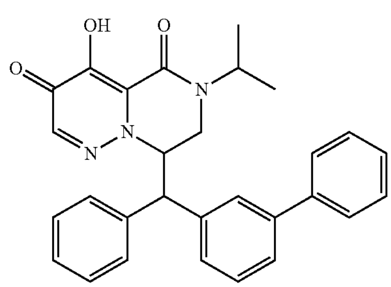 [SMILES: CC(C)N1CC(C(c2ccccc2)c2cccc(-c3ccccc3)c2)n2ncc(=O)c(O)c2C1=O] | 78 | Ex 10 | M + H: 466 |

TABLE 1A-continued
| Structure | # | General Procedure(s) | Mass |
|---|---|---|---|
| 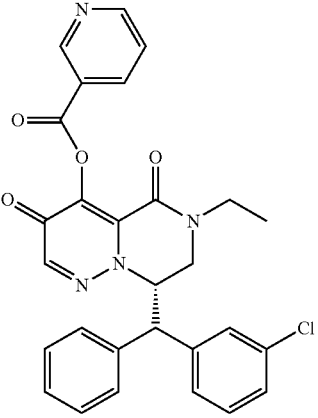 [SMILES: CCN1C[C@H](C(c2ccccc2)c2cccc(Cl)c2)n2ncc(=O)c(OC(=O)c3cccnc3)c2C1=O] | 79-A | Ex 11 | M + H: 515 |
| 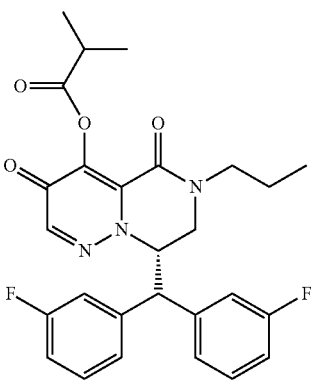 [SMILES: CCCN1C[C@H](C(c2cccc(F)c2)c2cccc(F)c2)n2ncc(=O)c(OC(=O)C(C)C)c2C1=O] | 80-A | Ex 11 | M + H: 496 |
| 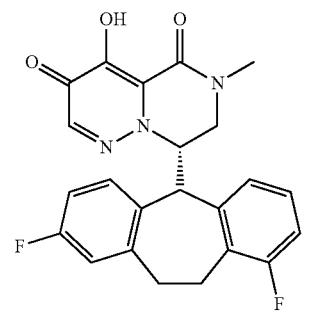 [SMILES: CN1C[C@H](C2c3ccc(F)cc3CCc3c(F)cccc32)n2ncc(=O)c(O)c2C1=O] | 81-A | Ex 14; Ex 7 (using Pt$_2$O in place of Pd/C) | M + H: 424 |
| 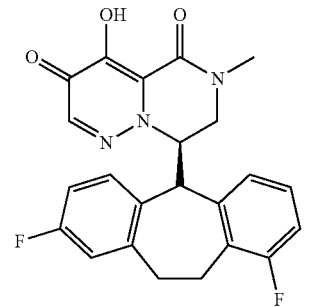 [SMILES: CN1C[C@@H](C2c3ccc(F)cc3CCc3c(F)cccc32)n2ncc(=O)c(O)c2C1=O] | 81-B | Ex 14; Ex 7 (using Pt$_2$O in place of Pd/C) | M + H: 424 |

TABLE 1A-continued

| Structure | # | General Procedure(s) | Mass |
|---|---|---|---|
| (structure) | 82-A | Ex 16 & Ex 10 | M + H: 424 |
| (structure) | 82-B | Ex 16 & Ex 10 | M + H: 424 |
| (structure) | 83 | Ex 14 & Ex 7 | M + H: 424 |
| (structure) | 83-A | Ex 14 & Ex 7 | M + H: 424 |
| (structure) | 83-B | Ex 14 & Ex 7 | M + H: 424 |

TABLE 1A-continued

| Structure | # | General Procedure(s) | Mass |
|---|---|---|---|
| 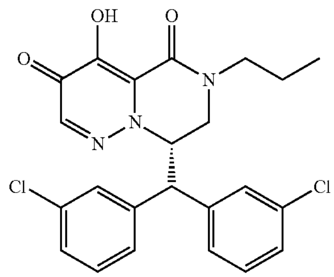 [SMILES: CCCN1C[C@H](C(c2cccc(Cl)c2)c2cccc(Cl)c2)n2ncc(=O)c(O)c2C1=O] | 84-A | Ex 16 & Ex 7 | M + H: 458 |
| 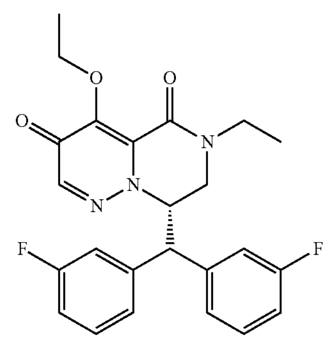 [SMILES: CCOc1c2n(ncc1=O)[C@@H](C(c1cccc(F)c1)c1cccc(F)c1)CN(CC)C2=O] | 85-A | Ex 13 | M + H: 440 |
| 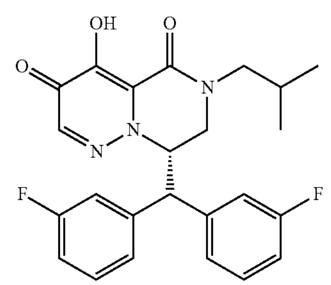 [SMILES: CC(C)CN1C[C@H](C(c2cccc(F)c2)c2cccc(F)c2)n2ncc(=O)c(O)c2C1=O] | 86-A | Ex 16 & Ex 7 (using Compound L) | M + H: 440 |
| 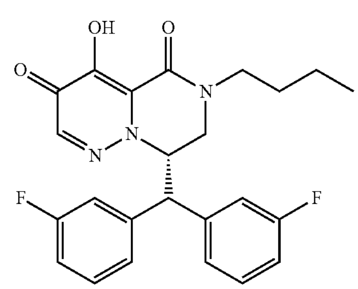 [SMILES: CCCCN1C[C@H](C(c2cccc(F)c2)c2cccc(F)c2)n2ncc(=O)c(O)c2C1=O] | 87-A | Ex 16 & Ex 7 (using Compound L) | M + H: 440 |

TABLE 1A-continued

| Structure | # | General Procedure(s) | Mass |
|---|---|---|---|
| 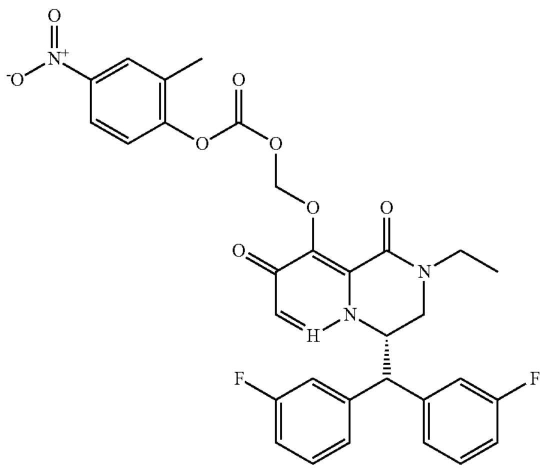 | 88-A | Ex 12 | M + H: 621 |
| 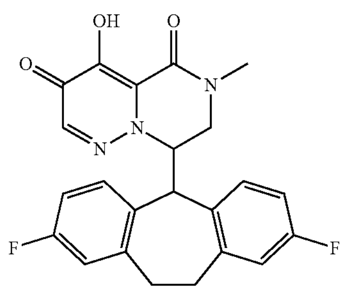 [SMILES: CN1CC(C2c3ccc(F)cc3CCc3cc(F)ccc32)n2ncc(=O)c(O)c2C1=O] | 89 | Ex 17 & Ex 7 | M + H: 424 |
| 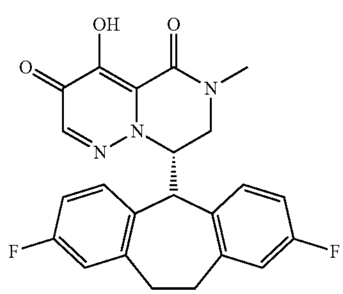 [SMILES: CN1C[C@H](C2c3ccc(F)cc3CCc3cc(F)ccc32)n2ncc(=O)c(O)c2C1=O] | 89-A | Ex 17 & Ex 7 | M + H: 424 |
| 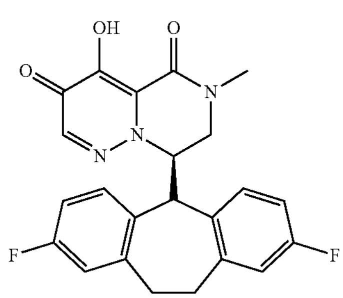 [SMILES: CN1C[C@@H](C2c3ccc(F)cc3CCc3cc(F)ccc32)n2ncc(=O)c(O)c2C1=O] | 89-B | Ex 17 & Ex 7 | M + H: 424 |

TABLE 1A-continued

| Structure | # | General Procedure(s) | Mass |
|---|---|---|---|
| (structure) | 90 | Ex 3 & Ex 10 | M + H: 434 |
| (structure) | 91-A | Ex 12 | M + H: 598 |
| (structure) | 92-A | Ex 16 & Ex 7 (using Compound L) | M + H: 428 |
| (structure) | 93-A | Ex 7 | M + H: 438 |

TABLE 1A-continued

| Structure | # | General Procedure(s) | Mass |
|---|---|---|---|
| 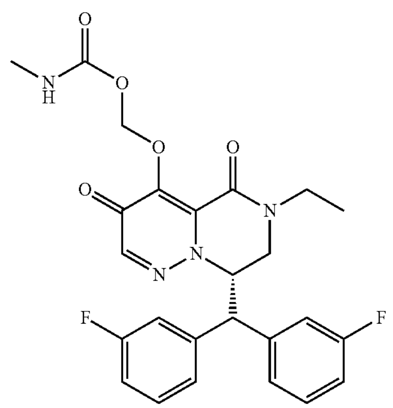 [SMILES: CCN1C[C@H](C(c2cccc(F)c2)c2cccc(F)c2)n2ncc(=O)c(OCOC(=O)NC)c2C1=O] | 94-A | Ex 12 | M + H: 499 |
| 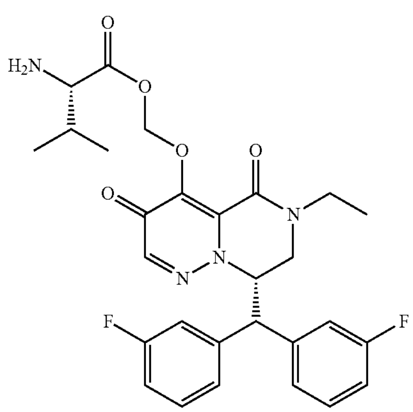 [SMILES: CCN1C[C@H](C(c2cccc(F)c2)c2cccc(F)c2)n2ncc(=O)c(OCOC(=O)[C@@H](N)C(C)C)c2C1=O] | 95-A | Ex 12 | M + H: 541 |
| 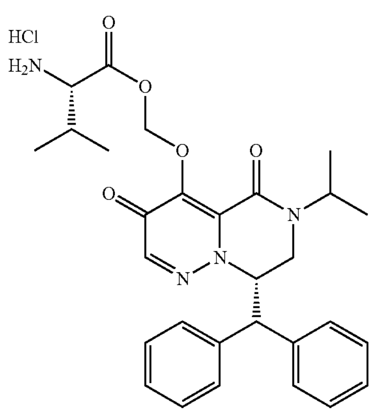 [SMILES: Cl ; CC(C)[C@H](N)C(=O)OCOc1c2n(ncc1=O)[C@@H](C(c1ccccc1)c1ccccc1)CN(C(C)C)C2=O] | 96-A | Ex 12 | M + H: 519 |
| 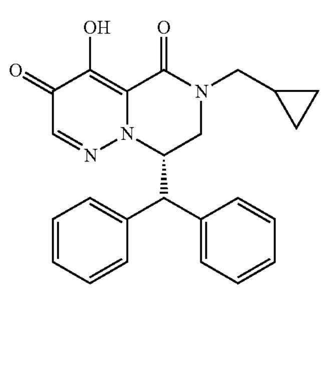 [SMILES: O=C1c2c(O)c(=O)cnn2[C@@H](C(c2ccccc2)c2ccccc2)CN1CC1CC1] | 97-A | Ex 7 | M + H: 402 |

TABLE 1A-continued

| Structure | # | General Procedure(s) | Mass |
|---|---|---|---|
| 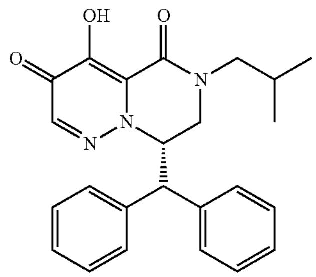 [SMILES: CC(C)CN1C[C@H](C(c2ccccc2)c2ccccc2)n2ncc(=O)c(O)c2C1=O] | 98-A | Ex 7 | M + H: 404 |
| 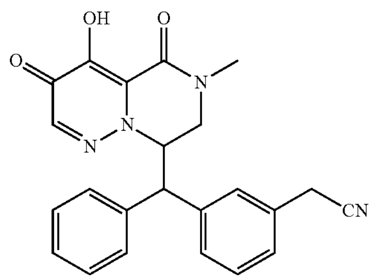 [SMILES: CN1CC(C(c2ccccc2)c2cccc(CC#N)c2)n2ncc(=O)c(O)c2C1=O] | 99 | Ex 3 & Ex 7 | M + H: 401 |
| 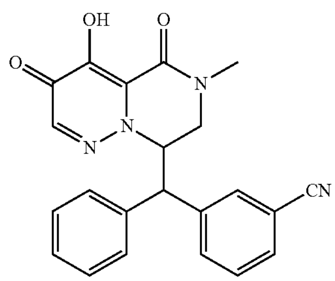 [SMILES: CN1CC(C(c2ccccc2)c2cccc(C#N)c2)n2ncc(=O)c(O)c2C1=O] | 100 | Ex 3 & Ex 7 | M + H: 387 |
| 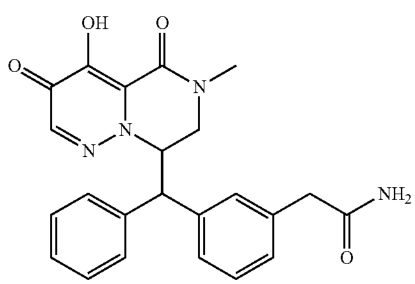 [SMILES: CN1CC(C(c2ccccc2)c2cccc(CC(N)=O)c2)n2ncc(=O)c(O)c2C1=O] | 101 | Using compound 99; followed by hydrolysis with K$_2$CO$_3$/ 30% H$_2$O$_2$ | M + H: 419 |
| 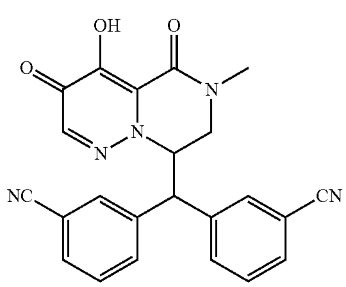 [SMILES: CN1CC(C(c2cccc(C#N)c2)c2cccc(C#N)c2)n2ncc(=O)c(O)c2C1=O] | 102 | Ex 16 & Ex 7 | M + H: 412 |

TABLE 1A-continued

| Structure | # | General Procedure(s) | Mass |
|---|---|---|---|
| 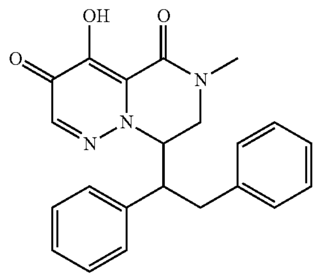 [SMILES: CN1CC(C(Cc2ccccc2)c2ccccc2)n2ncc(=O)c(O)c2C1=O] | 103 | Ex 3 & Ex 7 | M + H: 376 |
| 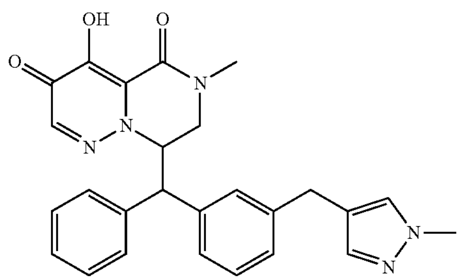 [SMILES: CN1CC(C(c2ccccc2)c2cccc(Cc3cnn(C)c3)c2)n2ncc(=O)c(O)c2C1=O] | 104 | Ex 3 & Ex 7 | M + H: 456 |
| 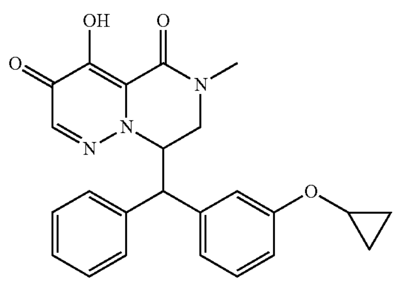 [SMILES: CN1CC(C(c2ccccc2)c2cccc(OC3CC3)c2)n2ncc(=O)c(O)c2C1=O] | 105 | Ex 3 & Ex 7 | M + H: 418 |
| 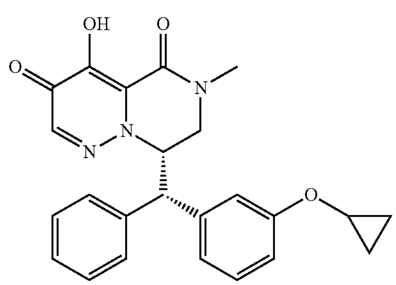 [SMILES: CN1C[C@H]([C@@H](c2ccccc2)c2cccc(OC3CC3)c2)n2ncc(=O)c(O)c2C1=O] | 105-A | Ex 3 & Ex 7 | M + H: 418 |
| 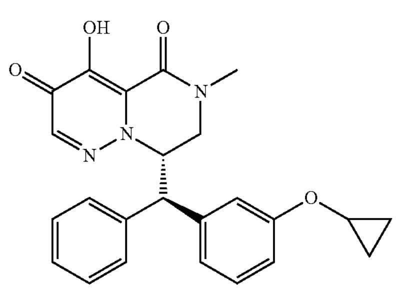 [SMILES: CN1C[C@H]([C@H](c2ccccc2)c2cccc(OC3CC3)c2)n2ncc(=O)c(O)c2C1=O] | 105-B | Ex 3 & Ex 7 | M + H: 418 |

TABLE 1A-continued

| Structure | # | General Procedure(s) | Mass |
|---|---|---|---|
| 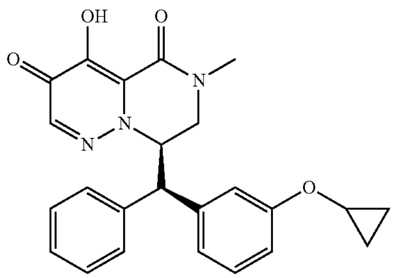 [SMILES: CN1C[C@@H]([C@H](c2ccccc2)c2cccc(OC3CC3)c2)n2ncc(=O)c(O)c2C1=O] | 105-C | Ex 3 & Ex 7 | M + H: 418 |
| 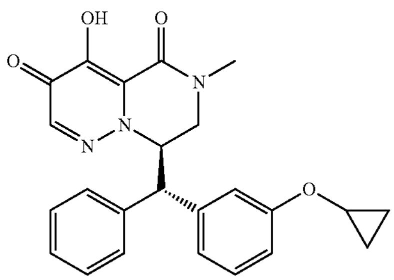 [SMILES: CN1C[C@@H]([C@@H](c2ccccc2)c2cccc(OC3CC3)c2)n2ncc(=O)c(O)c2C1=O] | 105-D | Ex 3 & Ex 7 | M + H: 418 |
| 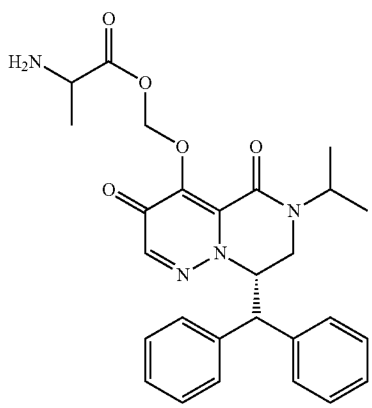 [SMILES: CC(N)C(=O)OCOc1c2n(ncc1=O)[C@@H](C(c1ccccc1)c1ccccc1)CN(C(C)C)C2=O] | 106-A | Ex 12 | M + H: 491 |
| 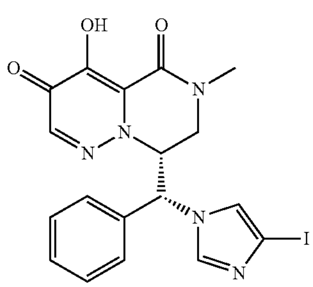 [SMILES: CN1C[C@H]([C@@H](c2ccccc2)n2cnc(I)c2)n2ncc(=O)c(O)c2C1=O] | 107-A | Ex 6 (rte 2) & Ex 7 | M + H: 478 |
| 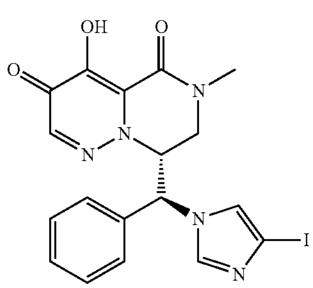 [SMILES: CN1C[C@H]([C@H](c2ccccc2)n2cnc(I)c2)n2ncc(=O)c(O)c2C1=O] | 107-B | Ex 6 (rte 2) & Ex 7 | M + H: 478 |

TABLE 1A-continued

| Structure | # | General Procedure(s) | Mass |
|---|---|---|---|
| 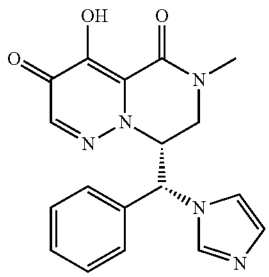 [SMILES: CN1C[C@H]([C@@H](c2ccccc2)n2ccnc2)n2ncc(=O)c(O)c2C1=O] | 108-A | Ex 6 (rte 2) & Ex 7 | M + H: 352 |
| 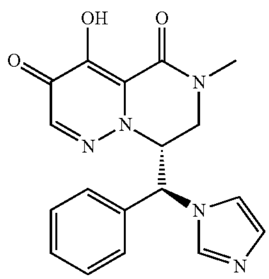 [SMILES: CN1C[C@H]([C@H](c2ccccc2)n2ccnc2)n2ncc(=O)c(O)c2C1=O] | 108-B | Ex 6 (rte 2) & Ex 7 | M + H: 352 |
| 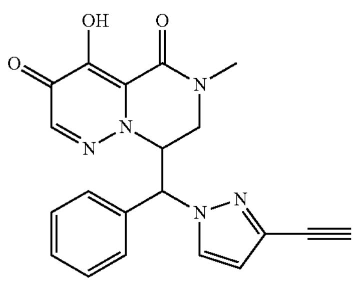 [SMILES: C#Cc1ccn(C(c2ccccc2)C2CN(C)C(=O)c3c(O)c(=O)cnn32)n1] | 109 | Ex 6 (rte 2) & Ex 7 | M + H: 376 |
| 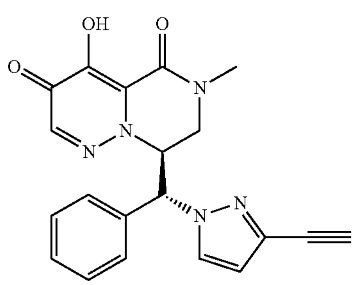 [SMILES: C#Cc1ccn([C@H](c2ccccc2)[C@@H]2CN(C)C(=O)c3c(O)c(=O)cnn32)n1] | 109-A | Ex 6 (rte 2) & Ex 7 | M + H: 376 |
| 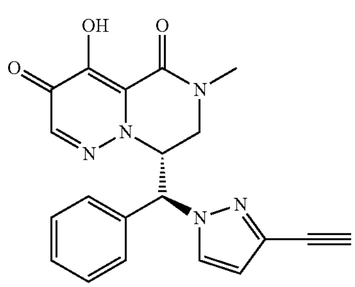 [SMILES: C#Cc1ccn([C@@H](c2ccccc2)[C@H]2CN(C)C(=O)c3c(O)c(=O)cnn32)n1] | 109-B | Ex 6 (rte 2) & Ex 7 | M + H: 376 |

TABLE 1A-continued

| Structure | # | General Procedure(s) | Mass |
|---|---|---|---|
| 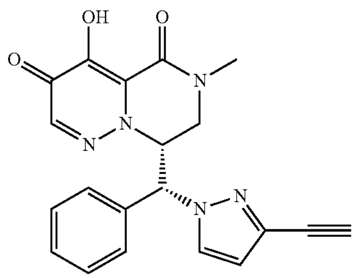 [SMILES: C#Cc1ccn([C@H](c2ccccc2)[C@H]2CN(C)C(=O)c3c(O)c(=O)cnn32)n1] | 109-C | Ex 6 (rte 2) & Ex 7 | M + H: 376 |
| 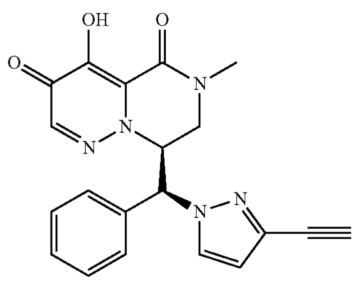 [SMILES: C#Cc1ccn([C@@H](c2ccccc2)[C@@H]2CN(C)C(=O)c3c(O)c(=O)cnn32)n1] | 109-D | Ex 6 (rte 2) & Ex 7 | M + H: 376 |
| 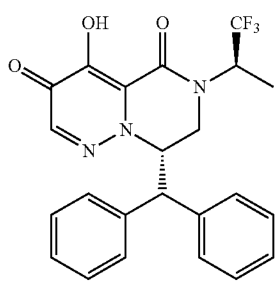 [SMILES: C[C@@H](N1C[C@H](C(c2ccccc2)c2ccccc2)n2ncc(=O)c(O)c2C1=O)C(F)(F)F] | 110-A | Ex 3 & Ex 10 | M + H: 444 |
| 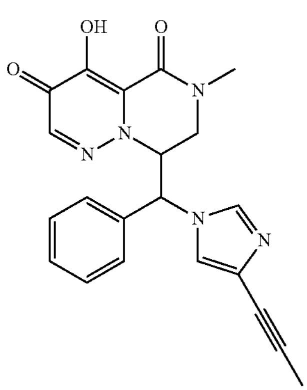 [SMILES: CC#Cc1cn(C(c2ccccc2)C2CN(C)C(=O)c3c(O)c(=O)cnn32)cn1] | 111 | Ex 6 (rte 2) & Ex 7 | M + H: 390 |

TABLE 1A-continued

| Structure | # | General Procedure(s) | Mass |
|---|---|---|---|
| 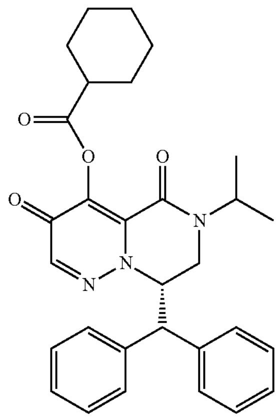 | 112 | Ex 11 | M + H: 500 |
| 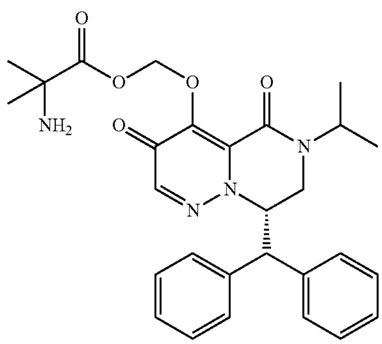 [SMILES: CC(C)N1C[C@H](C(c2ccccc2)c2ccccc2)n2ncc(=O)c(OCOC(=O)C(C)(C)N)c2C1=O] | 113-A | Ex 12 | M + H: 505 |
| 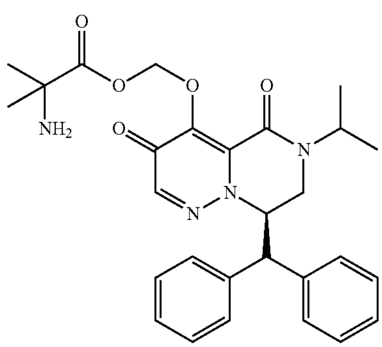 [SMILES: CC(C)N1C[C@@H](C(c2ccccc2)c2ccccc2)n2ncc(=O)c(OCOC(=O)C(C)(C)N)c2C1=O] | 113-B | Ex 12 | M + H: 505 |
| 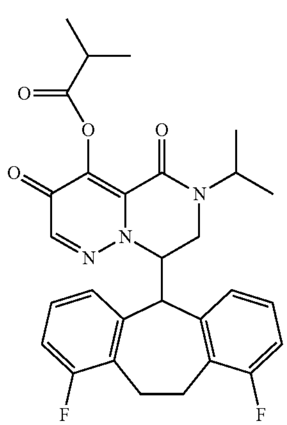 [SMILES: CC(C)C(=O)Oc1c2n(ncc1=O)C(C1c3cccc(F)c3CCc3c(F)cccc31)CN(C(C)C)C2=O] | 114 | Ex 11 | M + H: 522 |

TABLE 1A-continued

| Structure | # | General Procedure(s) | Mass |
|---|---|---|---|
| 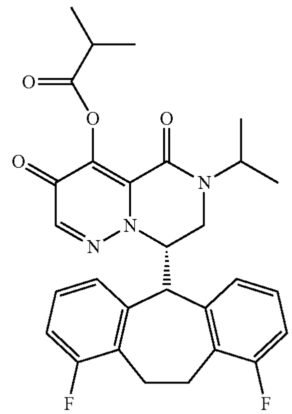 [SMILES: CC(C)C(=O)Oc1c2n(ncc1=O)[C@@H](C1c3cccc(F)c3CCc3c(F)cccc31)CN(C(C)C)C2=O] | 114-A | Ex 11 | M + H: 522 |
| 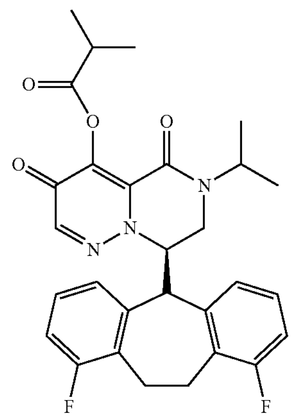 [SMILES: CC(C)C(=O)Oc1c2n(ncc1=O)[C@H](C1c3cccc(F)c3CCc3c(F)cccc31)CN(C(C)C)C2=O] | 114-B | Ex 11 | M + H: 522 |
| 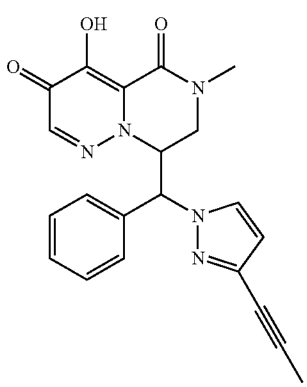 [SMILES: CC#Cc1ccn(C(c2ccccc2)C2CN(C)C(=O)c3c(O)c(=O)cnn32)n1] | 115 | Ex 6 (rte 2) & Ex 7 | M + H: 390 |
| 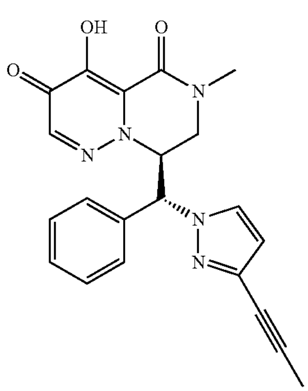 [SMILES: CC#Cc1ccn([C@H](c2ccccc2)[C@@H]2CN(C)C(=O)c3c(O)c(=O)cnn32)n1] | 115-A | Ex 6 (rte 2) & Ex 7 | M + H: 390 |

TABLE 1A-continued

| Structure | # | General Procedure(s) | Mass |
|---|---|---|---|
| 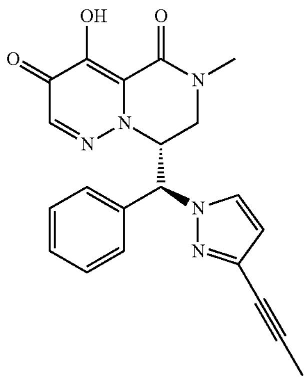 [SMILES: CC#Cc1ccn([C@@H](c2ccccc2)[C@H]2CN(C)C(=O)c3c(O)c(=O)cnn32)n1] | 115-B | Ex 6 (rte 2) & Ex 7 | M + H: 390 |
| 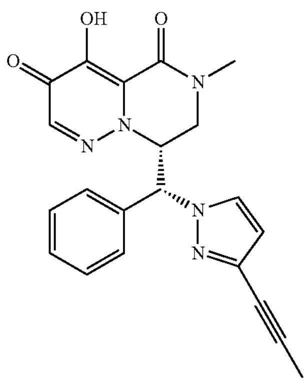 [SMILES: CC#Cc1ccn([C@H](c2ccccc2)[C@H]2CN(C)C(=O)c3c(O)c(=O)cnn32)n1] | 115-C | Ex 6 (rte 2) & Ex 7 | M + H: 390 |
| 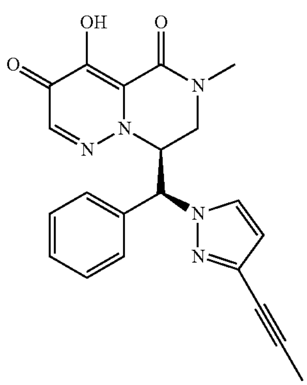 [SMILES: CC#Cc1ccn([C@@H](c2ccccc2)[C@@H]2CN(C)C(=O)c3c(O)c(=O)cnn32)n1] | 115-D | Ex 6 (rte 2) & Ex 7 | M + H: 390 |
| 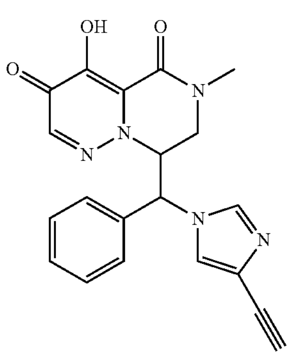 [SMILES: C#Cc1cn(C(c2ccccc2)C2CN(C)C(=O)c3c(O)c(=O)cnn32)cn1] | 116 | Ex 6 (rte 2) & Ex 7 | M + H: 376 |

TABLE 1A-continued
| Structure | # | General Procedure(s) | Mass |
|---|---|---|---|
| 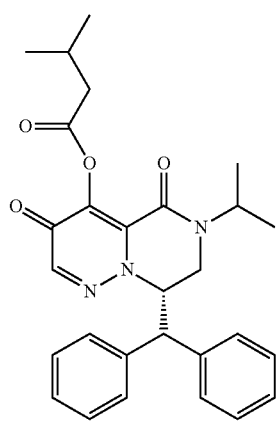 | 117 | Ex 6 (rte 2) & Ex 7 | M + H: 404 |
| 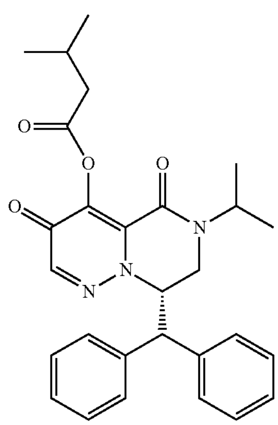 [SMILES: CC(C)CC(=O)Oc1c2n(ncc1=O)[C@@H](C(c1ccccc1)c1ccccc1)CN(C(C)C)C2=O] | 118 | Ex 11 | M + H: 474 |
| 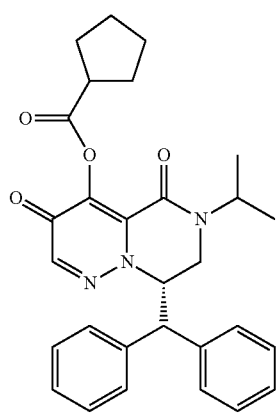 [SMILES: CC(C)N1C[C@H](C(c2ccccc2)c2ccccc2)n2ncc(=O)c(OC(=O)C3CCCC3)c2C1=O] | 119 | Ex 11 | M + H: 486 |

TABLE 1A-continued

| Structure | # | General Procedure(s) | Mass |
|---|---|---|---|
| 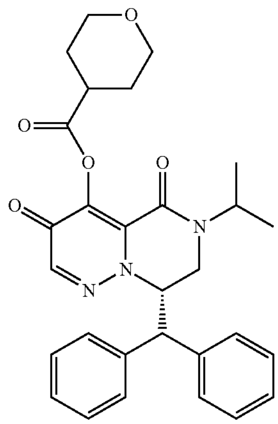 [SMILES: CC(C)N1C[C@H](C(c2ccccc2)c2ccccc2)n2ncc(=O)c(OC(=O)C3CCOCC3)c2C1=O] | 120 | Ex 11 | M + H: 502 |
| 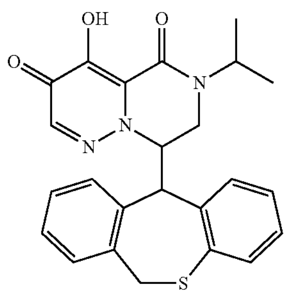 [SMILES: CC(C)N1CC(C2c3ccccc3CSc3ccccc32)n2ncc(=O)c(O)c2C1=O] | 121 | Ex 21 | M + H: 434 |
| 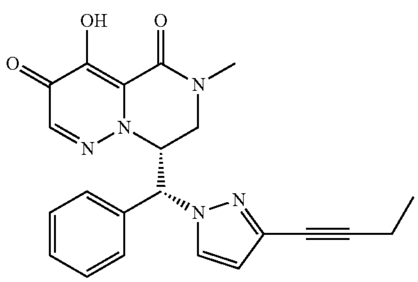 [SMILES: CCC#Cc1ccn([C@H](c2ccccc2)[C@H]2CN(C)C(=O)c3c(O)c(=O)cnn32)n1] | 122 | Ex 6 (rte 2) & Ex 7 | M + H: 404 |
| 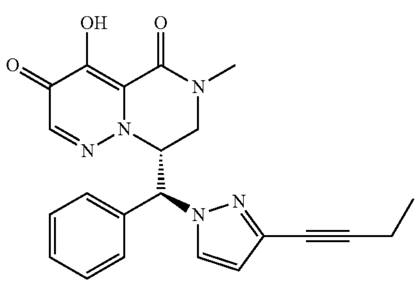 [SMILES: CCC#Cc1ccn([C@@H](c2ccccc2)[C@H]2CN(C)C(=O)c3c(O)c(=O)cnn32)n1] | 123 | Ex 6 (rte 2) & Ex 7 | M + H: 404 |
| 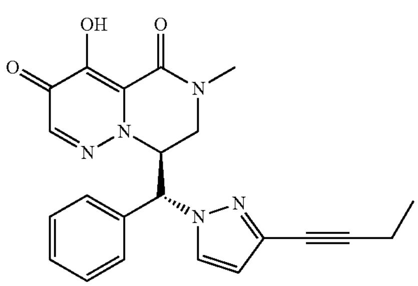 [SMILES: CCC#Cc1ccn([C@H](c2ccccc2)[C@@H]2CN(C)C(=O)c3c(O)c(=O)cnn32)n1] | 124 | Ex 6 (rte 2) & Ex 7 | M + H: 404 |

TABLE 1A-continued

| Structure | # | General Procedure(s) | Mass |
|---|---|---|---|
| 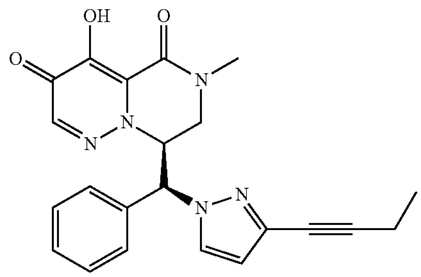 [SMILES: CCC#Cc1ccn([C@@H](c2ccccc2)[C@@H]2CN(C)C(=O)c3c(O)c(=O)cnn32)n1] | 125 | Ex 6 (rte 2) & Ex 7 | M + H: 404 |
| 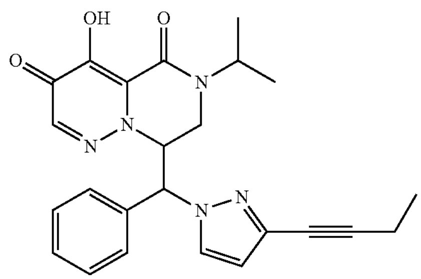 [SMILES: CCC#Cc1ccn(C(c2ccccc2)C2CN(C(C)C)C(=O)c3c(O)c(=O)cnn32)n1] | 126 | Ex 6 (rte 2) & Ex 21 (step 4) | M + H: 432 |
| 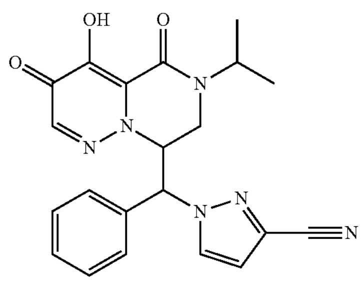 [SMILES: CC(C)N1CC(C(c2ccccc2)n2ccc(C#N)n2)n2ncc(=O)c(O)c2C1=O] | 127 | Ex 6 (rte 2) & Ex 21 (step 4) | M + H: 405 |
| 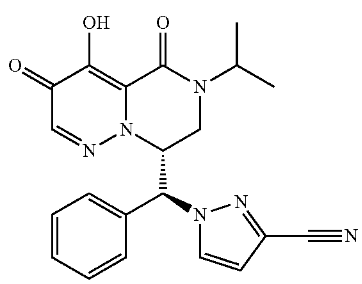 [SMILES: CC(C)N1C[C@H]([C@H](c2ccccc2)n2ccc(C#N)n2)n2ncc(=O)c(O)c2C1=O] | 127-A | Ex 6 (rte 2) & Ex 21 (step 4) | M + H: 405 |
| 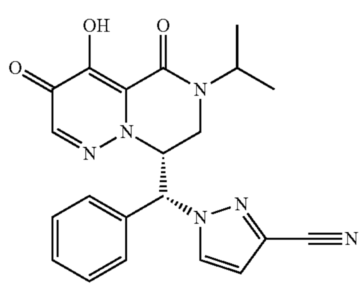 [SMILES: CC(C)N1C[C@H]([C@@H](c2ccccc2)n2ccc(C#N)n2)n2ncc(=O)c(O)c2C1=O] | 127-B | Ex 6 (rte 2) & Ex 21 (step 4) | M + H: 405 |

TABLE 1A-continued

| Structure | # | General Procedure(s) | Mass |
|---|---|---|---|
| (structure) | 127-C | Ex 6 (rte 2) & Ex 21 (step 4) | M + H: 405 |
| (structure) | 127-D | Ex 6 (rte 2) & Ex 21 (step 4) | M + H: 405 |
| (structure) | 128 | Ex 6 (rte 2) & Ex 21 (step 4) | M + H: 363 |
| (structure) | 131 | Ex 6 (rte 2) & Ex 21 (step 4) | M + H: 363 |
| (structure) | 132 | Ex 6 (rte 2) & Ex 21 (step 4) | M + H: 391 |

TABLE 1A-continued

| Structure | # | General Procedure(s) | Mass |
|---|---|---|---|
| 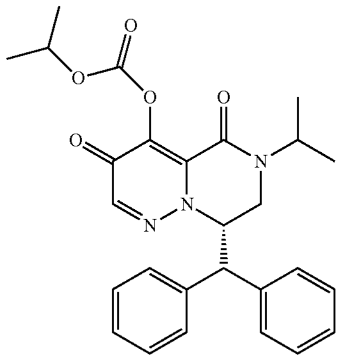 [SMILES: CC(C)OC(=O)Oc1c2n(ncc1=O)[C@@H](C(c1ccccc1)c1ccccc1)CN(C(C)C)C2=O] | 133 | Ex 11 | M + H: 476 |
| 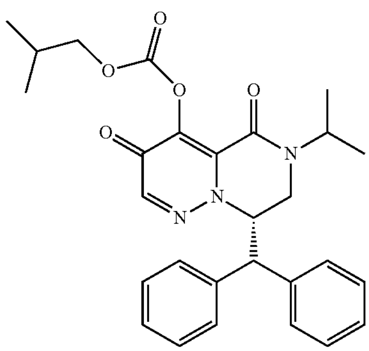 [SMILES: CC(C)COC(=O)Oc1c2n(ncc1=O)[C@@H](C(c1ccccc1)c1ccccc1)CN(C(C)C)C2=O] | 134 | Ex 11 | M + H: 490 |
| 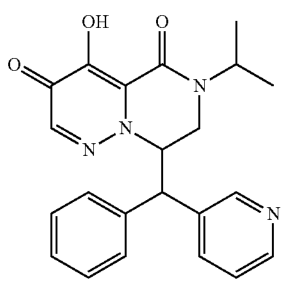 [SMILES: CC(C)N1CC(C(c2ccccc2)c2cccnc2)n2ncc(=O)c(O)c2C1=O] | 135 | Ex 6 (rte 2) & Ex 21 (step 4) | M + H: 391 |
| 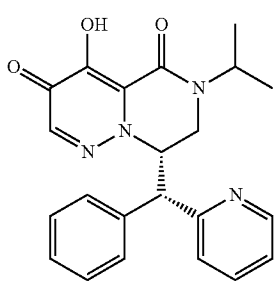 [SMILES: CC(C)N1C[C@H]([C@@H](c2ccccc2)c2ccccn2)n2ncc(=O)c(O)c2C1=O] | 136 | Ex 6 (rte 2) & Ex 21 (step 4) | M + H: 391 |
| 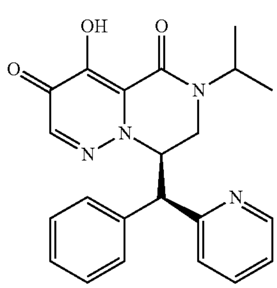 [SMILES: CC(C)N1C[C@@H]([C@H](c2ccccc2)c2ccccn2)n2ncc(=O)c(O)c2C1=O] | 137 | Ex 6 (rte 2) & Ex 21 (step 4) | M + H: 391 |

TABLE 1A-continued

| Structure | # | General Procedure(s) | Mass |
|---|---|---|---|
| (structure) | 138 | Ex 6 (rte 2) & Ex 21 (step 4) | M + H: 391 |

Example 25

Influenza Antiviral Assay

Human lung carcinoma A549 cells (ATCC, Manassas, Va.) were plated at a density of $5\times10^4$ cells/mL ($5\times10^3$ cells/well) in assay media (Ham's F12 media supplemented with 0.3% FBS, 1% penicillin/streptomycin (all Mediatech, Manassas, Va.) and 1% DMSO (Sigma-Aldrich, St Louis, Mo.)) in black 96-well plates. Alternatively, Madin-Darby canine kidney epithelial cells (MDCK, ATCC), were plated at a density of $1\times10^5$ cells/mL ($1\times10^4$ cells/well) in assay media (DMEM supplemented with 0.3% FBS, 1% penicillin/streptomycin and 1% DMSO) in 96-well plates. After 24 hours, serially diluted test compounds were added to cells and incubated for an additional 24 hours. Cells were infected with 250 IU/well of Influenza strain A549_A/WSN/33 (H1N1) (Virapur, San Diego Calif.) and incubated for 20 hours at 37° C., 5% $CO_2$. The cell culture supernatant was aspirated off and 50 µL of 25 µM 2'-(4-Methylumbelliferyl)-a-D-N-acetylneuraminic acid (Sigma-Aldrich) dissolved in 33 mM MES, pH 6.5 (Emerald Biosystems, Bainbridge Island, Wash.) was added to the cells. After incubation for 45 min at 30° C., reactions were stopped by addition of 150 µL stop solution (100 mM glycine, pH 10.5, 25% ethanol, all Sigma-Aldrich). Fluorescence was measured with excitation and emission filters of 355 and 460 nm, respectively, on a Victor X3 multi-label plate reader (Perkin Elmer, Waltham, Mass.). Cytotoxicity of uninfected parallel cultures was determined by addition of 100 µL of CellTiter-Glo® reagent (Promega, Madison, Wis.), and incubation for 10 min at RT. Luminescence was measured on a Victor X3 multi-label plate reader.

Compounds of Formula (I) are active in the assay as noted in Table 2, where 'A' indicates an $EC_{50}$<20 µM, 'B' indicates an $EC_{50}$ of ≥20 µM and <100 µM and 'C' indicates an $EC_{50}$≥100 µM.

TABLE 2

| No. | % Inhibition |
|---|---|
| 1 | A |
| 1-A | A |
| 1-B | A |
| 5 | A |
| 5-A | A |
| 5-B | A |
| 6 | A |
| 6-A | A |
| 6-B | A |
| 7 | A |
| 7-A | A |
| 7-B | A |
| 8 | A |
| 9 | A |
| 9-A | A |
| 9-B | A |
| 10 | A |
| 12 | A |
| 12-A | A |
| 12-B | A |
| 13 | A |
| 13-A | A |
| 13-B | A |
| 14 | A |
| 14-A | A |
| 16 | A |
| 17 | A |
| 17-B | A |
| 18 | A |
| 18-A | A |
| 18-B | A |
| 19 | A |
| 20 | A |
| 21 | A |
| 21-A | A |
| 21-B | A |
| 22 | A |
| 23 | A |
| 24 | A |
| 25 | A |
| 26 | A |
| 27 | A |
| 28 | A |
| 29 | A |
| 30 | B |
| 31 | A |
| 32 | A |
| 33-A | A |
| 33-B | A |
| 34 | A |
| 35-A | A |
| 35-B | A |
| 36 | A |
| 36-B | A |
| 37-A | A |
| 38 | A |
| 39 | A |
| 39-A | A |
| 39-B | A |
| 40 | A |
| 41 | A |
| 41-A | A |
| 42 | A |
| 42-A | A |
| 42-B | B |
| 45 | A |

TABLE 2-continued

| No. | % Inhibition |
|---|---|
| 45-A | A |
| 45-B | B |
| 46-A | A |
| 46-B | B |
| 47 | A |
| 48 | A |
| 49 | A |
| 50 | A |
| 51 | A |
| 51-A | A |
| 52 | A |
| 52-A | A |
| 52-B | A |
| 53-A | A |
| 54 | B |
| 55 | B |
| 56 | A |
| 57 | A |
| 58-A | A |
| 59-A | A |
| 60 | A |
| 61 | A |
| 62 | A |
| 63 | A |
| 63-A | A |
| 63-B | A |
| 64 | A |
| 65-A | A |
| 66-A | A |
| 67-A | A |
| 68-A | A |
| 68-B | A |
| 69-A | A |
| 70-A | A |
| 71 | B |
| 71-A | A |
| 71-B | A |
| 72-A | A |
| 73-A | A |
| 73-B | A |
| 74-A | A |
| 75-A | A |
| 76-A | A |
| 78 | A |
| 79-A | A |
| 80-A | A |
| 81-A | A |
| 81-B | B |
| 82-A | A |
| 83 | A |
| 83-A | A |
| 83-B | B |
| 84-A | A |
| 85-A | B |
| 86-A | A |
| 87-A | A |
| 88-A | A |
| 89 | A |
| 89-A | A |
| 89-B | A |
| 90 | A |
| 91-A | B |
| 92-A | A |
| 93-A | A |
| 94-A | B |
| 95-A | A |
| 96-A | A |
| 97-A | A |
| 98-A | A |
| 99 | B |
| 100 | A |
| 101 | B |
| 102 | B |
| 103 | B |
| 104 | A |
| 105 | B |
| 105-A | A |
| 105-B | A |
| 105-C | A |
| 105-D | B |
| 106-A | A |
| 107-A | B |
| 107-B | B |
| 108-A | B |
| 108-B | B |
| 109 | A |
| 109-A | A |
| 109-B | A |
| 109-C | A |
| 109-D | A |
| 110-A | A |
| 111 | C |
| 112 | A |
| 113-A | A |
| 113-B | B |
| 114 | A |
| 114-A | A |
| 114-B | A |
| 115 | A |
| 115-A | A |
| 115-B | A |
| 115-C | A |
| 115-D | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 127-A | A |
| 127-B | A |
| 127-C | A |
| 127-D | A |
| 128 | A |
| 129 | A |
| 130 | A |
| 131 | A |
| 132 | A |
| 133 | A |
| 134 | A |
| 135 | A |
| 138 | A |

Example 26

EN PA FRET Inhibition Assay

EN PA FRET inhibition assay was performed using a 19 nucleotide synthetic oligoribonucleotide substrate: 5'-FAM-AUUUUGUUUUUAAUAUUUC-BHQ-3' (Integrated DNA Technologies, Inc., Coralville, Iowa) (SEQ. ID. NO. 1). Upon RNA cleavage, the fluorescent FAM group is released from the BHQ quencher. The PA sequence used to produce active enzyme is derived from any one of multiple influenza A virus strains (e.g., A/goose/Nanchang/3-120/01 (H3N2), A/Victoria/3/1975 (H3N2), A/Brisbane/10/2007 (H3N2), A/WSN/33 (H1N1), A/CA/4/2009 (H1N1), A/CA/5/2009 (H1N1), A/Shanghai/1/2013 (H7N9), A/Guizhou/1/2009 (H5N1)). The full length recombinant protein was expressed from a baculovirus vector in insect cells. Full length EN PA was used in this assay at an effective concentration of 1 to 10 Nm, together with 50 Nm FRET probe with a final volume of 20 ml cleavage buffer (20 Mm Tris Ph8, 100 Mm NaCl, 5% Glycerol, 10 Mm β-ME, 0.01% Tween-20, 2 Mm $MnCl_2$).

Compounds described herein were added to a 384-well black polypropylene plate. Fluorescence was measured in a continuous mode up to 30 minutes with a Wallac 1420 Victor³V multilabel counter (PerkinElmer Life Sciences, Shelton, Conn.) (excitation 485 nm; emission 535 nm). Measured $IC_{50}$ is defined as the concentration at which fluorescence is 50% that of the uninhibited control (DMSO). $IC_{50}$ was calculated by fitting the data to the sigmoidal equation Y=% Min+(% Max−% Min)/(1+X/$IC_{50}$), where Y corresponds to the percent relative enzyme activity, Max is the maximum enzyme activity in the presence of DMSO, Min is the inhibited activity at saturating concentration of compound, and X corresponds to the compound concentration. The $IC_{50}$ values were derived from the mean of a minimum of two independent experiments.

Compounds of Formula (I) are potent in the assay as noted in Table 3, where 'A' indicates an $IC_{50}$<250 Nm, 'B' indicates an $IC_{50}$ of ≥250 Nm and <1000 Nm and 'C' indicates an $IC_{50}$≥1000 Nm.

TABLE 3

| No. | Potency |
| --- | --- |
| 1 | A |
| 1-A | A |
| 1-B | B |
| 2 | A |
| 3 | A |
| 4 | A |
| 5 | A |
| 5-A | A |
| 5-B | B |
| 6 | A |
| 6-A | A |
| 6-B | B |
| 7 | A |
| 7-A | A |
| 7-B | A |
| 8 | A |
| 9 | A |
| 9-A | A |
| 9-B | A |
| 10 | A |
| 11 | A |
| 12 | A |
| 12-A | A |
| 12-B | A |
| 12-C | A |
| 12-D | B |
| 12-E | A |
| 13 | A |
| 13-A | A |
| 13-B | B |
| 14 | A |
| 14-A | A |
| 14-B | A |
| 15 | C |
| 16 | B |
| 17 | A |
| 17-A | A |
| 17-B | A |
| 18 | A |
| 18-A | A |
| 18-B | A |
| 19 | A |
| 20 | A |
| 21 | A |
| 21-A | A |
| 21-B | A |
| 22 | A |
| 23 | A |
| 24 | A |
| 25 | A |
| 26 | A |
| 27 | A |
| 28 | A |

TABLE 3-continued

| No. | Potency |
| --- | --- |
| 29 | A |
| 30 | A |
| 31 | A |
| 32 | A |
| 33-A | A |
| 33-B | A |
| 34 | A |
| 35-A | A |
| 35-B | B |
| 36 | A |
| 36-B | C |
| 37-A | A |
| 38 | A |
| 39 | A |
| 39-A | A |
| 39-B | B |
| 40 | A |
| 41 | A |
| 41-A | A |
| 41-B | B |
| 42 | A |
| 42-A | A |
| 42-B | B |
| 43 | A |
| 44 | A |
| 45 | A |
| 45-A | A |
| 45-B | A |
| 46-A | A |
| 46-B | A |
| 47 | A |
| 48 | A |
| 49 | A |
| 50 | A |
| 51 | A |
| 51-A | A |
| 52 | A |
| 52-A | A |
| 52-B | A |
| 53-A | A |
| 54 | A |
| 55 | A |
| 56 | A |
| 57 | A |
| 58-A | A |
| 59-A | A |
| 60 | A |
| 61 | A |
| 62 | A |
| 63 | A |
| 63-A | A |
| 63-B | B |
| 64 | A |
| 65-A | A |
| 66-A | A |
| 67-A | A |
| 68-A | A |
| 68-B | B |
| 69-A | A |
| 70-A | A |
| 71 | B |
| 71-A | A |
| 71-B | A |
| 72-A | A |
| 73-A | A |
| 73-B | B |
| 74-A | A |
| 75-A | A |
| 76-A | A |
| 78 | A |
| 79-A | A |
| 80-A | A |
| 81-A | A |
| 81-B | A |
| 82-A | A |
| 82-B | B |
| 83 | A |
| 83-A | A |

TABLE 3-continued

| No. | Potency |
|---|---|
| 83-B | B |
| 84-A | A |
| 85-A | C |
| 86-A | A |
| 87-A | A |
| 88-A | B |
| 89 | A |
| 89-A | A |
| 89-B | A |
| 90 | A |
| 91-A | C |
| 92-A | A |
| 93-A | A |
| 94-A | C |
| 95-A | A |
| 96-A | A |
| 97-A | A |
| 98-A | A |
| 99 | A |
| 100 | A |
| 101 | A |
| 102 | A |
| 103 | A |
| 104 | A |
| 105 | A |
| 105-A | A |
| 105-B | A |
| 105-C | B |
| 105-D | C |
| 106-A | A |
| 107-A | A |
| 107-B | A |
| 108-A | A |
| 108-B | A |
| 109 | A |
| 109-A | A |
| 109-B | A |
| 109-C | A |
| 109-D | B |
| 110-A | A |
| 111 | B |
| 112 | B |
| 113-A | A |
| 113-B | B |
| 114 | A |
| 114-A | A |
| 114-B | C |
| 115 | A |
| 115-A | C |
| 115-B | A |
| 115-C | A |
| 115-D | C |
| 116 | A |
| 117 | A |
| 118 | B |
| 119 | A |
| 120 | A |
| 121 | A |
| 122 | A |
| 123 | A |
| 124 | B |
| 125 | A |
| 126 | A |
| 127 | A |
| 127-A | A |
| 127-B | A |
| 127-C | B |
| 127-D | B |
| 128 | A |
| 129 | A |
| 131 | A |
| 132 | A |
| 133 | C |
| 134 | C |
| 135 | A |
| 138 | A |

Example 27

Influenza B Assay

Viruses:

The influenza virus strains B/Malaysia/2506/2004 and B/Victoria/504/2000 were purchased from Virapur (San Diego, Calif.). The viruses had been previously titrated on MDCK cells at Virapur using the $TCID_{50}$ method.

Human Cell Lines:

Human lung carcinoma A549 cells were purchased from the ATCC (Manassas, Va., cat# CCL-185) and cultured in Ham's F12 media supplemented with 10% FBS, 1% penicillin/streptomycin, 1% HEPES, 1% non-essential amino acids and 1% Glutamine (all Mediatech, Manassas, Va.). A549 cells were maintained at 37° C. in a humidified 5% $CO_2$ atmosphere.

Fluorescence-Based Influenza Neuraminidase Assay:

Determination of the $EC_{50}$ and $CC_{50}$ in the fluorescence-based Influenza neuraminidase assay was performed by the following procedure. 24 hours prior to infection, A549 cells in assay media (Ham's F12 media supplemented with 0.3% FBS, 1% penicillin/streptomycin, 1% HEPES, 1% non-essential amino acids and 1% Glutamine) were plated at a density of $1 \times 10^5$ cells/ml ($1 \times 10^4$ cells/well) in white 96-well plates. On the day of infection, serially diluted compounds were added to cells. Cells were infected with 500 IU/well of influenza strains B/Malaysia/2506/2004 or B/Victoria/504/2000 and incubated for 20 h at 37° C., 5% $CO_2$. The cell culture supernatant was aspirated off and 50 µl of 25 µM 2'-(4-Methylumbelliferyl)-a-D-N-acetylneuraminic acid (Sigma-Aldrich) dissolved in 33 mM MES, pH 6.5 (Emerald Biosystems, Bainbridge Island, Wash.) was added to the cells. After incubation for 45 minutes at 37° C., reactions were stopped by the addition of 150 µl stop solution (100 mM glycine, pH 10.5, 25% ethanol, all Sigma-Aldrich). Fluorescence was measured with excitation and emission filters of 355 and 460 nm, respectively, on a Victor X3 multi-label plate reader (Perkin Elmer, Waltham, Mass.).

Cell Viability Assay:

Promega's CellTiter-Glo Luminescent Cell Viability Assay (Cat. #G7572) was used to measure cell viability. Assay plates were set up as described above and CellTiter-Glo reagent (100 µL) was added to each well and incubated at room temperature for 10 minutes. Luminescence was recorded using a Perkin Elmer multilabel counter Victor3V. The $CC_{50}$, the concentration of the drug required to reduce the number of viable cells by 50% in relation to the untreated cell control value, was calculated from the plot of percentage reductions of the luminescence value against the drug concentrations using the Microsoft Excel forecast function. All compound tested had $CC_{50}$ values >1 µM.

Compounds of Formula (I) are active in the assay as noted in Table 4, where 'A' indicates an $EC_{50}<20$ µM, 'B' indicates an $EC_{50}$ of ≥20 µM and <100 µM and 'C' indicates an $EC_{50} \geq 100$ µM.

TABLE 4

| No. | Potency |
|---|---|
| 6-A | A |
| 7-A | A |
| 21-A | A |
| 39-A | A |
| 41-A | A |
| 68-A | A |
| 76-A | A |

Example 28

Combination Studies 24 hours prior to infection, dog kidney epithelial MDCK cells (ATCC, Manassas, Va.) were plated in maintenance media (DMEM media supplemented with 10% FBS, 1% penicillin/streptomycin, 1% non-essential amino acids, 1% Glutamine and 1% HEPES (all Mediatech, Manassas, Va.) at a density of $15 \times 10^4$ cells/ml ($15 \times 10^3$ cells/well) in white 96-well plates with clear bottoms. At the day of infection, maintenance media was removed from cells. Compounds were serially diluted in assay media (MEM media without phenol-red, supplemented with 0.3% FBS, 1% penicillin/streptomycin, 1% non-essential amino acids, 1% Glutamine and 1% HEPES (all Mediatech, Manassas, Va.) and 4 µg/ml TPCK-treated trypsin (Affymetrix, Santa Clara, Calif.)) and added to cells. To determine drug-drug interactions (synergy), one compound was diluted horizontally and the second compound vertically to create a checker-board matrix of compound combinations at variable concentrations. Cells were infected at a MOI of 0.001 to 0.05 with Influenza strain A/Port Chalmers/1/73 (H3N2) (Virapur, San Diego Calif.) and incubated for three days at 37° C., 5% $CO_2$. 100 µL of the cell culture supernatant was aspirated off and 100 µl CellTiter-Glo® reagent (Promega, Madison, Wis.) was added to the cells. After incubation for 10 mins at R.T., Luminescence was measured on a Victor X3 multi-label plate reader (Perkin Elmer, Waltham, Mass.). Cytotoxicity of uninfected parallel cultures was determined at the same time. Drug interactions were calculated using the MacSynergy™ II tool developed by M. N. Prichard and C. Shipman Jr. (Prichard, M. N. et al., *Antiviral Res.* (1990) 14(4-5):181-205).

The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

The synergy volume results for the combinations are provided in Table 5.

TABLE 5

| Compound 1 | Compound 2 | Class of Compound 2 | Synergy Volume ($\mu M^2$ %) | Observed Result |
|---|---|---|---|---|
| 6-A | Oseltamivir | Neuraminidase-Inhibitor | 233 | strongly synergistic |
| 114-A | Oseltamivir | Neuraminidase-Inhibitor | 205 | strongly synergistic |
| 6-A | Zanamivir | Neuraminidase-Inhibitor | 217 | strongly synergistic |
| 114-A | Zanamivir | Neuraminidase-Inhibitor | 127 | strongly synergistic |
| 6-A | Laninamivir | Neuraminidase-Inhibitor | 276 | strongly synergistic |
| 6-A | Peramivir | Neuraminidase-Inhibitor | 308 | strongly synergistic |
| 114-A | Peramivir | Neuraminidase-Inhibitor | 100 | strongly synergistic |
| 6-A | Amantadine | M2 Channel-Inhibitor | 22.5 | additive |
| 114-A | Amantadine | M2 Channel-Inhibitor | 86 | moderately synergistic |
| 6-A | Rimantadine | M2 Channel-Inhibitor | 4.6 | additive |
| 114-A | Rimantadine | M2 Channel-Inhibitor | 45 | synergistic |
| 6-A | Ribavirin | Polymerase Inhibitor | 109 | strongly synergistic |
| 114-A | Ribavirin | Polymerase Inhibitor | 55 | moderately synergistic |
| 6-A | Favipiravir (T-705) | Polymerase Inhibitor | 185 | strongly synergistic |
| 114-A | Favipiravir (T-705) | Polymerase Inhibitor | 132 | strongly synergistic |

TABLE 5-continued

| Compound 1 | Compound 2 | Class of Compound 2 | Synergy Volume ($\mu M^2$ %) | Observed Result |
|---|---|---|---|---|
| 6-A | 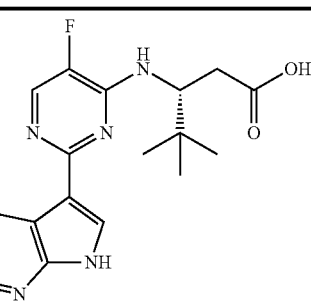 | Polymerase Inhibitor | 440 | strongly synergistic |
| 6-A | 21-A | PA Inhibitor | 4.1 | additive |
| 6-A | Consensus Interferon alpha⁺ | Immuno-modulator | 70 | moderately synergistic |

⁺obtained from Three Rivers Pharmaceuticals, LLC.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for ameliorating or treating an influenza virus infection comprising administering an effective amount of a compound of Formula (I), or a pharmaceutically acceptable salt thereof, to a subject suffering from the influenza virus infection, wherein the compound of Formula (I) has the structure:

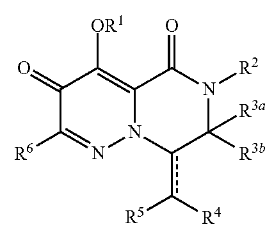

(I)

wherein:

- - - - is a single bond or double bond;

$R^1$ is selected from the group consisting of hydrogen, an unsubstituted $C_{1-4}$ alkyl, $—C(=O)Y^1$, $—C(=O)—O—Y^1$, $—(CH_2)—O—C(=O)—Y^1$, $—(CH_2)—O—C(=O)—O—Y^1$, $—(CHCH_3)—O—C(=O)—Y^1$ and $—(CHCH_3)—O—C(=O)—O—Y^1$;

$R^2$ is selected from the group consisting of hydrogen, an optionally substituted $C_{1-6}$ alkyl, an optionally substituted heterocyclyl, an optionally substituted cycloalkyl ($C_{1-6}$ alkyl), an optionally substituted aryl($C_{1-6}$ alkyl), an optionally substituted heteroaryl($C_{1-6}$ alkyl) and an optionally substituted heterocyclyl($C_{1-6}$ alkyl);

$R^{3a}$ and $R^{3b}$ are independently hydrogen or an optionally substituted $C_{1-4}$ alkyl;

$R^4$ and $R^5$ are independently selected from the group consisting of hydrogen, an optionally substituted aryl, an optionally substituted aryl($C_{1-6}$ alkyl), an optionally substituted heteroaryl and an optionally substituted heteroaryl($C_{1-6}$ alkyl), provided that at least one of $R^4$ and $R^5$ is not hydrogen; or $R^4$ and $R^5$ are taken together with the carbon to which they are attached to form an optionally substituted tricyclic cycloalkenyl or an optionally substituted tricyclic heterocyclyl;

$R^6$ is selected from the group consisting of hydrogen, halogen, —CN, an optionally substituted $C_{1-6}$ alkyl, an optionally substituted aryl, an optionally substituted heteroaryl, —CH$_2$OH, —CH($Y^2$)(OH) and —C(O)$Y^2$; and $Y^1$ and $Y^2$ are independently selected from the group consisting of an optionally substituted $C_{1-6}$ alkyl, an optionally substituted $C_{3-6}$ cycloalkyl, an optionally substituted aryl, an optionally substituted heteroaryl, an optionally substituted heterocyclyl, a mono-substituted amino group, and a di-substituted amino group.

2. A method for ameliorating or treating an influenza virus infection comprising contacting a cell infected with the influenza virus with an effective amount of a compound of Formula (I), or a pharmaceutically acceptable salt thereof, wherein the compound of Formula (I) has the structure:

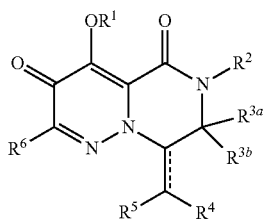

wherein:

═══ is a single bond or double bond;

$R^1$ is selected from the group consisting of hydrogen, an unsubstituted $C_{1-4}$ alkyl, —C(═O)$Y^1$, —C(═O)—O—$Y^1$, —(CH$_2$)—O—C(═O)—$Y^1$, —(CH$_2$)—O—C(═O)—O—$Y^1$, —(CHCH$_3$)—O—C(═O)—$Y^1$ and —(CHCH$_3$)—O—C(═O)—O—$Y^1$;

$R^2$ is selected from the group consisting of hydrogen, an optionally substituted $C_{1-6}$ alkyl, an optionally substituted heterocyclyl, an optionally substituted cycloalkyl ($C_{1-6}$ alkyl), an optionally substituted aryl($C_{1-6}$ alkyl), an optionally substituted heteroaryl($C_{1-6}$ alkyl) and an optionally substituted heterocyclyl($C_{1-6}$ alkyl);

$R^{3a}$ and $R^{3b}$ are independently hydrogen or an optionally substituted $C_{1-4}$ alkyl;

$R^4$ and $R^5$ are independently selected from the group consisting of hydrogen, an optionally substituted aryl, an optionally substituted aryl($C_{1-6}$ alkyl), an optionally substituted heteroaryl and an optionally substituted heteroaryl($C_{1-6}$ alkyl), provided that at least one of $R^4$ and $R^5$ is not hydrogen; or $R^4$ and $R^5$ are taken together with the carbon to which they are attached to form an optionally substituted tricyclic cycloalkenyl or an optionally substituted tricyclic heterocyclyl;

$R^6$ is selected from the group consisting of hydrogen, halogen, —CN, an optionally substituted $C_{1-6}$ alkyl, an optionally substituted aryl, an optionally substituted heteroaryl, —CH$_2$OH, —CH($Y^2$)(OH) and —C(O)$Y^2$; and $Y^1$ and $Y^2$ are independently selected from the group consisting of an optionally substituted $C_{1-6}$ alkyl, an optionally substituted $C_{3-6}$ cycloalkyl, an optionally substituted aryl, an optionally substituted heteroaryl, an optionally substituted heterocyclyl, a mono-substituted amino group, and a di-substituted amino group.

3. The method of claim 2, further comprising contacting the cell with one or more anti-influenza agents.

4. The method of claim 3, wherein the one or more anti-influenza agents is selected from the group consisting of a neuraminidase inhibitor, a M2 protein inhibitor, a polymerase inhibitor, a PB2 inhibitor, amantadine, rimantadine, zanamivir, oseltamivir, peramivir, laninamivir, laninamivir octanoate, favipiravir, fludase, ADS-8902, an immunomodulator, ribavirin, (R)-3-((5-fluoro-2-(5-fluoro-1H-pyrrolo[2,3-b]pyridin-3-yl)pyrimidin-4-yl)amino)-4,4-dimethylpentanoic acid, and (2S, 3S)-3-((5-fluoro-2-(5-fluoro-1H-pyrrolo[2,3-b]pyridin-3-yl)pyrimidin-4-yl)amino)bicycle[2.2.2]octane-2-carboxylic acid (VX-787).

5. The method of claim 2, wherein the influenza virus is influenza A virus.

6. The method of claim 2, wherein the influenza virus is influenza B virus.

7. The method of claim 1, wherein $R^4$ is an optionally substituted aryl; and $R^5$ is an optionally substituted aryl.

8. The method of claim 7, wherein $R^4$ is an optionally substituted phenyl; and $R^5$ is an optionally substituted phenyl.

9. The method of claim 1, wherein $R^2$ is an optionally substituted $C_{1-6}$ alkyl.

10. The method of claim 1, wherein $R^1$ is hydrogen.

11. The method of claim 1, wherein $R^1$ is —C(═O)$Y^1$, —C(═O)—O—$Y^1$, —(CH$_2$)—O—C(═O)—$Y^1$, —(CH$_2$)—O—C(═O)—O—$Y^1$, —(CHCH$_3$)—O—C(═O)—$Y^1$ and —(CHCH$_3$)—O—C(═O)—O—$Y^1$.

12. The method of claim 11, wherein $R^1$ is —C(═O)$Y^1$.

13. The method of claim 12, wherein $Y^1$ is an optionally substituted $C_{1-6}$ alkyl.

14. The method of claim 1, wherein $R^6$ is hydrogen.

15. The method of claim 1, wherein ═══ is a single bond.

16. The method of claim 1, wherein $R^{3a}$ is hydrogen; and $R^{3b}$ is hydrogen.

17. The method of claim 1, wherein the compound is selected from the group consisting of:

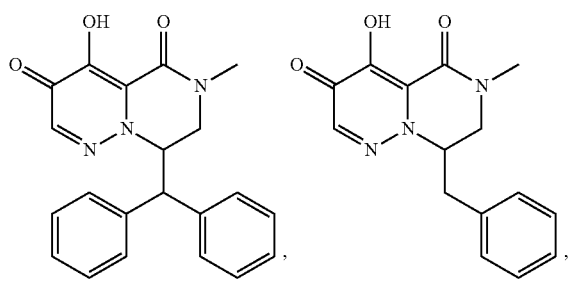

211
-continued
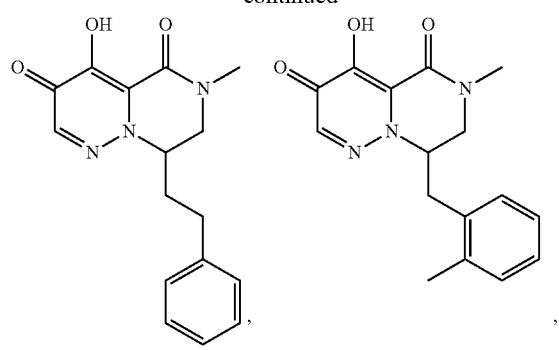
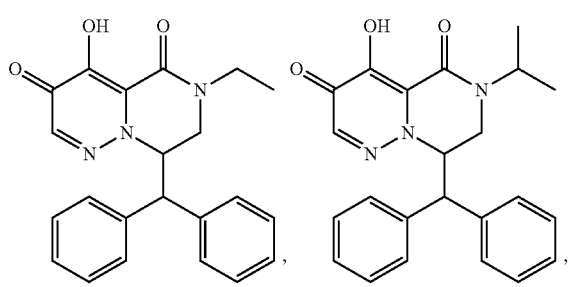
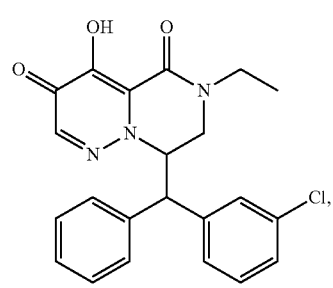
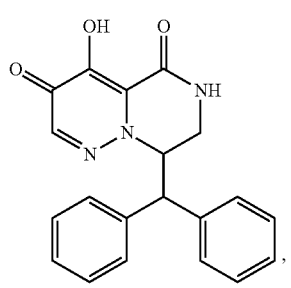
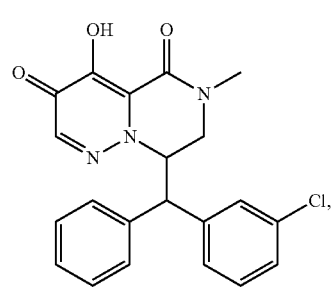
212
-continued
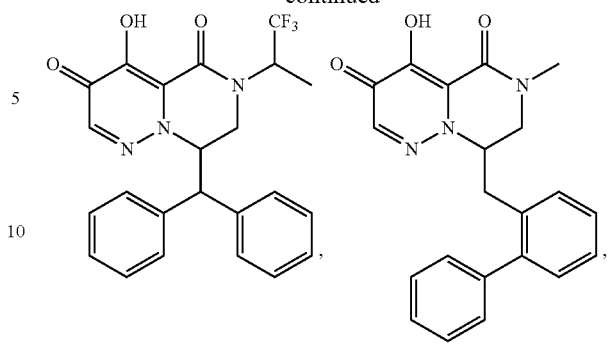
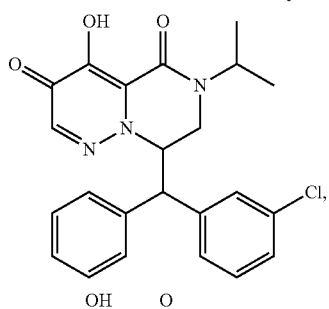
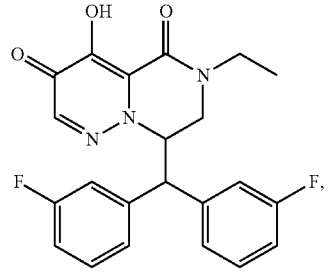
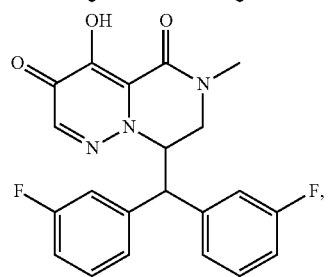
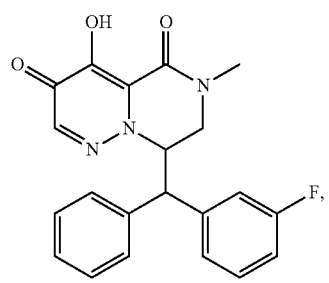
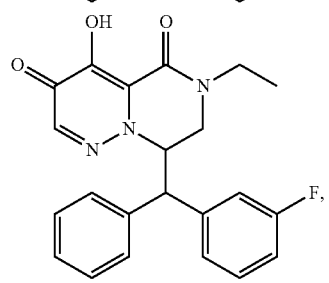

-continued
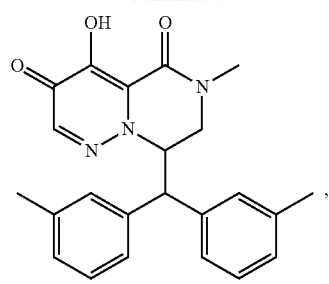
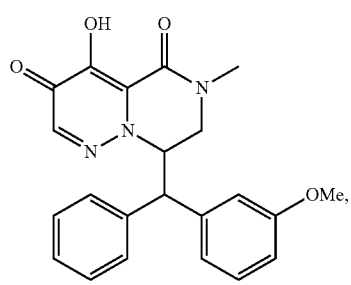
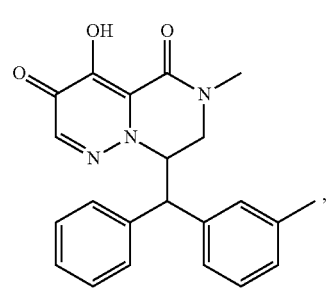
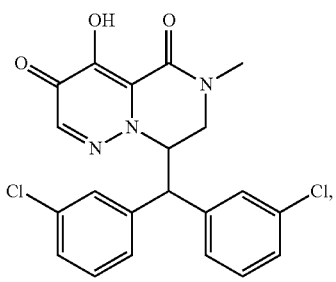
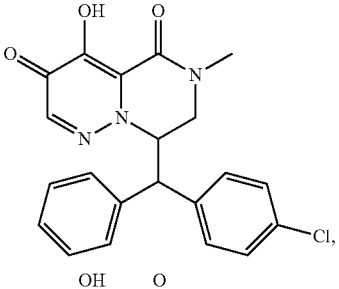
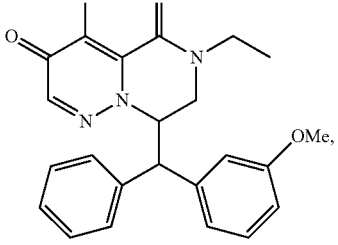
-continued
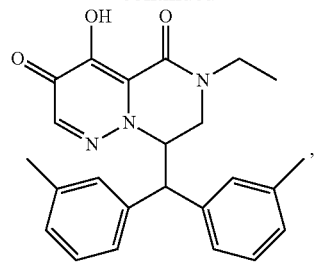
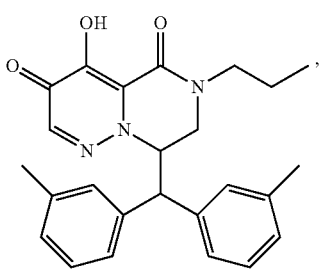
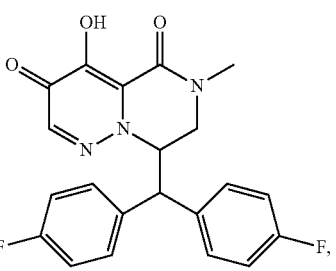
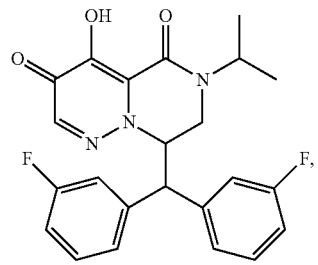
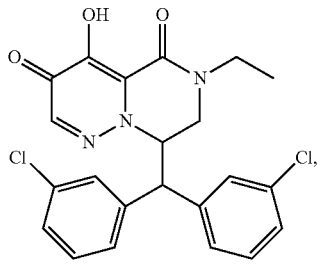
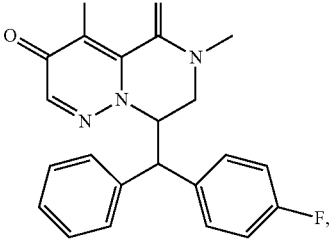

215
-continued
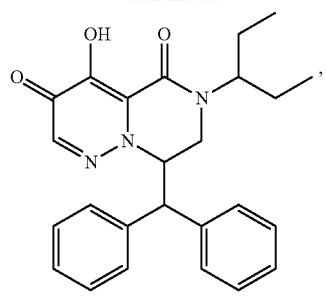
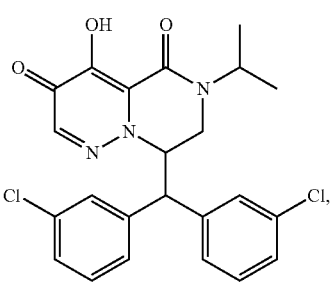
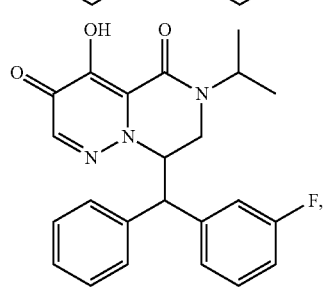
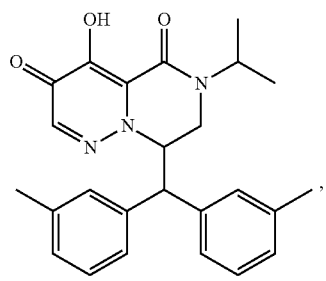
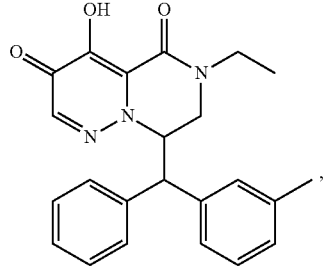
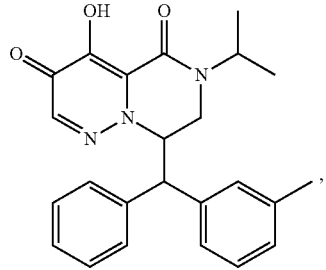
216
-continued
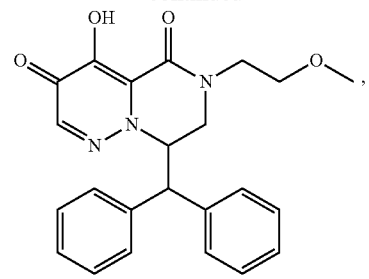
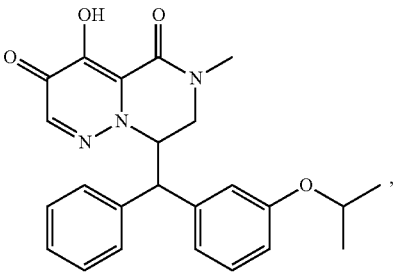
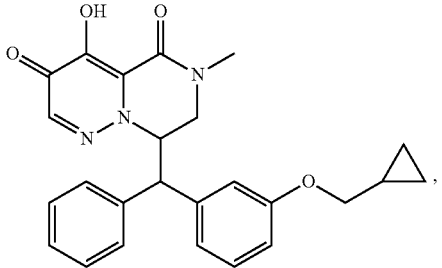
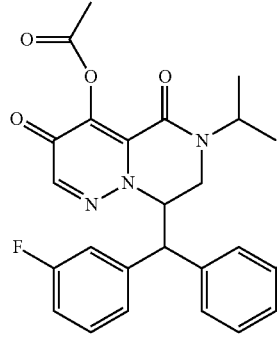
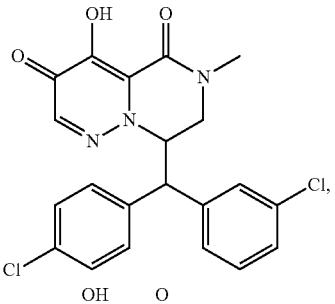
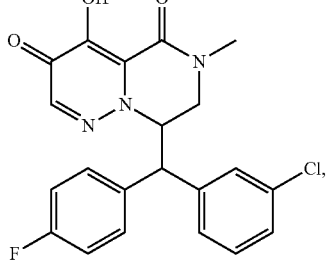

217
-continued
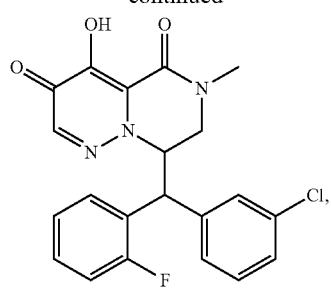
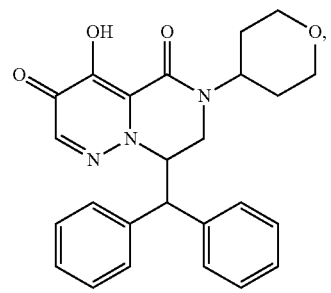
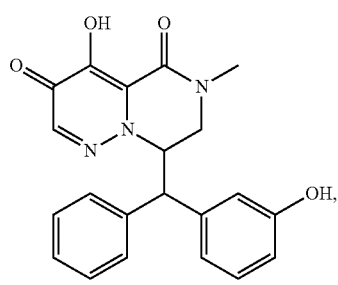
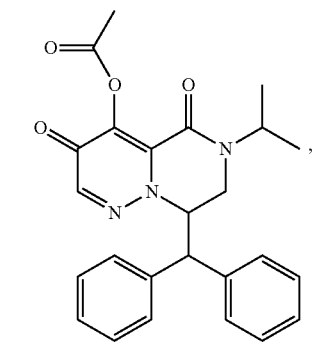
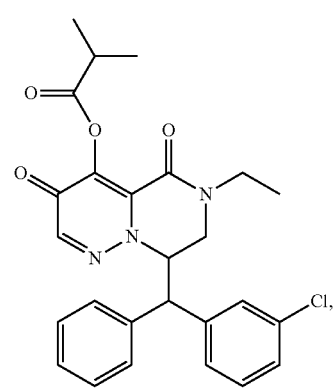
218
-continued
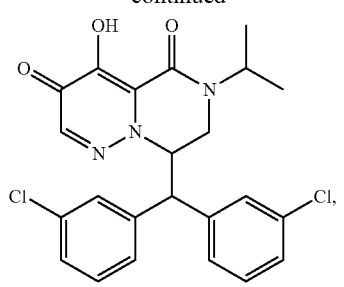
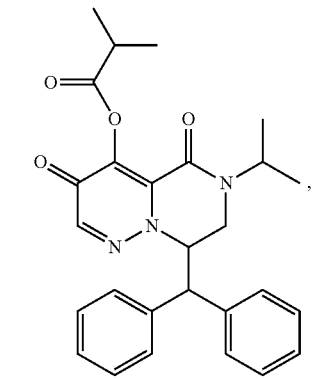
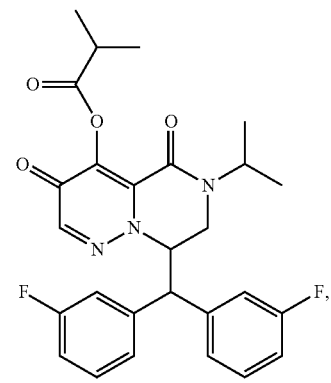
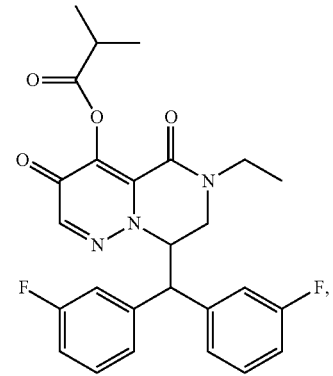
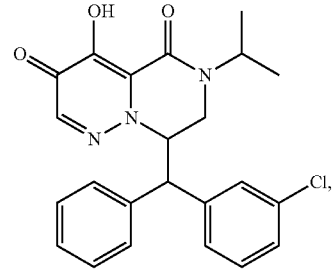

219
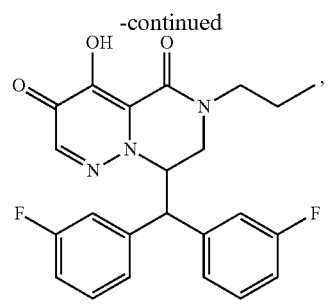
,
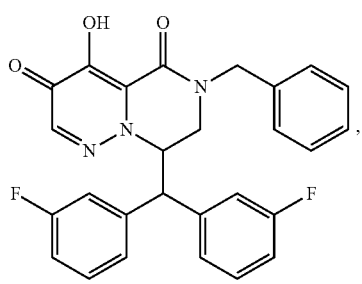
,
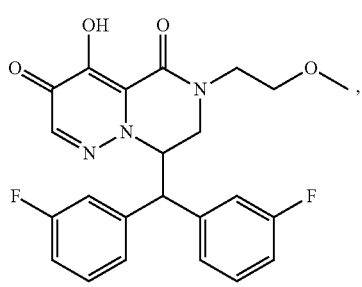
,
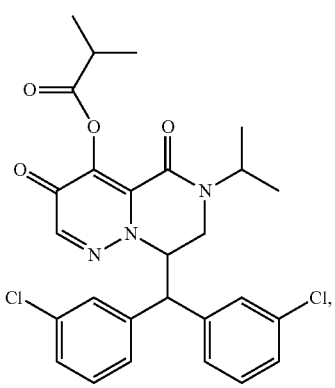
,
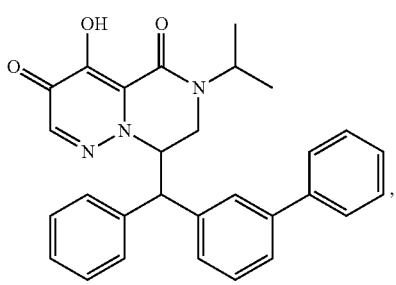
,
220
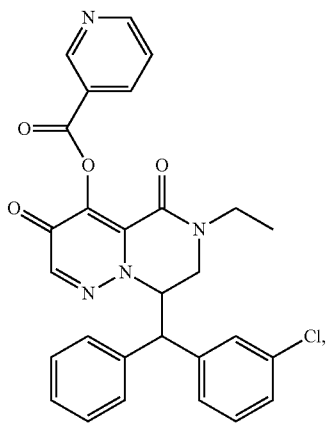
,
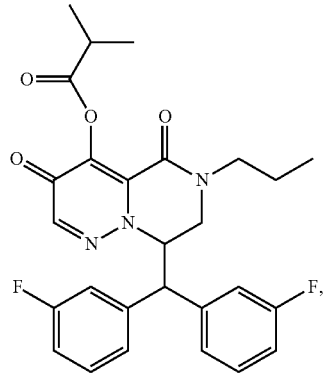
,
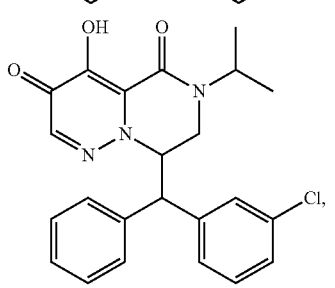
,
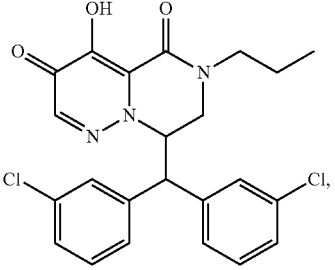
,
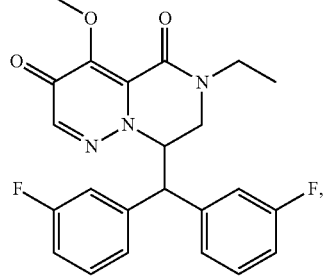
, 221
-continued
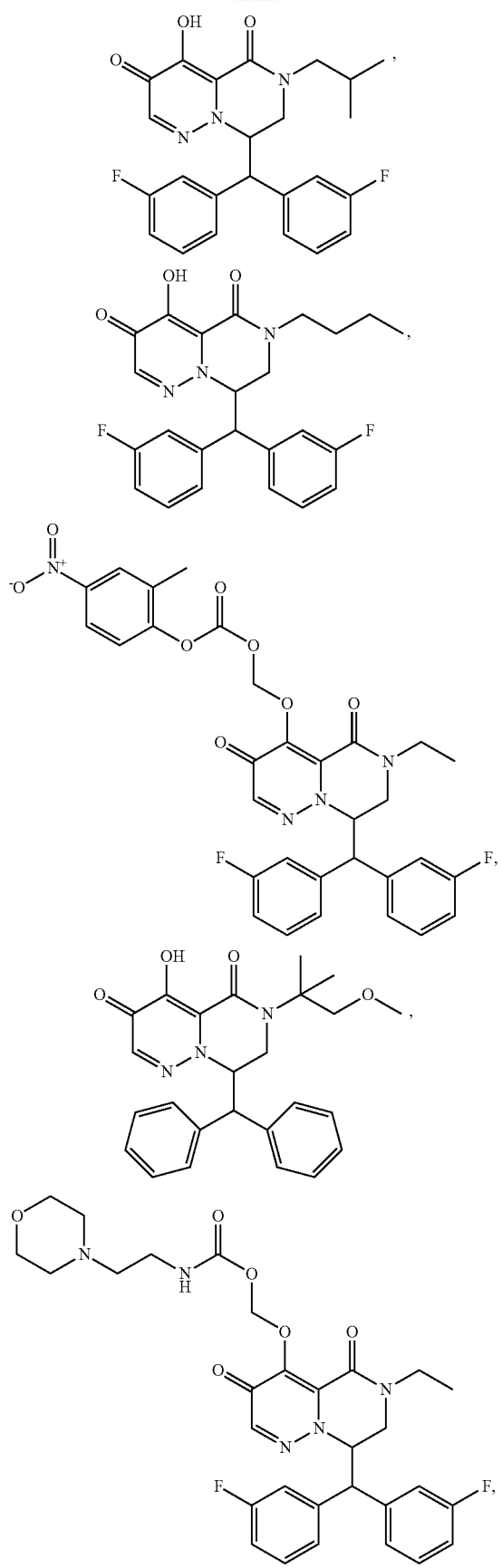
222
-continued
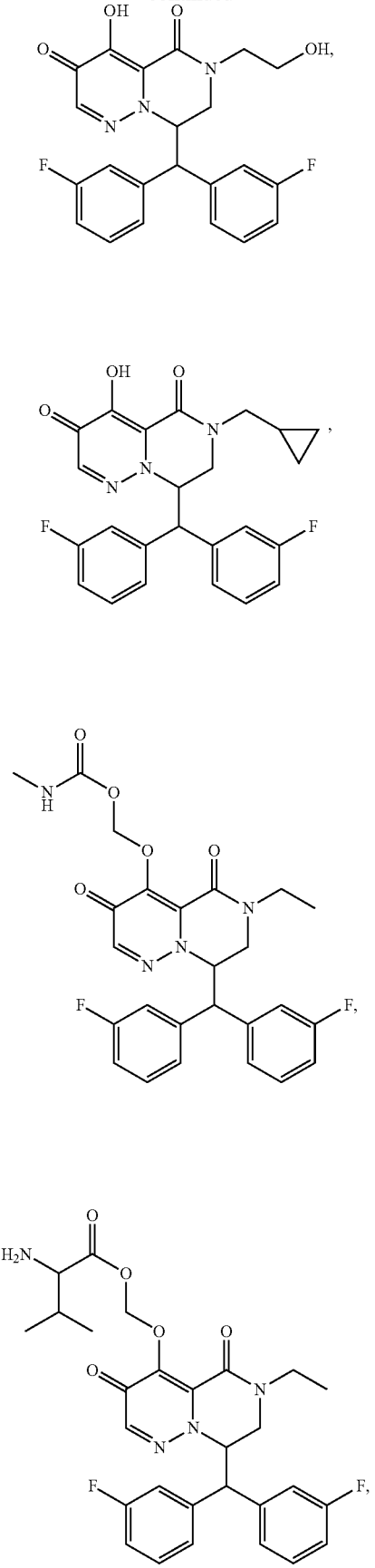

223
-continued
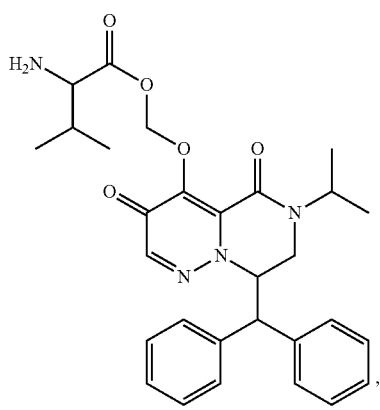
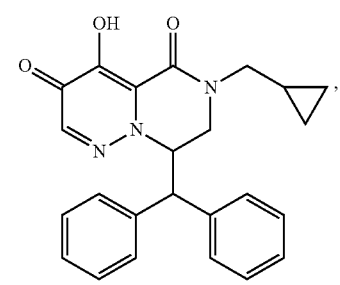
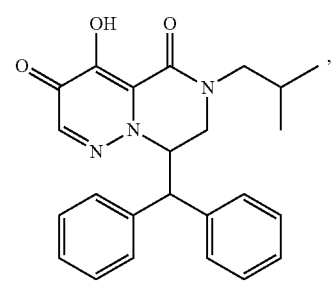
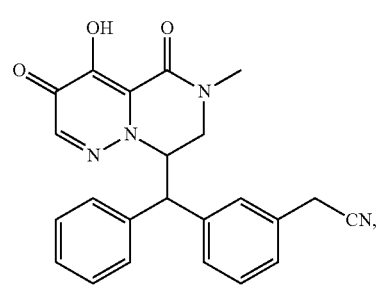
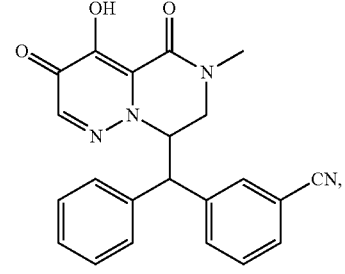
224
-continued
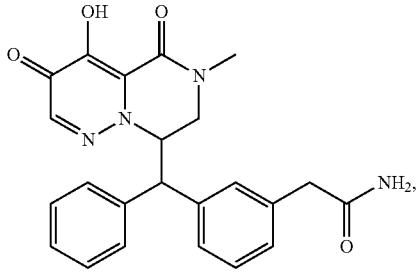
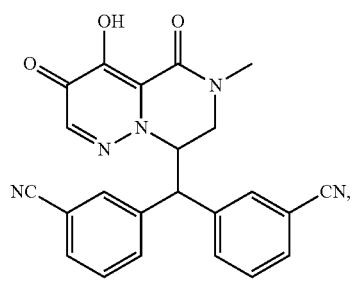
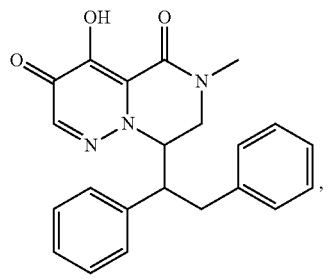
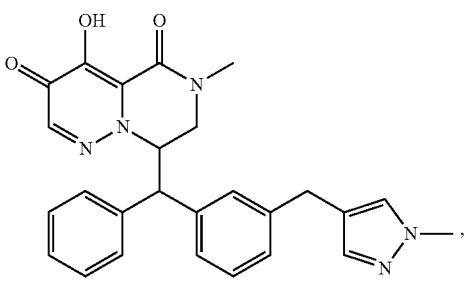
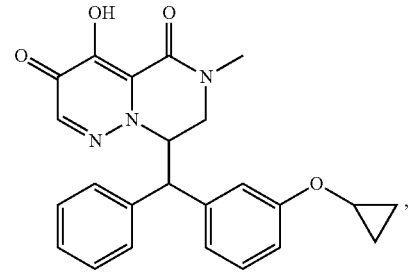

225
-continued
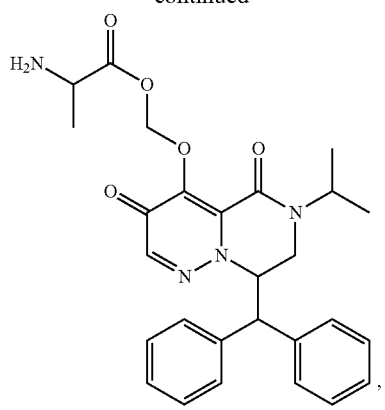
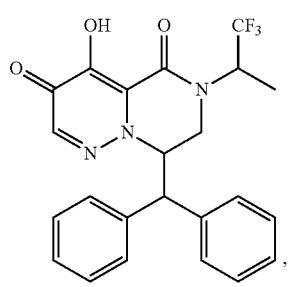
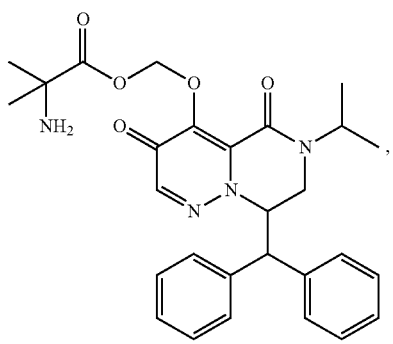
226
-continued
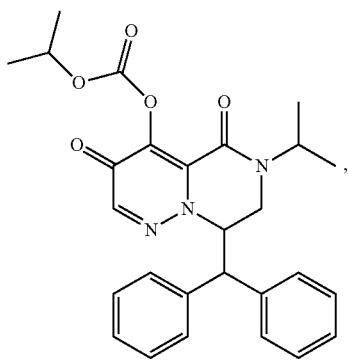
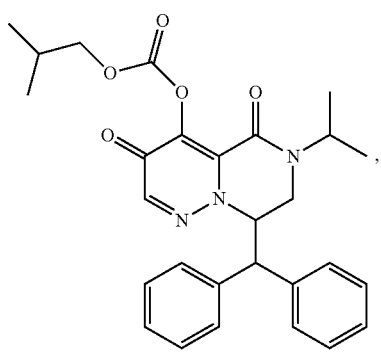
or a pharmaceutically acceptable salt of any of the foregoing.
18. The method of claim 1, wherein the compound is selected from the group consisting of:
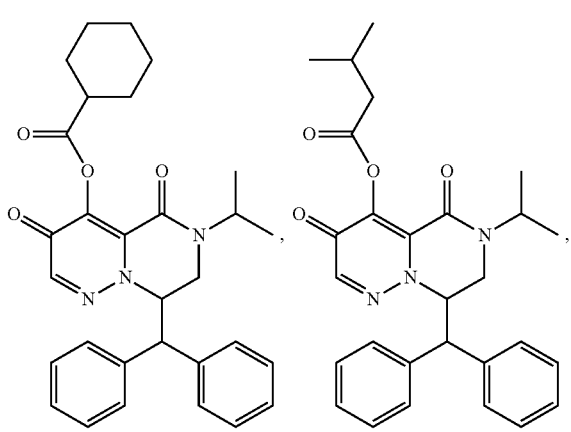
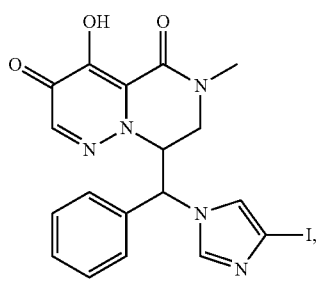

227
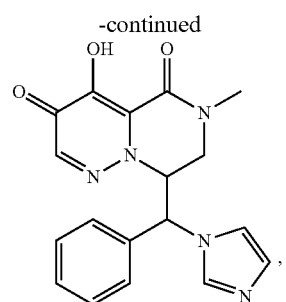,
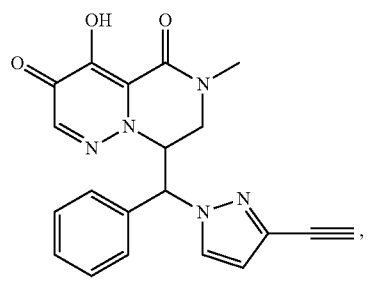,
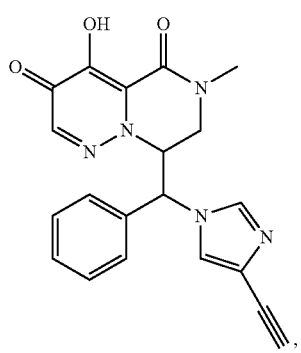,
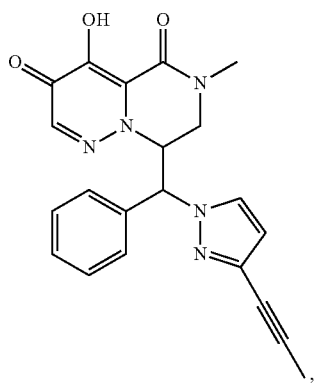,
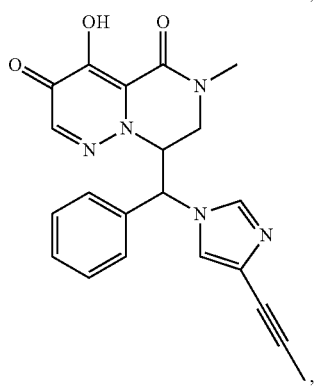,
228
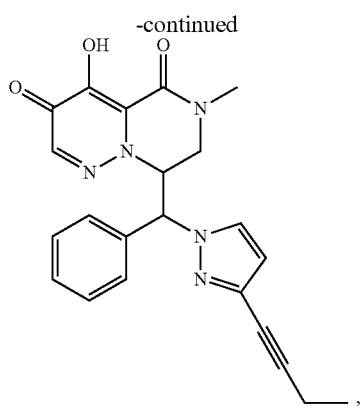,
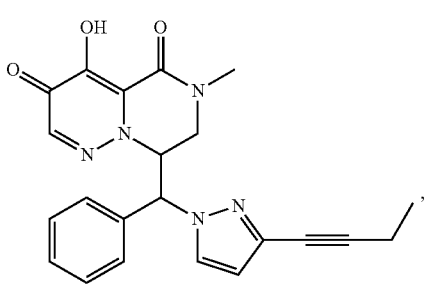,
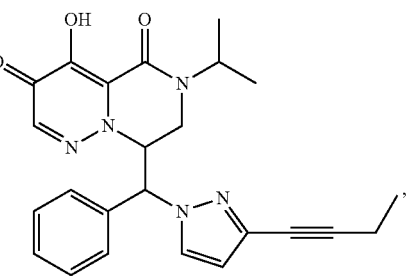,
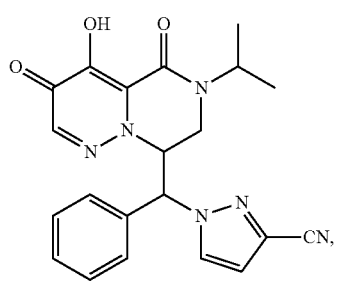,
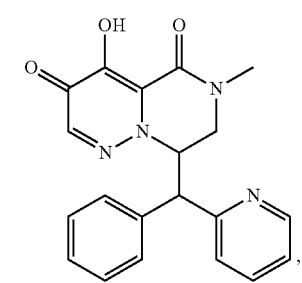, -continued

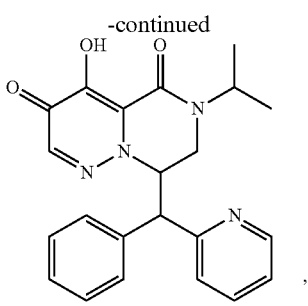

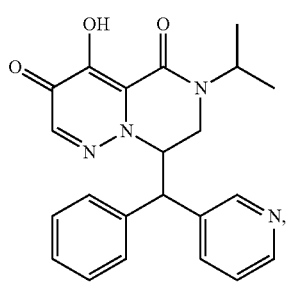

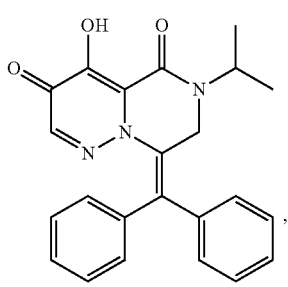

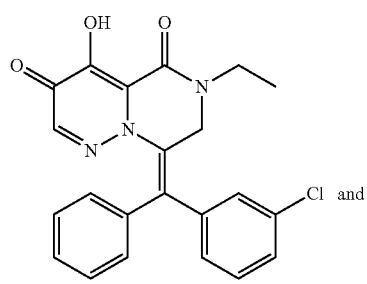

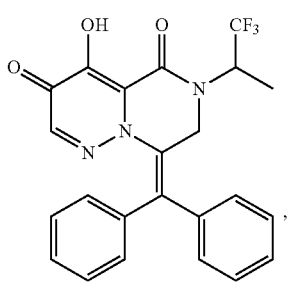

or a pharmaceutically acceptable salt of any of the foregoing.

19. The method of claim 1, wherein the compound is

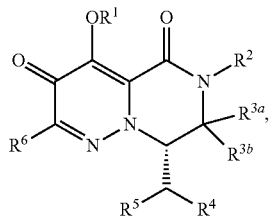

or a pharmaceutically acceptable salt thereof.

20. The method of claim 1, wherein the compound is

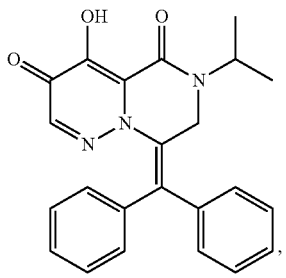

or a pharmaceutically acceptable salt thereof.

21. The method of claim 1, wherein the compound is

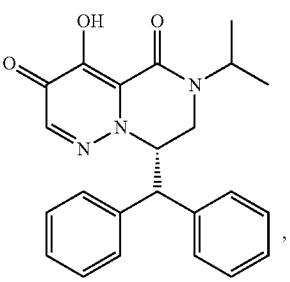 [SMILES: CC(C)N1C[C@H](C(c2ccccc2)c2ccccc2)n2ncc(=O)c(O)c2C1=O]

or a pharmaceutically acceptable salt thereof.

22. The method of claim 1, wherein the compound is

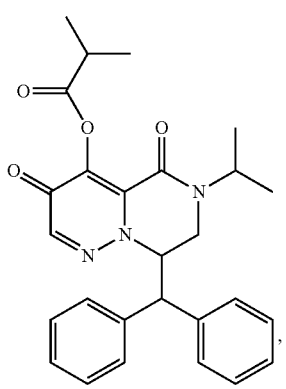

or a pharmaceutically acceptable salt thereof.

23. The method of claim 1, wherein the compound is

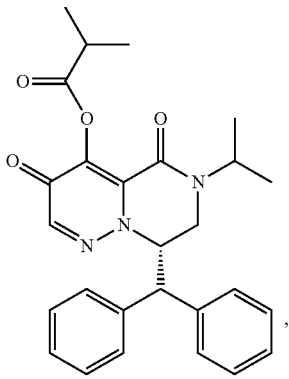 [SMILES: CC(C)C(=O)Oc1c2n(ncc1=O)[C@@H](C(c1ccccc1)c1ccccc1)CN(C(C)C)C2=O]

or a pharmaceutically acceptable salt thereof.

24. The method of claim 1, wherein the compound is

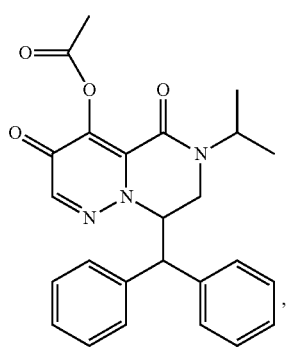 [SMILES: CC(=O)Oc1c2n(ncc1=O)C(C(c1ccccc1)c1ccccc1)CN(C(C)C)C2=O]

or a pharmaceutically acceptable salt thereof.

25. The method of claim 1, wherein the compound is

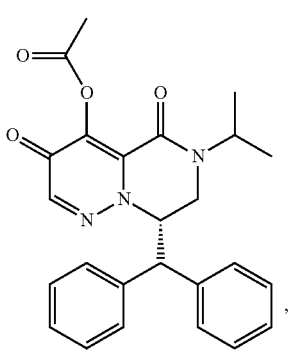 [SMILES: CC(=O)Oc1c2n(ncc1=O)[C@@H](C(c1ccccc1)c1ccccc1)CN(C(C)C)C2=O]

or a pharmaceutically acceptable salt thereof.

26. The method of claim 1, wherein the compound is

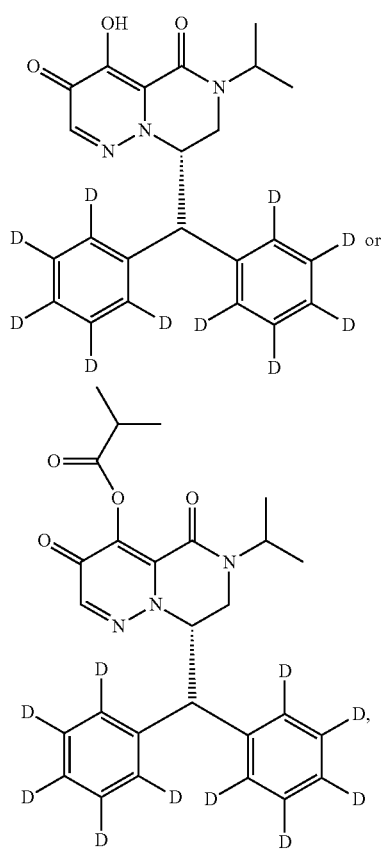

or a pharmaceutically acceptable salt of any of the foregoing.

27. The method of claim 1, wherein $R^4$ and $R^5$ are taken together with the carbon to which they are attached to form an optionally substituted tricyclic heterocyclyl.

28. The method of claim 1, wherein the influenza virus is influenza A virus.

29. The method of claim 1, wherein the influenza virus is influenza B virus.

30. A method for ameliorating or treating an influenza virus infection comprising administering an effective amount of a compound selected from the group consisting

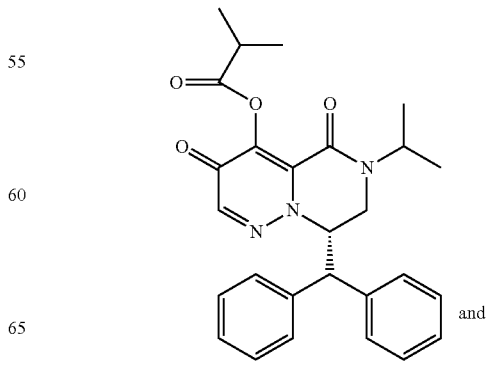

and

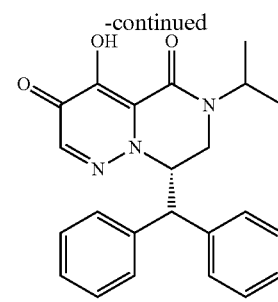

of or a pharmaceutically acceptable salt of any of the foregoing, to a subject suffering from the influenza virus infection.

31. The method of claim 1, further comprising administering one or more additional agents.

32. The method of claim 31, wherein the one or more additional agents is selected from the group consisting of a neuraminidase inhibitor, a M2 protein inhibitor, a polymerase inhibitor, a PB2 inhibitor, amantadine, rimantadine, zanamivir, oseltamivir, peramivir, laninamivir, laninamivir octanoate, favipiravir, fludase, ADS-8902, an immunomodulator, ribavirin, (R)-3-((5-fluoro-2-(5-fluoro-1H-pyrrolo[2,3-b]pyridin-3-yl)pyrimidin-4-yl)amino)-4,4-dimethylpentanoic acid, and (2S, 3S)-3-((5-fluoro-2-(5-fluoro-1H-pyrrolo[2,3-b]pyridin-3-yl)pyrimidin-4-yl)amino)bicycle[2.2.2]octane-2-carboxylic acid (VX-787).

33. A method for ameliorating or treating an influenza virus infection comprising contacting a cell infected with the influenza virus with an effective amount of a compound selected from the group consisting of

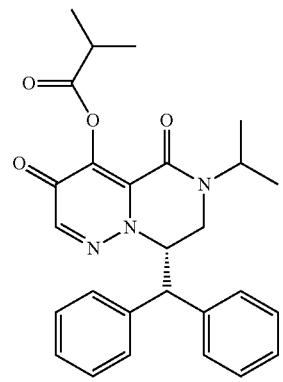

and

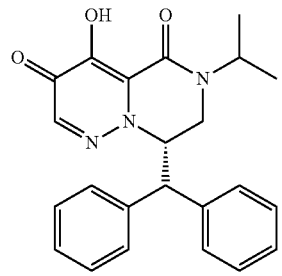

a pharmaceutically acceptable salt of any of the foregoing.

* * * * *

UNITED STATES PATENT AND TRADEMARK OFFICE
CERTIFICATE OF CORRECTION

PATENT NO.        : 10,251,882 B2
APPLICATION NO.   : 15/141387
DATED             : April 9, 2019
INVENTOR(S)       : Robert Than Hendricks et al.

Page 1 of 2

It is certified that error appears in the above-identified patent and that said Letters Patent is hereby corrected as shown below:

In the Claims

At Column 214, Claim number 17, Line numbers 13-22, please replace

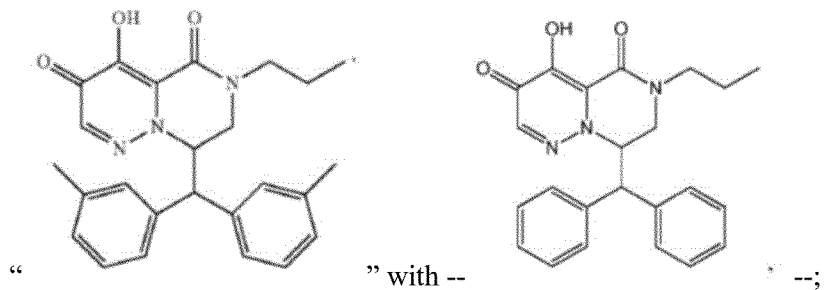

" with -- --;

At Column 226, Claim number 17, Line numbers 19-33, please replace

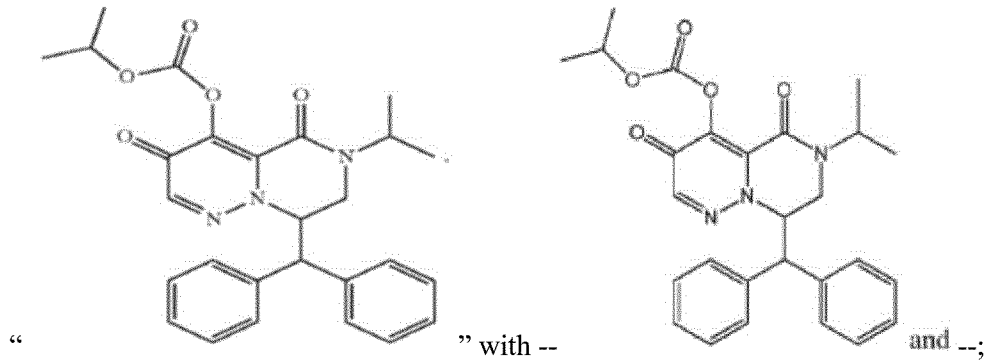

" with -- and --;

Signed and Sealed this
Third Day of December, 2019

Andrei Iancu
*Director of the United States Patent and Trademark Office*

CERTIFICATE OF CORRECTION (continued)
U.S. Pat. No. 10,251,882 B2

At Column 230, Claim number 20, Line numbers 19-28, please replace

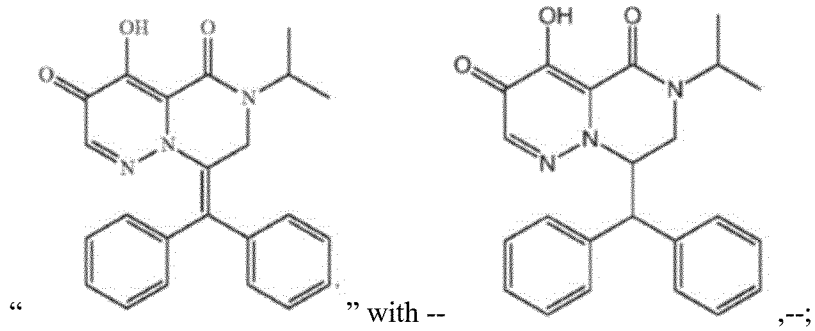

" " with -- ,--;

At Column 232, Claim number 30, Line number 51, please insert -- of -- after "consisting;";

At Column 233, Claim number 30, Line number 14, please delete "of" before "or;";

At Column 234, Claim number 33, Line number 30, please insert -- or -- before "a.".